US011339400B2

(12) United States Patent
Sayre et al.

(10) Patent No.: US 11,339,400 B2
(45) Date of Patent: May 24, 2022

(54) SYSTEMS, METHODS, AND COMPOSITIONS FOR HIGH-LEVEL PRODUCTION OF WATER-SOLUBLE CANNABINOIDS IN A PLANT TRICHOME

(71) Applicant: Trait Biosciences Inc., Los Alamos, NM (US)

(72) Inventors: Richard T. Sayre, Los Alamos, NM (US); Elton Carvalho Gonçalves, Los Alamos, NM (US); Tawanda Zidenga, White Rock, NM (US)

(73) Assignee: Trait Biosciences, Inc., Los Alamos, NM (US)

( * ) Notice: Subject to any disclaimer, the term of this patent is extended or adjusted under 35 U.S.C. 154(b) by 0 days.

(21) Appl. No.: 16/242,922

(22) Filed: Jan. 8, 2019

(65) Prior Publication Data

US 2019/0153461 A1    May 23, 2019

Related U.S. Application Data

(60) Division of application No. 16/110,728, filed on Aug. 23, 2018, which is a continuation-in-part of application No. PCT/US2018/024409, filed on Mar. 26, 2018.

(60) Provisional application No. 62/476,080, filed on Mar. 24, 2017, provisional application No. 62/588,662, filed on Nov. 20, 2017, provisional application No. 62/621,166, filed on Jan. 24, 2018.

(51) Int. Cl.
*C12N 15/82* (2006.01)
*A01H 6/28* (2018.01)
*C12N 9/08* (2006.01)

(52) U.S. Cl.
CPC ....... *C12N 15/8243* (2013.01); *C12N 9/0065* (2013.01); *C12Y 111/01006* (2013.01)

(58) Field of Classification Search
None
See application file for complete search history.

(56) References Cited

U.S. PATENT DOCUMENTS

| | | | |
|---|---|---|---|
| 5,292,899 A | 3/1994 | Tius et al. | |
| 5,990,697 A | 11/1999 | Kazama et al. | |
| 6,403,126 B1 | 6/2002 | Webster et al. | |
| 7,807,711 B2 | 10/2010 | Korthout et al. | |
| 8,410,064 B2 | 4/2013 | Radominska-Pandya et al. | |
| 8,673,368 B2 | 3/2014 | Guy et al. | |
| 8,829,043 B2 | 9/2014 | Riggs-Sauthier et al. | |
| 8,884,100 B2 * | 11/2014 | Page | C12N 9/1085 800/278 |
| 9,155,797 B2 | 10/2015 | Riggs-Sauthier et al. | |
| 9,205,063 B2 | 12/2015 | Guy et al. | |
| 9,394,510 B2 | 7/2016 | Peet et al. | |
| 9,512,391 B2 | 12/2016 | Peet et al. | |
| 9,546,362 B2 | 1/2017 | Page et al. | |
| 9,611,460 B2 | 4/2017 | Page et al. | |
| 9,822,384 B2 | 11/2017 | Poulos et al. | |
| 9,861,609 B2 | 1/2018 | Winnicki et al. | |
| 10,378,020 B2 | 8/2019 | Sayre et al. | |
| 2006/0106212 A1 | 5/2006 | Hollingsworth et al. | |
| 2006/0174377 A1 | 8/2006 | Nakamura et al. | |
| 2010/0021967 A1 | 1/2010 | Draborg | |
| 2012/0311744 A1 | 12/2012 | Sirkowski | |
| 2015/0099277 A1 | 4/2015 | Devaraj et al. | |
| 2016/0010126 A1 | 1/2016 | Poulos et al. | |
| 2016/0298151 A1 | 10/2016 | Butt et al. | |
| 2016/0326130 A1 | 11/2016 | Changoer et al. | |
| 2016/0355853 A1 | 12/2016 | Winnicki et al. | |
| 2017/0044552 A1 | 2/2017 | Kumar | |
| 2018/0264122 A1 * | 9/2018 | Zipp | A61K 31/352 |
| 2019/0153460 A1 | 5/2019 | Sayre et al. | |

FOREIGN PATENT DOCUMENTS

| | | |
|---|---|---|
| CA | 2454644 A1 | 2/2004 |
| EP | 3067058 A1 | 9/2016 |
| WO | 2007005604 A2 | 1/2007 |
| WO | 2011/017798 A1 | 2/2011 |
| WO | 2016/189384 A1 | 12/2016 |
| WO | 2017034942 A1 | 3/2017 |
| WO | 2017053574 A1 | 3/2017 |

OTHER PUBLICATIONS

Sevrioukova et al, 2013, Dalton Trans, 42:3116-3126.*
Wang et al., 2011, The Pharmacogenomics Journal, 11:274-286.*
Richman et al., 2005, The Plant J., 41:56-67.*
Andre et al, 2016, Frontiers in Plant Science, 7:1-17.*
Wahby et al, 2013, Journal of Plant Interactions, 8:312-320.*
Hardman et al, 2017, bioRxiv, Cannabinoid glycosides: In vitro Production of a New Class of Cannabinoids with Improved Physiochemical Properties, p. 1-37.*
https://en.wikipedia.org/wiki/List_of_EC_numbers_(EC_2)#EC_2.4:_Glycosyltransferases (2021).*
Sirikantaramas et al, 2005, Plant Cell Physiol., 46:1578-1582.*
Von Ossowski, et al., "Necleotide Sequence of *Escherichia coli* katE, Which Encodes Catalase HPII", Journal of Bacteriology, Jan. 1991, pp. 514-520, vol. 173, No. 2, American Society for Microbiology.
Holland, et al., "The multidrug transporter ABCG2 (BCRP) is inhibited by plant-derived cannabinoids", British Journal of Pharmacology, Oct. 1, 2007, pp. 815-824, vol. 152, Nature Publishing Group.
Ivanchenko, et al., "Maize ROP7 GTPase contains a unique, CaaX box-independent plasma membrane targeting signal", The Plant Journal, Jul. 12, 2000, pp. 79-90, vol. 24, Issue 1, Blackwell Science Ltd.

(Continued)

*Primary Examiner* — Jason Deveau Rosen
(74) *Attorney, Agent, or Firm* — Berg Hill Greenleaf Ruscitti LLP

(57) ABSTRACT

The inventive technology relates to systems and methods for enhanced in vivo production, accumulation and modification of cannabinoids. In one embodiment, the invention may include systems and methods for enhanced in vivo biosynthesis of chemically-modified water-soluble cannabinoids in a whole plant, or a cell suspension culture system.

5 Claims, 34 Drawing Sheets

Specification includes a Sequence Listing.

(56) References Cited

OTHER PUBLICATIONS

Rini, et al., "Chaper 5: Glycosyltransferases and Glycan-processing Enzymes", Essentials of Glycobiology, 2009, retrieved online on Aug. 17, 2018 from https://www.ncbi.nlm.nih.gov/books/NBK1921/, pp. 1-8, 2nd edition, Cold Spring Harbor, New York, USA.
Marks, et al., "Identification of candidate genes affecting Δ9-tetrahydrocannabinol biosynthesis in Cannabis sativa", Journal of Experimental Botany, Jul. 6, 2009, pp. 3715-3726, vol. 60, No. 13, Advance Access.
Nagaya, et al., "The HSP Terminator of *Arabidopsis thaliana* Increases Gene Expression in Plant Cells", Plant & Cell Physiology, 2010, pp. 328-332, vol. 51, Issue 2, Oxford University Press on behalf of Japanese Society of Plant Physiologists.
Norambuena, et al., "Transport of UDP-galactose in Plants: Identification and Functional Characterization of AtUTr1, An *Arabidopsis thaliana* UDP-galactose/UDP-glucose Transporter", The Journal of Biological Chemistry, May 31, 2002, pp. 32923-32929, vol. 277, No. 36, The American Society for Biochemistry and Molecular Biology, Inc.
Onofri, et al., "Sequence heterogeneity of cannabidiolic- and tetrahydrocannabinolic acid-synthase in *Cannabis sativa* L. and its relationship with chemical phenotype", Phytochemistry, Apr. 9, 2015, pp. 57-68, vol. 116, Elsevier Ltd.
Priest, et al., "Use of the glucosyltransferase UGT71B6 to disturb abscisic acid homeostasis in *Arabidopsis thaliana*", The Plant Journal, Jan. 12, 2006, pp. 492-502, vol. 46, Blackwell Publishing Ltd.
Siritunga, et al., "Generation of cyanogen-free transgenic cassava", Planta, Mar. 18, 2003, pp. 367-373, vol. 217, Springer-Verlag.
Sparkes, et al., "Rapid, transient expression of fluorescent fusion proteins in tobacco plants and generation of stably transformed plants", Nature Protocols, Nov. 30, 2006, pp. 2019-2025, vol. 1, No. 4, Nature Publishing Group.
Taura, et al., "Purification and Characterization of Cannabidiolic-acid Synthase from *Cannabis sativa* L.: Biochemical Analysis of a Novel Enzyme that Catalyzes the Oxidocyclization of Cannabigerolic Acid to Cannabidiolic Acid", The Journal of Biological Chemistry, Apr. 26, 1996, pp. 17411-17416, vol. 271, No. 29, Issue of Jul. 19, The American Society of Biochemistry and Molecular Biology, Inc. U.S.A.
Taura, et al., "Cannabidiolic-acid synthase, the chemotype-determining enzyme in the fiber-type Cannabis sativa", FEBS Letters, May 25, 2007, pp. 2929-2934, vol. 581, Elsevier B.V.
Yoo, et al., "*Arabidopsis mesophyll* protoplasts: a versatile cell system for transient gene expression analysis", Nature Protocol, Jun. 21, 2007, pp. 1565-1572, vol. 2, No. 7, Nature Publishing Group.
Matsui, et al., "High level expression of transgenes by use of 5'-untranslated region of the *Arabidopsis thaliana* arabinogalactan-protein 21 gene in dicotyledons", Plant Biotechnology, Mar. 22, 2012, pp. 319-322, vol. 29, The Japanese Society for Plant Cell and Molecular Biology.
Murashige, et al., "A Revised Medium for Rapid Growth and Bio Assays with Tobacco Tissue Cultures", Physiologia Plantarum, Apr. 1, 1962, pp. 473-497, vol. 15.
Hardman, et al., "Cannabinoid glycosides: In vitro production of a new class of cannabinoids with improved physicochemical properties", BioRxiv, Jan. 30, 2017, pp. 1-37.
Mohamed, et al., "Overexpression of bacterial catalase in tomato leaf chloroplasts enhances photo-oxidative stress tolerance", Plant, Cell and Environment, 2003, pp. 2037-2046, vol. 26, Blackwell Publishing Ltd.
Akhtar, "Cannabinoids and zebrafish", Universiteit Leiden dissertation, May 22, 2013, pp. 1-179.
Hussein, "Cannabinoids production in *Cannabis sativa* L.: An in vitro approach", University Dortmund dissertation, Nov. 26, 2014, pp. 1-138.

Watanabe, et al., "Cytochrome P450 enzymes involved in the metabolism of tetrahydrocannabinols and cannabinol by human hepatic microsomes", Life Sciences, Dec. 27, 2006, pp. 1415-1419, vol. 80, Elsevier Inc.
Flores-Sanchez, et al., "Elicitation studies in cell suspension cultures of *Cannabis sativa* L.", Journal of Biotechnology, May 12, 2009, pp. 157-168, vol. 143, Elsevier B.V.
Stout, et al., "Exogenous cannabinoids as substrates, inhibitors, and inducers of human drug metabolizing enzymes: a systematic review", Drug Metabolism Reviews, Oct. 25, 2013, pp. 86-95, vol. 46, Issue 1, informa healthcare.
Andre, et al., "*Cannabis sativa*: The Plant of the Thousand and One Molecules", Frontiers in Plant Science, Feb. 4, 2016, pp. 1-17, vol. 7, Article 19, CrossMark.
Mahlberg, et al., "Accumulation of Cannabinoids in Glandular Trichomes of Cannabis (Cannabaceae)", Journal of Industrial Hemp, Sep. 25, 2008, pp. 15-36 and cover page, vol. 9, Issue 1, The Haworth Press, Inc.
Solymosi, et al., "Cannabis: A Treasure Trove or Pandora's Box?", Mini Reviews in Medicinal Chemistry, Aug. 31, 2016, pp. 1-70 and cover page, vol. 17, Bentham Science Publishers.
Sirikantaramas, et al., "Tetrahydrocannabinolic Acid Synthase, the Enzyme Controlling Marijuana Psychoaclivily, is Secreted into the Storage Cavity of the Glandular Trichomes", Plant Cell Physiology, 2005, pp. 1578-1582, vol. 46, Issue 9, JSPP.
Schilmiller, et al., "Harnessing plant trichome biochemistry for the production of useful compounds", The Plant Journal, Dec. 6, 2007, pp. 702-711, vol. 54, Blackwell Publishing Ltd.
Matias-Hernandez, et al., "AaMYB1 and its orthologue AtMYB61 affect terpene metabolism and trichome development in Artemisia annua and *Arabidopsis thaliana*". The Plant Journal, Feb. 16, 2017, pp. 520-534, vol. 90, John Wiley & Sons Ltd.
Invitation to Pay Additional Fees and, Where Applicable, Protest Fee dated Sep. 18, 2018 in International Application No. PCT/US18/41710 filed Jul. 11, 2018.
International Search Report and Written Opinion dated Nov. 8, 2018 in International Application No. PCT/US18/41710 filed Jul. 11, 2018.
International Search Report and Written Opinion dated Oct. 22, 2018 in International Application No. PCT/US18/24409 filed Mar. 26, 2018.
GenBank accession No. AB176523.1 "Nicotiana tabacum NtGT5a mRNA for glycosyltransferase, complete cds", Mar. 11, 2009 [online]. [Retrieved on Oct. 29, 2018]. Retrieved from the internet <URL:https://www.ncbi.nlm.nih.gov/nuccore/AB176523.1?report=genbank > sequence.
Logrono, "In Vitro Cell Culture of Cannabis Sativa for the Production of Cannabinoids" Poster [online]. Universitat Autonoma de Barcelona, Bellaterra. 2014 [Retrieved on Sep. 6, 2018]. Retrieved from the Internet: <URL: https://ddd.uab.cat/pub/tfg/2014/119249/TFG-javierlidoylogrono.pdf>; 1st column, 2nd paragraph; 3rd column, cell suspension Figures 3 and 4.
Akhtar, et al., "Hydrozylation and glycosylation of Delta 9-tetrahydrocannabinol by Catharanthus roseus cell suspension culture", Biocatalysis and Biotransformation, 2015, pp. 279-286, vol. 33 (5-6), Taylor & Francis Group.
Schachtsiek, et al., "Current Perspectives on Biotechnological Cannabinoid Production in Plants", Planta Med, 2018, pp. 214-220.
Wang et al., Glycosyltransferases: key players involved int he modification of plant secondary metabolites, Front Biol. China, 2009, pp. 39-46.
Nelson et al., "A P450-centric view of plant evolution", The Plant Journal, 2011, pp. 194-211.
Carvalho, et al., "Designing microorganisms for heterologous biosynthesis of cannabinoids", FEMS, 2017, pp. 1-11.
Aryal, et al., "Distribution of cannabinoid synthase genes in non-Cannabis organisms", Journal of Cannabis Research, 2019, pp. 1-6.
Christelle M. Andre et al, "*Cannabis sativa*: The Plant of the Thousand and One Molecules", Frontiers in Plant Science, (Feb. 4, 2016), vol. 7, doi:10.3389/fpls.2016.00019, pp. 1-17, XP055581704 [Y] 1,2 * p. 11, col. 1, paragraph 3-col. 2, paragraph 3 *.
M. Feeney et al, "Tissue culture and Agrobacterium-mediated transformation of hemp (*Cannabis sativa* L.)", in Vitro Cellular &

(56) References Cited

OTHER PUBLICATIONS

Development Biology. Plant, US, (Nov. 1, 2003), vol. 39, No. 6, doi:10.1079/IVP2003454, ISSN 1054-5476, pp. 578-585, XP055332883 [Y] 1,2 * p. 580, col. 2, paragraph I-p. 583, col. 2, paragraph I; figure 4 *.

Janee' M. Hardman et al, "Cannabinoid glycosides: In vitro production of a new class of cannabinoids with improved physicochemical properties", bioRxiv, doi:10.1101/104349, (Jan. 30, 2017), URL: https://www.biorxiv.org/content/biorxiv/early/2017/01/30/104349.full.pdf, XP055564615 [Y] 1,2 * p. 2, paragra.

Beaune P H et al, "Isolation and Sequence Determination of a CDNA Clone Related to Human Cytchrome P-450 Nifedipine Oxidase", Proceedings of the National Academy of Sciences, National Academy of Sciences, (Jan. 1, 1996), vol. 83, No. 83, ISSN 0027-8424, pp. 8064-8068, XP000907192 [Y] 1,2 * figures 3,4 *.

Alex Richman et al, "Functional genomics uncovers three glucosyltransferases involved in the synthesis of the major sweet glucosides of Stevia rebaudiana", The Plant Journal, Blackwell Scientific Publications, Oxford, GB, vol. 41, No. 1, doi:10.1111/J.1365-313X.2004.02275.X, ISSN 0960-7412, (Jan. 1, 2005), pp. 56-67, (Nov. 11, 2004), XP002686584 [Y] 1,2 * figure 10 *.

Mitsuru Haniu et al, "Biochemistry (preceding paper in this issue) Structural and Functional Analysis of NADPH-Cytochrome P-450 Reductase from Human Liver: Complete Sequence of Human Enzyme and NADPH-Binding Sites* 1", Biochemistry Biophys. J. Biochem. Soc. Trans, (Jan. 1, 1989), vol. 28, No. 21, doi:10.1021/bi00447a054, pp. 8639-8645, XP055722680 [Y] 1,2 * figure 1; table 3 *.

Supplementary European Search Report in U.S. Appl. No. 18/770,434, dated Dec. 3, 2020.

Sevrioukova, et al., "Understanding the Mechanism of Cytochrome P4503A4: Recent Advances and Remaining Problems", Dalton Trans., 2013, pp. 3116-3126, NIH-PA Author Manuscript.

Wang, et al., "Intronic polymorphism in CYP3A4 affects hepatic expression and response to statin drugs", The Pharmacogenomics Journal, 2011, pp. 274-286, Macmillan Publishers Limited.

Wahby, et al., "Agrobacterium infection of hemp (*Cannabis sativa* L.): establishment of hairy root cultures", Journal of Plant Interactions, 2013, pp. 312-320, Taylor & Francis Group.

* cited by examiner

```
        10         20         30         40         50         60         70         80         90        100
         |          |          |          |          |          |          |          |          |          |
CAT1  MDPYNVRPSSAHDSPFFTTNSGAPVWNNSSLTVGTRGPILLEDYHLLEKLANFDRERIPERVVHARGASAKGFFEVTHDITQLTSADFLRGPGVQTPVI
CAT2  MDPYKYRPASSVNSPFFTTNSGAPVWNNSSMTVGPRGPILLEDYHLVEKLANFDRERIPERVVHARGASAKGFFEVTHDISNLTCADFLRAPGVQTPVI
CAT3  MDPYKYRPASAVNAPFYTTNGGAPVSNNISSLTIGERGPVLLEDYHLIEKVANFTRERIPERVVHARGISAKGFFEVTHDISNLTCADFLRAPGVQTPVI 110        120        130        140        150        160        170        180        190        200
         |          |          |          |          |          |          |          |          |          |
CAT1  VRFSTVIHERGSPETIRDPRGFAVKFYTREGNFDLVGNNFPVFFVRDGMKFPDMVHALKPNPKSHIQENWRILDFFSHHPESLHMFSFLFDDIGIPQDYR
CAT2  VRFSTVIHERGSPETIRDPRGFAVKFYTREGNFDLVGNNFPVFFIRDGMKFPDMVHALKPNPKSHIQENWRILDFFSHHPESLNMFTFLFDDIGIPQDYR
CAT3  VRFSTVHERASPETRRDIRGFAVKFYTREGNFDLVGNNTPVFFIRDGIQFPDVVHALKPNPKTHIQEYWRILDYMSHLPESLLTWCMFDDVGIPQDYR 210        220        230        240        250        260        270        280        290        300
         |          |          |          |          |          |          |          |          |          |
CAT1  HMEGAGVNTYMLINKAGKAHYVKFHWKPTCGIKCLSDEEAIRVGGANHSHATKDLYDSIAAGYNPQWNLFVQVMDPAHEDKFDFPLDVTKINPEDILPL
CAT2  HMDGSGVNTYMLINKAGKAHYVKFHWKPTCGVKSLLEEDAIRVGGTNHSHATQDLVLYDSIAAGYNPEWKLFIQIIDPADEDKFDFPLDVTKINPEDILPL
CAT3  HMEGGVHTYTLIARSGKVLFVKFHWKPTCGIKNLTIDEFAKVGGANHSHATKDLHDATASGYNPEWKLFIQIIDPADEDKFDFPLDVTKINPEDILPL 310        320        330        340        350        360        370        380        390        400
         |          |          |          |          |          |          |          |          |          |
CAT1  QPVGRILVLNKNIDNFFNENEQIAFCPALVPGIHYSDDKLLQTRIFSYADSQRHRLGPNYLQLPVNAPKCAHHNNHDGFMNFMHRDEEVNYFPSRLDPV
CAT2  QPVGRMLNKNIDNFFAENEQLAFCPAIIVPGIHYSDDKLLQTRVFESYADTQRHRLGPNYLQLPVNAPKCAHHNNHHEGFMNFMHRDEEVNYFPSRYDQV
CAT3  QPVGRIVLNRTIDNFFNETEQLAFNPGLWPGIYYSDDKLLQCRIFAYGDTQRHRLGPNYLQLPVNAPKCAHHNNHHEGFMNFMHRDEEINYYPSKEDPV 410        420        430        440        450        460        470        480        490
         |          |          |          |          |          |          |          |          |
CAT1  RHAEKVPTTPIVCSGNREKCFIGKENNFKQPGERYRSMDSDRQERFVKRFVEALSFPRVTHEIRSTWISYWSQADKSLGQKIATRIRNVRPNE
CAT2  RHAEKVPTPPAVCSGKRERCIEKENNFKEPGERYRTPERQERFIQRWIDALSDPRITHEIRSTWISYWSQADKSLGQKIASRIRNVRPSI
CAT3  RCAEKVPTFNSYTGIRTKCVIKKENNFKQAGDRYRSWAPDRQDRFVKRWVEILSEPRLTHEIRGTWISYWSQADRSLGQKIASRIRNVRPSH
```

FIG. 33

SYSTEMS, METHODS, AND COMPOSITIONS FOR HIGH-LEVEL PRODUCTION OF WATER-SOLUBLE CANNABINOIDS IN A PLANT TRICHOME

This application is a Division of U.S. application Ser. No. 16/110,728, filed Aug. 23, 2018; which is a Continuation-in-Part of International Application No. PCT/US18/24409, filed Mar. 26, 2018; which claims the benefit of and priority to U.S. Provisional Application No's. 62/476,080, filed Mar. 24, 2017; 62/588,662, filed Nov. 20, 2017; and 62/621,166, filed Jan. 24, 2018. The entire specifications and figures of the above-referenced applications are hereby incorporated, in their entirety by reference.

SEQUENCE LISTING

The instant application contains a Sequence Listing which has been submitted electronically in ASCII format and is hereby incorporated by reference in its entirety.

TECHNICAL FIELD

The field of the present invention relates generally to plant molecular biology and plant biotechnology. More specifically, it relates to novel systems, methods and compositions for the in vivo production, modification and isolation of cannabinoid compounds from plant systems, including whole plants and/or plant cell cultures systems. In certain preferred embodiments, the inventive technology includes a novel system of genetically modifying a plant or plant cell suspension culture to produce, modify and/or accumulate one or more target cannabinoids in *Cannabis* and/or *Nicotiana benthamiana* and/or *Nicotiana tabacum*

BACKGROUND

Cannabinoids are a class of specialized compounds synthesized by *Cannabis*. They are formed by condensation of terpene and phenol precursors. They include these more abundant forms: Delta-9-tetrahydrocannabinol (THC), cannabidiol (CBD), cannabichromene (CBC), and cannabigerol (CBG). Another cannabinoid, cannabinol (CBN), is formed from THC as a degradation product and can be detected in some plant strains. Typically, THC, CBD, CBC, and CBG occur together in different ratios in the various plant strains.

Cannabinoids are generally classified into two types, neutral cannabinoids and cannabinoid acids, based on whether they contain a carboxyl group or not. It is known that, in fresh plants, the concentrations of neutral cannabinoids are much lower than those of cannabinoid acids. One strain *Cannabis sativa* contains approximately 61 compounds belonging to the general class of cannabinoids. These cannabinoids are generally lipophilic, nitrogen-free, mostly phenolic compounds, and are derived biogenetically from a monoterpene and phenol, the acid cannabinoids from a monoterpene and phenol carboxylic acid, and have a C21 to base material.

Cannabinoids also find their corresponding carboxylic acids in plant products. In general, the carboxylic acids have the function of a biosynthetic precursor. For example, these compounds arise in vivo from the THC carboxylic acids by decarboxylation the tetrahydrocannabinols Δ9- and Δ8-THC and CBD from the associated cannabidiol. As generally shown in FIG. 28, THC and CBD may be derived artificially from their acidic precursor's tetrahydrocannabinolic acid (THCA) and cannabidiolic acid (CBDA) by non-enzymatic decarboxylation.

Cannabinoids are widely consumed, in a variety of forms around the world. Cannabinoid-rich preparations of *Cannabis*, either in herb (i.e. marijuana) or resin form (i.e., hash oil), are used by an estimated 2.6-5.0% of the world population (UNODC, 2012). Cannabinoid containing pharmaceutical products, either containing natural *cannabis* extracts (Sativex®) or the synthetic cannabinoids dronabinol or nabilone, are available for medical use in several countries As noted above, Δ-9-tetrahydrocannabinol (also known as THC) is one of the main biologically active components in the *Cannabis* plant which has been approved by the Food and Drug Administration (FDA) for the control of nausea and vomiting associated with chemotherapy and, more recently, for appetite stimulation of AIDS patients suffering from wasting syndrome. The drug, however, shows other biological activities which lend themselves to possible therapeutic applications, such as in the treatment of glaucoma, migraine headaches, spasticity, anxiety, and as an analgesic.

Indeed, it is well documented that agents, such as cannabinoids and endocannabinoids that activate cannabinoid receptors in the body modulate appetite, and alleviate nausea, vomiting, and pain (Martin B. R. and Wiley, J. L, *Mechanism of action of cannabinoids: how it may lead to treatment of cachexia, emesis and pain*, Journal of Supportive Oncology 2: 1-10, 2004), multiple sclerosis (Pertwee, R. G., *Cannabinoids and multiple sclerosis*, Pharmacol. Ther. 95, 165-174, 2002), and epilepsy (Wallace, M. J., Blair, R. E., Falenski, K. WW., Martin, B. R., and DeLorenzo, R. J. Journal Pharmacology and Experimental Therapeutics, 307: 129-137, 2003). In addition, CB2 receptor agonists have been shown to be effective in treating pain (Clayton N., Marshall F. H., Bountra C., O'Shaughnessy C. T., 2002. CB1 and CB2 cannabinoid receptors are implicated in inflammatory pain. 96, 253-260; Malan T. P., Ibrahim M. M., Vanderah T. W., Makriyannis A., Porreca F., 2002. Inhibition of pain responses by activation of CB(2) cannabinoid receptors. Chemistry and Physics of Lipids 121, 191-200; Malan T. P., Jr., Ibrahim M. M., Deng H., Liu Q., Mata H. P., Vanderah T., Porreca F., Makriyannis A., 2001. *CB2 cannabinoid receptor-mediated peripheral antinociception*. 93, 239-245; Quartilho A., Mata H. P., Ibrahim M. M., Vanderah T. W., Porreca F., Makriyannis A., Malan T. P., Jr., 2003. *Inhibition of inflammatory hyperalgesia by activation of peripheral CB2 cannabinoid receptors*. Anesthesiology 99, 955-960) and multiple sclerosis (Pertwee, R. G., *Cannabinoids and multiple sclerosis*, Pharmacol. Ther. 95, 165-174, 2002) in animal models.

More recently, several states have approved use of *Cannabis* and cannabinoid infused products for both recreational and medical uses. As these new medical and commercial markets have developed, there has grown a need to develop more efficient production and isolation of cannabinoid compounds. Traditional methods of cannabinoid production typically focus on extraction and purification of cannabinoids from raw harvested *Cannabis*. However, traditional cannabinoid extraction and purification methods have a number of technical and practical problems that limits its usefulness.

Limitations of Traditional Cannabinoid Production and Extraction Methods

For example, in U.S. Pat. No. 6,403,126 (Webster et al.), cannabinoids, and other related compounds are isolated from raw harvested *Cannabis* and treated with an organic solvent, typically a petroleum derived hydrocarbon, or a low molecular-weight alcohol to solubilize the cannabinoids for later isolation. This traditional method is limited in that it relies on naturally grown plant matter that may have been exposed to various toxic pesticides, herbicides and the like. In addition, such traditional extraction methods are imprecise resulting in unreliable and varied concentrations of extracted THC. In addition, many *Cannabis* strains are grown in hydroponic environments which are also not regulated and can results in the widespread contamination of such strains with chemical and other undesired compounds.

In another example, US Pat. App. No. 20160326130 (Lekhram et al.), cannabinoids, and other related compounds are isolated from raw harvested *Cannabis* using, again, a series of organic solvents to convert the cannabanoids into a salt, and then back to its original carboxylic acid form. Similar to Webster, this traditional method is limited in that is relies on naturally grown plant matter that may have been exposed to various toxic pesticides, herbicides and the like. In addition, the multiple organic solvents used in this traditional process must be recovered and either recycled and/or properly disposed of.

Another traditional method of cannabinoid extraction involves the generation of hash oils utilizing supercritical carbon-dioxide ($sCO_2$). Under this traditional method, again the dried plant matter is ground and subjected to a $sCO_2$ extraction environment. The primary extract being initially obtained and further separated. For example, as generally described by CA2424356 (Muller et al.) cannabinoids are extracted with the aid of $sCO_2$ under supercritical pressure and temperature conditions and by the addition of accessory solvents (modifiers) such as alcohols. Under this process, this supercritical $CO_2$ evaporates and dissolves into the cannabinoids. However, this traditional process also has certain limiting disadvantages. For example, due to the low solubility in supercritical $sCO_2$, recovery of the cannabinoids of interest is inconsistent. Additionally, any solvents used must be recycled and pumped back to the extractor, in order to minimize operating costs.

Another method utilizes butane to extract cannabinoids, in particular high concentrations of THC, from raw harvested *Cannabis*. Because butane is non-polar, this process does not extract water soluble by-products such as chlorophyll and plant alkaloids. That said, this process may take up to 48 hours and as such is limited in its ability to scale-up for maximum commercial viability. The other major drawback of traditional butane-based extraction processes is the potential dangers of using flammable solvents, as well as the need to ensure all of the butane is fully removed from the extracted cannabinoids.

Another limiting factor in the viability of these traditional methods of cannabinoid extraction methods is the inability to maintain *Cannabis* strain integrity. For example, cannabanoids used in medical and research applications, or that are subject to controlled clinical trials, are tightly regulated by various government agencies in the United States and elsewhere. These regulatory agencies require that the *Cannabis* strains remain chemically consistent over time. Unfortunately, the genetic/chemical compositions of the *Cannabis* strains change over generations such that they cannot satisfy regulatory mandates present in most clinical trials or certified for use in other pharmaceutical applications.

Several attempts have been made to address these concerns. For example, efforts have been made to produce cannabinoids in genetically engineered organisms. For example, in U.S. patent application Ser. No. 14/795,816 (Poulos, et al.) Here, the applicant claims to have generated a genetically modified strain of yeast capable of producing a cannabinoid by inserting genes that produce the appropriate enzymes for its metabolic production. However, such application is limited in its ability to produce only a single or very limited number of cannabinoid compounds. This limitation is clinically significant. Recent clinical studies have found that the use of a single isolated cannabinoid as a therapeutic agent is not as effective as treatment with the naturally-occurring "entourage" of primary and secondary cannabinoids associated with various select strains.

Additional attempts have been made to chemically synthesize cannabinoids, such as THC. However, the chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*.

Efforts to generate large-scale *Cannabis* cell cultures have also raised a number of technical problems. Chief among them is the fact that cannabinoids are cytotoxic. Under natural conditions cannabinoids are generated and then stored extracellularly in small glandular structures called trichomes. Trichomes can be visualized as small hairs or other outgrowths from the epidermis of a *Cannabis* plant. As a result, in *Cannabis* cell cultures, the inability to store cannabanoids extracellularly means any accumulation of cannabinoids would be toxic to the cultured cells. Such limitations impair the ability of *Cannabis* cell cultures to be scaled-up for industrial levels of production.

Cannabinoid Biosynthesis Toxicity Limits In Vivo Production Systems

Efforts to generate *Cannabis* strains/cell cultures that produce or accumulate high-levels of cannabinoids have raised a number of technical problems. Chief among them is the fact that cannabinoid synthesis produces toxic by-products. Notably, both CBDA and THCA synthases require molecular oxygen, in conjunction with a molecule of FAD, to oxidize Cannabigerolic acid (CBGA). Specifically, as shown in FIG. 29, two electrons from the substrate are accepted by an enzyme-bound FAD, and then transferred to molecular oxygen to re-oxidize FAD. CBDA and THCA are synthesized from the ionic intermediates via stereoselective cyclization by the enzymes. The hydride ion is transferred from the reduced flavin to molecular oxygen, resulting in the formation of hydrogen peroxide and re-activation of the flavin for the next cycle. As a result, in addition to producing CBDA and THCA respectively, this reaction produces hydrogen peroxide ($H_2O_2$) which is naturally toxic to the host cell. Due to this production of a toxic hydrogen peroxide byproduct, cannabinoid synthesis generates a self-limiting feed-back loop preventing high-level production and/or accumulation of cannabinoids in in vivo systems. One way that *Cannabis* plants deal with these cellular cytotoxic effects is through the use of trichomes for Cannabinoid production and accumulations.

*Cannabis* plants deal with this toxicity by sequestering cannabinoid biosynthesis and storage extracellularly in small glandular structures called trichomes as note above. For example, THCA synthase is a water soluble enzyme that is responsible for the production of THC. For example, THC biosynthesis occurs in glandular trichomes and begins with condensation of geranyl pyrophosphate with olivetolic acid to produce cannabigerolic acid (CBGA); the reaction is catalyzed by an enzyme called geranylpyrophosphate:olivatolate geranyltransferase. CBGA then undergoes oxidative cyclization to generate tetrahydrocannabinolic acid (THCA) in the presence of THCA synthase. THCA is then transformed into THC by non-enzymatic decarboxylation. Subcellular localization studies using RT-PCR and enzymatic activity analyses demonstrate that THCA synthase is expressed in the secretory cells of glandular trichomes, and then is translocated into the secretory cavity where the end product THCA accumulates. THCA synthase present in the secretory cavity is functional, indicating that the storage cavity is the site for THCA biosynthesis and storage. In this way, the *Cannabis* is able to produce cannabinoids extracellularly and thereby avoid the cytotoxic effects of these compounds. However, as a result, the ability to access and chemically alter cannabinoids in vivo is impeded by this cellular compartmentalization.

To address these concerns, some have proposed chemically modifying cannabinoid compounds to reduce their cytotoxic effects. For example, Zipp, et al. have proposed utilizing an in vitro method to produce cannabinoid glycosides. However, this application is limited to in vitro systems only. Specifically, as noted above, cannabinoid synthase enzymes, such as THCA synthase, are water soluble proteins that are exported out of the basal trichome cells into the storage compartment where it is active and catalyzes the synthesis of THCA. Specifically, in order to effectively mediate the cellular export of such cannabinoid synthase, this enzyme contains a 28 amino acid signal peptide that directs its export out of the cell and into the extracellular trichrome where cannabinoid synthesis occurs. As a result of this signal-dependent extracellular compartmentalization of, in this instance, THCA synthase, this means that the THCA is made outside of the cytoplasm and would not be accessible to genetically engineered glycosylation enzymes. As such, simple expression of a UDP glycosyltransferase in plant cells, as vaguely alluded to in Zipp, et al., would not result in effective glycosylation of cannabinoid molecules in the compartmentalized and extracellular trichrome structure where cannabinoid synthesis occurs. Neither can the method of Zipp generate acetylated cannabinoids, as well as 0 acetyl glycoside cannabinoid molecules.

The foregoing problems regarding the production, detoxification and isolation of cannabinoids may represent a long-felt need for an effective—and economical—solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

As will be discussed in more detail below, the current inventive technology overcomes the limitations of traditional cannabinoid production systems while meeting the objectives of a truly effective and scalable cannabinoid production, modification and isolation system.

SUMMARY OF THE INVENTION(S)

The inventive technology may encompass systems, methods and compositions for the in vivo production, modification and isolation of cannabinoid compounds from *Cannabis* plants. In particular, the invention provides systems and methods for high level in vivo biosynthesis of water-soluble cannabinoids.

The current inventive technology includes systems and methods for enhanced production and/or accumulation of cannabinoids. In one embodiment, the invention may include systems and methods for enhanced production and/or accumulation of cannabinoids in an in vivo system, such as a plant, or plant cell culture.

Another aim of the current invention may include the generation of genetically modified plants overexpressing certain endogenous/exogenous genes that result in the overproduction and/or accumulation of cannabinoids above wild-type levels. In one preferred embodiment, such transgenic plants may exhibit enhanced production and localized accumulation of cannabinoid precursor compounds, such as THCA (tetrahydrocannabinolic acid), CBCA (cannabichromenic acid), and CBDA (cannabidiolic acid). Such transgenic plants may additionally exhibit enhanced production and localized accumulation of cannabinoids, such as THCs, CBCs and CBDs. An additional aim of the current invention may include the generation of genetically modified plants expressing certain endogenous/exogenous genes that result in the enhanced modification of cannabinoids. In one preferred embodiment, such transgenic plants may exhibit enhanced modification of cannabinoids including hydroxylation, and/or acetylation, and/or glycosylation. In additional preferred embodiments, such transgenic plants may exhibit enhanced modification of cannabinoids including acetylation and glycosylation, such as an O acetyl glycoside form. For example, acetylation adds an acetyl group ($—CH_3OOH$) to a cannabinoid such that the carboxylate group is acidic and charged at neutral pH making it highly water-soluble.

One aim of the current inventive technology may be to generate a genetically modified or transgenic *Cannabis* plant that overexpresses one or more transcription factors, such as myb, that enhance metabolite flux through the cannabinoid biosynthetic pathway. In one preferred embodiment, these transcription factors may include various analogues. In certain preferred embodiment, one or more of these transgenes may be operably-linked to one or more promoters.

Another aim of the current inventive technology may be to generate a genetically modified or transgenic *Cannabis* cell culture that overexpresses one or more transcription factors that enhance metabolite flux through the cannabinoid biosynthetic pathway. In one preferred embodiment, these transgenes may be operably linked to one or more promoters.

Another aim of the current inventive technology may be to generate a genetically modified or transgenic *Cannabis* plant that expresses one or more exogenous/heterologous transcription factors that up-regulated trichome formation to increase cannabinoid accumulation. In certain preferred embodiments, one or more of these exogenous transgenes may be operably linked to one or more promoters.

Yet, another aim of the current inventive technology may be to generate a genetically modified or transgenic *Cannabis* plant that expresses an enzyme that is configured to be capable of reducing hydrogen peroxide ($H_2O_2$) levels that may be generated during cannabinoid synthesis. In one preferred embodiment, the current inventive technology may be to generate a genetically modified or transgenic *Cannabis* plant that expresses a chimeric protein. In this embodiment, this chimera protein may include a first domain that may reduce hydrogen peroxide ($H_2O_2$) levels that may be generated during cannabinoid synthesis. This chimera/fusion protein may further include a second domain that may comprise a trichome targeting domain that may allow targeted localization of the chimeric protein to locations of active cannabinoid synthesis. In some embodiments, a third domain may include a linker which may further separate the first domain from the second domain, such that said first domain and said second domain can each fold into its appropriate three-dimensional shape and retains its activity and said linker ranges in length.

Another aim of the current inventive technology may include the generation of one or more of the above referenced genetically modified plant or plant cell cultures utilizing *Agrobacterium* Ti-plasmid mediated transformation.

Another aim of the present inventive technology relates methods and systems for the in vivo cellular localization of cannabinoid biosynthesis and modification. More specifically, the present inventive technology relates methods and systems for the in vivo cellular localization of cannabinoid hydroxylation, acetylation and/or glycosylation. The inventive technology may include systems and methods for high-efficiency localized chemical modification and isolation of cannabinoid compounds from suspension cultures. In this embodiment, various select cannabinoid compounds may be chemically modified into soluble and non-toxic configurations.

Additional embodiments of the inventive technology may include the transient modification of cannabinoid compounds to reduce and/or eliminate their cytotoxicity in plants or plant cell culture systems. In a preferred embodiment, such transiently modified cannabinoids may be allowed to accumulate at levels that would normally have a deleterious effect on the cell. Additional embodiments may include the isolation of these transiently modified cannabinoids followed by enzymatic conversion or reconstitution to their original and/or partially modified structure.

Another aim of the invention may include the generation of a transgenic plant and or plant cell cultures that may express heterologous genes that coupled cannabinoid synthesis and hydroxylation and/or glycosylation in planta. Specifically, one aim of the technology may include using *Nicotiana benthamiana* to demonstrate the coupling CBDA synthesis and glycosylation in planta. An, additional aim of this embodiment may include additional modifications in the CBDA molecule, such as hydroxylation and acetylation. In yet another aim, this cannabinoid modification may be specifically localized, for example in the cytosol and/or trichome.

Another aim of the invention may include the generation of a transgenic plant and or plant cell cultures that may over express endogenous genes that may be configured to modify cannabinoids. Additional aim may include the co-expression of heterologous transcription factors that may increase cannabinoid production. Another aim of the invention may include the co-expression of heterologous genes that detoxify the hydrogen peroxide byproducts generated through cannabinoid biosynthesis. Co-expression of such genes may be additive with the co-expression of genes configured to modify and/or localize cannabinoid biomodifications.

BRIEF DESCRIPTION OF THE FIGURES

FIG. 33. Amino Acid sequence comparison of exemplary *Arabidopsis* catalase protein sequences. FIG. 33 also contains SEQ ID NO. 51 which represents CAT gene 1; SEQ ID NO. 52 which represents CAT gene 2; and SEQ ID NO. 53 which represents CAT gene 3.

MODE(S) FOR CARRYING OUT THE INVENTION(S)

Figure 1:
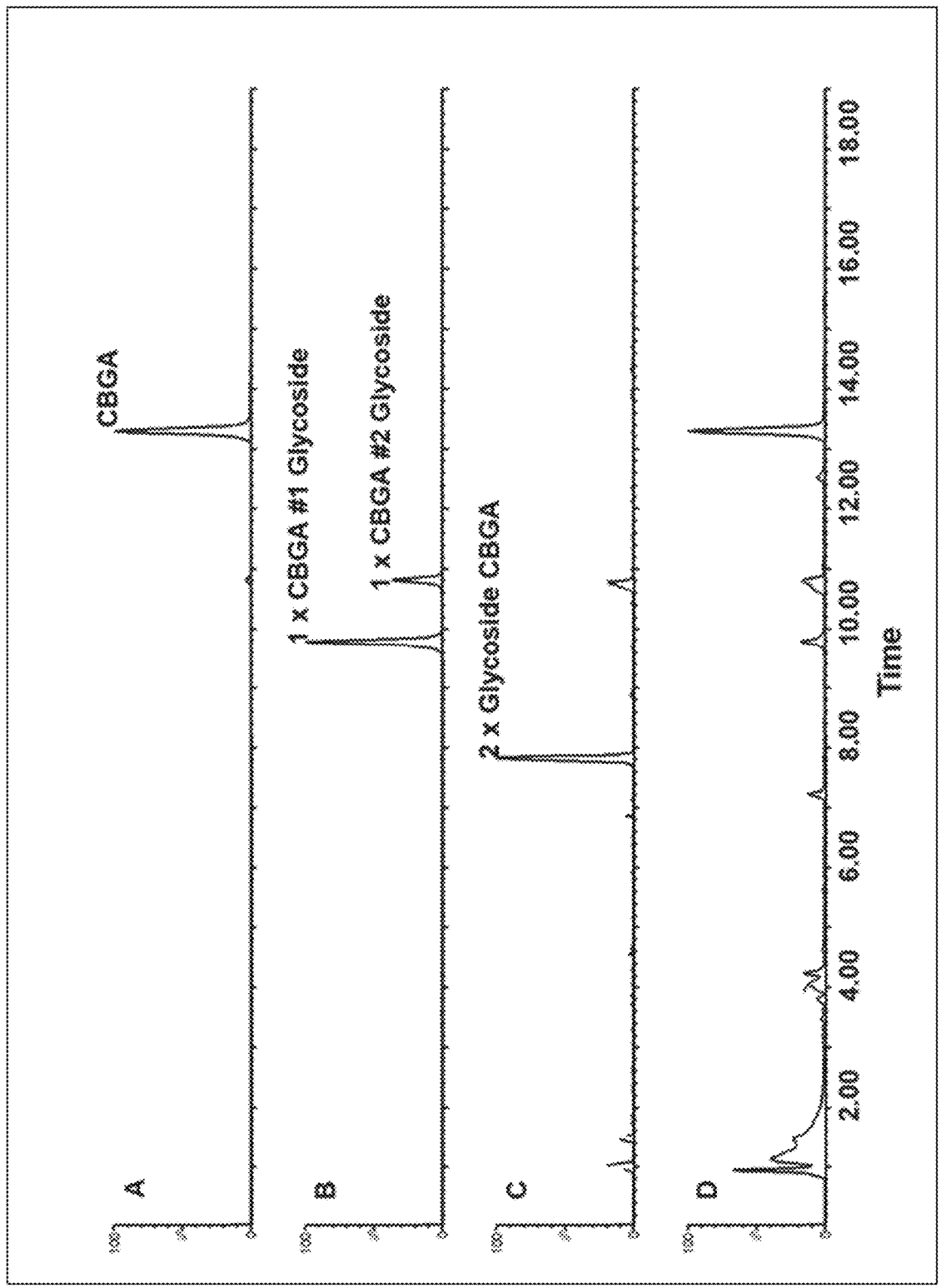
FIG. 1. Representative Chromatographic Elution profile of CBGA Glycosides found in in vitro Assays. Chromatograms A, B, and C represent respective extracted ion chromatograms for each glycoside product. Chromatogram D is representative of the total ion chromatogram. Peak Intensities are illustrated as relative abundance to most abundant peak in each respective chromatogram.
Figure 2:
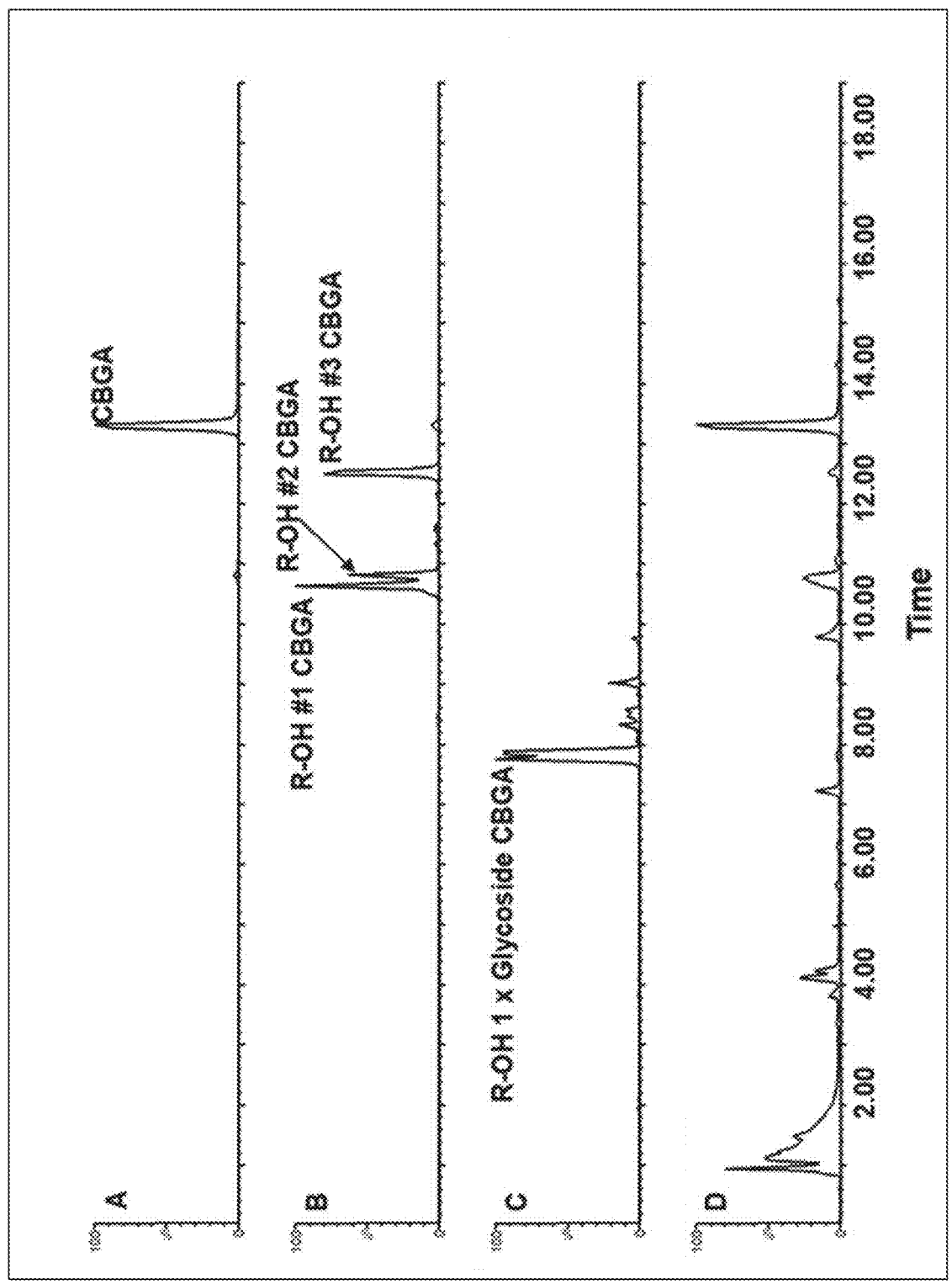
FIG. 2. Representative Chromatographic Elution profiles of Functionalized CBGA and Glycosides found in in vitro assays. Chromatograms A, B, and C represent respective extract rated ion chromatograms for each product. Chromatogram D is representative of the total ion chromatogram. Peak Intensities are illustrated as relative abundance to most abundant peak in each respective chromatogram.
Figure 3:
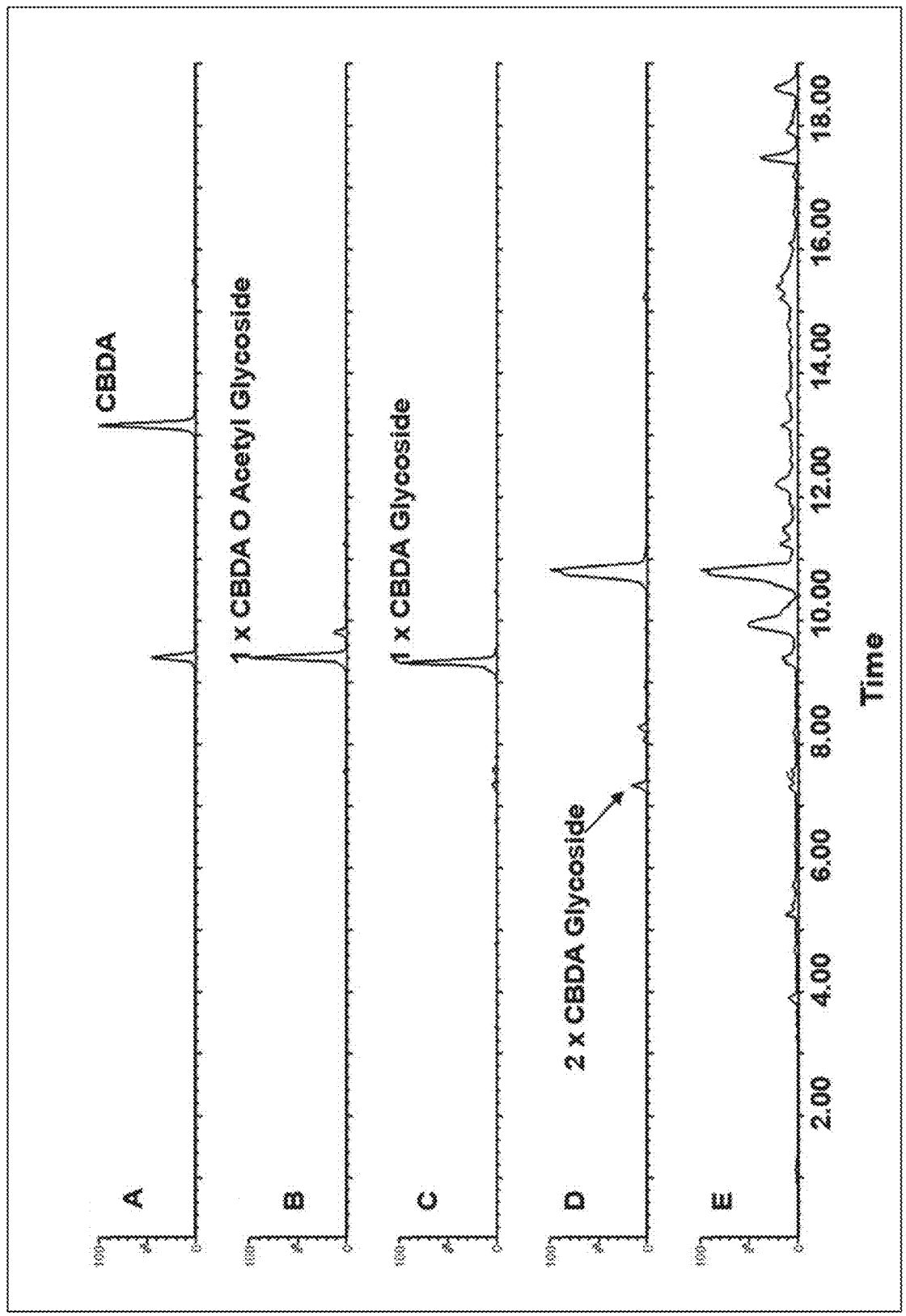
FIG. 3. Representative Chromatographic Elution profile of CBDA Glycosides profiles found in Leaf Extracts. Chromatograms A, B, C, and D represent respective extract rated ion chromatograms for each glycoside product. Chromatogram E is representative of the total ion chromatogram. Peak Intensities are illustrated as relative abundance to most abundant peak in each respective chromatogram.
Figure 4:
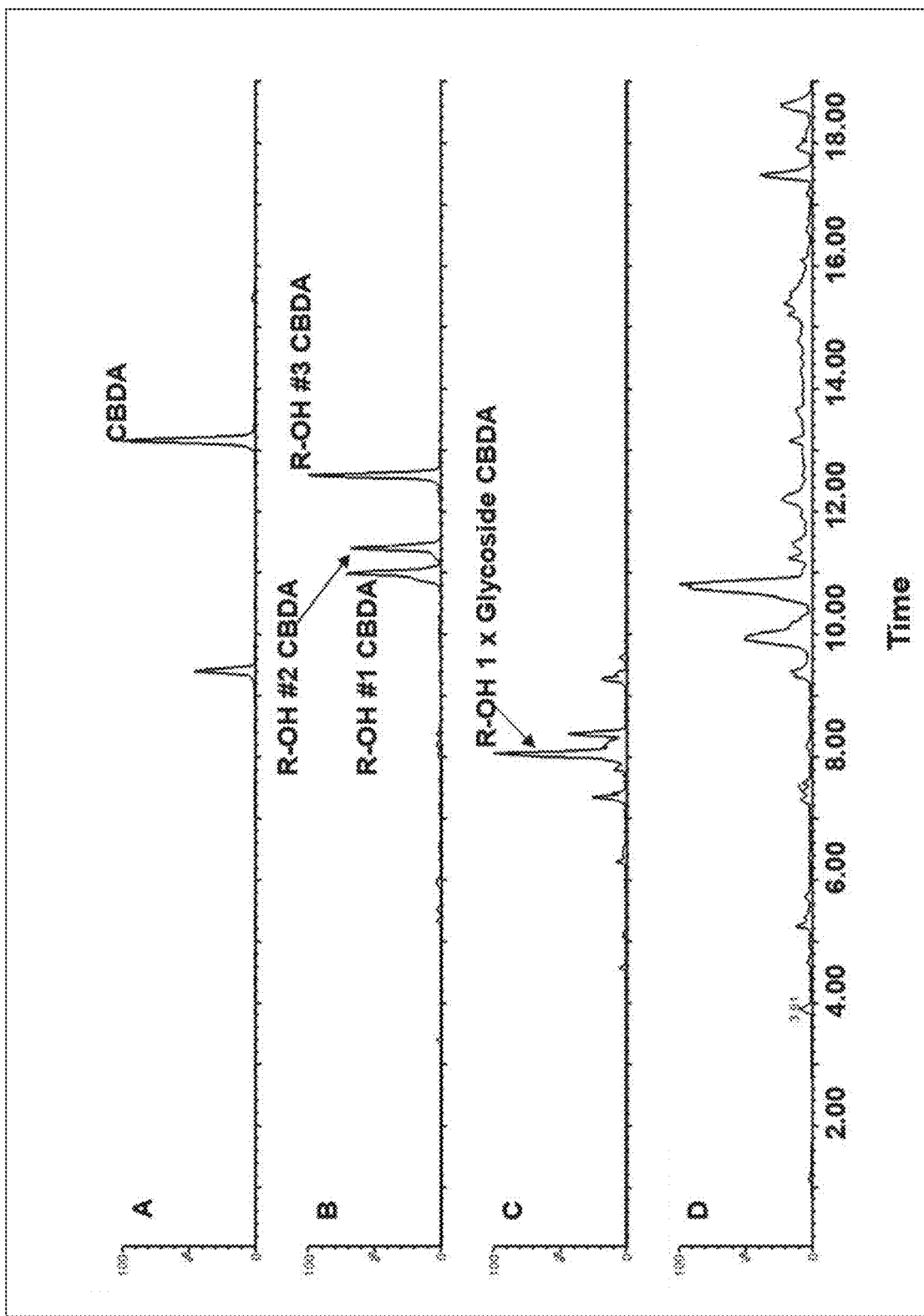
FIG. 4. Chromatographic Elution of Functionalized CBDA and Functionalized Glycosides in Leaf Extracts. Chromatograms A, B, and C represent respective extract rated ion chromatograms for each product. Chromatogram D is representative of the total ion chromatogram. Peak Intensities are illustrated as relative abundance to most abundant peak in each respective chromatogram.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The inventive technology includes systems and methods for high-level production of cannabinoid compounds. As used herein, the term "high level" in this instance may mean higher than wild-type biosynthesis or accumulation of one or more cannabinoids in a plant or plant cell. In one embodiment, a suspension or hairy root or cell suspension culture of one or more plant strains may be established. In one preferred embodiment, a suspension or hairy root or cell suspension culture of one or more *Cannabis* or tobacco plant strains may be established. It should be noted that the term strain may refer to a plant strain, as well as a cell culture, or cell line derived from a plant, such as *Cannabis*.

In one preferred embodiment, a suspension or hairy root or cell suspension culture of *Cannabis sativa* or tobacco plant may be established in a fermenter or other similar apparatus. It should be noted that the use of *C. sativa* in this embodiment is exemplary only. For example, in certain other embodiments, various *Cannabis* strains, mixes of strains, hybrids of different strains or clones, as well as different varieties may be used to generate a suspension or hairy root culture. For example, strains such as *C. sativa, C. indica* and *C. ruderalis* may all be used with the inventive technology. In yet further embodiments, other cannabinoid or cannabinoid-like producing plants may be used. For example, in a certain embodiment a cell suspension or hairy root culture may be established for one or more of the following: *Echinacea; Acmella Oleracea; Helichrysum Umbraculigerum; Radula Marginata* (Liverwort), *Theobroma Cacao* or tobacco.

In certain embodiments, such fermenters may include large industrial-scale fermenters allowing for a large quantity of cannabinoid producing *C. sativa* cells to be cultured. In this embodiment, it may be possible to culture a large quantity of unadulterated cells from a single-strain of, for example, tobacco or *C. sativa*, which may establish a cell culture having a consistent production and/or modification of cannabinoid compounds in both quantity and type. Such cultured growth may be continuously sustained with the supplementation of nutrient and other growth factors to the culture. Such features may be automated or accomplished manually.

Another embodiment of the inventive technology may include systems and methods for high level production of modified cannabinoid compounds. In one embodiment, a suspension or hairy root culture of one or more tobacco plant strains may be established. It should be noted that the term strain may refer to a plant strain, as well as a cell culture, or cell line derived from a tobacco plant. In one preferred embodiment, a suspension or hairy root culture of *Nicotiana benthamiana* plant may be established in a fermenter or other similar apparatus. It should be noted that the use of *N. benthamiana* in this embodiment is exemplary only. For example, in certain other embodiments, various *Nicotiana* strains, mixes of strains, hybrids of different strains or clones, as well as different varieties may be used to generate a cell suspension or hairy root culture.

In certain cases, such fermenters may include large industrial-scale fermenters allowing for a large quantity of *N. benthamiana* cells to be cultured. In this embodiment, harvested cannabinoids may be introduced to this suspension culture, and modified as generally described herein. Similarly, such cultured growth of tobacco cells may be continuously sustained with the continual addition of nutrient and other growth factors being added to the culture. Such features may be automated or accomplished manually.

Another embodiment of the invention may include the production of genetically modified *Cannabis* and/or tobacco cells to express varying exogenous and/or endogenous genes that may modify the chemical structure of cannabinoid compounds. Such transgenic strains may be configured to produce and/or modify large quantities of cannabinoid compounds generally, as well as targeted increases in the production of specific cannabanoids such as THC, Cannabidiol (CBD) or Cannabinol (CBN) and the like.

Another embodiment of the invention may include the production of genetically modified *Cannabis* cell cultures that express a mix of cannabinoids that may be optimized for the treatment of specific medical conditions. For example, CBD is a non-psychoactive cannabinoid that may be used to treat seizures in those with epilepsy. However, decades of selective breeding has resulted in the majority of *Cannabis* strains having low concentrations of CBD when compared to the psychoactive cannabinoid THC. As such, in certain embodiments, disease or syndrome specific cell cultures may be developed that express a calibrated mix of cannabinoids for the downstream treatment of such conditions.

Additional embodiments of the inventive technology may include novel systems, methods and compositions for the production and in vivo modification of cannabinoid compounds in a plant system. In certain embodiment, these in vivo modifications may lead to the production of different forms of cannabinoids with special properties, e.g. water-soluble, slow-release cannabinoids or prodrugs. In one preferred embodiment, the inventive technology may include novel systems, methods and compositions for the hydroxylation, acetylation and/or glycosylation. Modified cannabinoids can be made water-soluble, for example by glycosylation.

Figure 13:
FIG. 13. Exemplary monooxygenase reaction, catalyzed by cytochromes P450.

As noted above, production and/or accumulation of high-levels of cannabinoids would be toxic for a plant cell host. As such, one embodiment of the inventive technology may include systems and methods to transiently modify cannabinoids in vivo. One aim of the current invention may include the use of cytochrome P450's (CYP) monooxygenases to transiently modify or functionalize the chemical structure of the cannabinoids. CYPs constitute a major enzyme family capable of catalyzing the oxidative biotransformation of many pharmacologically active chemical compounds and other lipophilic xenobiotics. For example, as shown in FIG. 13, the most common reaction catalyzed by cytochromes P450 is a monooxygenase reaction, e.g., insertion of one atom of oxygen into the aliphatic position of an organic substrate (RH) while the other oxygen atom is reduced to water.

Figure 30:
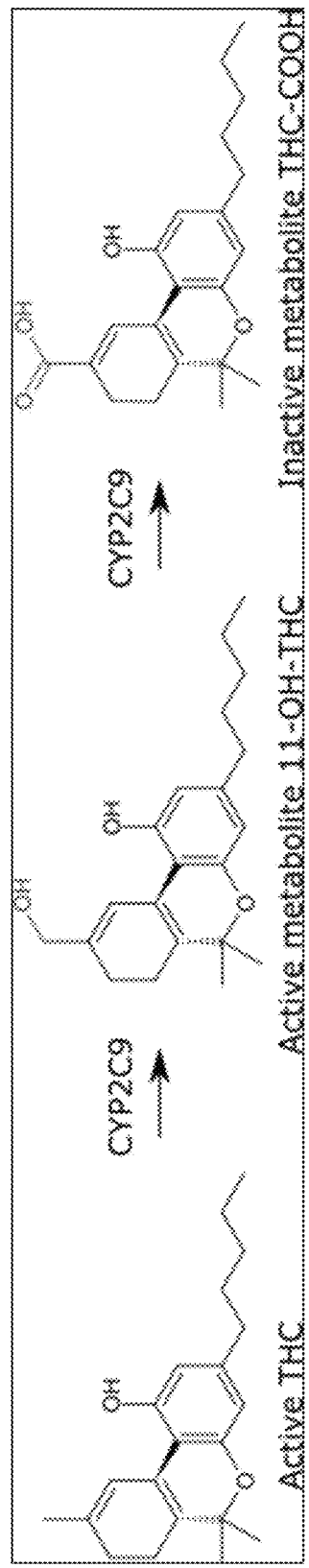
FIG. 30. Hydroxylation followed by oxidation of THC by CYP2C9/FIG. 31. Transfer of a glucuronic acid component to a cannabinoid substrate by UGT.

Several cannabinoids, including THC, have been shown to serve as a substrate for human CYPs (CYP2C9 and CYP3A4). Similarly, CYPs have been identified that metabolize cannabidiol (CYPs 2C19, 3A4); cannabinol (CYPs 2C9, 3A4); JWH-018 (CYPs 1A2, 2C9); and AM2201 (CYPs 1A2, 2C9). For example, as shown generally in FIG. 30, in one exemplary system, CYP2C9 may "functionalize" or hydroxylate a THC molecule resulting in a hydroxyl-form of THC. Further oxidation of the hydroxyl form of THC by CYP2C9 may convert it into a carboxylic-acid form which loses its psychoactive capabilities, rendering it an inactive metabolite.

As such, another embodiment of the invention may include the creation of a *Cannabis* strain or cell culture that may be transformed with artificially created genetic constructs encoding one or more exogenous CYPs. In one preferred embodiment, genes encoding one or more non-human isoforms and/or analogs, as well as possibly other CYPs that may functionalize cannabinoids, may be expressed in transgenic *Cannabis sativa* or other plant. In another preferred embodiment, genes encoding one or more non-human isoforms and/or analogs, as well as possibly other CYPs that may functionalize cannabinoids, may be expressed in transgenic *Cannabis sativa* or tobacco strains grown in a suspension culture. Additional embodiments may include genetic control elements such as promotors and/or enhancers as well as post-transcriptional regulatory elements that may also be expressed in transgenic *Cannabis* strains such that the presence, quantity and activity of any CYPs present in the suspension or hairy root culture may be modified and/or calibrated.

Another embodiment of the invention may include the creation of a tobacco strain or cell culture may be transformed with artificially created genetic constructs encoding one or more exogenous CYPs. In one preferred embodiment, genes encoding one or more non-human isoforms and/or analogs, as well as possibly other CYPs that may functionalize cannabinoids introduced to a transgenic *N. benthamiana* plant or suspension culture. Additional embodiments may include genetic control elements such as promotors and/or enhancers as well as post-transcriptional regulatory elements that may also be expressed in transgenic *N. benthamiana* strains such that the presence, quantity and activity of any CYPs present in the suspension or hairy root culture may be modified and/or calibrated.

Figure 31:
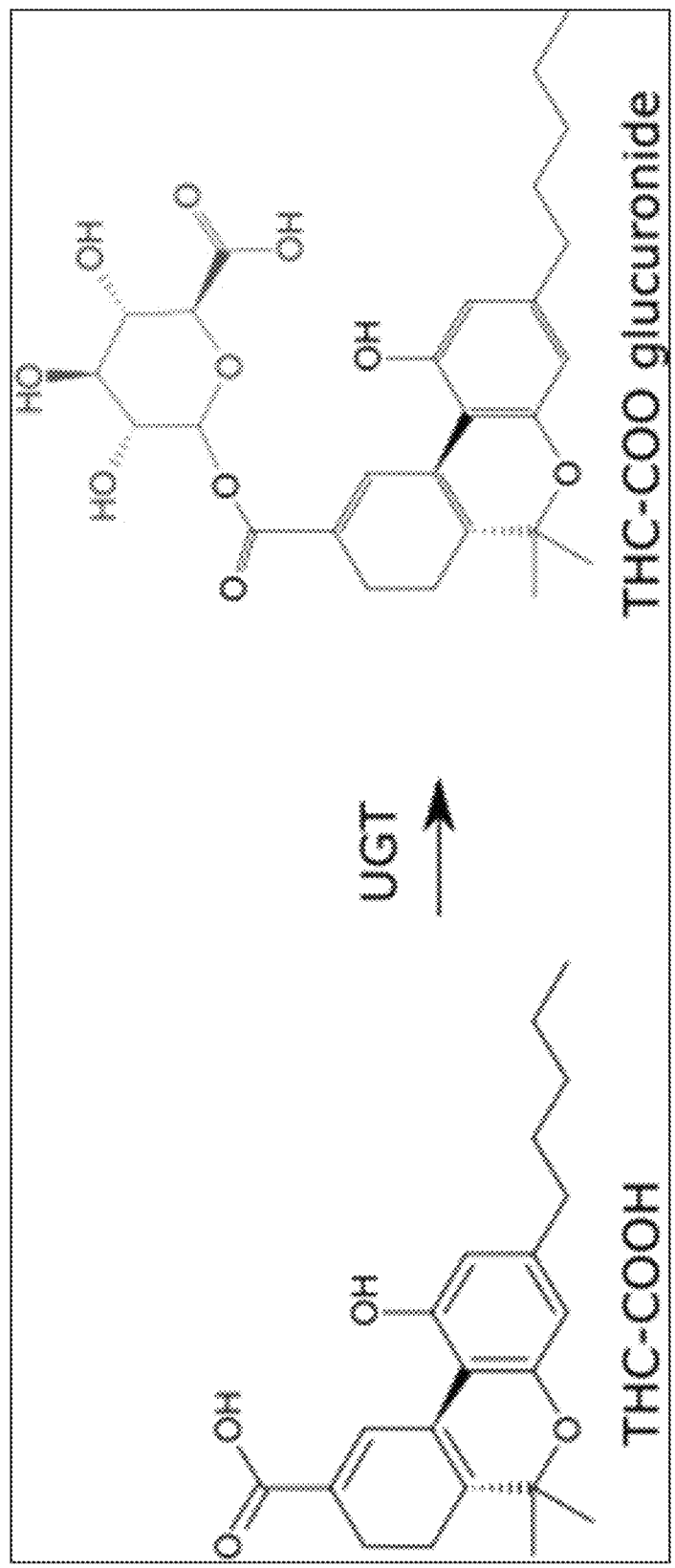

Another aim of the invention may be to further modify, in vivo, cannabinoids and/or already functionalized cannabinoids. In a preferred embodiment, glycosylation of cannabinoids and/or functionalized cannabinoids may covert to them into a water-soluble form. In an exemplary embodiment shown in FIG. 31, the inventive technology may utilize one or more glycosyltransferase enzymes, such as UDP-glycosyltransferase (UGT), to catalyze, in vivo the glucuronosylation or glucuronidation of cannabinoids, such as primary (CBD, CBN) and secondary cannabinoids (THC, JWH-018, JWH-073). In this embodiment, glucuronidation may consist of the transfer of a glucuronic acid component of uridine diphosphate glucuronic acid to a cannabinoid substrate by any of several types of glycosyltransferases as described herein. Glucuronic acid is a sugar acid derived from glucose, with its sixth carbon atom oxidized to a carboxylic acid.

Yet another embodiment of the current invention may include the in vivo conversion of a functionalized cannabinoid, in this example a carboxylic acid form of the cannabinoid, to a glycosylated form of cannabinoid that may be both water-soluble and non-toxic to the cell host. These chemical modifications may allow for greater levels of cannabinoid accumulation in a plant cell culture without the deleterious cytotoxic effects that would be seen with unmodified cannabinoids due to this water-solubility.

Another embodiment of the invention may include the generation of transgenic or genetically modified strains of *Cannabis*, or other plants such as tobacco, having artificial genetic constructs that may express one or more genes that may increase cannabinoids solubility and/or decrease cannabinoid cytotoxicity. For example, the inventive technology may include the generation of transgenic plant strains or cell lines having artificial genetic constructs that may express one or more endogenous/or exogenous glycosyltransferases or other enzymes capable of glycosylating cannabinoid compounds. For example, in one embodiment one or more glycosyltransferases from *N. benthamiana*, or other non-*cannabis* plants may be introduced into a *cannabis* plant or cell culture and configured to glycosylate cannabinoids in vivo. In other embodiment, endogenous glycosyltransferases from *N. benthamiana* may be over-expressed to as to increase in vivo cannabinoid glycosylation.

In an additional embodiment, of the inventive technology may include the generation of artificial genetic constructs having genes encoding one or more glycosyltransferases, including non-human analogues of those described herein as well as other isoforms, that may further may be expressed in transgenic *Cannabis sativa, N. benthamiana* or other plant system which may further be grown in a suspension culture. Additional embodiments may include genetic control elements such as promotors and/or enhancers as well as post-transcriptional regulatory control elements that may also be expressed in a transgenic plant system such that the presence, quantity and activity of any glycosyltransferases present in the suspension or hairy root culture may be regulated.

An additional embodiment of the invention may include artificial genetic constructs having one or more genes encoding one or more UDP- and/or ADP-glycosyltransferases having localization sequences or domains that may assist in the movement of the protein to a certain portion of the cell, such as the cellular locations were cannabinoids and/or functionalized cannabinoids may be modified, produced, stored, and/or excreted from the cell.

An additional embodiment of the invention may include artificial genetic constructs having one or more genes encoding one or more UDP- and/or ADP-glycosyltransferases being co-expressed with one or more exogenous genes that may assist in the movement of the protein to a certain portion of the cell, such as the cellular locations were cannabinoids and/or functionalized cannabinoids may be stored, and/or excreted from the cell.

One preferred embodiment of the inventive technology may include the high level in vivo production of water-soluble, glycosylated cannabinoids, generally being referred to as transiently modified cannabinoids that may be harvested from a plant or a cell culture. In one embodiment, transiently modified cannabinoids may accumulate within the cell that is part of a suspension culture. In this example, the cell culture may be allowed to grow to a desired level of cell or optical density, or in other instances until a desired level of transiently modified cannabinoids have accumulated in the cultured *Cannabis* cells. Such exogenous genes may be localized, for example to the cytosol or trichome as generally described herein, and may further be co-expressed with other exogenous genes that may reduce cannabinoid biosynthesis toxicity and/or facilitate cannabinoid transport through, or out of the cell.

All or a portion of the *Cannabis* cells containing the accumulated transiently modified cannabinoids may then be harvested from the culture, which in a preferred embodiment may be an industrial-scale fermenter or other apparatus suitable for the large-scale culturing of plant cells. The harvested *Cannabis* cells may be lysed such that the accumulated transiently modified cannabinoids may be released to the surrounding lysate. Additional steps may include treating this lysate. Examples of such treatment may include filtering or screening this lysate to remove extraneous plant material as well as chemical treatments to improve later cannabinoid yields.

Another embodiment of inventive technology may include the high level in vivo generation of water-soluble, glycosylated cannabinoids, generally being referred to as transiently modified cannabinoids that may be harvested from a plant or a cell culture. In one embodiment, cannabinoids may be introduced to a non-cannabinoid producing cell culture, such as *N. benthamiana*. In this preferred embodiment, the non-cannabinoid producing cell culture may be genetically modified to express one or more endogenous or exogenous genes that may modify the cannabinoids, for example through hydroxylation, acetylation and/or glycosylation. Such endogenous or exogenous genes may be localized, for example to the cytosol or trichome as generally described herein, and may further be co-expressed with other exogenous genes that may reduce cannabinoid biosynthesis toxicity and/or facilitate cannabinoid transport through, or out of the cell.

This non-cannabinoid producing the cell culture may be allowed to grow to a desired level of cell or optical density, or in other instances until a desired level of transiently modified cannabinoids have accumulated in the cultured cells. All or a portion of the *N. benthamiana* cells containing the accumulated cannabinoids may then be harvested from the culture, which in a preferred embodiment may be an industrial-scale fermenter or other apparatus suitable for the large-scale culturing of plant cells. The harvested *N. benthamiana* cells may be lysed such that the accumulated transiently modified cannabinoids may be released to the surrounding lysate. Additional steps may include treating this lysate. Examples of such treatment may include filtering or screening this lysate to remove extraneous plant material as well as chemical treatments to improve later cannabinoid yields.

Another aim of the inventive technology may include methods to isolate and purified transiently modified cannabinoids from a plant or suspension culture. In one preferred embodiment, a *Cannabis* lysate may be generated and processed utilizing affinity chromatography or other purification methods. In this preferred embodiment, an affinity column having a ligand or protein receptor configured to bind with the transiently modified cannabinoids, for example through association with a glycosyl or glucuronic acid functional group among others, may be immobilized or coupled to a solid support. The lysate may then be passed over the column such that the transiently modified cannabinoids, having specific binding affinity to the ligand become bound and immobilized. In some embodiments, non-binding and non-specific binding proteins that may have been present in the lysate may be removed. Finally, the transiently modified cannabinoids may be eluted or displaced from the affinity column by, for example, a corresponding sugar or other compound that may displace or disrupt the cannabinoid-ligand bond. The eluted transiently modified cannabinoids may be collected and further purified or processed.

An aim of the invention may include an embodiment where transiently modified cannabinoids may be passively and/or actively excreted from a cell or into a cell wall. In one exemplary model, an exogenous ATP-binding cassette transporter (ABC transporters) or other similar molecular structure may recognize the glycosyl or glucuronic acid functional group (conjugate) on the transiently modified cannabinoid and actively transport it across the cell wall/membrane and into the surrounding media. In this embodiment, the cell culture may be allowed to grow until an output parameter is reached. In one example, an output parameter may include allowing the cell culture to grow until a desired cell/optical density is reach, or a desired concentration of transiently modified cannabinoid is reached. In this embodiment, the culture media containing the transiently modified cannabinoids may be harvested for later cannabinoid extraction. In some embodiments, this harvested media may be treated in a manner similar to the lysate generally described above. Additionally, the transiently modified cannabinoids present in the raw and/or treated media may be isolated and purified, for example, through affinity chromatography in a manner similar to that described above.

In certain embodiments, this purified cannabinoid isolate may contain a mixture of primary and secondary glycosylated cannabanoids. As noted above, such purified glycosylated cannabinoids may be water-soluble and metabolized slower than unmodified cannabinoids providing a slow-release capability that may be desirable in certain pharmaceutical applications, such as for use in tissue-specific applications, or as a prodrug. As such, it is one aim of the invention to incorporate such purified glycosylated cannabinoids into a variety of pharmaceutical and/or nutraceutical applications.

For example, the purified glycosylated cannabinoids may be incorporated into various solid and/or liquid delivery vectors for use in pharmaceutical applications. As noted above, these transiently modified cannabinoids may no longer possess their psychoactive component, making their application in research, therapeutic and pharmaceutical applications especially advantageous. For example, the treatment of children may be accomplished through administration of a therapeutic dose of isolated and purified transiently modified cannabinoids, without the undesired psychoactive effect. Additional therapeutic applications may include the harvesting and later administration of a therapeutic dose of an "entourage" of isolated and purified transiently modified cannabinoids.

Another embodiment of the invention may include a system to convert or reconstitute transiently modified cannabinoids. In one preferred embodiment, glycosylated cannabinoids may be converted into non-glycosylated cannabinoids through their treatment with one or more generalized or specific glycosidases. The use and availability of glycosidase enzymes would be recognized by those in the art without requiring undue experimentation. In this embodiment, these glycosidase enzymes may remove a sugar moiety. Specifically, these glycosidases may remove the glycosyl or glucuronic acid moiety reconstituting the cannabinoid compound to a form exhibiting psychoactive activity. This reconstitution process may generate a highly purified "entourage" of primary and secondary cannabinoids. These reconstituted cannabinoid compounds may also be incorporated into various solid and/or liquid delivery vectors for use in a variety of pharmaceutical and other commercial applications.

As noted above, in one embodiment of the invention, cannabinoid producing strains of *Cannabis*, as well as other plants may be utilized with the inventive technology. In certain preferred embodiments, in lieu of growing the target cannabinoid producing plant in a cell culture, the raw plant material may be harvested and undergo cannabinoid extraction utilizing one or more of the methods described herein. These traditionally extracted cannabinoids may then be modified from their native forms through the in vitro application of one or more CYP's that may generate hydroxyl and carboxylic acid forms of these cannabinoids respectively. These functionalized cannabinoids may be further modified through the in vitro application of one or more glycosyl-transferases as generally described herein. In this embodiment, the new transiently modified cannabinoids may be isolated and purified through a process of affinity chromatography, or other extraction protocol, and then applied to various commercial and other therapeutic uses. In other embodiments, the transiently modified cannabinoids may be restored and reconstituted through the in vitro application of one or more glycosidase enzymes. These restored cannabinoids may also be applied to various commercial and other therapeutic uses.

Another embodiment of the invention may include the use of other non-cannabinoid producing plants in lieu of growing a cannabinoid producing plant in a cell culture. Here, cannabinoid may be introduced to genetically modified plants, or plant cell cultures that express one or more CYP's that may generate hydroxyl and carboxylic acid forms of these cannabinoids respectively. These functionalized cannabinoids may be further modified through the action of one or more glycosidases that may also be expressed in the non-cannabinoid producing plant or cell culture. In one preferred embodiment, a non-cannabinoid producing cell culture may include tobacco plant or cell cultures.

One embodiment of the invention may include an in vivo method of trichome-targeted cannabinoid accumulation and modification. One preferred embodiment of this in vivo system may include the creation of a recombinant protein that may allow the translocation of a CYP or glycosyltransferases to a site of extracellular cannabinoid synthesis in a whole plant. More specifically, in this preferred embodiment, one or more CYPs or glycosyltransferases may either be engineered to express all or part of the N-terminal extracellular targeting sequence as present in cannabinoid synthase protein, such as THCA synthase or CBDA synthase.

One another embodiment of the invention may include an in vivo method of high-level trichome-targeted cannabinoid biosynthesis, accumulation and/or modification. One preferred embodiment of this in vivo system may include the creation of a recombinant protein that may allow the translocation of a catalase to a site of extracellular cannabinoid synthesis in a whole plant. More specifically, in this preferred embodiment, one or more catalase enzymes may either be engineered to express all or part of the N-terminal extracellular targeting sequence as present in cannabinoid synthase protein, such as THCA synthase or CBDA synthase. In this embodiment, the catalase may be targeted to the site of cannabinoid biosynthesis allowing it to more efficiently neutralize hydrogen peroxide byproducts.

In this preferred embodiment, this N-terminal trichome targeting sequence or domain may generally include the first 28 amino acid residues of a generalized synthase. An exemplary trichome targeting sequence for THCA synthase is identified SEQ ID NO. 40, while trichome targeting sequence for CBDA synthase is identified SEQ ID NO. 41. This extracellular targeting sequence may be recognized by the plant cell and cause the transport of the glycosyltransferase from the cytoplasm to the plant's trichrome, and in particular the storage compartment of the plant trichrome where extracellular cannabinoid glycosylation may occur. More specifically, in this preferred embodiment, one or more glycosyltransferases, such as UDP glycosyltransferase may either be engineered to express all or part of the N-terminal extracellular targeting sequence as present in an exemplary synthase enzyme.

Another embodiment of the invention may include an in vivo method of cytosolic-targeted cannabinoid production, accumulation and/or modification. One preferred embodiment of this in vivo system may include the creation of a recombinant protein that may allow the localization of cannabinoid synthases and/or glycosyltransferases to the cytosol.

More specifically, in this preferred embodiment, one or more cannabinoid synthases may be modified to remove all or part of the N-terminal extracellular targeting sequence. An exemplary trichome targeting sequence for THCA synthase is identified SEQ ID NO. 40, while trichome targeting sequence for CBDA synthase is identified SEQ ID NO. 41. Co-expression with this cytosolic-targeted synthase with a cytosolic-targeted CYP or glycosyltransferase, may allow the localization of cannabinoid synthesis, accumulation and modification to the cytosol. Such cytosolic target enzymes may be co-expressed with catalase, ABC transporter or other genes that may reduce cannabinoid biosynthesis toxicity and or facilitate transport through or out of the cell.

Another embodiment of the invention may include the generation of an expression vector comprising this polynucleotide, namely a cannabinoid synthase N-terminal extracellular targeting sequence and glycosyltransferase genes, operably linked to a promoter. A genetically altered plant or parts thereof and its progeny comprising this polynucleotide operably linked to a promoter, wherein said plant or parts thereof and its progeny produce said chimeric protein, is yet another embodiment. For example, seeds and pollen contain this polynucleotide sequence or a homologue thereof, a genetically altered plant cell comprising this polynucleotide operably linked to a promoter such that said plant cell produces said chimeric protein. Another embodiment comprises a tissue culture comprising a plurality of the genetically altered plant cells.

Another embodiment of the invention provides for a genetically altered plant or cell expressing a chimeric or fusion protein having a cannabinoid synthase N-terminal extracellular targeting sequence (see i.e., SEQ ID: 40-41; see also SEQ ID NO. 42 for full amino acid sequence of THCA synthase) coupled with a UDP glycosyltransferase genes, operably linked to a promoter. Another embodiment provides a method for constructing a genetically altered plant or part thereof having glycosylation of cannabinoids in the extracellular storage compartment of the plant's trichrome compared to a non-genetically altered plant or part thereof, the method comprising the steps of: introducing a polynucleotide encoding the above protein into a plant or part thereof to provide a genetically altered plant or part thereof, wherein said chimeric protein comprising a first domain, a second domain, and wherein said first domain comprises a cannabinoid synthase N-terminal extracellular targeting sequence, and a second domain comprises a glycosyltransferase sequence. These domains may be separated by a third domain or linker. This linker may be any nucleotide sequence that may separate a first domain from a second domain such that the first domain and the second domain can each fold into its appropriate three-dimensional shape and retain its activity.

One preferred embodiment of the invention may include a genetically altered plant or cell expressing a cytosolic-targeted cannabinoid synthase protein having a cannabinoid synthase N-terminal extracellular targeting sequence (SEQ IDs. 40-41) inactivated or removed. In one embodiment, a cytosolic targeted THCA synthase (ctTHCAs) may be identified as SEQ ID NO. 46, while in another embodiment cytosolic targeted CBDA synthase (cytCBDAs) is identified as SEQ ID NO. 22-23). Such cytosolic-targeted cannabinoid synthase protein may be operably linked to a promoter. Another embodiment provides a method for constructing a genetically altered plant or part thereof having glycosylation of cannabinoids in the plant's cytosol compared to a non-genetically altered plant or part thereof, the method comprising the steps of: introducing a polynucleotide encoding the above protein into a plant or part thereof to provide a genetically altered plant or part thereof, wherein said a cannabinoid synthase N-terminal extracellular targeting sequence has been disrupted or removed.

Yet another embodiment of the invention may include an in vivo method of cannabinoid glycosylation in a *cannabis* cell culture. In one preferred embodiment, to facilitate glycosylation of cannabinoids in *cannabis* cell culture, which would lack an extracellular trichrome structure, a cannabinoid synthase gene may be genetically modified to remove or disrupt, for example through a directed mutation, the extra-cellular N-terminal targeting domain which may then be used to transform a *Cannabis* plant cell in a cell culture. In this embodiment, without this targeting domain the cannabinoid synthase, for example THCA or CBDA synthases, may remain within the plant cell, as opposed to being actively transported out of the cell, where it may be expressed with one or more glycosyltransferases, such as UDP glycosyltransferase in the cytoplasm.

Another embodiment of the inventive technology may include systems and methods for enhanced production and/or accumulation of cannabinoid compounds in an in vivo system. In one preferred embodiment, the invention may include the generation of a genetically modified or transgenic *Cannabis* plant that may produce and/or accumulate one or more cannabinoids at higher than wild-type levels. In one embodiment, a transgenic *Cannabis* plant may be generated to express one or more *Cannabis sativa* transcription factors that may enhance the cannabinoid metabolic pathway(s). In one preferred embodiment, a polynucleotide may be generated that encodes for one or more *Cannabis sativa* myb transcription factors genes, and/or one or more exogenous ortholog genes that enhance the metabolite flux through the cannabinoid biosynthetic pathway.

Figure 32:
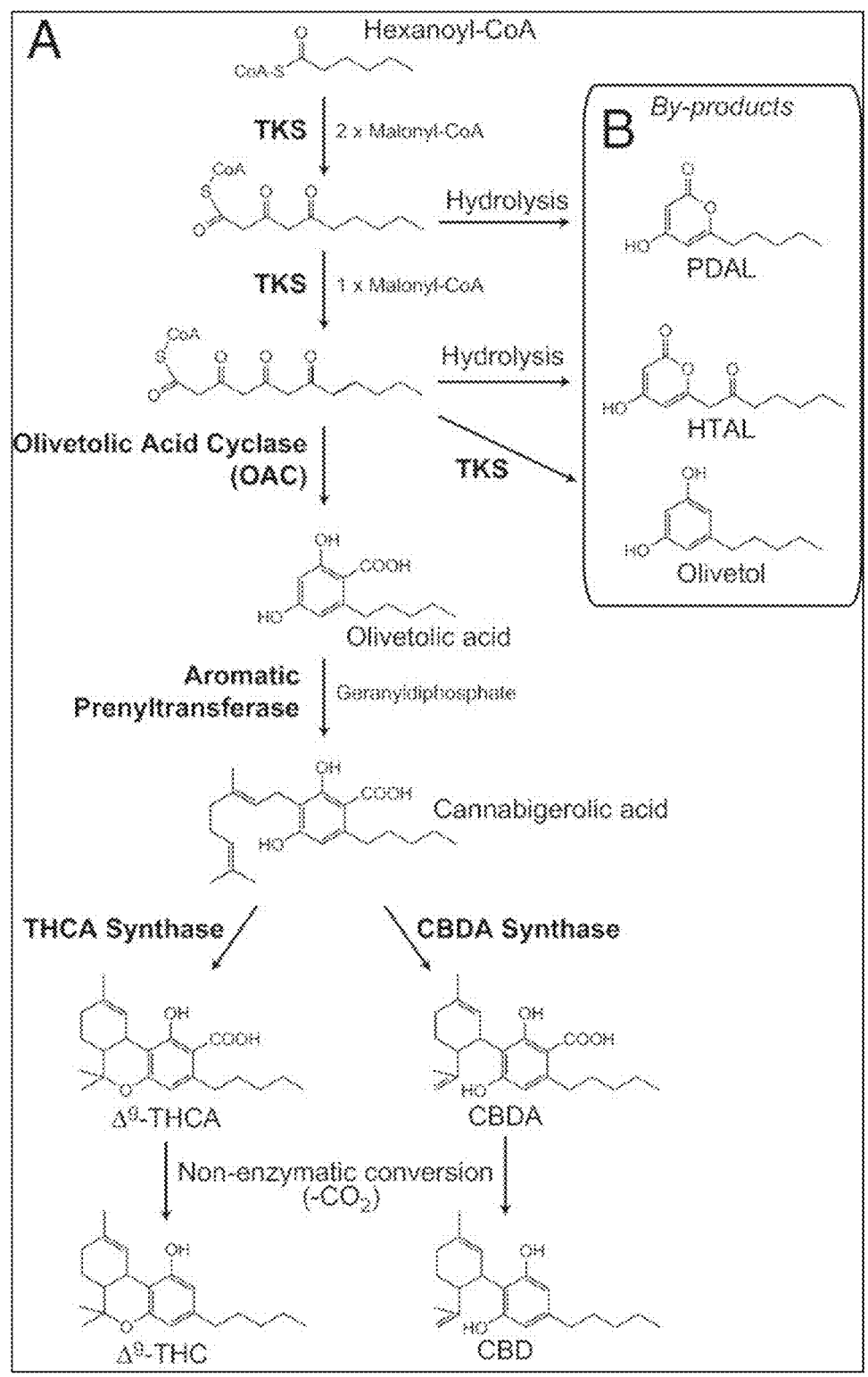
FIG. 32. (A) Synthesis Olivetolic Acid a precursor of CBGA; (B) Byproducts generated from the Synthesis Olivetolic Acid.

In this preferred embodiment, a polynucleotide may be generated that encodes for one or more *Cannabis sativa* myb transcription factors genes, such as CAN833 and/or CAN738 that. As shown in FIG. 32, these transcriptions factors may drive the production of olivetolic acid, which is a precursor of CBGA, which in turn is a precursor in the biosynthetic pathway of THCs, CBDs and CBC. In an alternative embodiment, a polynucleotide may be generated that encodes for one or more *Cannabis sativa* myb transcription factors genes orthologs, specifically *cannabis* Myb12 (SEQ IDs. 11-12), Myb8 (SEQ ID NO. 43), AtMyb12 (SEQ ID NO.44), and/or MYB112 (SEQ ID NO. 45) that may also drive the production of olivetolic acid, which is a precursor of CBGA, which in turn is a precursor in the biosynthetic pathway of THCs, CBDs and CBC.

In one preferred embodiment, the invention may include methods of generating a polynucleotide that expresses one or more of the SEQ IDs related to enhanced cannabinoid production identified herein. In certain preferred embodiments, the proteins of the invention may be expressed using any of a number of systems to obtain the desired quantities of the protein. Typically, the polynucleotide that encodes the protein or component thereof is placed under the control of a promoter that is functional in the desired host cell. An extremely wide variety of promoters may be available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

Additional embodiments of the invention may include selecting a genetically altered plant or part thereof that expresses the cannabinoid production transcription factor protein, wherein the expressed protein has increased cannabinoid biosynthesis capabilities. In certain embodiments, a polynucleotide encoding the cannabinoid production transcription factor protein is introduced via transforming said plant with an expression vector comprising said polynucleotide operably linked to a promoter. The cannabinoid production transcription factor protein may comprise a SEQ ID selected from the group consisting of SEQ ID NO: 11-2 or 43-45, or a homologue thereof.

As noted above, one embodiment of the invention may include systems and methods for general and/or localized detoxification of cannabinoid biosynthesis in an in vivo system. In one preferred embodiment, the invention may include the generation of a genetically modified or transgenic *Cannabis* or other plant that may be configured to be capable of detoxifying hydrogen peroxide by-products resulting from cannabinoid biosynthesis at higher than wild-type levels. In addition, this detoxification may be configured to be localized to the cytosol and/or trichome structure of the *Cannabis* plant where cannabinoids are actively being synthesized in a whole plant system. In this preferred embodiment of the invention, a transgenic plant, such as a *cannabis* or tobacco plant or cell, that express one or more genes that may up-regulate hydrogen peroxide detoxification.

In one preferred embodiment, a polynucleotide may be generated that encodes for one or more endogenous and/or exogenous transcription catalase genes, and/or orthologs that catalyze the reduction of hydrogen peroxide:

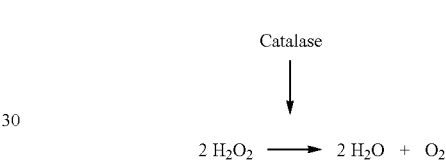

As such, in one embodiment, the invention comprises the generation of a polynucleotide encoding a exogenous catalase protein that may be expressed within a transformed plant and/or cell culture. In a preferred embodiment, a catalase enzyme configured reduce hydrogen peroxide ($H_2O_2$) generated during cannabinoid synthesis may be used to transform a cannabis or other plant, such as a tobacco plant. While a number of generic catalase enzymes may be included in this first domain, as merely one exemplary model, a first domain may include an exogenous catalase derived from *Arabidopsis* (SEQ ID NO. 13-14; see also FIG. 33), or *Escherichia coli* (SEQ ID NO. 15-16), or any appropriate catalase ortholog, protein fragment, or catalases with a homology between about 70%—and approximately 100% as herein defined.

Another embodiment of the current invention may include localization of the catalase enzyme to a trichome structure. As generally outlined above, in this embodiment a trichome targeting sequence from a cannabinoid synthase may be coupled with one or more catalase enzymes in a fusion or chimera—the terms being generally interchangeable in this application. This artificial trichome-target catalase gene may be used to transform a plant having trichome structures, such as *Cannabis* or tobacco. In a preferred embodiment, a trichome-targeted catalase from *Arabidopsis thaliana* with a THCA synthase trichome targeting domain is identified as SEQ ID NO. 47, while a trichome-targeted catalase *Arabidopsis thaliana* with a CBDA synthase trichome targeting domain is identified as SEQ ID NO. 48. In another embodiment, a trichome-targeted catalase from *Escherichia coli* with a THCA synthase trichome targeting domain is identified as SEQ ID NO. 49, while a trichome-targeted catalase *Escherichia coli* with a CBDA synthase trichome targeting domain is identified as SEQ ID NO. 50.

Another embodiment of the invention comprises generating a polynucleotide of a nucleic acid sequence encoding the chimeric/fusion catalase protein. Another embodiment includes an expression vector comprising this polynucleotide operably linked to a promoter. A genetically altered plant or parts thereof and its progeny comprising this polynucleotide operably linked to a promoter, wherein said plant or parts thereof and its progeny produce said fusion protein is yet another embodiment. For example, seeds and pollen contain this polynucleotide sequence or a homologue thereof, a genetically altered plant cell comprising this polynucleotide operably linked to a promoter such that said plant cell produces said chimeric protein. Another embodiment comprises a tissue culture comprising a plurality of the genetically altered plant cells.

In a preferred embodiment, a polynucleotide encoding a trichome-targeted fusion protein may be operably linked to a promoter that may be appropriate for protein expression in a *Cannabis*, tobacco or other plant. Exemplary promotors may include, but not be limited to: a non-constitutive promotor; an inducible promotor, a tissue-preferred promotor; a tissue-specific promotor, a plant-specific promotor, or a constitutive promotor. In a preferred embodiment, one or more select genes may be operably linked to a leaf-specific gene promotor, such as Cab 1. Additional promoters and operable configurations for expression, as well as co-expression of one or more of the selected genes are generally known in the art.

Another embodiment of the invention may provide for a method for constructing a genetically altered plant or part thereof having increased resistance to hydrogen peroxide cytotoxicity generated during cannabinoid synthesis compared to a non-genetically altered plant or part thereof, the method comprising the steps of: introducing a polynucleotide encoding a fusion protein into a plant or part thereof to provide a genetically altered plant or part thereof, wherein said fusion protein comprising a catalase and a trichome-targeting sequence from a cannabinoid synthase.

Figure 34:
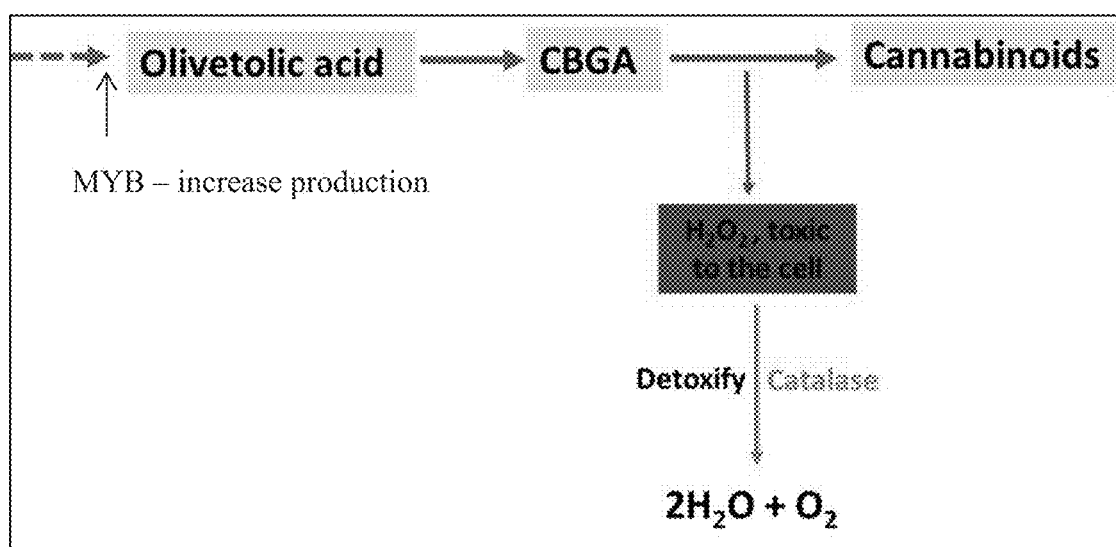
FIG. 34. Schematic diagram of increase cannabinoid production coupled with reduced oxidative damage system in one embodiment thereof

In one embodiment, the invention may encompass a system to increase overall cannabinoid production and accumulation in trichomes while preventing potential cytotoxicity effects. As generally shown in FIG. 34, the system may include, in a preferred embodiment, creating a transgenic *Cannabis*, tobacco or other plant or suspension culture plant that overexpresses at least one Myb transcription factor to increase overall cannabinoid biosynthesis In further preferred embodiments, this transgenic plant may co-express a catalase enzyme to reduce oxidative damage resulting from hydrogen peroxide production associated with cannabinoid synthesis reducing cell toxicity. In certain preferred embodiments, this catalase may be fused with an N-terminal synthase trichome targeting domain, for example from THCA and/or CBDA synthase, helping localize the catalase to the trichome in the case of whole plant systems, and reduce potentially toxic levels of hydrogen peroxide produced by THCA, CBCA and/or CBDA synthase activity.

Another embodiment of the invention may comprise a combination polynucleotide of a nucleic acid sequence encoding a combination of: 1) a cannabinoid production transcription factor protein, such as a myb gene; and/or a catalase protein, or any homologue thereof, which may further include a trichome targeting or localization signal. A genetically altered plant or parts thereof and its progeny comprising this combination polynucleotide operably linked to a promoter, wherein said plant or parts thereof and its progeny produce said protein is yet another embodiment. For example, seeds and pollen contain this polynucleotide sequence or a homologue thereof, a genetically altered plant cell comprising this polynucleotide operably linked to a promoter such that said plant cell produces said proteins. Another embodiment comprises a tissue culture comprising a plurality of the genetically altered plant cells.

Another embodiment of the invention may provide for a method for constructing a genetically altered plant or part thereof having: 1) increased cannabinoid production compared to a non-genetically altered plant or part thereof and/or and 2) increased resistance to hydrogen peroxide cytotoxicity generated during cannabinoid synthesis compared to a non-genetically altered plant or part thereof, the method comprising the steps of: introducing a combination polynucleotide into a plant or part thereof to provide a genetically altered plant or part thereof.

Additional embodiments of the invention may include selecting a genetically altered plant or part thereof that expresses one or more of the proteins, wherein the expressed protein(s) may have: 1) increased cannabinoid production capabilities, for example through overexpression of an endogenous myb gene; and 2) catalase with/or without a trichome localization capability, or any combination thereof. In certain embodiments, a combination polynucleotide encoding the proteins is introduced via transforming said plant with an expression vector comprising said combination polynucleotide operably linked to a promoter. The cannabinoid production transcription factor protein may comprise a SEQ ID selected from the sequences identified herein, or homologues thereof. Naturally, such combinations and expression combination strategies, such identified in Tables 7-8, 10 below and elsewhere, are exemplary, as multiple combinations of the elements as herein described is included in the invention.

In one preferred embodiment, the inventive technology may include systems, methods and compositions high levels of in vivo cannabinoid hydroxylation, acetylation and/or glycosylation and/or a combination of all three. In a preferred embodiment, the in vivo cannabinoid hydroxylation, acetylation and/or glycosylation and/or a combination of all three may occur in a cannabinoid-producing plant or cell culture system. While in alternative embodiments may include a non-cannabinoid producing plant or cell culture system such as a tobacco plant, like *N. benthamiana*.

In one embodiment, the invention may include a cannabinoid production, accumulation and modification system. In one preferred embodiment, a plant, such as *cannabis* or tobacco, may be genetically modified to express one or more heterologous cytochrome P450 genes. In this preferred embodiment, a heterologous human cytochrome P450 (CYP3A4) SEQ ID NO. 1 may be expressed in a cannabinoid-producing plant or cell culture system. While in alternative embodiments a heterologous human cytochrome P450 (CYP3A4) may be expressed non-cannabinoid producing plant or cell culture system such as a tobacco plant, like *N. benthamiana*. In this embodiment, the overexpression of a heterologous human cytochrome P450 protein, identified as SEQ ID NO. 2, may functionalize endogenously-created cannabinoids so that they can be more efficiently glycosylated and/or acetylated in vivo, rendering them water-soluble.

In an alternative embodiment, the invention may include a cannabinoid production, accumulation and modification system. In one preferred embodiment, a plant, such as *cannabis* or tobacco, may be genetically modified to express one or more heterologous cytochrome P450 oxidoreductase genes. In this preferred embodiment, a heterologous cytochrome P450 oxidoreductase (oxred) identified as SEQ ID NO. 3, may be expressed in a cannabinoid-producing plant or cell culture system. While in alternative embodiments a heterologous human heterologous cytochrome P450 oxidoreductase (oxred) may be expressed non-cannabinoid producing plant or cell culture system such as a tobacco plant, like *N. benthamiana*. In this embodiment, the overexpression of a heterologous cytochrome P450 oxidoreductase (oxred) protein, identified as SEQ ID NO. 4, may functionalize endogenously-created cannabinoids so that they can be more efficiently glycosylated and/or acetylated in vivo, rendering them water-soluble.

In one embodiment, the invention may include a cannabinoid production, accumulation and modification system in a non-cannabinoid producing plant. In one preferred embodiment, a plant, such as tobacco, may be genetically modified to express one or more heterologous cytochrome P450 oxidoreductase genes. In this preferred embodiment, a heterologous cytochrome P450 oxidoreductase (oxred) identified as SEQ ID NO. 3 may be expressed in a cannabinoid-producing plant or cell culture system. In alternative embodiments, While in alternative embodiments a heterologous cytochrome P450 oxidoreductase (oxred) may be expressed non-cannabinoid producing plant or cell culture system such as a tobacco plant, like *N. benthamiana*. In this embodiment, the overexpression of a heterologous cytochrome P450 oxidoreductase (oxred) protein, identified as SEQ ID NO. 4, may help to functionalize cannabinoids introduced to the genetically modified plant or plant cell culture system so that they can be more efficiently glycosylated and/or acetylated, in vivo, rendering them water-soluble.

In a preferred embodiment cytochrome 450 and P450 oxidoreductase are co-expressed.

In another embodiment, the invention may include the expression of one or more exogenous or heterologous, the terms being generally interchangeable, cannabinoid synthase gene in a non-cannabinoid producing plant or plant-cell culture system. In one preferred embodiment, such a gene may include one or more of a CBG, THCA, CBDA or CBCA synthase genes. For example in one embodiment, a Cannabidiolic acid (CBDA) synthase, identified as SEQ ID NO. 5 (gene) or SEQ ID NO. 6 (protein) from *Cannabis sativa* may use expressed in a non-*cannabis*-producing plant, such as or plant cell suspension culture of *N. benthamiana*. In another preferred embodiment, a Tetrahydrocannabinolic acid (THCA) synthase, identified as SEQ ID NO. 42 (gene) from *Cannabis sativa* may use expressed in a non-*cannabis*-producing plant, such as a plant cell suspension culture of *N. benthamiana*.

In another preferred embodiment, such cannabinoid synthase genes expressed in a cannabinoid and/or non-cannabinoid plant or plant-cell suspension culture may be target or localized to certain parts of a cell. For example, in one preferred embodiment, cannabinoid production may be localized to the cytosol allowing cannabinoids to accumulate in the cytoplasm. In one exemplary embodiment, an artificially modified cannabinoids synthase protein may be generated. In this example embodiment, a CBDA synthase may have the trichome targeting sequence remove forming a cytosolic CBDA synthase (cytCBDAs) identified as SEQ ID NO. 22, (gene) or 23 (protein). Alternative embodiments would include generation of other artificial cytosol target synthase genes, such as cytosolic THCA synthase (cytTHCAs) identified as SEQ ID NO. 46 (gene).

These preferred embodiments may be particularly suited for cannabinoid cell-suspension culture cannabinoid expression systems, as such culture systems lack the trichomes present in whole plants. As such, in one preferred embodiment, a cannabinoid producing plant may be transformed to one or more of the artificial cytosolic targeted cannabinoid synthase genes lacking a trichome-targeting signal. In an alternative embodiment, such artificial cytosolic targeted cannabinoid synthase genes may be expressed in a cannabinoid producing plant suspension culture where the corresponding endogenous wild-type synthase gene has been inhibited and/or knocked out.

In one embodiment, the invention may include a cannabinoid production, accumulation and modification system that may generate water-soluble cannabinoids. In one preferred embodiment, a plant, such as *cannabis* or tobacco, may be genetically modified to express one or more heterologous glycosyltransferase genes, such as UDP glycosyltransferase. In this preferred embodiment, UDP glycosyltransferase (76G1) (SEQ ID NO. 7) (gene)/SEQ ID NO. 8 (protein) from *Stevia rebaudiana* may be expressed in cannabinoid producing plant or cell suspension culture. In a preferred embodiment, the cannabinoid producing plant or cell suspension culture may be *Cannabis*. In another embodiment, one or more glycosyltransferase from *Nicotiana tabacum* and/or a homologous glycosyltransferase from *Nicotiana benthamiana*, may be expressed in a cannabinoid-producing plant, such as *cannabis*, or may be over-expressed in an endogenous plant and/or plant cell culture system. In a preferred embodiment, a glycosyltransferase gene and/or protein may be selected from the exemplary plant, such as *Nicotiana tabacum* Such glycosyltransferase gene and/or protein may include, but not limited to: Glycosyltransferase (NtGT5a) *Nicotiana tabacum* (SEQ ID NO. 26) (Amino Acid); Glycosyltransferase (NtGT5a) *Nicotiana tabacum* (SEQ ID NO. 27) (DNA); Glycosyltransferase (NtGT5b) *Nicotiana tabacum* (SEQ ID NO. 28) (Amino Acid); Glycosyltransferase (NtGT5b) *Nicotiana tabacum* (SEQ ID NO. 29) (DNA); UDP-glycosyltransferase 73C3 (NtGT4) *Nicotiana tabacum* (SEQ ID NO. 30) (Amino Acid); UDP-glycosyltransferase 73C3 (NtGT4) *Nicotiana tabacum* (SEQ ID NO. 31) (DNA); Glycosyltransferase (NtGT1b) *Nicotiana tabacum* (SEQ ID NO. 32) (Amino Acid); Glycosyltransferase (NtGT1b) *Nicotiana tabacum* (SEQ ID NO. 33) (DNA); Glycosyltransferase (NtGT1a) *Nicotiana tabacum* (SEQ ID NO. 34) (Amino Acid); Glycosyltransferase (NtGT1a) *Nicotiana tabacum* (SEQ ID NO. 35) (DNA); Glycosyltransferase (NtGT3) *Nicotiana tabacum* (SEQ ID NO. 36) (Amino Acid); Glycosyltransferase (NtGT3) *Nicotiana tabacum* (SEQ ID NO. 37) (DNA); Glycosyltransferase (NtGT2) *Nicotiana tabacum* (SEQ ID NO. 38) (Amino Acid); and/or Glycosyltransferase (NtGT2) *Nicotiana tabacum* (SEQ ID NO. 39) (DNA). The sequences from *Nicotiana tabacum* are exemplary only as other tobacco Glycosyltransferase may be used.

As noted above, such glycosyltransferases may glycosylate the cannabinoids and/or functionalized cannabinoids in a plant or plant cell suspension culture as generally described here. Naturally, other glycosyltransferase genes from alternative sources may be included in the current invention.

As noted above, in one embodiment, one or more glycosyltransferases may be targeted or localized to a portion of the plant cell. For example, in this preferred embodiment, cannabinoid glycosylation may be localized to the trichome allowing cannabinoids to accumulate at higher-then wild-type levels in that structure. In one exemplary embodiment, an artificially modified glycosyltransferase may be generated. In this example embodiment, a UDP glycosyltransferase (76G1) may be fused with a trichome-targeting sequence at its N-terminal tail. This trichome targeting sequence may be recognized by the cell and cause it to be transported to the trichome. This artificial gene construct is identified as SEQ ID NO. 19 (gene), or SEQ ID NO. 20 (protein). In one embodiment, a trichome targeting sequence or domain may be derived from any number of synthases. For example, in one embodiment a THCA Synthase Trichome domain (SEQ ID NO. 40) may be coupled with a glycosyltransferase as generally described above. Moreover, in another example, a CBDA Synthase Trichome targeting domain (SEQ ID NO. 41) may be coupled with a glycosyltransferase as generally described above.

In one embodiment, the inventive technology may include the in vivo generation of one or more cannabinoid glucuronides. As also noted above, UDP-glucuronosyltransferases catalyze the transfer of the glucuronosyl group from uridine 5'-diphospho-glucuronic acid (UDP-glucuronic acid) to substrate molecules that contain oxygen, nitrogen, sulfur or carboxyl functional groups. Glucuronidation of a compound, such as a cannabinoid may modulate the bioavailability, activity, and clearance rate of a compound. As such, in one embodiment, the invention may include a cannabinoid production, accumulation and modification system that may generate water-soluble cannabinoid glucuronides. In one preferred embodiment, a plant, such as *cannabis* or tobacco, may be genetically modified to express one or more endogenous and/or heterologous UDP-glucuronosyltransferases. Such a UDP-glucuronosyltransferases may be expressed in cannabinoid producing plant, non-cannabinoid producing plant, or cell suspension culture. Non-limiting examples of UDP-glucuronosyltransferases may include UGT1A1, UGT1A3, UGT1A4, UGT1A6, UGT1A7, UGT1A8, UGT1A9, UGT1A1O, UGT2B4, UGT2B7, UGT2BI5, and UGT2BI7—there nucleotide and amino acid sequences being generally know to those of ordinary skill in the art. These UDP-glucuronosyltransferases may be a recombinant UDP-glucuronosyltransferases. Methods of making, transforming plant cells, and expressing recombinant UDP-glucuronosyltransferases are known in the art. In a preferred embodiment, the cannabinoid producing plant or cell suspension culture may be *cannabis*. In another embodiment, one or more UDP-glucuronosyltransferases and/or a homolog/ortholog of a UDP-glucuronosyltransferase, may be expressed in a cannabinoid-producing plant, such as *cannabis*, or may be over-expressed in an endogenous plant and/or plant cell culture system. In a preferred embodiment, a UDP-glucuronosyltransferase may be targeted or localized to a portion of the plant cell. For example, in this preferred embodiment, cannabinoid glucuronidation may be localized to the trichome allowing cannabinoids to accumulate at higher-then wild-type levels in that structure. In one exemplary embodiment, an artificially modified UDP-glucuronosyltransferase may be generated. In this embodiment, a UDP-glucuronosyltransferase may be fused with a trichome-targeting sequence at its N-terminal tail. This trichome targeting sequence may be recognized by the cell and cause it to be transported to the trichome. In one embodiment, a trichome targeting sequence or domain may be derived from any number of synthases. For example, in one embodiment a THCA Synthase trichome domain (SEQ ID NO. 40) may be coupled with a UDP-glucuronosyltransferase as generally described above. Moreover, in another example, a CBDA Synthase trichome targeting domain (SEQ ID NO. 41) may be coupled with a UDP-glucuronosyltransferase as generally described above.

In another embodiment, a UDP-glucuronosyltransferase may further be targeted to the cytosol as generally described herein.

In another embodiment, invention may include an embodiment where transiently modified cannabinoids may be passively and/or actively excreted from a cell or into a cell wall. In one exemplary model, an exogenous ATP-binding cassette transporter (ABC transporters or ABCt) or other similar molecular structure may recognize the glycosyl or glucuronic acid or acetyl functional group (conjugate) on the transiently modified cannabinoid and actively transport it across the cell wall/membrane and into the surrounding media.

In one embodiment, a plant may be transformed to express a heterologous ABC transporter. In this embodiment, an ABCt may facilitate cannabinoid transport outside the cells in suspension cultures, such as a *cannabis* or tobacco cell suspension culture. In this preferred embodiment, a human multi-drug transported (ABCG2) may be expressed in a plant cell suspension culture of the same respectively. ABCG2 is a plasma membrane directed protein and may further be identified as SEQ ID NO. 9 (gene), or 10 (protein).

Generally, a trichome structure, such as in *Cannabis* or tobacco, will have very little to no substrate for a glycosyltransferase enzyme to use to effectuate glycosylation. To resolve this problem, in one embodiment, the invention may include systems, methods and compositions to increase substrates for glycosyltransferase, namely select sugars in a trichome. In one preferred embodiment, the invention may include the targeted or localization of sugar transport to the trichome. In this preferred embodiment, an exogenous or endogenous UDP-glucose/UDP-galactose transporter (UTR1) may be expressed in a trichome producing plant, such as *cannabis* or tobacco and the like. In this embodiment, the UDP-glucose/UDP-galactose transporter (UTR1) may be modified to include a plasma-membrane targeting sequence and/or domain. With this targeting domain, the UDP-glucose/UDP-galactose transporter (UTR1) may allow the artificial fusion protein to be anchored to the plasma membrane. In this configuration, sugar substrates from the cytosol may pass through the plasma membrane bound UDP-glucose/UDP-galactose transporter (PM-UTR1) into the trichome. In this embodiment, substrates for glycosyltransferase may be localized to the trichome and allowed to accumulate further allowing enhanced glycosylation of cannabinoids in the trichome. In one example, SEQ ID NO. 21 is identified as the polynucleotide gene sequence for a heterologous UDP-glucose/galactose transporter (UTR1) from *Arabidopsis thaliana* having a plasma-membrane targeting sequence replacing a tonoplast targeting sequence. The plasma membrane targeting sequence of this exemplary fusion protein may include the following sequence (see SEQ ID NO 21) TGCTCCATAATGAACTTAATGTGTGGGTC-TACCTGCGCCGCT (SEQ ID NO. 74), or a sequence having 70-99% homology with the sequence.

It should be noted that a number of combinations and permutations of the genes/proteins described herein may be co-expressed and thereby accomplish one or more of the goals of the current invention. Such combinations are exemplary of preferred embodiments only, and not limiting in any way.

In one embodiment, a gene, such as a cannabinoid synthase, or a gene fragment corresponding with, for example a signal domain may be inhibited, downregulated, disrupted, or may even be knocked-out. One of ordinary skill in the art will recognize the many processes that can accomplish this without undue experimentation. In other embodiment, a knock-out may mean overexpression of a modified endo- or exogenous gene compared to the wt version.

For example, in one embodiment high levels of cannabinoid glycosylation may be generated by co-expressing CYP3A4 and CYP oxidoreductase (cytochrome P450 with P450 oxidoreductase) and at least one endogenous glycosyltransferases in *N. benthamiana*. In another embodiment, one or more of the endogenous or exogenous gene may be expressed in a plant or plant cell culture with the co-expression of myb and/or a catalase. In this configuration, there exists an additive effect of over-expressing a Myb transcription factor and a catalase, one or more of which may be targeted or localized, in the synthesis of water-soluble cannabinoids (glycosylated and hydroxylated) in *Cannabis sativa*.

In certain embodiments, endocannabinoids may be functionalized and/or acetylated and/or glycosylated as generally described herein.

All sequences described herein include sequences having between 70-99% homology with the sequence identified The modified cannabinoids compounds of the present invention are useful for a variety of therapeutic applications. For example, the compounds are useful for treating or alleviating symptoms of diseases and disorders involving CB1 and CB2 receptors, including appetite loss, nausea and vomiting, pain, multiple sclerosis and epilepsy. For example, they may be used to treat pain (i.e. as analgesics) in a variety of applications including but not limited to pain management. In additional embodiments, such modified cannabinoids compounds may be used as an appetite suppressant. Additional embodiment may include administering the modified cannabinoids compounds By "treating" the present inventors mean that the compound is administered in order to alleviate symptoms of the disease or disorder being treated. Those of skill in the art will recognize that the symptoms of the disease or disorder that is treated may be completely eliminated, or may simply be lessened. Further, the compounds may be administered in combination with other drugs or treatment modalities, such as with chemotherapy or other cancer-fighting drugs.

Implementation may generally involve identifying patients suffering from the indicated disorders and administering the compounds of the present invention in an acceptable form by an appropriate route. The exact dosage to be administered may vary depending on the age, gender, weight and overall health status of the individual patient, as well as the precise etiology of the disease. However, in general, for administration in mammals (e.g. humans), dosages in the range of from about 0.1 to about 30 mg of compound per kg of body weight per 24 hr., and more preferably about 0.1 to about 10 mg of compound per kg of body weight per 24 hr., are effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.). In a preferred embodiment of the invention, the water-soluble cannabinoid analogs are provided orally or intravenously.

In particular, the phenolic esters of the invention (Formula 1) are preferentially administered systemically in order to afford an opportunity for metabolic activation via in vivo cleavage of the ester. In addition, the water soluble compounds with azole moieties at the pentyl side chain (Formula 2, e.g. with imidazole moieties) do not require in vivo activation and may be suitable for direct administration (e.g. site specific injection).

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the compounds of the present invention may be intermittent, bolus dose, or at a gradual or continuous, constant or controlled rate to a patient. In addition, the time of day and the number of times per day that the pharmaceutical formulation is administered may vary are and best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

Genes encoding by a combination polynucleotide and/or a homologue thereof, may be introduced into a plant, and/or plant cell using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants.

As used herein, a "cannabinoid" is a chemical compound (such as cannabinol, THC or cannabidiol) that is found in the plant species *Cannabis* among others like *Echinacea; Acmella Oleracea*; Helichrysum Umbraculigerum; Radula *Marginata* (Liverwort) and *Theobroma Cacao*, and metabolites and synthetic analogues thereof that may or may not have psychoactive properties. Cannabinoids therefore include (without limitation) compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3 S,4R)-7-hydroxy-Δ6-tetrahydrocannabinol homologs and derivatives described in U.S. Pat. No. 4,876,276, incorporated by reference; (+)-4-[4-DMH-2,6-diacetoxy-phenyl]-2-carboxy-6,6-dimethylbicyclo[3.1.1]hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., J. Clin. Phannacol. 21:428S-436S, 1981, which is also incorporated by reference. Many other cannabinoids are similarly disclosed in Agurell et al., Pharmacol. Rev. 38:31-43, 1986, which is also incorporated by reference.

As claimed herein, the term "cannabinoid" may also include different modified forms of a cannabinoid such as a hydroxylated cannabinoid or cannabinoid carboxylic acid. For example, if a glycosyltransferase were to be capable of glycosylating a cannabinoid, it would include the term cannabinoid as defined elsewhere, as well as the aforementioned modified forms. It may further include multiple glycosylation moieties.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid,delta-9-tetrahydrocannabivarin, delta-9-tetrahydrocannabiorcolic acid, delta-9-tetrahydrocannabiorcol,delta-7-cis-iso-tetrahydrocannabivarin, delta-8-tetrahydrocannabiniolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol, trihydroxy-delta-9-tetrahydrocannabinol, and cannabinol. Examples of cannabinoids within the context of this disclosure include tetrahydrocannabinol and cannabidiol.

The term "endocannabinoid" refer to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexanoyl ethanolamide, linolenoyl ethanolamide, 5(Z),8(Z),1 1 (Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

Hydroxylation is a chemical process that introduces a hydroxyl group (—OH) into an organic compound. Acetylation is a chemical reaction that adds an acetyl chemical group. Glycosylation is the coupling of a glycosyl donor, to a glycosyl acceptor forming a glycoside.

The term "prodrug" refers to a precursor of a biologically active pharmaceutical agent (drug). Prodrugs must undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety to form the biologically active pharmaceutical agent.

As used herein, the term "homologous" with regard to a contiguous nucleic acid sequence, refers to contiguous nucleotide sequences that hybridize under appropriate conditions to the reference nucleic acid sequence. For example, homologous sequences may have from about 70%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific."

A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most cell or tissue types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone are general examples (Schena et al. (1991) Proc. Natl. Acad. Sci. USA 88:0421).

As used herein, the term "transformation" or "genetically modified" refers to the transfer of one or more nucleic acid molecule(s) into a cell. A plant is "transformed" or "genetically modified" by a nucleic acid molecule transduced into the plant when the nucleic acid molecule becomes stably replicated by the plant. As used herein, the term "transformation" or "genetically modified" encompasses all techniques by which a nucleic acid molecule can be introduced into, such as a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria.

As is known in the art, different organisms preferentially utilize different codons for generating polypeptides. Such "codon usage" preferences may be used in the design of nucleic acid molecules encoding the proteins and chimeras of the invention in order to optimize expression in a particular host cell system.

An "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 1a, infra, contains information about which nucleic acid codons encode which amino acids.

TABLE 4

Amino acid Nucleic acid codons

| Amino Acid | Nucleic Acid Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "plant" or "plant system" includes whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The invention may also include Cannabaceae and other *Cannabis* strains, such as *C. sativa* generally.

The term "expression," as used herein, or "expression of a coding sequence" (for example, a gene or a transgene)

refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

The term "sequence identity" or "identity," as used herein in the context of two nucleic acid or polypeptide sequences, refers to the residues in the two sequences that are the same when aligned for maximum correspondence over a specified comparison window.

The term "recombinant" when used with reference, e.g., to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed—over-expressed, under expressed or not expressed at all.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

As used herein, "heterologous" or "exogenous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct. Host cells may be prokaryotic cells such as E. coli, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell

EXAMPLES

Example 1: Functionalization of Cannabinoids by Cytochrome P450s

The present inventors have demonstrated that cannabinoids can be functionalized in an in vivo plant system.

Specifically, the present inventors utilized cytochrome P450 monooxygenases (CYP) to modify or functionalize the chemical structure of cannabinoids. As shown below, CYPs do this by inserting an oxygen atom into hydrophobic molecules to make them more reactive and hydrophilic. A representative reaction may include the generalized reaction in FIG. 13.

Figure 5:
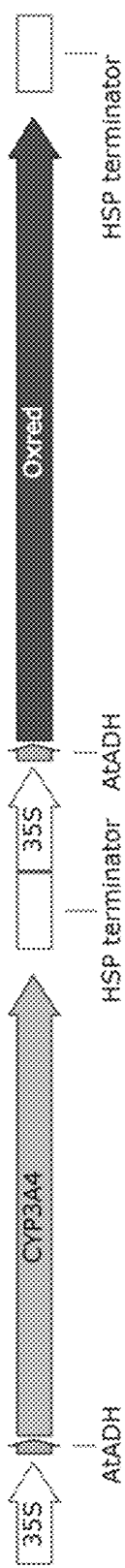
FIG. 5. Gene construct for expression of cytochrome P450 (CYP3A4) gene, (SEQ ID NO. 1), expressing the cytochrome P450 (CYP3A4) protein (SEQ ID NO. 2) and P450 oxidoreductase gene (oxred) (SEQ ID NO. 3) expressing the P450 oxidoreductase protein (SEQ ID NO. 4), in plants. Both genes were driven by the constitutive 35S promoter (35S) and featured 5' untranslated regions from *Arabidopsis thaliana* alcohol dehydrogenase (AtADH) as translational enhancers.

The P450 enzyme system involves several cytochrome P450 species and nonspecific cytochrome P450 oxidoreductases. As shown in FIG. 5, the present inventors used a human cytochrome P450 (CYP3A4) in a double construct with an exemplary human cytochrome P450 oxidoreductase, both expressed under the control of the constitutive CaMV 35S promoter with 5' untranslated regions to enhance translation. Protein and DNA sequences for the functionalization of cannabinoids (CYP3A4 and P450 oxidoreductase) are identified as SEQ ID NO's. 1-4. Expression was confirmed using RT-PCR utilizing the forward and reverse primers identified in Table 3 below. As noted above, the present inventors demonstrated that overexpressing of P450s generated functionalized cannabinoids which could then be glycosylated, rendering them water-soluble.

Figure 6:
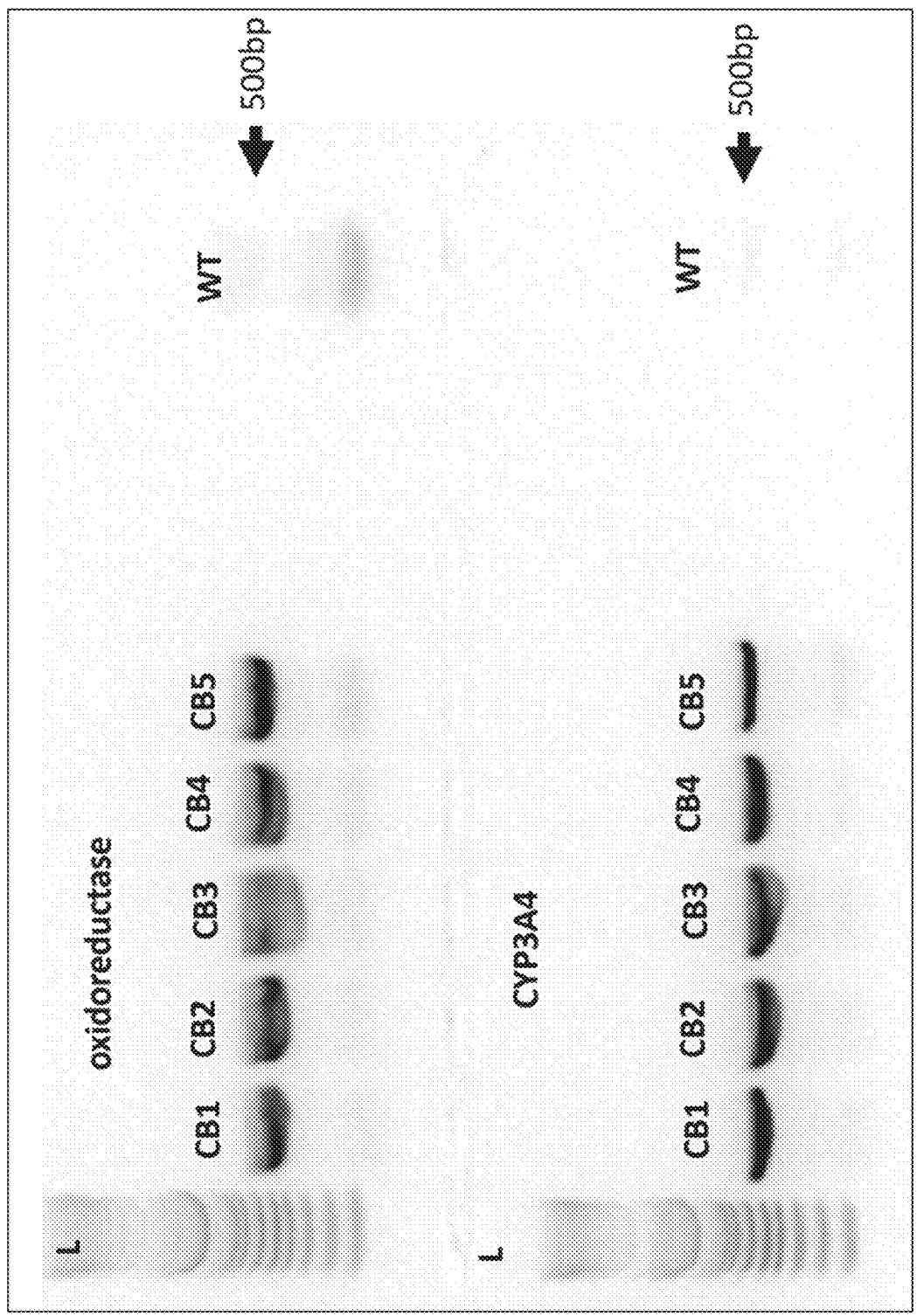
FIG. 6. Confirmation of expression of CYP3A4 and P450 oxidoreductase in tobacco leaves. CB1-CB5, biological replicates of leaves infiltrated with the CYP3A4/P450 oxidoreductase; WT=wild type tobacco leaves with no infiltration. L=1 kb plus ladder (Thermo Fisher Scientific, USA). The arrows show the expected (500 bp) band indicating expression of the transgene.

Example 2: P450 Overexpression Enhances In Vivo Hydroxylation and Glycosylation of Cannabinoids in Plant Systems The present inventors have demonstrated that overexpression enhanced in vivo hydroxylation and glycosylation of CBDA in an exemplary plant system. Specifically, as generally shown in FIG. 6, the present inventors demonstrate that infiltration of tobacco leaves with *Agrobacterium* carrying CYP3A4 and P450 oxidoreductase was accomplished as described in herein. Confirmation of expression was done using RT-PCR 2-3 days after infiltration (FIG. 6).

Figure 7:
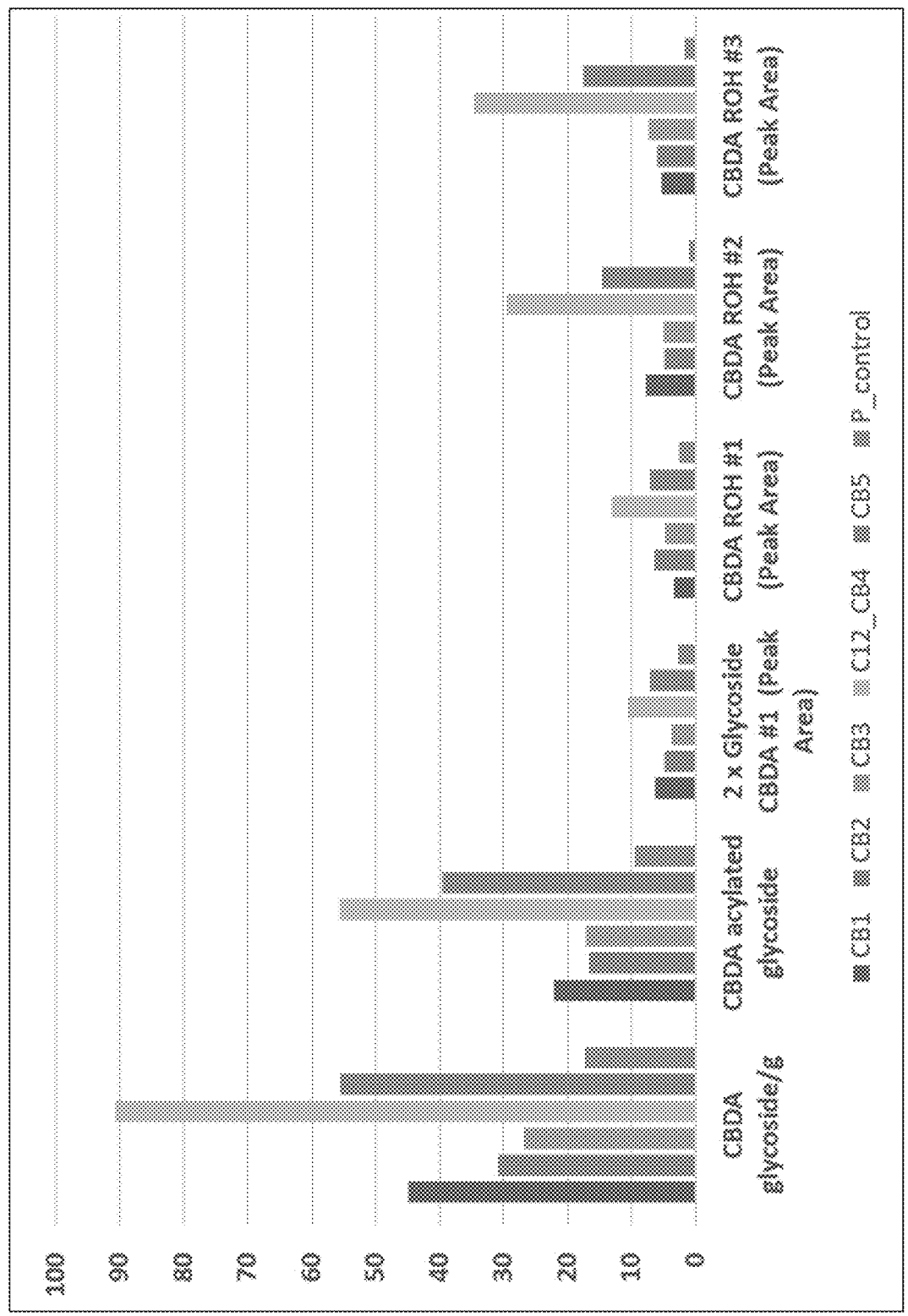
FIG. 7. Enhanced glycosylation of cannabinoids in P450-over expressing *N. benthamiana* plants. CB1-CB5 are biological reps overexpressing CYP3A4+P450 oxidoreductase, P control is the P19 silencing suppressor ('empty vector' control). Vertical axis shows relative amounts expressed as peak area per g fresh weight.

As generally shown in FIG. 7, the present inventors demonstrate that overexpression of the CYP3A4+P450 oxidoreductase construct and subsequent feeding of at least one cannabinoid, in this case CBDA, upon confirmation of expression resulted in in vivo glycosylation of CBDA in tobacco leaves (FIG. 7). On average, glycosylation increased 3-fold in transgenic *N. benthamiana* plants compared to the control while hydroxylation increased up to 13-fold. As such, in certain embodiment, tobacco glycosyltransferases may be utilized as key targets in the current inventive technology for glycosylation of cannabinoids.

Example 3: Identification of Modified Water-Soluble Cannabinoids by Mass Spectrometry The present inventors demonstrated the biosynthesis of modified functionalized as well as water-soluble cannabinoids in both in vitro as well as in vivo plant system. Specifically, the present inventors identified the cannabinoid biotransformations associated with the gene constructs in both in vitro assays and transient leaf expression. Through the use of accurate mass spectrometry measurements, the present inventors were able to identify and confirm the biosynthesis of modified water-soluble cannabinoids.

Specifically, as generally shown in FIGS. 1-4, the present inventors were able to identify the glycosylated water-soluble cannabinoids in the chromatographic analysis and were able to produce extracted ion chromatograms for peak integration. For example, FIG. 1 panel B, illustrates the identification of multiple constitutional cannabinoid isomers of a single glycoside moiety, while in FIG. 2 panel B, an example of multiple constitutional isomers of the cytochrome P450 oxidation are illustrated. Peak areas for each identified molecule were used for relative quantification between treatments. Based on these results we confirmed biosynthesis of modified cannabinoid molecules containing up to two glycosides moieties, 0 acetyl glycoside, as well as hydroxylation (R-OH) biotransformations.

Tables 1 and 2 are provided below further demonstrating the production of the select modified cannabinoid molecules. Generally referring to Tables 1-2 below, the present inventors demonstrated that based on the reduced retention time in the water: acetonitrile HPLC gradient, the glycosylated and hydroxylated cannabinoids, which eluted earlier than their non-modified forms, are demonstrated to be more water soluble than their non-modified forms.

Figure 8:
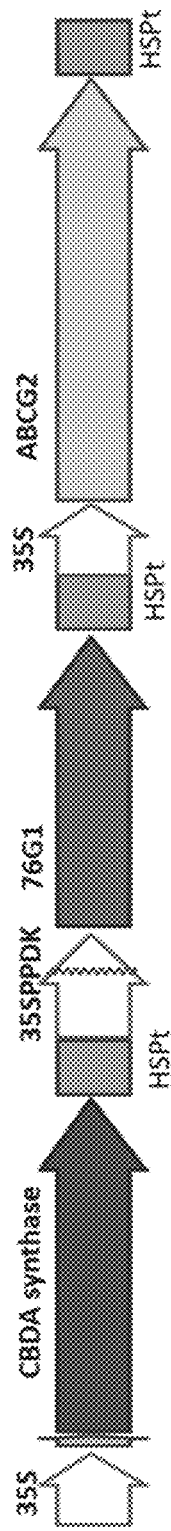
FIG. 8. Gene construct for the cytosol and suspension culture cannabinoid production system. 35S, Cauliflower mosaic 35S promoter; HSPt, HSP terminator; 35PPDK, hybrid promoter consisting of the cauliflower mosaic virus 35S enhancer fused to the maize C4PPDK basal promoter (Yoo et al. 2007); 76G1, UDP glycosyltransferase from *Stevia rebaudiana*; ABCG2, human multi-drug transporter.

Example 4: Generation of Heterologous Cytosolic Synthesis and Glycosylation Gene Constructs for Expressions in Tobacco Leaves and Cell Suspensions As shown in FIG. 8, the present inventors generated a triple gene construct for expression of cannabidiolic acid (CBDA) synthase in which the trichome targeting sequence had been removed, and the glycosyltransferase 76G1 from *Stevia rebaudiana*. In this construct the multi-drug ABC transporter ABCG2 was also included.

In one embodiment of the present inventive technology, the gene construct may be used to transform a plant cell that may further be configured to be cultured in a suspension culture. In one preferred embodiment, a *cannabis* cell may be transformed with the construct generally outline in FIG. 8. In this preferred embodiment, cannabinoids produced by the *cannabis* cells in the cell culture may be functionalize through the overexpression of the CYP3A4+P450 oxidoreductase as described above, and further glycosylated by the expression and action of the heterologous UDP glycosyltransferase (76G1) from *Stevia rebaudiana* referend above. Moreover, as generally outline herein, the cannabinoids may be modified so as to be functionalized and/or glycosylated, or generally water-soluble, and may then be secreted into the cell wall area, in the case of a whole plant, or the surrounding media in suspension cultures, with the aid of the ABC transporter. In one embodiment, this construct may be used for synthesis and modification of cannabinoids in cell suspension cultures, utilizing tobacco bright yellow cells or *cannabis* cells.

Figure 9:
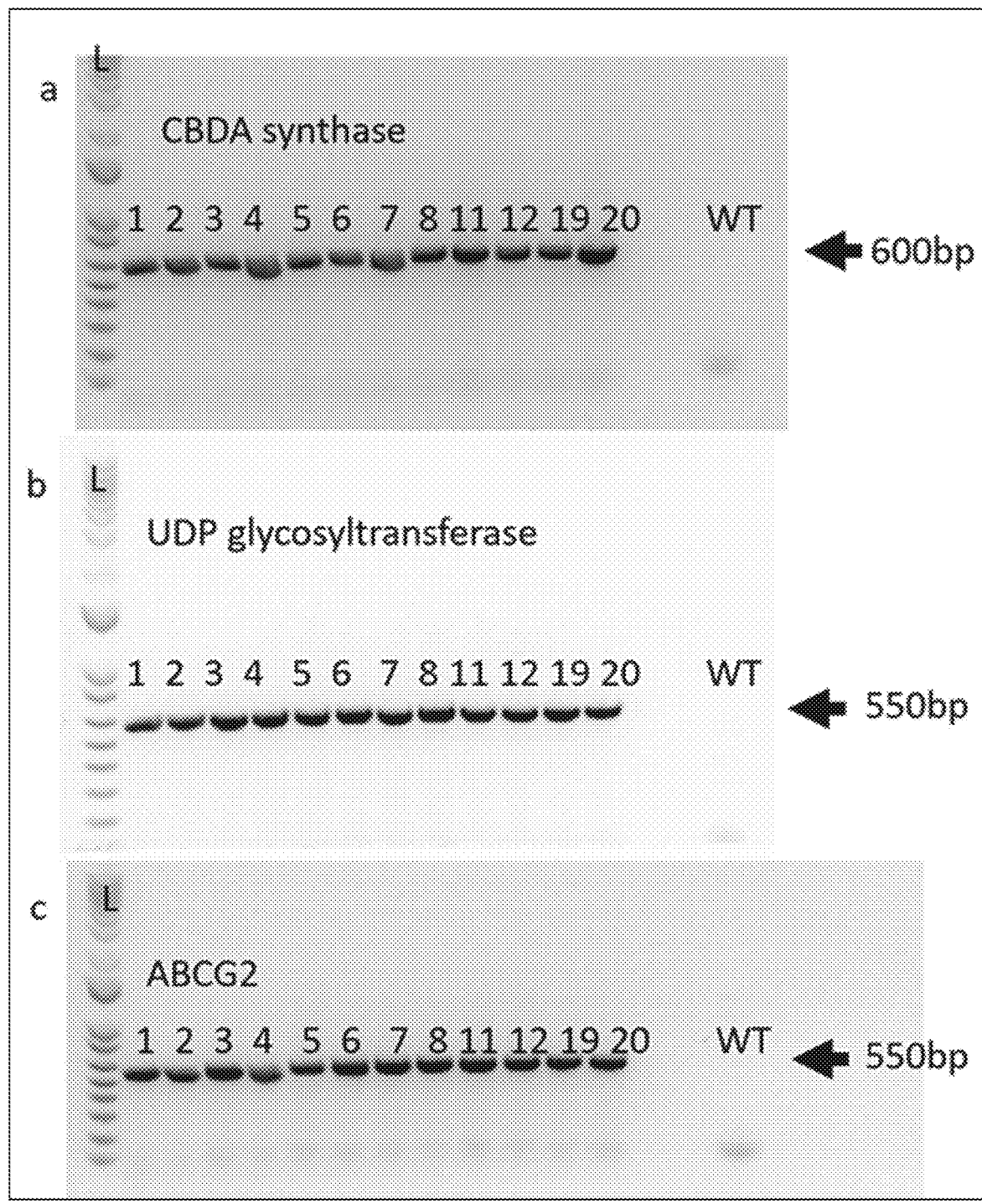
FIG. 9. Demonstrates RT-PCR confirmation of expression of CBDA synthase (a), UDP glycosyltransferase (b) and ABCG2 (c) in tobacco leaf cells. L is the 1 kb plus ladder (Thermo Fisher Scientific, USA). Numbers on the lanes represent independent transgenic lines. The arrows point to the expected band that shows expression of the transgene.

As generally shown in FIG. 9, in vivo expression of CBDA synthase, UDP glycosyltransferase 76G1 and ABCG2 was confirmed. Reverse and forward primers used in the RT-PCR reactions are provided below in Table 4 below.

The gene and protein sequence identifications for CBDA synthase are provided as SEQ ID NO's 5 and 6 respectively. It should be noted that a variety of cannabinoid synthase genes/proteins may be used with the current inventive technology, CBDA synthase being exemplary only. Indeed, it is specifically contemplated that the synthase enzyme associated with any of the cannabinoids identified herein may be incorporated into the current invention without undue experimentation. In one embodiment, one or more of such exogenous or endogenous synthase enzyme may further have the trichome targeting sequence excised, again, a step that can be readily accomplished without undue experimentation. Example may THCA synthase, CBG synthase, THCA synthase, CBDA synthase or CBCA synthase, which may in this embodiment have their trichome targeting sequence had been removed.

The gene and protein sequence identifications for glycosyltransferase 76G1 from *Stevia rebaudiana* are provided as SEQ ID NO's. 7, and 8 respectively. The gene and protein sequence identifications for the multi-drug ABC transporter ABCG2 are provided as SEQ ID NO's 9 and 10 respectively.

Figure 10:
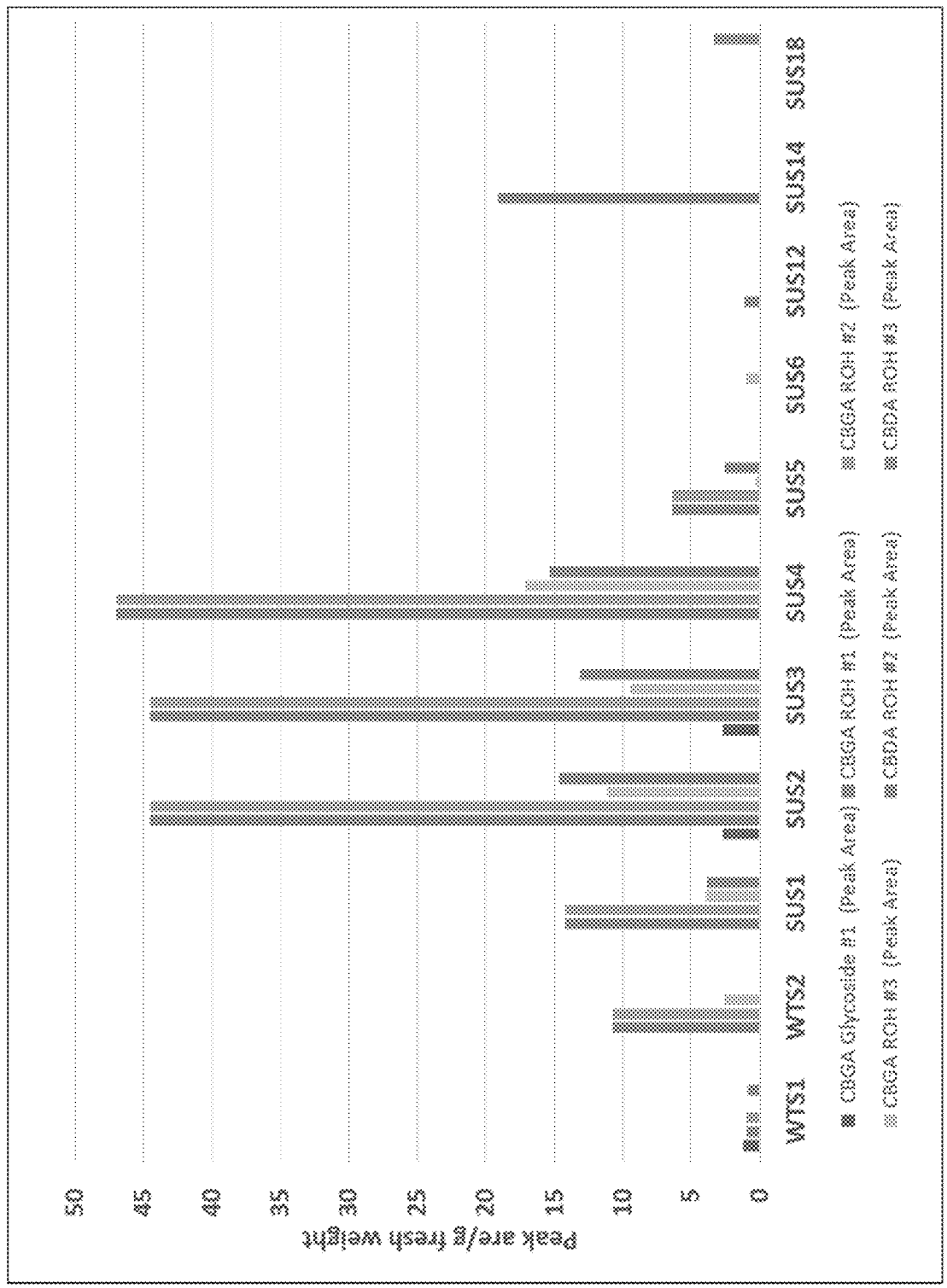
FIG. 10. Hydroxylation and glycosylation of cannabinoids in transgenic tobacco (SUS, numbered) overexpressing CBDA synthase, UDP glycosyltransferase and ABC transporter. WTS1 and 2 are wild type fed with substrate for endogenous reactions. There was some endogenous glycosylation of CBGA, as well as evidence for enhanced transgenic glycosyltransferase activity (e.g. SUS2, SUS3 and SUS4). The data has been corrected to peak area per g fresh weight.

Example 5: In Vivo Cytosolic Synthesis and Glycosylation of Cannabinoids in *N. benthamiana* Leaves and Cell Suspensions As shown in FIG. 10, the present inventors demonstrate that in plants, in this embodiment *N. benthamiana*, expressing the above referenced cytosolic construct, glycosylation of CBGA occurred as well as formation of modified or hydroxylated CBDA. The glycosylation of CBGA evidences in vivo glycosylation of cannabinoids by overexpressing a glycosyltransferase in *N. benthamiana* plants. The presence of glycosylated cannabinoids in wild type plants suggests the presence of a strong glycosyltransferase in tobacco. As such, in one embodiment, over expression of a heterologous or homologous tobacco glycosyltransferase may expressed or overexpressed resulting in the enhanced in vivo biosynthesis of water-soluble cannabinoids in whole plants, as well as in suspension cultures. For example, in one embodiment, a heterologous tobacco glycosyltransferase may be expressed in a *cannabis* plant or cell culture resulting in the in vivo biosynthesis of water-soluble cannabinoids in the *Cannabis* plant and/or a *Cannabis* suspension cultures.

Figure 27:
FIG. 27. Gene construct used to boost cannabinoid production and mitigate toxicity. CsMYB12, predicted *Cannabis sativa* MYB transcription factor for enhancing flavonol biosynthesis; HSPt, efficient transcription terminator from the *Arabidopsis thaliana* heat shock protein 18.2 gene; 35S, constitutive promoter from cauliflower mosaic virus; Catalase, *Arabidopsis thaliana* catalase gene.
Figure 28:
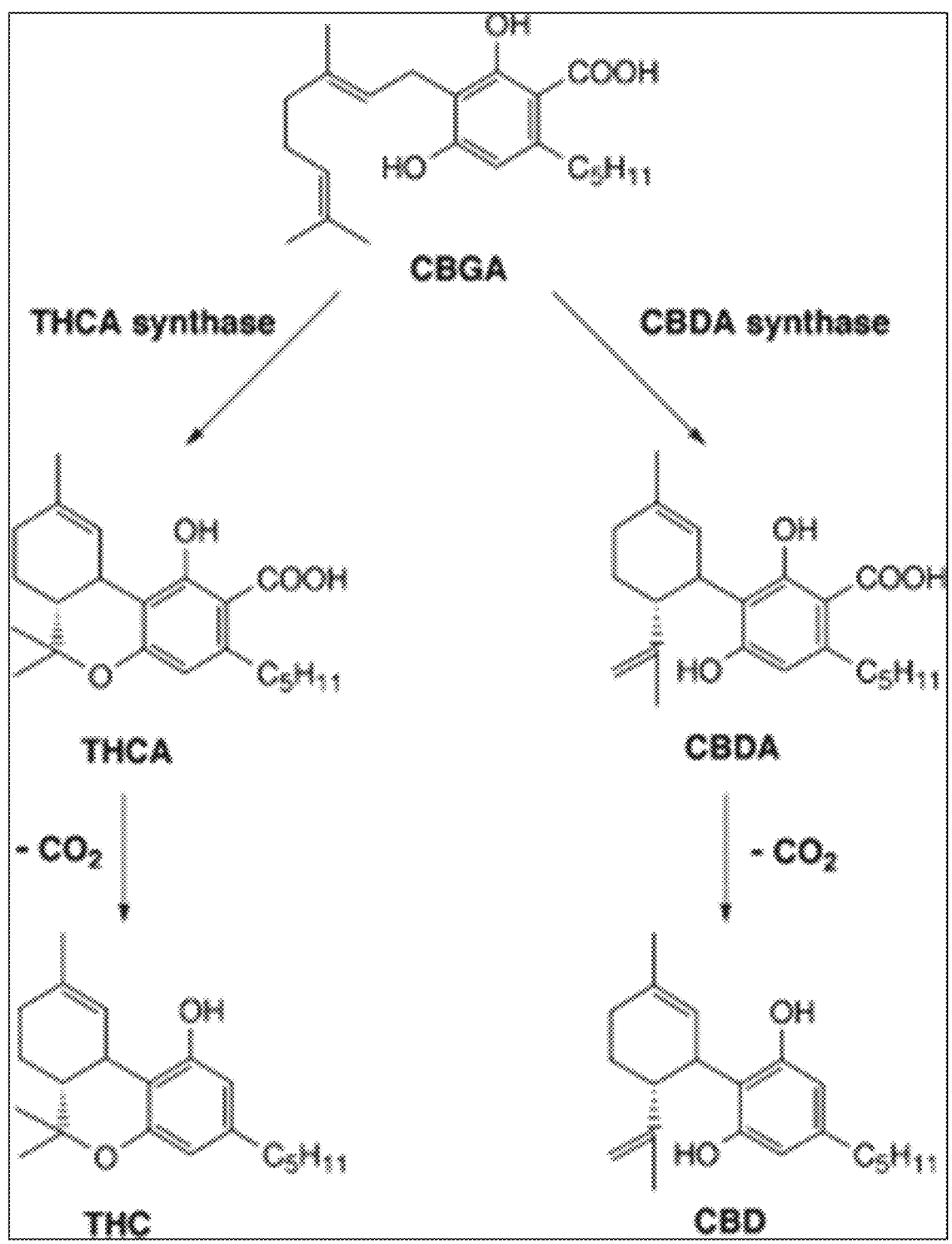
FIG. 28. Synthesis of THC and CBD from common precursor CBGA.
Figure 29:
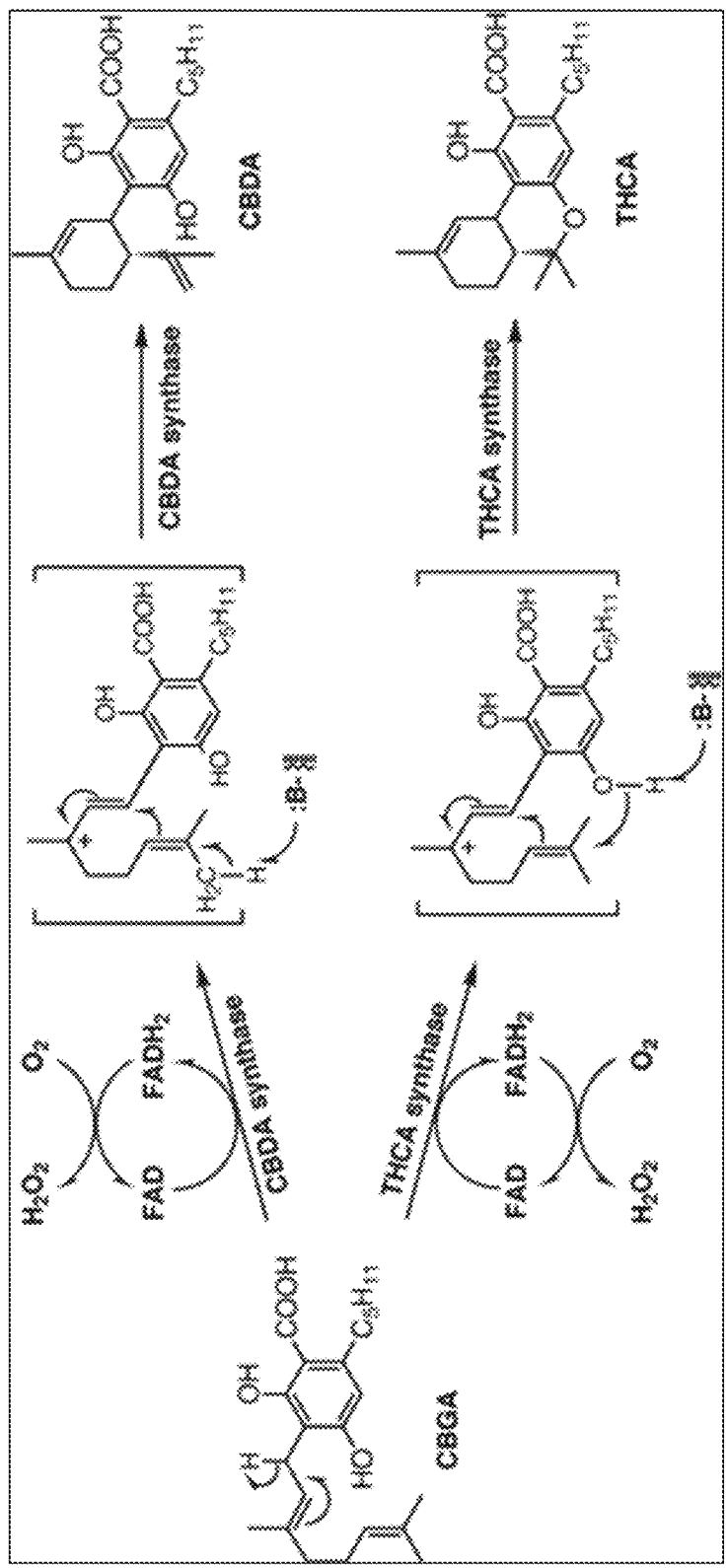
FIG. 29. Generation of hydrogen peroxide during cannabinoid biosynthesis.

Example 6: Water Soluble Cannabinoid Production Systems Utilizing MYB Transcription Factor and/or Catalase The present inventors have developed a plurality of systems for the biosynthesis and modification of cannabinoids based on cellular location using novel methods of protein targeting. As shown in Table 10, the present inventors designed such novel systems and methods to enhance production and modification (glycosylation, acetylation and functionalization) of cannabinoids as well as to mitigate toxicity resulting from cannabinoid accumulation. Certain embodiments, included the expression of a MYB transcription factor and a catalase (FIG. 27) to degrade hydrogen peroxide resulting from CBDA synthase activity. In one preferred embodiment, the present inventors used *Arabidopsis thaliana* or an *E. coli* catalase gene and a predicted *Cannabis* MYB transcription factor involved in elevating genes involved in cannabinoid biosynthesis. DNA and protein sequences for *Cannabis* predicted MYB transcription factor (SEQ ID NOs. 11-12, DNA and amino acid sequences respectively), *Arabidopsis thaliana* catalase SEQ ID NOs. 13-14, DNA and amino acid sequences respectively) and/or *E. coli* catalase (SEQ ID NO. 15-16, DNA and amino acid sequences).

Figure 11:
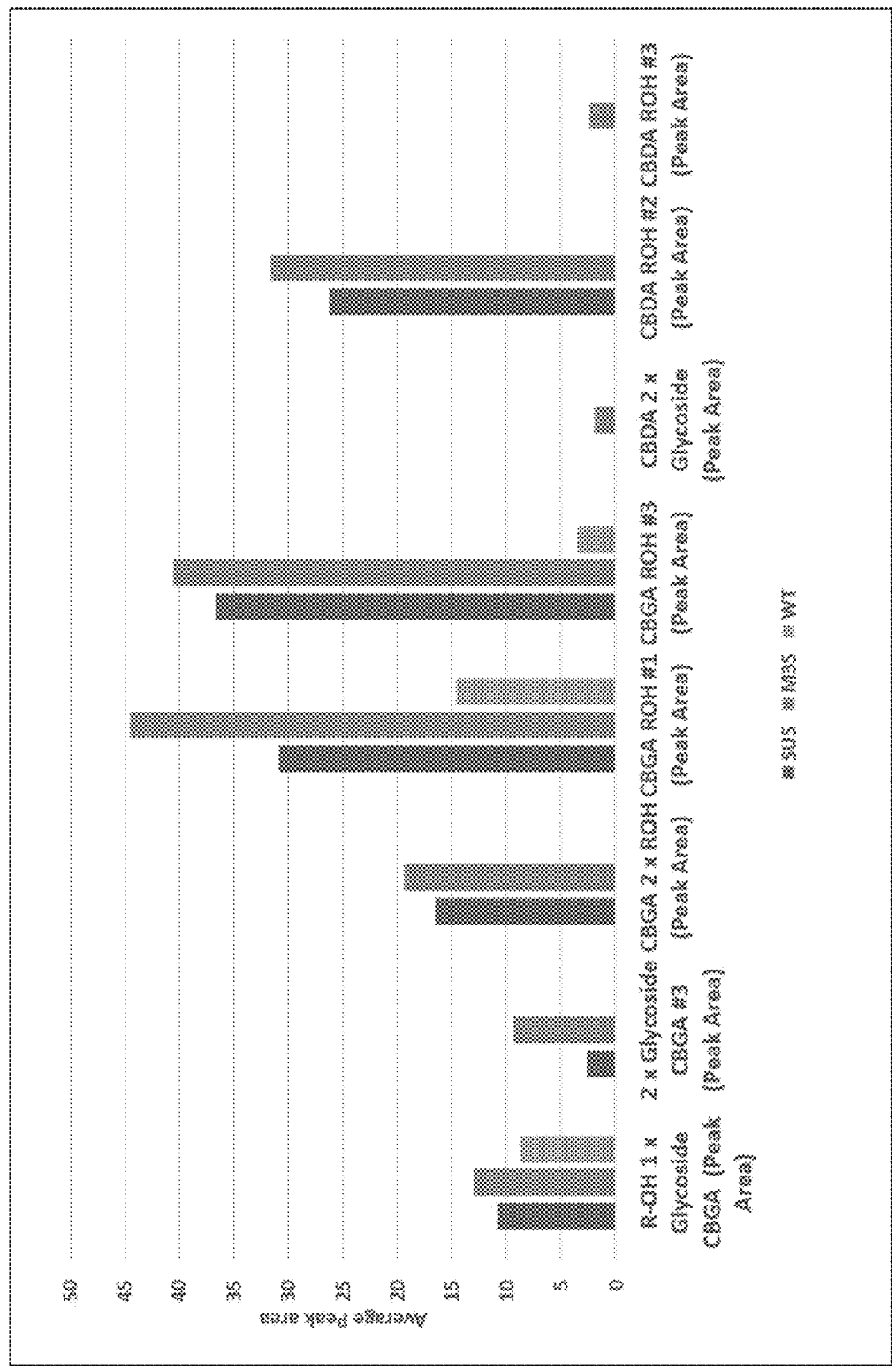
FIG. 11. Enhanced modification of cannabinoids in transgenic *N. benthamiana* plants co-infected with constructs for glycosylation, P450-mediated functionalization (hydroxylation) and detoxification of hydrogen peroxide by catalase. SUS=construct for overexpressing CBDA synthase, UDP glycosyltransferase and ABC transporter; M3 S=construct for overexpressing CBDA synthase, UDP glycosyltransferase and ABC transporter with *Cannabis* MYB12-like and *Arabidopsis thaliana* catalase.

Example 7: Enhanced In Vivo Cytosolic Synthesis and Glycosylation of Cannabinoids in Tobacco Leaves and Cell Suspensions The present inventors have demonstrated the enhanced in vivo modification of cannabinoids in transgenic plants co-infected with constructs for glycosylation, P450-mediated functionalization (hydroxylation) and detoxification of hydrogen peroxide by catalase. As further shown in FIG. 11, functionalization and glycosylation, mainly of the substrate CBGA was observed in transgenic tobacco plants overexpressing CBDA synthase, UDP glycosyltransferase and ABC transporter but increased when overexpression of this construct was coupled with cytochrome P450, MYB transcription factor and catalase. As previously noted, overexpression of a cytochrome P450 enhanced glycosylation of cannabinoids. As such, the present inventor demonstrated the formation and glycosylation of CBDA in vivo in transiently transformed tobacco leaves fed with the precursor CBGA.

Figure 12:
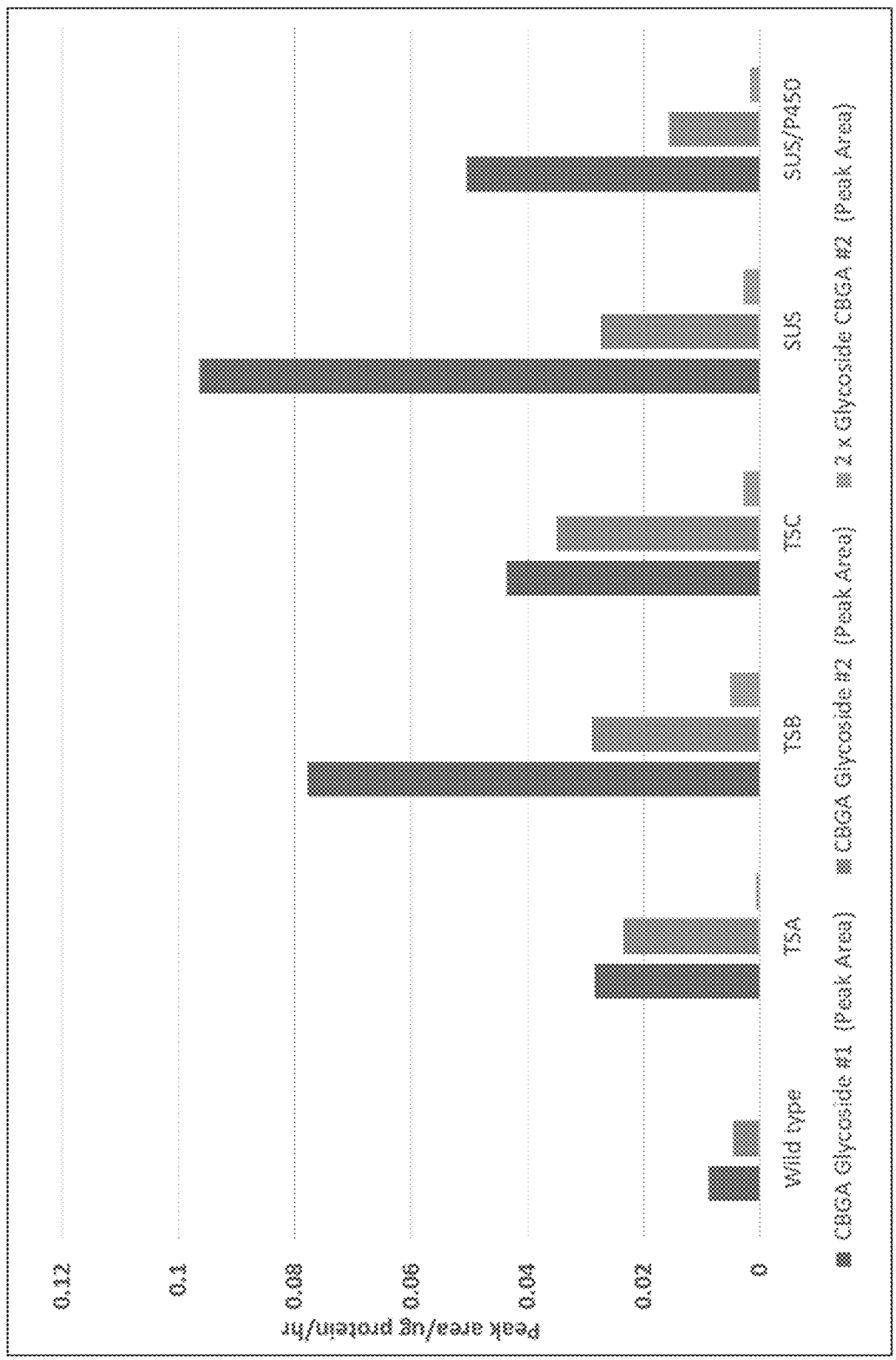
FIG. 12. Increased glycosylation activity in transgenic *N. benthamiana* plants (TSA, TSB, TSC, SUS, SUS/P450) overexpressing a glycosyltransferase compared to wild type in 14-hour transient expression assays.

The present inventors also compared the activities of endogenous and transgenic glycosyltransferase activities in tobacco. Specifically, as shown in FIG. 12, the present inventor performed in vitro assays of UDP glycosyltransferase and CBDA synthase. Short assays of 3 hours at 30° C. did not reveal any difference in glycosylation of CBGA between the wild type and transgenic *N. benthamiana* plants, suggesting endogenous glycosylation. In extended assays (14 hours), there was a significant difference in the detection of glycosylated CBGA in transgenic plants compared to the wild type demonstrating increased glycosylation activity in transgenic plants.

In certain embodiment, glycosyltransferases from tobacco, or other plants may be used as herein described. In one embodiment, one or more heterologous or homologous glycosyltransferases may be expressed or over expressed in a plant, such as tobacco or *Cannabis*. Gene and protein sequences for exemplary glycosyltransferases are identified below in Table 9.

Example 8: Generation of Trichome-Targeted Cannabinoid Synthesis and Glycosylation Constructs of Cannabidiolic Acid (CBDA)

Figure 14:
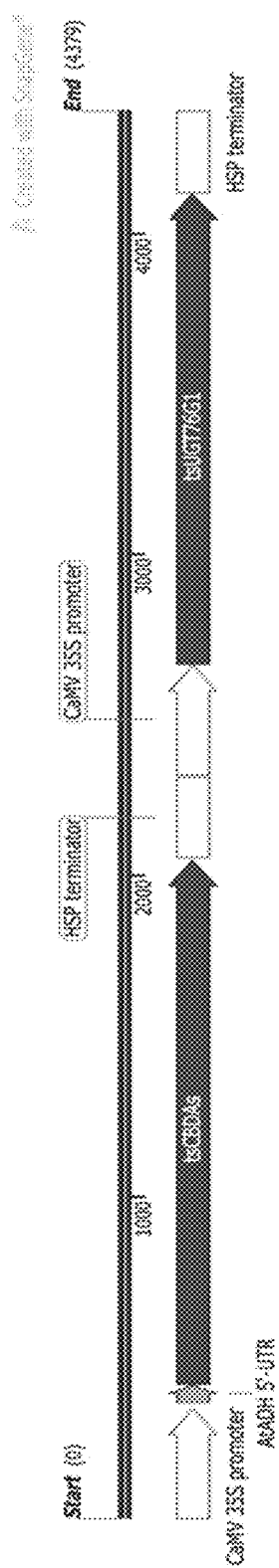
FIG. 14. Gene construct 1 for the trichome cannabinoid production system. Cauliflower mosaic 35S promoter; AtADH 5'-UTR, translation enhancer element (Matsui et al. 2012); tsCBDAs, cannabidiolic acid synthase with its original trichome target sequence; HSP terminator; tsUGT76G1, UDP glycosyltransferase from *Stevia rebaudiana* with CBDAs trichome target sequence.
Figure 15:
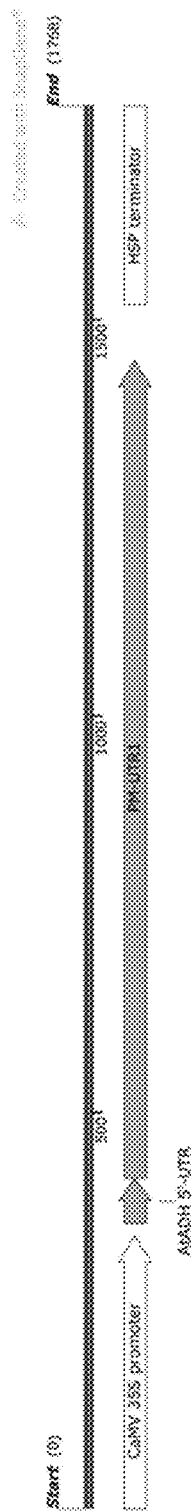
FIG. 15. Gene construct 2 for the trichome cannabinoid production system. Cauliflower mosaic 35S promoter; AtADH 5'-UTR, enhancer element; PM-UTR1, *Arabidopsis thaliana* UDP-glucose/galactose transporter targeted to the plasma membrane; HSP terminator.

As shown in FIGS. 14-15, the present inventors demonstrated a system of trichome-targeted synthesis and synthesis and glycosylation of cannabinoid compounds, such as CBDA. By targeting CBDA synthase, a UDP-glucose/UDP-galactose transporter (PM-UTR1) targeted to the plasma, and a *Stevia* UDP-glycosyltransferase 76G1 (tsUGT) to the trichomes, these genes may produce and accumulate, in this case CBDA and its glycosylated derivatives (primary, secondary glycoside), as well as novel CBDA derivatives, in the trichomes.

SEQ ID NO. 17 is identified as the polynucleotide gene sequence for a CBDA synthase having a trichome targeting sequence. SEQ ID NO. 18 is identified as the corresponding protein sequence for a CBDA synthase having a trichome targeting domain.

SEQ ID NO. 19 is identified as the polynucleotide gene sequence for a trichome-targeted UDP-glycosyltransferase (76G1) coding sequence, in this instance being optimized for *Arabidopsis thaliana* expression, although other codon optimized versions fall within the scope of this invention. SEQ ID NO. 20 is identified as the corresponding protein sequence for a UDP-glycosyltransferase (76G1) having a trichome targeting domain.

SEQ ID NO. 21 is identified as the polynucleotide gene sequence for a UDP-glucose/galactose transporter (UTR1) having a plasma-membrane targeting sequence.

Example 9: Trichome-Targeted Synthesis and Glycosylation of Cannabidiolic Acid (CBDA)

Figure 16:
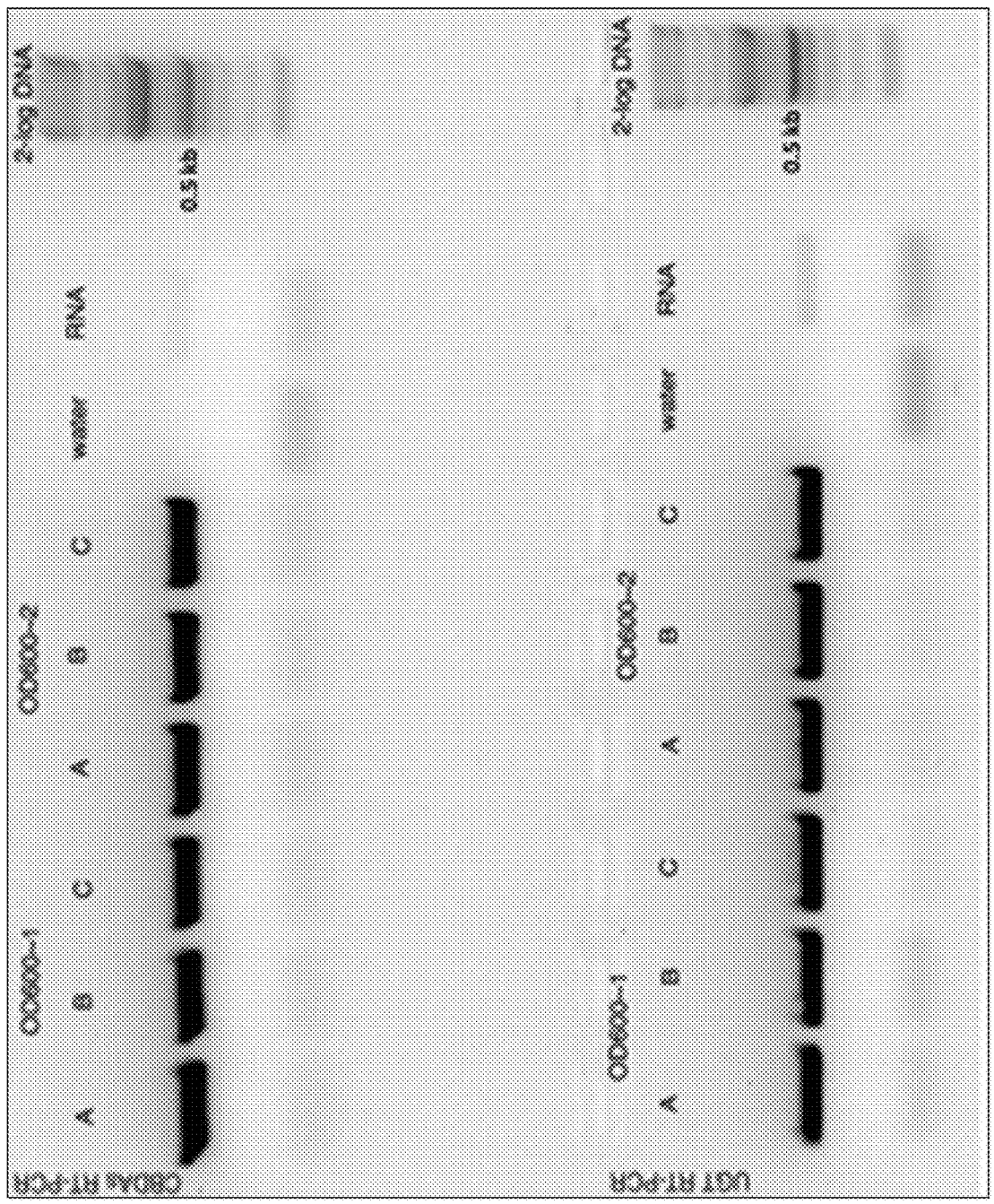
FIG. 16. Trichome-targeted CBDA synthase RT-PCR (top), Trichome-targeted UDP glycosyltransferase (76G1) UGT RT-PCR (bottom). A, B, and C are biological replicates collected after 2 DPI.
Figure 17:
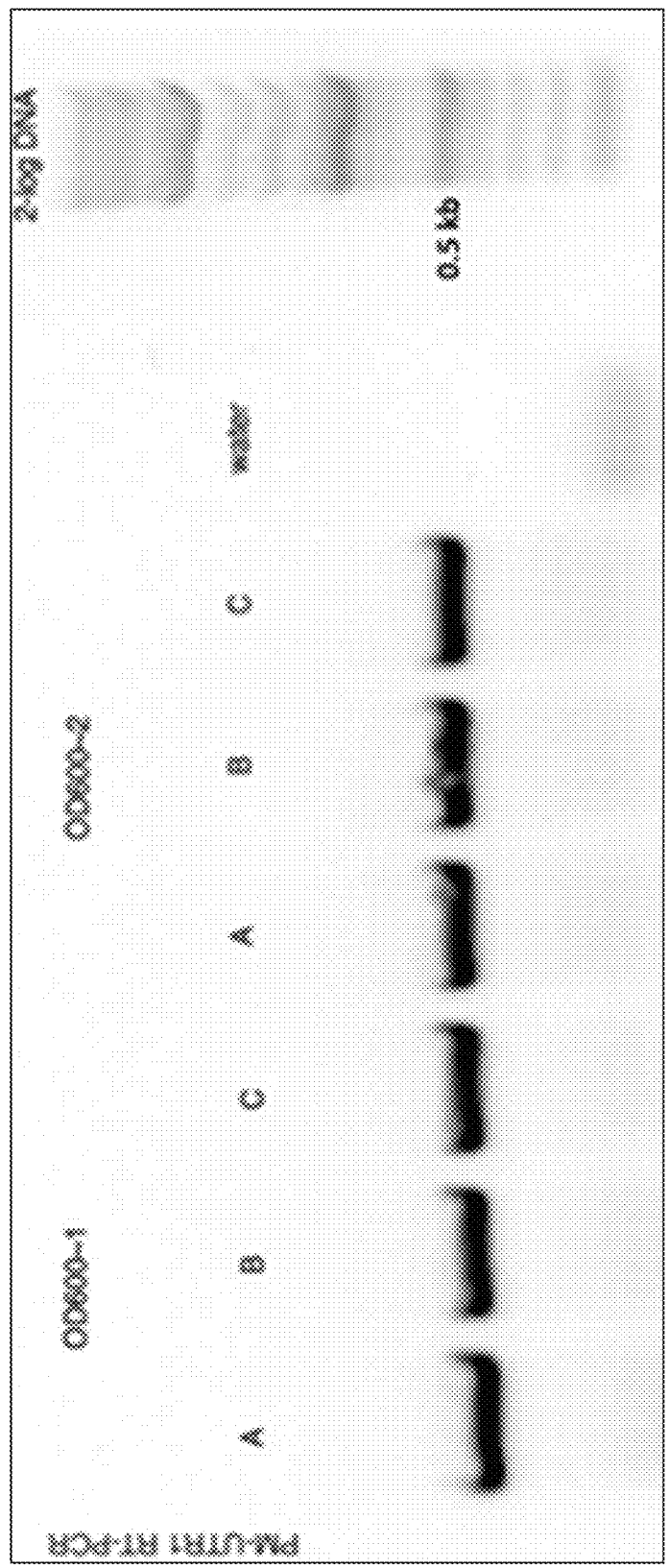
FIG. 17. PM-UTR1 RT-PCR. A, B, and C are biological replicates collected after 2 DPI.
Figure 19:
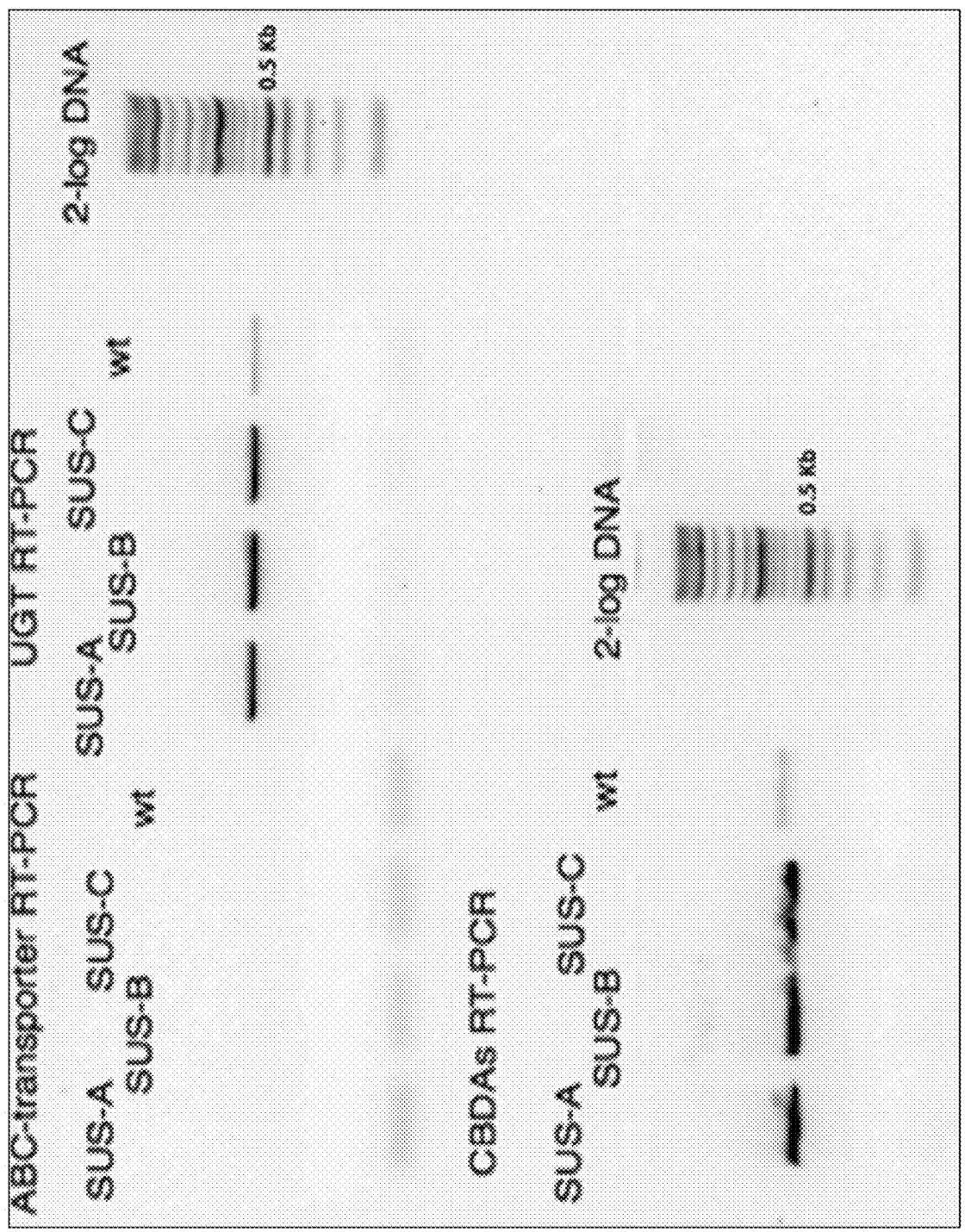
FIG. 19. SUS-A to SUS-C are biological replicates for the cell suspension (201-SUS) transformation after 1 DPI.
Figure 20:
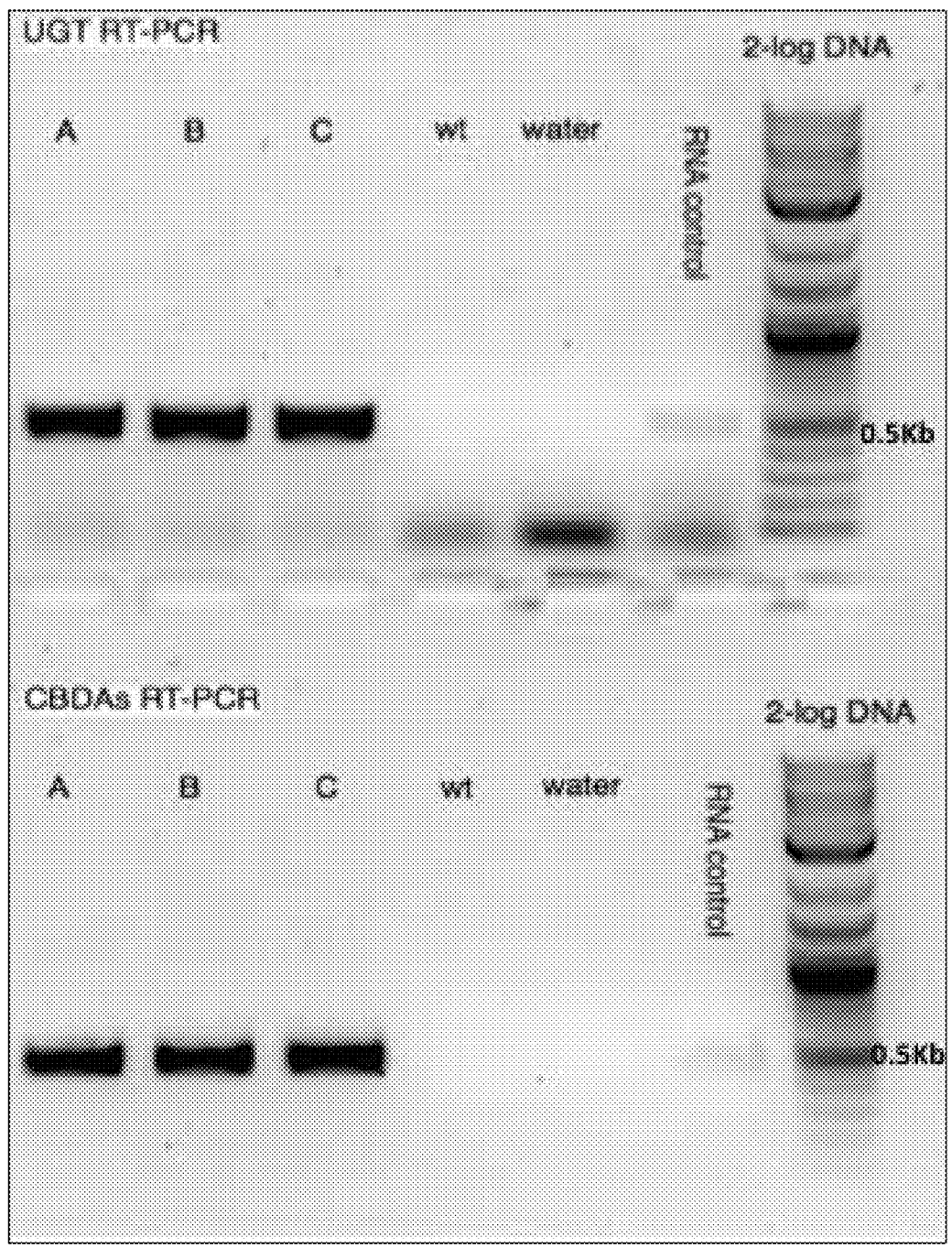
FIG. 20. cytUGT RT-PCR (top), cytCBDAs RT-PCR (bottom). A, B, and C are biological replicates for cytosolic construct infiltration after 2 DPI.

As shown in FIGS. 16-17, gene expression of CBDA synthase, tsUGT and PM-UTR1 in *N. benthamiana* infiltrated leaves was confirmed 2 DPI (Days Post Infiltration of *Agrobacterium* Ti-plasmid constructs) via RT-PCR (FIGS. 19 and 20). As expected, CBGA substrate was detected in all infiltrated leaves and wild type control (no *Agrobacterium* infiltration). CBGA primary and secondary glycosides were also detected in all infiltrated leaves and wild-type control, further demonstrating an endogenous glycosyltransferase activity acting upon CBGA. Moreover, CBGA acetylated primary glycoside was detected in all samples, including WT control, providing evidence of endogenous acetylation. CBDA was detected at marginal levels in samples infiltrated with both trichome and cell suspension constructs, but not in wild type plants.

Example 10: Cytosolic-Targeted Synthesis and Glycosylation of Cannabidiolic Acid (CBDA)

Figure 18:
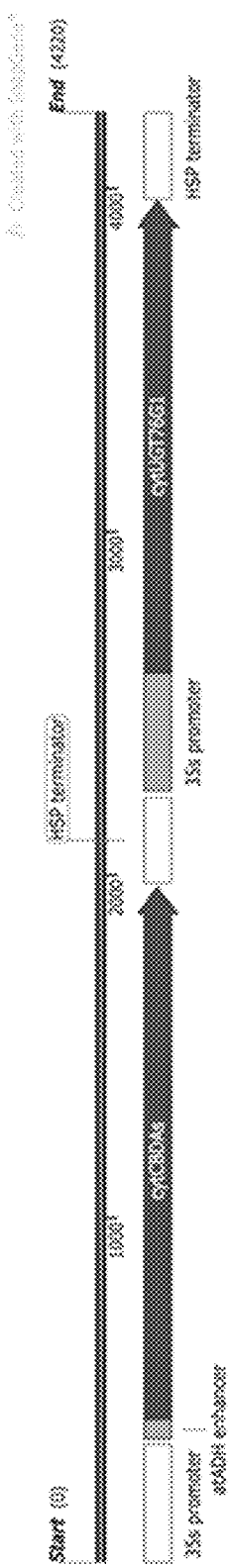
FIG. 18. Gene construct for the cytosolic cannabinoid production system. Cauliflower mosaic 35S promoter; AtADH 5'-UTR, enhancer element; cytCBDAs, cannabidiolic acid synthase with the trichome target sequence removed; HSP terminator; cytUGT76G1, UDP glycosyltransferase from *Stevia rebaudiana*.

The present inventors have demonstrated a system of cytosolic-targeted cannabinoid synthesis and glycosylation. By targeting or localizing, CBDA synthase (CBDAs) and UDP-glycosyltransferase 76G1 (UGT) to the cytosol, the present inventors demonstrated that plants expressing these heterologous genes produce and accumulate, in this embodiment, CBDA and its glycosylated derivatives (primary, secondary glycoside), as well as other CBDA derivatives, in the cytosol. As shown in FIG. 18, a gene expression vector for the cytosolic cannabinoid production system was generated. This construct included a cauliflower mosaic 35S promoter; AtADH 5'-UTR, enhancer element; cytCBDAs, cannabidiolic acid synthase with the trichome target sequence removed; HSP terminator; cytUGT76G1, UDP glycosyltransferase from *Stevia rebaudiana*.

SEQ ID NO. 22 is identified as the polynucleotide gene sequence for a, cannabidiolic acid synthase with the trichome target sequence removed (cytCBDAs). SEQ ID NO. 23 is identified as the corresponding protein sequence of cytCBDAs.

SEQ ID NO. 24 is identified as the polynucleotide gene sequence for a, Cytosolic-targeted UDP-glycosyltransferase (UGT76G1) coding sequence (optimized for *Arabidopsis thaliana* expression) (cytUGT76G1 or cytUTG). SEQ ID NO. 25 is identified as the corresponding protein sequence of cytUGT76G1 or cytUTG.

As an exemplary plant model, *N. benthamiana* plants were grown from seed and after 4 weeks of vegetative growth, leaves were co-infiltrated with *Agrobacterium tumefaciens* GV3101 carrying the following constructs: Cytosolic CBDAs+Cytosolic UGT in pRI201-AN or cell suspension construct, Myb/catalase in pRI201-AN, and p19 silencing suppressor in pDGB3alpha2. *Agrobacterium* density was normalized to 2 at absorbance of 600 nm using a spectrophotometer and cultures co-infiltrated in same ratio (1:1:1). After 2 and 4 days post-*Agrobacterium* infiltration (DPI), 1 mL CBGA (2.7 mM) dissolved in 0.1% Tween 20 (Sigma-Aldrich) or 0.1% Triton X-100 (Sigma-Aldrich) was infiltrated to each leaf. In a second embodiment using the cytosolic construct, 4 mM UDP-glucose was added to the CBGA media before feeding. Three biological replicates were used. RT-PCR primers are outlined in Table 5 below.

Figure 21:
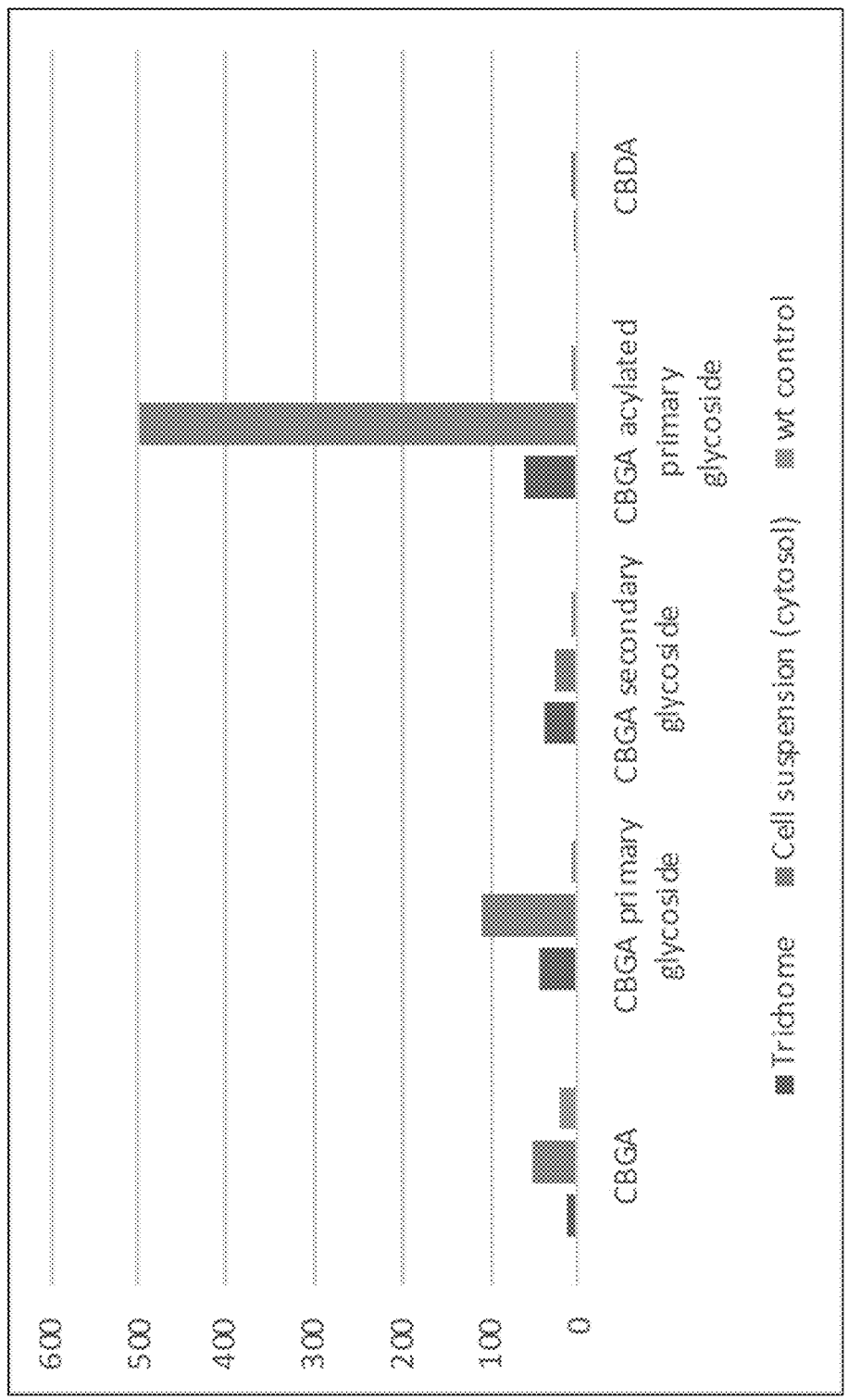
FIG. 21. Cannabinoid detection in leaves infiltrated with trichome or cell suspension constructs and fed with CBGA 2.7 mM. The color code refers to the target compartment for CBDAs and UGT76G1 protein accumulation, either trichome or cell suspension cytostol. Y-axis: CBGA and CBDA expressed as parts per million (ppm). Primary, secondary, and acylated glycosides expressed as peak area.
Figure 22:
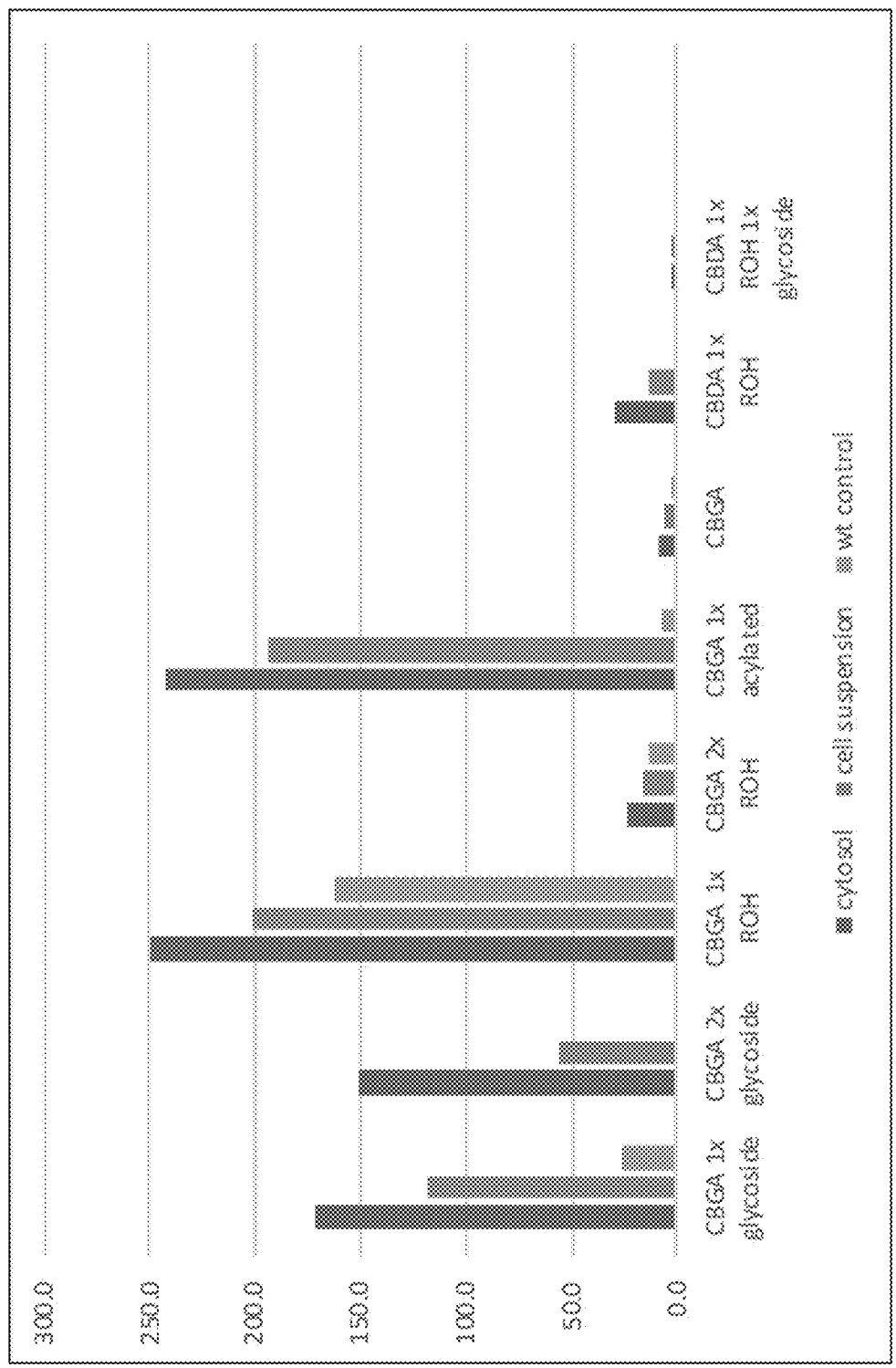
FIG. 22. Cannabinoid detection in leaves infiltrated with cytosolic or cell suspension construct and fed with CBGA 2.7 mM and UDP-glucose 4 mM. The color code refers to the target compartment for CBDAs and UGT76G1 protein accumulation. Y-axis: CBGA expressed as parts per million (ppm). All other cannabinoid derivatives expressed as peak area (no standards available).
Figure 23:
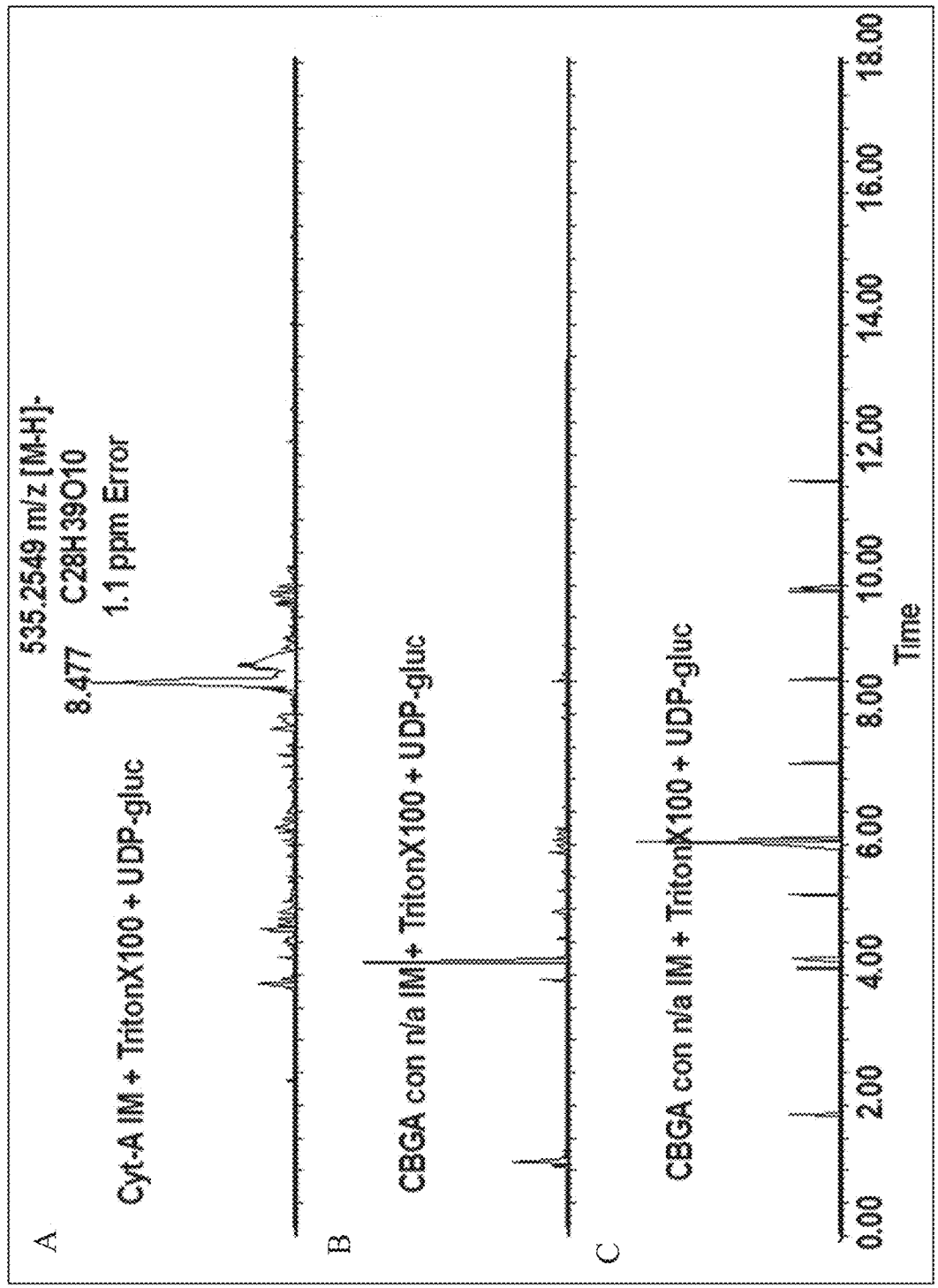
FIG. 23. Extracted Ion Chromatograms of R-OH Functionalized 1× Glycosylated CBDA Analog. (A) Chromatographic trace, ion m/z, calculated elemental composition, confirming presence of trace levels of CBDA analog (B) Absence of CBDA analog in control extract (C) Absence of CBDA analog in biological duplicate control extract.

As shown in FIGS. 19-20, gene expression of cytCBDAs and cytUGT was confirmed via RT-PCR after 1 and 2 DPI. No expression of ABC transporter (ABCt) was observed after 1 DPI in leaves infiltrated cells suspension construct. This does not impact this experiment as the role of ABCt was to facilitate cannabinoid transport outside the cells in suspension cultures. As shown in FIG. 21, CBGA and its glycosylated and acylated derivatives were detected in concentrations higher than in the trichome construct infiltrated leaves, except for secondary glycosides. Moreover, CBDA was detected in higher concentrations (up to 34 ppm) in leaves infiltrated with the cell suspension construct, compared to the trichome construct experiments (up to 2.6 ppm). As shown in FIG. 22, when UDP-glucose 4 mM (substrate for UGT) was provided together with CBGA (substrate for CBDAs), the present inventors detected low levels of glycosylated and hydroxylated CBDA in leaves infiltrated with both the cytosolic and cell suspension construct, but not in the WT control. This result demonstrates the novel in plant synthesis, glycosylation and hydroxylation of CBDA in the surrogate plant *N. benthamiana*, as demonstrated by the Extracted Ion Chromatograms shown in FIG. 23.

Example 11: Hydroxylation and Glycosylation of Cannabinoids in *Cannabis Sativa*

Figure 24:
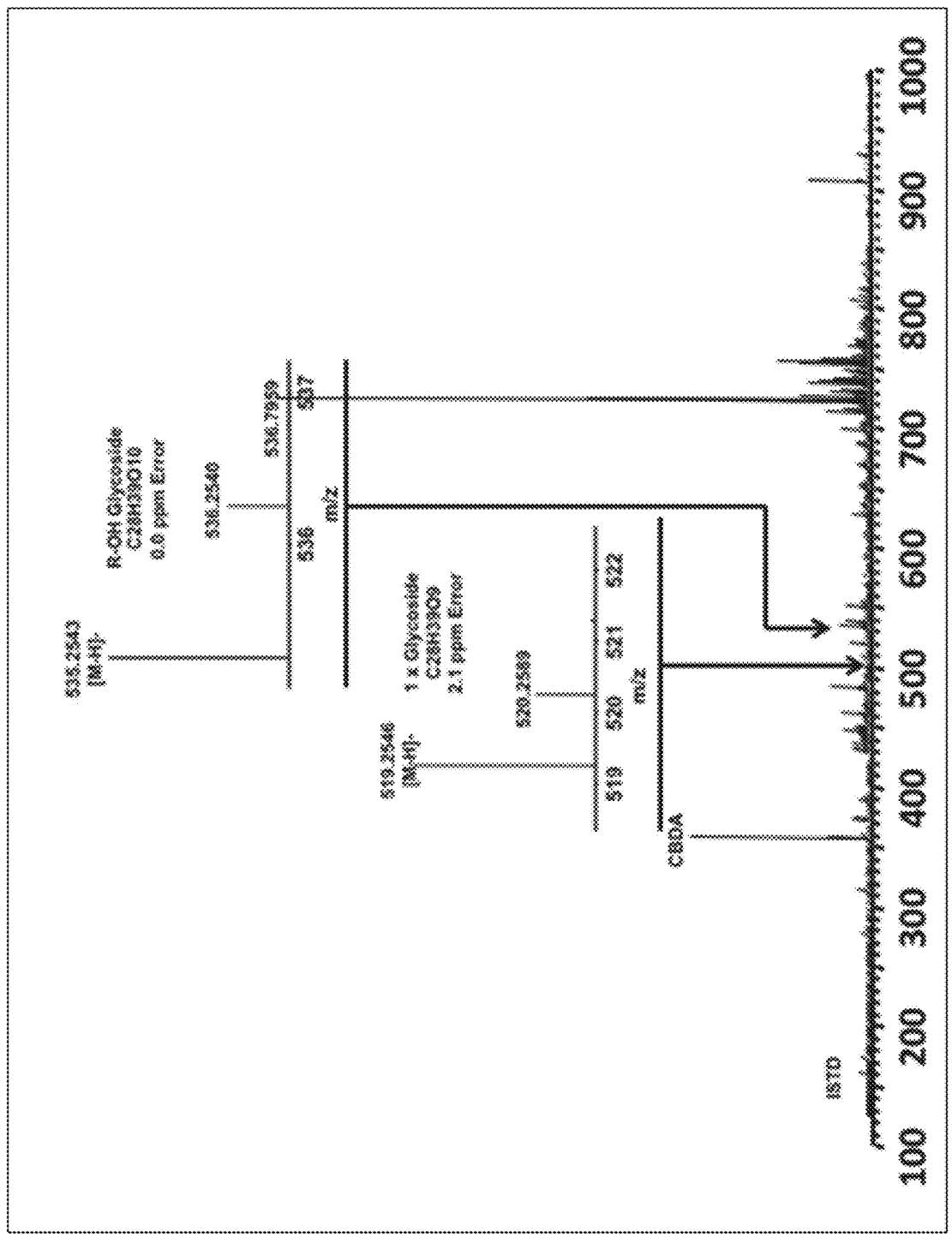
FIG. 24. Direct Infusion Mass Spectrum of *Cannabis sativa* extract. Spectral insets represent CBDA with a single glycosylation (519.2546 m/z), and CBDA functionalized with R-OH and a single glycosylation (535.2543 m/z). Peak Intensities are illustrated as relative abundance to most intense ion.
Figure 25:
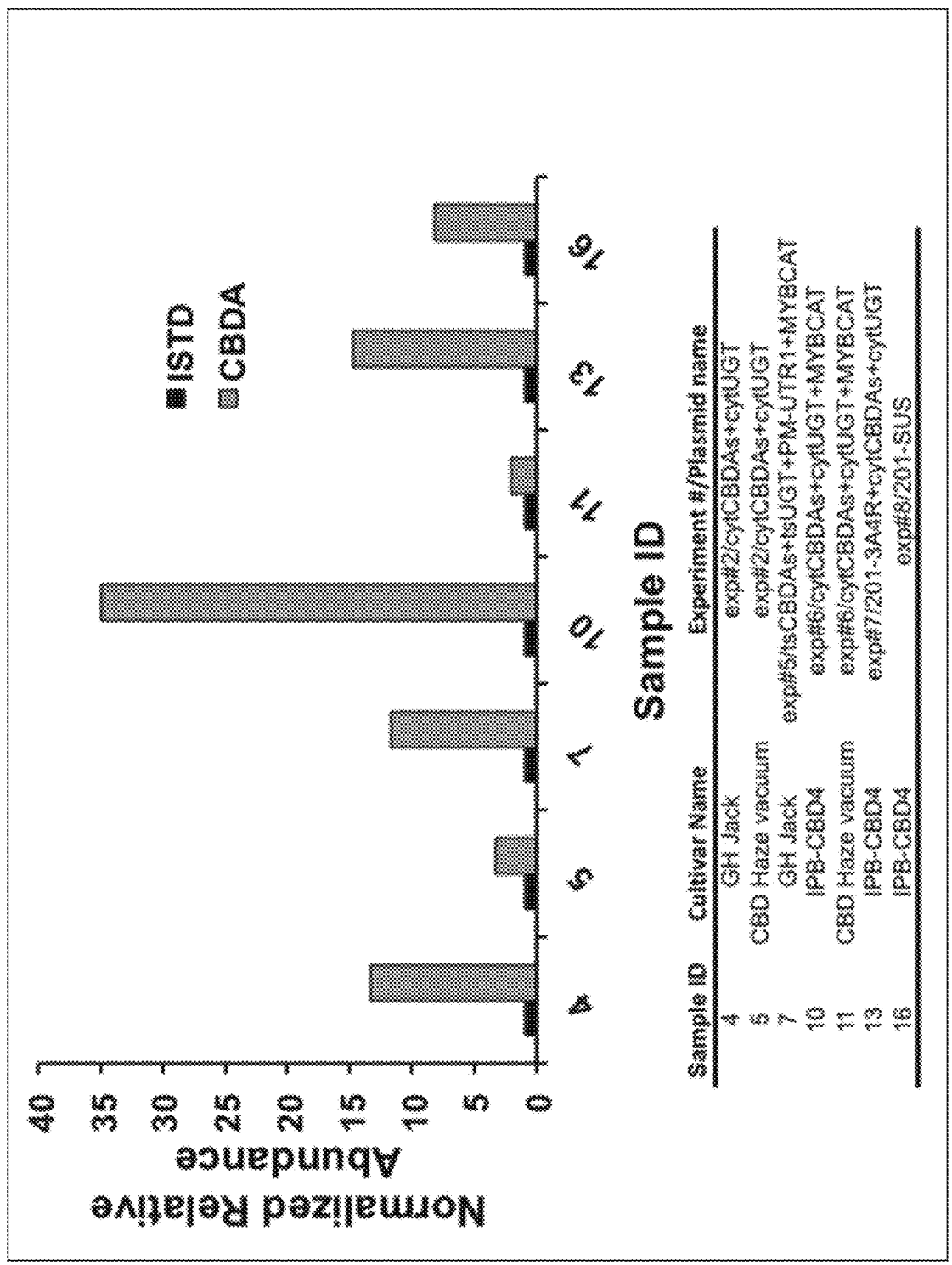
FIG. 25. Relative abundance of CBDA in extracts of various *Cannabis sativa* strains infiltrated with *Agrobacterium* cultures harboring CBDA synthase (CBDAs) and UGT plasmid combinations. Normalized relative abundance data is presented as the ion intensity of each compound divided by the ion intensity of the internal standard 7-hydroxycoumarin (20 ppm).
Figure 26:
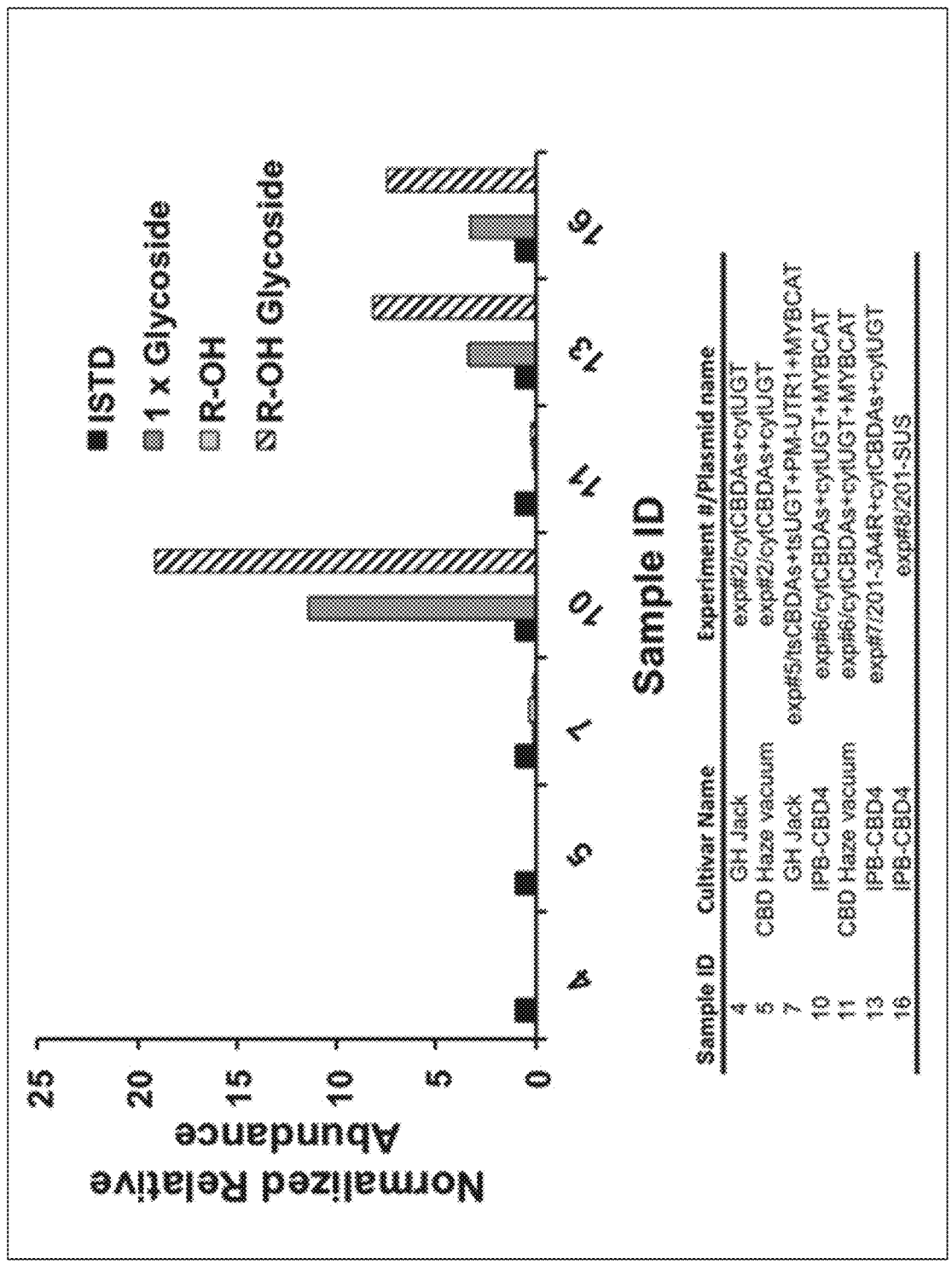
FIG. 26. Relative abundance of modified CBDA (glycosylated and/or hydroxylated) in extracts of various *Cannabis sativa* strains infiltrated with *Agrobacterium* cultures harboring CBDAs and UGT plasmid combinations. Normalized relative abundance data is presented as the ion intensity of each compound divided by the ion intensity of the internal standard 7-hydroxycoumarin (20 ppm).

The present inventors demonstrate the glycosylation and hydroxylation of cannabinoids in *Cannabis sativa*. To further confirm our findings using *N. benthamiana* as a plant model, we performed *Agrobacterium* infiltration of the same plasmid constructs described in the section above in various strains of *Cannabis sativa* (see FIG. 24 Sample IDs). As shown in FIGS. 24-26, expression of the select genetic constructs in *C. sativa*, as in *N. benthamiana*, demonstrate synthesis and accumulation of hydroxylated and/or glycosylated cannabinoids, in this case CBDA. A comparison of the results using different *Agrobacterium* genetic constructs is presented in Table 8 below.

As the present inventors have demonstrated, in one embodiment, where the cytosolic construct was con-transformed with the Myb/catalase (MYBCAT) expression vector, yielded the highest detection of CBDA and CBDA glycoside, demonstrating the role of these genes in mitigating toxicity effects due to hydrogen peroxide accumulation (catalase) and overall increase in cannabinoid synthesis (Myb transcription factor).

Materials and Methods

Example 12: Use of a Tobacco as an Exemplary Plant System for the In Vivo Functionalization and Glycosylation of Cannabinoids The present inventors demonstrated the in vivo functionalization and glycosylation of cannabinoids in a model plant system. Specifically, the present inventors used *N. benthamiana* (tobacco) as a model system to demonstrate in vivo functionalization and glycosylation of cannabinoids. In this embodiment, transient transformation through *Agrobacterium* infiltration was performed in *N. benthamiana*. The present inventors demonstrated expression of heterologous genes that were expressed in transformed *N. benthamiana* using a number of heterologous gene expression vectors (described below). In this exemplary embodiment, upon confirmation of expression of the heterologous genes that would functionalize and glycosylate cannabinoid molecules, the present inventors introduced to the plants select cannabinoid compounds. In this embodiment, the present inventors introduced to the transgenic *N. benthamiana* plants cannabigerolic acid (CBGA) and/or cannabidiolic acid (CBDA). The present inventors also demonstrated the in vivo functionalization and glycosylation of cannabinoids in a cell suspension culture. Specifically, the inventors used exemplary tobacco bright yellow (BY2) cells as a cell suspension system for studies of cannabinoid production, functionalization and/or glycosylation.

Example 13: Transient Transformation of the Exemplary Plant Model *Nicotiana benthamiana*

The present inventors used *Agrobacterium tumefaciens* Ti-plasmid-mediated transformation with the plant expression vector pRI201-AN (Takara Bio USA), a binary vector for high-level expression of a foreign gene in dicotyledonous plants carrying the constitutive 35S promoter and an *Arabidopsis thaliana* Alcohol dehydrogenase (AtAdh) as a translational enhancer (Matsui et al. 2012). *N. benthamiana* was transiently transformed according to the method described by Sparkes et al. 2006. Overnight cultures of *Agrobacterium* strain GV3101 were transferred to a 250 mL flask with 50 mL LB medium supplemented with 50 mg/L of Kanamycin, 50 mg/L of Gentamycin and 10 mg/L of Rifampicin and grown for 4-8 hours until the optical density at 600 nm (OD600) reached approximately between 0.75 and 1. The cells were pelleted in a centrifuge at room temperature and resuspended in 45 mL of infiltration medium containing 5 g/L D-glucose, 10 mM MES, 10 mM MgCl2 and 100 µM acetosyringone. 1 ml of the solution was used to infiltrate the leaves using a 1 mL syringe. Expression of the transgene(s) was confirmed 2-4 days after infiltration by RT-PCR. For RT-PCR analysis, 100 mg of leaf tissue were frozen in liquid nitrogen and ground in a TissueLyser (QIAGEN Inc, USA). RNA was extracted following the EZNA plant RNA extraction kit (Omega Bio-tek Inc, USA). Up to a microgram of total RNA was used to synthesize cDNA using the superscript III cDNA synthesis kit (Thermo Fisher Scientific, USA). The cDNA was used to check for the expression of transgene(s) by RT-PCR.

Example 14: Introduction of Select Cannabinoid Substrate(s) to the Transgenic *N. benthamiana* Strain Select enzyme substrates were introduced to the transgenic or genetically modified *N. benthamiana* strain two days after *Agrobacterium* infiltration and upon confirmation of transgene expression by RT-PCR. In this example, approximately 277 µM cannabigerolic acid (CBGA) and/or cannabidiolic acid (CBDA) was dissolved in 1 mL of buffer containing 10 mM MES, 10 mM MgCl$_2$ and 0.1% Triton X100 or 0.1% Tween20 and applied to the transformed leaves either by infiltration or by dabbing with a cotton applicator. Plants were harvested after 1-4 days, weighed for fresh weight and frozen at −80° C. before conducting LC-MS analysis for the presence of modified cannabinoids.

Example 15: In Vitro Assays for CBDA Synthase and Glycosyltransferase Activity

CBDA synthase is generally active in the pH range 4-6 (Taura et al. 1996) while glycosyltransferases are typically active in the pH range 5.0 to 7.0 (Rini and Esko, 2017). Based on this difference in optimal pH for enzyme activity, the present inventors generated a single extraction buffer for a combined assay of CBDA synthase and UDP glycosyltransferase at pH 6 and 30° C. in in vitro assays (Priest et al., 2006). The present inventors ground the transformed leaf tissue in liquid nitrogen. A grinding buffer was added consisting of 50 mM MES, pH 6, 1 mM EDTA, 5 mM β-mercaptoethanol and 0.1% Triton X-100 was added at 5:1 ratio of buffer to fresh weight of plant using a mortar and pestle. The extract was filtered on ice through 2 layers of cheesecloth to remove debris and centrifuged at 21000 g for 5 minutes at 4° C. The supernatant was used in subsequent assays. Protein concentration of the supernatant was quantified by the Bradford assay, using bovine serum albumin as the standard. To start the reaction, 100-200 µg of crude total protein was used. The assay was carried out with and without UDP-glucose to check if glycosylation of cannabinoid substrate was preventing downstream reactions or transport of CBGA. Wild type plants were used as controls to separate endogenous from overexpressed UDP glycosyltransferase activity. The reaction was started by adding 100 µg of protein, and 8 mM uridine diphosphate glucose (UDPG) as the sugar-nucleotide donor to a reaction mixture consisting of approximately 277 µM CBGA, 0.1% (w/v) Triton X-100, 3 mM MgCl$_2$ and 50 mM MES (pH 6.0). The reaction was incubated at 30° C. for 3 h or overnight for 14 hours. The reaction was terminated by freezing in liquid nitrogen and the samples were stored at −80° C. before LC-MS analysis.

Example 16: Trichome-Targeted Synthesis and Glycosylation

As an exemplary plant model, *N. benthamiana* plants were grown from seed and, after 4 weeks of vegetative growth, the leaves were co-infiltrated with *Agrobacterium tumefaciens* GV3101 carrying the following constructs: Trichome CBDAs+trichome UGT in pRI201-AN (trichome construct), PM-UTR1 in pRI201-AN, and p19 silencing suppressor in pDGB3alpha2. In a second experiment, leaves were also infiltrated with the *Agrobacterium* expressing a Ti-plasmid with the Myb/catalase genes. *Agrobacterium* density was normalized to 1 or 2 at absorbance of 600 nm using a spectrophotometer and cultures co-infiltrated in same ratio (1:1:1). After 1 and 4 days post *Agrobacterium* infiltration (DPI), 1 mL CBGA (277 µM) dissolved in 0.1% Tween20 (Sigma-Aldrich) or 3% DMSO (Sigma-Aldrich) was infiltrated to each leaf. Three biological replicates were used. The experiment was repeated twice. After preliminary results, *Agrobacterium* densities of 2 at OD$_{600}$ were selected for all following infiltration experiments. Moreover, 0.1% Tween20 was chosen over DMSO 3% due to better solubilizing CBGA substrate.

In this embodiment, leaf samples were collected at 2 DPI and immediately frozen in liquid nitrogen. RNA extraction was done using RNA plant mini-kit as described by manufacturer (Qiagen). cDNA was synthesized using RNA to cDNA Ecodry Premix as described by manufacturer (Takara). Template cDNA was normalized to 50ng of corresponding total RNA per reaction. Annealing temperature in Celsius: 60. Extension time: 15 s. 35 cycles. Q5 DNA polymerase kit used as described by manufacturer (New England Biolabs). RT-PCR primers are outlined in Table 5 below.

Example 17: Transient Transformation of *Cannabis sativa*

The present inventors performed *Agrobacterium tumefaciens*-mediated transient transformation of *Cannabis sativa*. The experimental groups consisted of young leaves of high CBD variety (~10% in dried flowers) and trichome leaves of high THC variety (~20% dried flowers).

To transform leaves of high CBD varieties, the present inventors germinated 100 seeds three times; this was done to ensure that a sufficient number of plants would be available for all 9 independent transformation events. To transform trichome leaves, the present inventors used small trichome-containing leaves of several varieties known to be high THC varieties. Experimental set up consisted of 2 different *Agrobacterium tumefaciens* strains. For transient transformation of *Agrobacterium* strain EHA 105, the present inventors grew cells in 10 ml of LB medium supplemented with 100 mg/L of Rifampicin and 50 mg/L of Kanamycin and for *Agrobacterium* strain GV3101:6000 cells were grown with 50 mg/L of Kanamycin, 25 mg/L of Gentamycin and 50 mg/L of Rifampicin. A single *Agrobacterium* colony was used for inoculation and grown overnight. Then, 1 ml of this culture was inoculated into 500 ml of aforementioned LB medium supplemented with 20 µM acetosyringone. Agrobacteria were grown to OD$_{600}$ of approximately between 1 and 1.5. The cells were pelleted in a centrifuge at room temperature and resuspended in infiltration medium containing 10 mM MES, 10 mM MgCl$_2$ and 200 µM acetosyringone to an OD$_{600}$ of 0.5.

Bacterial culture was then used for three different types of *Cannabis Sativa* transformations. In all cases, transformation was done in the form of co-transformation, mixing all relevant strains (plasmids) in equal proportion of cell numbers. First, for the present inventors infiltrated young (two weeks old) fully expended *Cannabis sativa* plants using 1 ml syringe. Prior to transformation, plants were kept under plastic cover, to ensure maximum softness of the leaves. Infiltration was performed from abaxial side, ensuring that the entire surface of the leaf is infiltrated at 12/h/12 h day/night at 22° C.

Second, the present inventors vacuum infiltrated detached young (two weeks old) fully expended *Cannabis sativa* leaves. Prior to transformation, plants were kept under plastic cover, to ensure maximum softness of the leaves. Leaves were then placed on half-strength Murashige and Skoog (1962) (½ MS) agar supplemented with 61.8 mM ammonium nitrate and incubated for 5 days at 12/h/12 h day/night at 22° C.

Third, trichome leaves were detached, placed into 50 ml Falcon tubes and vacuum infiltrated with aforementioned bacterial solution 2× for 10 min each. Leaves were then placed on ½ MS agar supplemented with 61.8 mM ammonium nitrate and incubated for 5 days.

All experiments were done in triplicates, with the fourth replicate done for collection of DNA/RNA and staining X-gluc for measuring the activity of beta-glucuronidase (GUS) after co-infiltration with *Agrobacterium*-containing GUS gene. In all cases, leaves were harvested after 5 days of transformation, frozen in liquid nitrogen and stored at −80° C.

Example 18: Extraction of Water-Soluble Cannabinoids from *N. Benthamiana*

Fresh transformed plant material was harvested from greenhouse experiments in 15 or 50 mL polypropylene centrifuge tubes and flash frozen in liquid $N_2$. The frozen plant material was enzymatically quenched by submersing the plant material in boiling methanol for 2 min. The methanol-quenched material was homogenised using a P-10-35 homogenizer (Kinematica, Bohemia N.Y.). The homogenate was extracted by brief agitation in a final volume of 10 mL or 30 mL 70% methanol (v/v) respective to tube size. The resulting extracts were clarified by centrifugation at 2,500 rpm at 4° C. for 15 minutes in a Beckman J-6B floor centrifuge (Beckman Coulter, Indianapolis Ind.). The supernatant was transferred into a polypropylene tube and evaporated under a stream of $N_2$ at 45° C. until dried. The extracts were reconstituted in methanol containing 20 µg/mL of the internal standard 7-Hydroxyoumarin (Sigma-Aldrich, H24003). The reconstituted extracts were placed into 1.5 mL microfuge tubes and clarified in a microcentrifuge at 10,000 g for 15 min. 500 µL of the supernatant was transferred to a 2 mL auto sampler vial and kept at 4° C. until analysis. In vitro assays sample preparation: samples were syringed filtered through 0.45 µm PVDF membrane into a 2 mL auto sampler vial.

Example 19: Extraction of Water-Soluble Cannabinoids from *Cannabis sativa*

Fresh plant material was harvested from plants grown in chamber in 1.5 mL polypropylene centrifuge tubes and flash frozen in liquid $N_2$. The frozen plant material was homogenized using pestle and mortar and enzymatically quenched by submersing the plant material in boiling 100% ethanol for 2 min. Homogenized solution was diluted to 70% ethanol. The resulting extracts were clarified by centrifugation at 2,500 rpm at 4° C. for 15 minutes in Eppendorf centrifuge (Centrifuge 5415 R). The supernatant was transferred into a polypropylene tube and concentrated three times using vacuum centrifuge (Speedvac SC110, Savant). 2 µl of 20 µg/mL of the internal standard Umbelliferone (Sigma-Aldrich, H24003) was added to 98 µl of concentrated extract and taken for analysis.

Example 20: Liquid Chromatography Mass Spectrometry Used to Confirm Functionalization and Glycosylation of Cannabinoids The present inventor used liquid chromatography mass spectrometry to confirm functionalization and glycosylation of cannabinoids in the exemplary plant systems described herein. Specifically, mass spectrometry was performed on a quadrupole time-of-flight (QTOF) mass spectrometer (QTOF Micro, Waters, Manchester, UK) equipped with a Lockspray™ electrospray ion source coupled to a Waters Acquity UPLC system (Waters, Manchester, UK). Mass spectra were collected in the negative electrospray ionization mode (ESI−). The nebulization gas was set to 400 L/h at a temperature of 350° C., the cone gas was set to 15 L/H and the source temperature was set to 110° C. A capillary voltage and cone voltage were set to 2500 and 35 V, respectively. The MCP detector voltage was set to 2500 V. The Q-TOF micro MS acquisition rate was set to 1.0 s with a 0.1 s interscan delay. The scan range was from 100 to 1500 m/z. Data was collected in continuum mode. A lockmass solution of 50 ppm raffinose (503.1612 m/z) in 50:50 water:methanol was delivered at 20 µL/min through an auxiliary pump and acquired every 10 s during the MS acquisition. Separations were performed on a Waters HSS T3 C18 column (2.1×100 mm, particle size 1.8 µm) using a Waters ACQUITY UPLC System, equipped with an ACQUITY Binary Solvent Manager, ACQUITY Column Manager and ACQUITY Sample Manager (10 µL sample loop, partial loop injection mode, 5 µL injection volume, 4° C.). Eluents A and B were water and acetonitrile, respectively, both containing 0.1% formic acid. Elution was performed isocratically for 0.5 min at 10% eluent B and then linear gradient 100% eluent B in 14.5 min, and isocratically for 3 min at 100% eluent B. The column was re-equilibrated for 6 min. The flow rate was set to 250 µL/min and the column temperature was maintained at 30° C.

Example 21: Demonstrates Materials and Methods for Data Processing

Identification of individual cannabinoid analogs was performed by the present inventors, by their corresponding accurate mass shifts by Metabolynx (Waters Corp., Milford, USA). The method parameters for data processing were set as follows: retention time range 0.1-18 min, mass range 100-1500 Da, retention time tolerance 0.2 min, mass tolerance 0.05 Da, peak intensity threshold 14. Accurate mass measure of the continuum data was performed using the raffinose lock mass. Raw chromatographic data were additionally processed for extracted ion chromatogram sand peak area integration using Masslynx 4.1 (Waters Corp., Milford, USA). The select cannabinoids, CBGA and CBDA were identified and quantitated using certified reference materials (Cerilliant, Round Rock, Tex.). All chemical structures and physiochemical and constitutional properties were generated using ChemDoodle version 8.1.0 (IChemLabs™ Chesterfield, Va.).

Tables

TABLE 1

CBGA Biotransformed Products

| Product | RRT to Parent | Expected m/z | Found m/z | Error (mDa) | Error (ppm) | Molecular Formula [M—H]- |
|---|---|---|---|---|---|---|
| R—OH 1 × Glycoside | 0.58 | 537.2700 | 537.2703 | −0.30 | 0.6 | $C_{28}H_{41}O_{10}$ |
| 2 × Glycoside | 0.59 | 683.3279 | 683.3258 | 2.10 | −3.1 | $C_{34}H_{51}O_{14}$ |
| 1 × O acetyl Glycoside | 0.73 | 563.2856 | 563.2844 | 1.20 | −2.1 | $C_{30}H_{43}O_{10}$ |
| 1 × Glycoside #1 | 0.74 | 521.2751 | 521.2734 | 1.70 | −3.3 | $C_{28}H_{41}O_9$ |
| R—OH #1 | 0.80 | 375.2171 | 375.2224 | −5.30 | 14.1 | $C_{22}H_{31}O_5$ |
| 1 × Glycoside #2 | 0.81 | 521.2751 | 521.2727 | 2.40 | −4.6 | $C_{28}H_{41}O_9$ |
| R—OH #2 | 0.81 | 375.2171 | 375.2237 | −6.60 | 17.6 | $C_{22}H_{31}O_5$ |
| R—OH #3 | 0.94 | 375.2171 | 375.2192 | −2.10 | 5.6 | $C_{22}H_{31}O_5$ |
| CBGA | 1.00 | 359.2222 | 359.2245 | −2.30 | 6.4 | $C_{22}H_{31}O_4$ |

RRT Relative Retention Time to Parent Molecule
R—OH Functionalized by addition of O atom

TABLE 2

CBDA Biotransformed Products

| Product | RRT to Parent | Expected m/z | Found m/z | Error (mDa) | Error (ppm) | Molecular Formula [M—H]- |
|---|---|---|---|---|---|---|
| 2 × Glycoside | 0.56 | 681.3122 | 681.3097 | 2.50 | −3.7 | $C_{34}H_{49}O_{14}$ |
| R—OH 1 × Glycoside | 0.61 | 535.2543 | 535.2599 | −5.60 | 10.5 | $C_{28}H_{39}O_{10}$ |
| 1 × Glycoside | 0.71 | 519.2601 | 519.2594 | 0.70 | 1.3 | $C_{28}H_{39}O_9$ |
| 1 × O acetyl Glycoside | 0.71 | 561.2700 | 561.2700 | 0.00 | 0 | $C_{30}H_{41}O_{10}$ |
| R—OH #1 | 0.84 | 373.2015 | 373.2074 | −5.90 | 15.8 | $C_{22}H_{29}O_5$ |
| R—OH #2 | 0.87 | 373.2015 | 373.2034 | −1.90 | 5.1 | $C_{22}H_{29}O_5$ |
| R—OH #3 | 0.96 | 373.2015 | 373.2040 | −2.50 | −8 | $C_{22}H_{29}O_5$ |
| CBDA | 1.00 | 357.2066 | 357.2122 | −5.60 | 15.7 | $C_{22}H_{29}O_4$ |

RRT Relative Retention Time to Parent Molecule
R—OH Functionalized by addition of O atom'

TABLE 3

Forward and reverse primers for RT-PCR of CYP3A4 and P450 oxidoreductase. SEQ ID NO. 54 represents the forward primer of CYP3A4; SEQ ID NO. 55 represents the reverse primer of CYP3A4; SEQ ID NO. 56 represents the forward primer of P450 oxidoreductase; and SEQ ID NO. 57 represents the reverse primer of P450 oxidoreductase.

| Sequence | | CYP3A4 | | P450 oxidoreductase |
|---|---|---|---|---|
| Primers for RT-PCR | Forward | TGCCTAATAAAGCTCCTCCTACT | Forward | GGAAGAGCTTTGGTTCCTATGT |
| | Reverse | GCTCCTGAAACAGTTCCATCTC | Reverse | GCTCCCAATTCAGCAACAATATC |

TABLE 4

Forward and reverse primers for CBDA synthase, UGT76G1 and ABCG2. SEQ ID NO. 58 represents the forward primer of CBDA synthase; SEQ ID NO. 59 represents the reverse primer of CBDA synthase; SEQ ID NO. 60 represents the forward primer of UGT76G1; SEQ ID NO. 61 represents the reverse primer of UGT76G1; SEQ ID NO. 62 represents the forward primer of ABCG2; and SEQ ID NO. 63 represents the reverse primer of ABCG2.

| Sequence | CBDA synthase | UGT76G1 | ABCG2 |
|---|---|---|---|
| Primer for RT-PCR | Forward primer: ACATCACAATCACACAAAACT AACAAAAG | Forward primer: GATTGGAAGAACAAGCTTCAGG ATTTCC | Forward primer: CCTTCAGGATTGTCAGGA GATG |

TABLE 4-continued

Forward and reverse primers for CBDA synthase, UGT76G1 and ABCG2. SEQ ID NO. 58 represents the forward primer of CBDA synthase; SEQ ID NO. 59 represents the reverse primer of CBDA synthase; SEQ ID NO. 60 represents the forward primer of UGT76G1; SEQ ID NO. 61 represents the reverse primer of UGT76G1; SEQ ID NO. 62 represents the forward primer of ABCG2; and SEQ ID NO. 63 represents the reverse primer of ABCG2.

| Sequence | CBDA synthase | UGT76G1 | ABCG2 |
|---|---|---|---|
| | Reverse primer: GGCCATAGTTTCTCATCAATGG | Reverse primer: CCATCCTGAATGAGTCCAAAAAGCTC | Reverse primer: GCAGGTCCATGAAACATCAATC |

TABLE 5

Trichome-targeted CBDA synthase (CBDAs), Trichome-targeted UGT and PM-targeted UTR1. SEQ ID NO. 64 represents the forward primer of Trichome-targeted CBDAs; SEQ ID NO. 65 represents the reverse primer of Trichome-targeted CBDAs; SEQ ID NO. 66 represents the forward primer of Trichome-targeted UGT; SEQ ID NO. 67 represents the reverse primer of Trichome-targeted UGT; SEQ ID NO. 68 represents the forward primer of Plasma membrane-targeted UTRI; and SEQ ID NO. 69 represents the reverse primer of Plasma membrane-targeted UTR1.

| Sequence | Trichome-targeted CBDAs | Trichome-targeted UGT | Plasma membrane-targeted UTR1 |
|---|---|---|---|
| Primers for RT-PCR | Forward primer: AAAGATCAAAAGCAAGTTCTTCACTGT Reverse primer: CCATGCAGTTTGGCTATGAACATCT | Forward primer: AGTGCTCAACATTCTCCTTTTGGTT Reverse primer: TCTGAAGCCAACATCAACAATTCCA | Forward primer: TTGTTCCTTAAACCTCGCCTTGAC Reverse primer: TCATTATGGAGCACTCCACTCTCTG |

TABLE 6

Cytosolic-targeted CBDA synthase (cytCBDAs), Cytosolic-targeted UGT (cytUGT). SEQ ID NO. 70 represents the forward primer of Cytosolic-targeted CBDA synthase; SEQ ID NO. 71 represents the reverse primer of Cytosolic-targeted CBDA synthase; SEQ ID NO. 72 represents the forward primer of Cytosolic-targeted UGT; and SEQ ID NO. 73 represents the reverse primer of Cytosolic-targeted UGT.

| Sequence | Cytosolic-targeted CBDA synthase | Cytosolic-targeted UGT |
|---|---|---|
| Primers for RT-PCR | Forward primer: AAAGATCAAAAGCAAGTTCTTCACTGT Reverse primer: ATAAACTTCTCCAAGGGTAGCTCCG | Forward primer: AGAACTGGAAGAATCCGAACTGGAA Reverse primer: AAATCATCGGGACACCTTCACAAAC |

TABLE 7

Summary of results from glycosylation and functionalization experiments in *N. benthamiana* leaves.

| Agrobacterium Constructs | Substrate fed | CBGA (relative amount) | CBGA glycoside (relative amount) | CBGA glycoside + acetylated (relative amount) | CBDA (relative amount) | CBDA glycoside (relative amount) | CBDA Hydroxyl (relative amount) |
|---|---|---|---|---|---|---|---|
| Trichome CBDA synthase + trichome glycosyltransferase + PM-UTR1) + Myb/catalase* + P19 silencing supressor* | CBGA | + | + | + | + | ND | ND |
| Cytosolic CBDA synthase, glycosyltransferase and plasma membrane ABC transporter) + | CBGA | + | +++ | +++ | +++ | ND | ND |

TABLE 7-continued

Summary of results from glycosylation and functionalization experiments in *N. benthamiana* leaves.

| Agrobacterium Constructs | Substrate fed | CBGA (relative amount) | CBGA glycoside (relative amount) | CBGA glycoside + acetylated (relative amount) | CBDA (relative amount) | CBDA glycoside (relative amount) | CBDA Hydroxyl (relative amount) |
|---|---|---|---|---|---|---|---|
| Myb/catalase + P19 silencing suppressor 201-SUS (cytosolic CBDA synthase, glycosyltransferase and plasma membrane ABC transporter) | CBGA | + | +++ | ++++ | + | + | + |
| CYP3A4 + oxidoreductase (cytochrome P450 with P450 oxidoreductase) | CBDA | ND | + | ND | +++ | +++++ | +++++ |
| Cytosolic CBDA synthase + cytosolic glycosyltransferase + Myb/catalase* + P19 silencing suppressor* | CBGA | ++++ | +++++ | +++++ | ND | ++ | ++ |
| P450/MYBcatalase/ cytosolic CBDA synthase, glycosyltransferase and plasma membrane ABC transporter | CBGA | + | ++++ | + | ND | ++ | ++ |
| No agrobacterium (negative control) | CBGA | + | + | + | ND | ND | ND |

*Co-infiltration with and without construct was tested in different replicates

TABLE 8

Summary of results from glycosylation and functionalization experiments in *Cannabis sativa* leaves.

| Agrobacterium Constructs | CBDA (relative amount) | CBDA glycoside (relative amount) | CBDA Hydroxyl (relative amount) |
|---|---|---|---|
| Trichome CBDA synthase + trichome glycosyltransferase + plasma membrane-targeted sugar transporter) + Myb/catalase | ++ | trace | trace |
| cytosolic CBDA synthase, cytosolic glycosyltransferase + Myb/catalase | +++ | ++++ | +++++ |
| 201-SUS (cytosolic CBDA synthase, glycosyltransferase and plasma membrane ABC transporter) | ++ | ++ | ++ |

TABLE 9

Exemplary Glycosyltransferase sequence identification

| SEQ ID NO. | Name | Organism | Type |
|---|---|---|---|
| SEQ ID NO. 26 | NtGT5a | *Nicotiana tabacum* | Amino Acid |
| SEQ ID NO. 27 | NtGT5a | *Nicotiana tabacum* | DNA |
| SEQ ID NO. 28 | NtGT5b | *Nicotiana tabacum* | Amino Acid |
| SEQ ID NO. 29 | NtGT5b | *Nicotiana tabacum* | DNA |
| SEQ ID NO. 30 | NtGT4 | *Nicotiana tabacum* | Amino Acid |
| SEQ ID NO. 31 | NtGT4 | *Nicotiana tabacum* | DNA |
| SEQ ID NO. 32 | NtGT1b | *Nicotiana tabacum* | Amino Acid |
| SEQ ID NO. 33 | NtGT1b | *Nicotiana tabacum* | DNA |
| SEQ ID NO. 34 | NtGT1a | *Nicotiana tabacum* | Amino Acid |
| SEQ ID NO. 35 | NtGT1a | *Nicotiana tabacum* | DNA |
| SEQ ID NO. 36 | NtGT3 | *Nicotiana tabacum* | Amino Acid |
| SEQ ID NO. 37 | NtGT3 | *Nicotiana tabacum* | DNA |
| SEQ ID NO. 38 | NtGT2 | *Nicotiana tabacum* | Amino Acid |
| SEQ ID NO. 39 | NtGT2 | *Nicotiana tabacum* | DNA |

TABLE 10

Cannabinoid production cellular compartmentalization models. Different shaded columns and rows correspond to different exemplary expression constructs used.

| Cannabinoid production/ accumulation system | CBDA Synthase | UDP glycosyl transferase | Cannabinoid ABC transporter | UDP glucose transporter | Myb transcription factor for cannabinoids | Catalase to degrade $H_2O_2$ from CBDA Synthase |
|---|---|---|---|---|---|---|
| Cytoplasmic accumulation | Minus trichome target sequence | Required but no targeting change | No gene required | No gene required | Express | Express |

TABLE 10-continued

Cannabinoid production cellular compartmentalization models. Different shaded columns and rows correspond to different exemplary expression constructs used.

| Cannabinoid production/ accumulation system | CBDA Synthase | UDP glycosyl transferase | Cannabinoid ABC transporter | UDP glucose transporter | Myb transcription factor for cannabinoids | Catalase to degrade $H_2O_2$ from CBDA Synthase |
|---|---|---|---|---|---|---|
| Trichome (low pH) synthesis | No change | Add trichome target sequence | No gene required | Target to plasma membrane | Express | Express |
| Cell suspension cultures | Minus trichome target sequence | Required but no targeting change | Target to plasma membrane (PM) | No gene required | Express | Express |

REFERENCES

The following references are hereby incorporated in their entirety by reference:

[1] I von Ossowski, M R Mulvey, P A Leco, A Borys and P C Loewen, *J. Bacteriol.* 1991, 173(2):514.

[2] Behera, A., Behera, A., Mishra, S. C., Swain, S. K., & Author, C. (2003). Cannabinoid glycosides: In vitro production of a new class of cannabinoids with improved physicochemical properties. Proc. Intl. Soc. Mag. Reson. Med (Vol. 14).

[3] Holland, M. L., Lau, D. T. T., Allen, J. D., & Arnold, J. C. (2009). The multidrug transporter ABCG2 (BCRP) is inhibited by plant-derived cannabinoids. *British Journal of Pharmacology*, 152(5), 815-824.

[4] Ivanchenco. M., Vejlupkova. Z., Quatrano. R. S., Fowler. J. E. (2000) Maize ROP7 GTPase contains a unique, CaaX box-independent plasma membrane targeting signal. *The Plant Journal*, (24)1, 79-90.

[5] James M. Rini and Jeffrey D. Esko. Glycosyltransferases and Glycan-Processing Enzymes. In: Essentials of Glycobiology [Internet]. 3rd edition.

[6] Marks, M. D., Tian, L., Wenger, J. P., Omburo, S. N., Soto-Fuentes, W., He, J., . . . Dixon, R. A. (2009). Identification of candidate genes affecting Δ9-tetrahydrocannabinol biosynthesis in Cannabis sativa. *Journal of Experimental Botany*, 60(13), 3715-3726.

[7] Nagaya, S., Kawamura, K., Shinmyo, A., & Kato, K. (2010). The HSP terminator of Arabidopsis thaliana increases gene expression in plant cells. *Plant and Cell Physiology*, 51(2), 328-332.

[8] Norambuena, L., Marchant, L., Berninsone, P., Hirschberg, C. B., Silva, H., & Orellana, A. (2002). Transport of UDP-galactose in plants. Identification and functional characterization of AtUTr1, an Arabidopsis thaliana UDP-galactose/UDP-glucose transporter. *Journal of Biological Chemistry*, 277(36), 32923-32929.

[9] Onofri, C., De Meijer, E. P. M., & Mandolino, G. (2015). Sequence heterogeneity of cannabidiolic- and tetrahydrocannabinolic acid-synthase in Cannabis sativa L. and its relationship with chemical phenotype. *Phytochemistry*, 116(1), 57-68.

[9] Priest, D. M., Ambrose, S. J., Vaistij, F. E., Elias, L., Higgins, G. S., Ross, A. R. S., . . . Bowles, D. J. (2006). Use of the glucosyltransferase UGT71B6 to disturb abscisic acid homeostasis in Arabidopsis thaliana. *Plant Journal*, 46(3), 492-502.

[10] Siritunga, D., and Sayre, R. T. (2003). Generation of cyanogen-free transgenic cassava. Planta 217,367-373. doi: 10.1007/s00425-003-1005-8

[11] Sparkes, I. A., Runions, J., Kearns, A., & Hawes, C. (2006). Rapid, transient expression of fluorescent fusion proteins in tobacco plants and generation of stably transformed plants. *Nature Protocols*, 1(4), 2019-2025.

[13] Taura, F., Morimoto, S., & Shoyama, Y. (1996). Purification and characterization of cannabidiolic-acid synthase from Cannabis sativa L. Biochemical analysis of a novel enzyme that catalyzes the oxidocyclization of. *Journal of Biological Chemistry*, 271(29), 17411-17416.

[14] Taura, F., Sirikantaramas, S., Shoyama Y, Yoshikai K, Shoyama Y, Morimoto S. (2007) Cannabidiolic-acid synthase, the chemotype-determining enzyme in the fiber-type Cannabis sativa. *Febbs letters*, 581(16), 2929-34. DOI:10.1016/j.febslet.2007.05. 043

[15] Yoo, S. D., Cho, Y. H., & Sheen, J. (2007). Arabidopsis mesophyll protoplasts: A versatile cell system for transient gene expression analysis. *Nature Protocols*, 2(7), 1565-1572.

[16] Matsui, T., Matsuura, H., Sawada, K., Takita, E., Kinjo, S., Takenami, S., . . . Kato, K. (2012). High level expression of transgenes by use of 5'-untranslated region of the Arabidopsis thaliana arabinogalactan-protein 21 gene in dicotyledons. *Plant Biotechnology*, 29(3), 319-322.

[17] Murashige, T., and Skoog, F. (1962). A revised medium for rapid growth and bioassays with tobacco tissue culture. Physiol. Plant. 15, 473-497. doi: 10.1111/j.1399-3054.1962.tb08052.x

[18] Zipp, et al., Cannabinoid glycosides: In vitro production of a new class of cannabinoids with improved physicochemical properties. bioRxiv preprint doi:

[19] Mohamed, E. A., T. Iwaki, I. Munir, M. Tamoi, S. Shigeoka, and A. Wadano. 2003. Overexpression of bacterial catalase in tomato leaf chloroplasts enhances photooxidative stress tolerance. Plant Cell Environ. 26:2037-2046.

[20] Akhtar, M. T., 2013, Doctoral Thesis, Leiden University. Cannabinoids and zebrafish. 2013-05-22.

[21] Sayed Farag. Cannabinoids production in Cannabis sativa L.: An in vitro approach. Thesis•January 2014. DOI: 10.17877/DE290R-16298

[21] K, Watanabe, et al., Cytochrome P450 enzymes involved in the metabolism of tetrahydrocannabinols and cannabinol by human hepatic microsomes. Life Sciences. Volume 80, Issue 15, 20 Mar. 2007, Pages 1415-1419
[22] Flores-Sanchez I J. et al., Elicitation studies in cell suspension cultures of *Cannabis sativa* L. J Biotechnol. 2009 Aug. 20;143(2):157-68. doi: 10.1016/j.jbiotec.
[23] Stephen M. Stout & Nina M. Cimino (2013) Exogenous cannabinoids as substrates, inhibitors, and inducers of human drug metabolizing enzymes: a systematic review, Drug Metabolism Reviews, 46:1, 86-95, DOI: 10.3109/03602532.2013.849268
[24] Andre C M, Hausman J-F, Guerriero G. *Cannabis sativa*: The Plant of the Thousand and One Molecules. Frontiers in Plant Science. 2016; 7:19. doi:10.3389/fpls.2016.00019.
[25] Mahlberg Pl. et a., Accumulation of Cannabinoids in Glandular Trichomes of *Cannabis* (Cannabaceae). Journal of Industrial Hemp 9(1):15-36•June 2004 with 273 Reads DOI: 10.1300/J237v09n01_04.
[25] Katalin S., et al., Mini Rev Med Chem. 2017; 17(13): 1223-1291. doi: 10.2174/1389557516666161004162133.
[26] Sirikantaramas S., et al., Tetrahydrocannabinolic Acid Synthase, the Enzyme Controlling Marijuana Psychoactivity, is Secreted into the Storage Cavity of the Glandular Trichomes. Plant and Cell Physiology, Volume 46, Issue 9, 1 Sep. 2005, Pages 1578-1582.
[26] Schilmiller A L, Last R L, Pichersky E (2008) Harnessing plant trichome biochemistry for the production of useful compounds. Plant Journal 54: 702-711.
[27] Matias-Hernandez, L. et al. AaMYB1 and its orthologue AtMYB61 affect terpene metabolism and trichome development in *Artemisia annua* and *Arabidopsis thaliana*. Plant J. 2017; 90: 520-534

Sequence Listings

As noted above, the instant application contains a full Sequence Listing which has been submitted electronically in ASCII format and is hereby incorporated by reference in its entirety. The following sequences are further provided herewith and are hereby incorporated into the specification in their entirety:

```
DNA
Cytochrome P450 (CYP3A4)
Human
                                                      SEQ ID NO. 1
ATGGCTTTGATTCCTGATTTGGCTATGGAAACTAGATTGTTGTTGGCTGTTTCATTGGTTTTGT

TGTATTTGTATGGAACTCATTCACATGGATTGTTTAAAAAATTGGGAATTCCTGGACCTACTCC

TTTGCCTTTTTTGGGAAATATTTTGTCATATCATAAAGGATTTTGCATGTTTGATATGGAATGC

CATAAAAAATATGGAAAGTTTGGGGATTTTATGATGGACAACAACCTGTTTTGGCTATTACTG

ATCCTGATATGATTAAAACTGTTTTGGTTAAAGAATGCTATTCAGTTTTTACTAATAGAAGACC

TTTTGGACCTGTTGGATTTATGAAATCAGCTATTTCAATTGCTGAAGATGAAGAATGGAAAAGA

TTGAGATCATTGTTGTCACCTACTTTTACTTCAGGAAAATTGAAAGAAATGGTTCCTATTATTG

CTCAATATGGAGATGTTTTGGTTAGAAATTTGAGAAGAGAAGCTGAAACTGGAAAACCTGTTAC

TTTGAAAGATGTTTTTGGAGCTTATTCAATGGATGTTATTACTTCAACTTCATTTGGAGTTAAT

ATTGATTCATTGAATAATCCTCAAGATCCTTTTGTTGAAAATACTAAAAAATTGTTGAGATTTG

ATTTTTTGGATCCTTTTTTTTTGTCAATTACTGTTTTTCCTTTTTTGATTCCTATTTTGGAAGT

TTTGAATATTTGCGTTTTTCCTAGAGAAGTTACTAATTTTTTGAGAAAATCAGTTAAAAGAATG

AAAGAATCAAGATTGGAAGATACTCAAAAACATAGAGTTGATTTTTTGCAATTGATGATTGATT

CACAAAATTCAAAAGAAACTGAATCACATAAAGCTTTGTCAGATTTGGAATTGGTTGCTCAATC

AATTATTTTATTTTTGCTGGATGCGAAACTACTTCATCAGTTTTGTCATTTATTATGTATGAA

TTGGCTACTCATCCTGATGTTCAACAAAAATTGCAAGAAGAAATTGATGCTGTTTTGCCTAATA

AAGCTCCTCCTACTTATGATACTGTTTTGCAAATGGAATATTTGGATATGGTTGTTAATGAAAC

TTTGAGATTGTTTCCTATTGCTATGAGATTGGAAAGAGTTTGCAAAAAAGATGTTGAAATTAAT

GGAATGTTTATTCCTAAAGGAGTTGTTGTTATGATTCCTTCATATGCTTTGCATAGAGATCCTA

AATATTGGACTGAACCTGAAAAATTTTTGCCTGAAAGATTTTCAAAAAAAAATAAAGATAATAT

TGATCCTTATATTTATACTCCTTTTGGATCAGGACCTAGAAATTGCATTGGAATGAGATTTGCT

TTGATGAATATGAAATTGGCTTTGATTAGAGTTTTGCAAAATTTTTCATTTAAACCTTGCAAAG

AAACTCAAATTCCTTTGAAATTGTCATTGGGAGGATTGTTGCAACCTGAAAAACCTGTTGTTTT

GAAAGTTGAATCAAGAGATGGAACTGTTTCAGGAGCT
```

-continued

Amino Acid
Cytochrome P450 (CYP3A4)
Human

SEQ ID NO. 2

MALIPDLAMETRLLLAVSLVLLYLYGTHSHGLFKKLGIPGPTPLPFLGNILSYHKGFCMFDMEC

HKKYGKVWGFYDGQQPVLAITDPDMIKTVLVKECYSVFTNRRPFGPVGFMKSAISIAEDEEWKR

LRSLLSPTFTSGKLKEMVPIIAQYGDVLVRNLRREAETGKPVTLKDVFGAYSMDVITSTSFGVN

IDSLNNPQDPFVENTKKLLRFDFLDPFFLSITVFPFLIPILEVLNICVFPREVTNFLRKSVKRM

KESRLEDTQKHRVDFLQLMIDSQNSKETESHKALSDLELVAQSIIFIFAGCETTSSVLSFIMYE

LATHPDVQQKLQEEIDAVLPNKAPPTYDTVLQMEYLDMVVNETLRLFPIAMRLERVCKKDVEIN

GMFIPKGVVVMIPSYALHRDPKYWTEPEKFLPERFSKKNKDNIDPYIYTPFGSGPRNCIGMRFA

LMNMKLALIRVLQNFSFKPCKETQIPLKLSLGGLLQPEKPVVLKVESRDGTVSGA

DNA
P450 oxidoreductase gene (oxred)
Human

SEQ ID NO. 3

ATGATTAATATGGGAGATTCACATGTTGATACTTCATCAACTGTTTCAGAAGCTGTTGCTGAAG

AAGTTTCATTGTTTTCAATGACTGATATGATTTTGTTTTCATTGATTGTTGGATTGTTGACTTA

TTGGTTTTTGTTTAGAAAAAAAAAAGAAGAAGTTCCTGAATTTACTAAAATTCAAACTTTGACT

TCATCAGTTAGAGAATCATCATTTGTTGAAAAAATGAAAAAAACTGGAAGAAATATTATTGTTT

TTTATGGATCACAAACTGGAACTGCTGAAGAATTTGCTAATAGATTGTCAAAAGATGCTCATAG

ATATGGAATGAGAGGAATGTCAGCTGATCCTGAAGAATATGATTTGGCTGATTTGTCATCATTG

CCTGAAATTGATAATGCTTTGGTTGTTTTTGCATGGCTACTTATGGAGAAGGAGATCCTACTG

ATAATGCTCAAGATTTTTATGATTGGTTGCAAGAAACTGATGTTGATTTGTCAGGAGTTAAATT

TGCTGTTTTTGGATTGGGAAATAAAACTTATGAACATTTTAATGCTATGGGAAAATATGTTGAT

AAAAGATTGGAACAATTGGGAGCTCAAAGAATTTTTGAATTGGGATTGGGAGATGATGATGGAA

ATTTGGAAGAAGATTTTATTACTTGGAGAGAACAATTTTGGTTGGCTGTTTGCGAACATTTTGG

AGTTGAAGCTACTGGAGAAGAATCATCAATTAGACAATATGAATTGGTTGTTCATACTGATATT

GATGCTGCTAAAGTTTATATGGGAGAAATGGGAAGATTGAAATCATATGAAAATCAAAAACCTC

CTTTTGATGCTAAAAATCCTTTTTTGGCTGCTGTTACTACTAATAGAAAATTGAATCAAGGAAC

TGAAAGACATTTGATGCATTTGGAATTGGATATTTCAGATTCAAAAATTAGATATGAATCAGGA

GATCATGTTGCTGTTTATCCTGCTAATGATTCAGCTTTGGTTAATCAATTGGGAAAAATTTTGG

GAGCTGATTTGGATGTTGTTATGTCATTGAATAATTTGGATGAAGAATCAAATAAAAAACATCC

TTTTCCTTGCCCTACTTCATATAGAACTGCTTTGACTTATTATTTGGATATTACTAATCCTCCT

AGAACTAATGTTTTGTATGAATTGGCTCAATATGCTTCAGAACCTTCAGAACAAGAATTGTTGA

GAAAAATGGCTTCATCATCAGGAGAAGGAAAAGAATTGTATTTGTCATGGGTTGTTGAAGCTAG

AAGACATATTTTGGCTATTTTGCAAGATTGCCCTTCATTGAGACCTCCTATTGATCATTTGTGC

GAATTGTTGCCTAGATTGCAAGCTAGATATTATTCAATTGCTTCATCATCAAAAGTTCATCCTA

ATTCAGTTCATATTTGCGCTGTTGTTGTTGAATATGAAACTAAAGCTGGAAGAATTAATAAAGG

AGTTGCTACTAATTGGTTGAGAGCTAAAGAACCTGTTGGAGAAAATGGAGGAAGAGCTTTGGTT

CCTATGTTTGTTAGAAAATCACAATTTAGATTGCCTTTTAAAGCTACTACTCCTGTTATTATGG

TTGGACCTGGAACTGGAGTTGCTCCTTTTATTGGATTTATTCAAGAAAGAGCTTGGTTGAGACA

ACAAGGAAAAGAAGTTGGAGAAACTTTGTTGTATTATGGATGCAGAAGATCAGATGAAGATTAT

TTGTATAGAGAAGAATTGGCTCAATTTCATAGAGATGGAGCTTTGACTCAATTGAATGTTGCTT

TTTCAAGAGAACAATCACATAAAGTTTATGTTCAACATTTGTTGAAACAAGATAGAGAACATTT

```
GTGGAAATTGATTGAAGGAGGAGCTCATATTTATGTTTGCGGAGATGCTAGAAATATGGCTAGA

GATGTTCAAAATACTTTTTATGATATTGTTGCTGAATTGGGAGCTATGGAACATGCTCAAGCTG

TTGATTATATTAAAAAATTGATGACTAAAGGAAGATATTCATTGGATGTTTGGTCA
```

```
Amino Acid
P450 oxidoreductase
Human
                                                                SEQ ID NO. 4
MINMGDSHVDTSSTVSEAVAEEVSLFSMTDMILFSLIVGLLTYWFLFRKKKEEVPEFTKIQTLT

SSVRESSFVEKMKKTGRNIIVFYGSQTGTAEEFANRLSKDAHRYGMRGMSADPEEYDLADLSSL

PEIDNALVVFCMATYGEGDPTDNAQDFYDWLQETDVDLSGVKFAVFGLGNKTYEHFNAMGKYVD

KRLEQLGAQRIFELGLGDDDGNLEEDFITWREQFWLAVCEHFGVEATGEESSIRQYELVVHTDI

DAAKVYMGEMGRLKSYENQKPPFDAKNPFLAAVTTNRKLNQGTERHLMHLELDISDSKIRYESG

DHVAVYPANDSALVNQLGKILGADLDVVMSLNNLDEESNKKHPFPCPTSYRTALTYYLDITNPP

RTNVLYELAQYASEPSEQELLRKMASSSGEGKELYLSWVVEARRHILAILQDCPSLRPPIDHLC

ELLPRLQARYYSIASSSKVHPNSVHICAVVVEYETKAGRINKGVATNWLRAKEPVGENGGRALV

PMFVRKSQFRLPFKATTPVIMVGPGTGVAPFIGFIQERAWLRQQGKEVGETLLYYGCRRSDEDY

LYREELAQFHRDGALTQLNVAFSREQSHKVYVQHLLKQDREHLWKLIEGGAHIYVCGDARNMAR

DVQNTFYDIVAELGAMEHAQAVDYIKKLMTKGRYSLDVWS
```

```
DNA
cannabidiolic acid (CBDA) synthase
Cannabis sativa
                                                                SEQ ID NO. 5
ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAAGAT

CATGGAGATACATGAGCTTGTCAAGTTAGTTAACAAATGGCAAATATTGCTTACAAGTATGAC

AAAGATTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT

TGCTTGATAGATCCGCTGGGCAGAACGGTGCTTTCAAGATTAAGTTAGACTACGTTAAGAAACC

AATTCCAGAATCTGTATTTGTCCAAATTTTGGAAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAGAAGCAAGAAGATAA

CGAAAAGCATCTAAACTGGATTAGAAATATTTATAACTTCATGACTCCTTATGTGTCCAAAAAT

TCAAGATTGGCATATCTCAATTATAGAGACCTTGATATAGGAATAAATGATCCCAAGAATCCAA
```

-continued

```
ATAATTACACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCAA

CCACGGCATCGTCATTAA
```

Amino Acid
Cannabidiolic acid (CBDA) synthase
*Cannabis sativa*

SEQ ID NO. 6
```
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

SRLAYLNYRDLDIGINDPKNPNNYTQARIWGEKYFGKNFDRLVKVKTLVDPNNFFRNEQSIPPQ

PRHRH
```

DNA
UDP glycosyltransferase 76G1
*Stevia rebaudiana*

SEQ ID NO. 7
```
ATGGAAAATAAAACTGAAACTACTGTTAGAAGAAGAAGAAGAATTATTTTGTTTCCTGTTCCTT

TTCAAGGACATATTAATCCTATTTTGCAATTGGCTAATGTTTTGTATTCAAAAGGATTTTCAAT

TACTATTTTTCATACTAATTTTAATAAACCTAAAACTTCAAATTATCCTCATTTTACTTTTAGA

TTTATTTTGGATAATGATCCTCAAGATGAAAGAATTTCAAATTTGCCTACTCATGGACCTTTGG

CTGGAATGAGAATTCCTATTATTAATGAACATGGAGCTGATGAATTGAGAAGAGAATTGGAATT

GTTGATGTTGGCTTCAGAAGAAGATGAAGAAGTTTCATGCTTGATTACTGATGCTTTGTGGTAT

TTTGCTCAATCAGTTGCTGATTCATTGAATTTGAGAAGATTGGTTTTGATGACTTCATCATTGT

TTAATTTTCATGCTCATGTTTCATTGCCTCAATTTGATGAATTGGGATATTTGGATCCTGATGA

TAAAACTAGATTGGAAGAACAAGCTTCAGGATTTCCTATGTTGAAAGTTAAAGATATTAAATCA

GCTTATTCAAATTGGCAAATTTTGAAAGAAATTTTGGGAAAAATGATTAAACAAACTAGAGCTT

CATCAGGAGTTATTTGGAATTCATTTAAAGAATTGGAAGAATCAGAATTGGAAACTGTTATTAG

AGAAATTCCTGCTCCTTCATTTTTGATTCCTTTGCCTAAACATTTGACTGCTTCATCATCATCA

TTGTTGGATCATGATAGAACTGTTTTTCAATGGTTGGATCAACAACCTCCTTCATCAGTTTTGT

ATGTTTCATTTGGATCAACTTCAGAAGTTGATGAAAAAGATTTTTTGGAAATTGCTAGAGGATT

GGTTGATTCAAAACAATCATTTTTGTGGGTTGTTAGACCTGGATTGTTAAAGGATCAACTTGG

GTTGAACCTTTGCCTGATGGATTTTTGGGAGAAAGAGGAAGAATTGTTAAATGGGTTCCTCAAC

AAGAAGTTTTGGCTCATGGAGCTATTGGAGCTTTTTGGACTCATTCAGGATGGAATTCAACTTT

GGAATCAGTTTGCGAAGGAGTTCCTATGATTTTTTCAGATTTTGGATTGGATCAACCTTTGAAT

GCTAGATATATGTCAGATGTTTTGAAAGTTGGAGTTTATTTGGAAAATGGATGGGAAAGAGGAG

AAATTGCTAATGCTATTAGAAGAGTTATGGTTGATGAAGAAGGAGAATATATTAGACAAAATGC

TAGAGTTTTGAAACAAAAAGCTGATGTTTCATTGATGAAAGGAGGATCATCATATGAATCATTG

GAATCATTGGTTTCATATATTTCATCATTG
```

-continued

Amino Acid
UPD gycosyltransferase 76G1
Stevia rebaudiana
SEQ ID NO. 8

MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTRASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL

DNA
ABC transporter ABCG2
Human
SEQ ID NO. 9

ATGTCATCATCAAATGTTGAAGTTTTTATTCCTGTTTCACAAGGAAATACTAATGGATTTCCTG

CTACTGCTTCAAATGATTTGAAAGCTTTTACTGAAGGAGCTGTTTTGTCATTTCATAATATTTG

CTATAGAGTTAAATTGAAATCAGGATTTTTGCCTTGCAGAAAACCTGTTGAAAAAGAAATTTTG

TCAAATATTAATGGAATTATGAAACCTGGATTGAATGCTATTTTGGGACCTACTGGAGGAGGAA

AATCATCATTGTTGGATGTTTTGGCTGCTAGAAAAGATCCTTCAGGATTGTCAGGAGATGTTTT

GATTAATGGAGCTCCTAGACCTGCTAATTTTAAATGCAATTCAGGATATGTTGTTCAAGATGAT

GTTGTTATGGGAACTTTGACTGTTAGAGAAAATTTGCAATTTTCAGCTGCTTTGAGATTGGCTA

CTACTATGACTAATCATGAAAAAAATGAAAGAATTAATAGAGTTATTCAAGAATTGGGATTGGA

TAAAGTTGCTGATTCAAAAGTTGGAACTCAATTTATTAGAGGAGTTTCAGGAGGAGAAAGAAAA

AGAACTTCAATTGGAATGGAATTGATTACTGATCCTTCAATTTTGTTTTTGGATGAACCTACTA

CTGGATTGGATTCATCAACTGCTAATGCTGTTTTGTTGTTGTTGAAAAGAATGTCAAAACAAGG

AAGAACTATTATTTTTTCAATTCATCAACCTAGATATTCAATTTTTAAATTGTTTGATTCATTG

ACTTTGTTGGCTTCAGGAAGATTGATGTTTCATGGACCTGCTCAAGAAGCTTTGGGATATTTTG

AATCAGCTGGATATCATTGCGAAGCTTATAATAATCCTGCTGATTTTTTTTGGATATTATTAA

TGGAGATTCAACTGCTGTTGCTTTGAATAGAAGAAGATTTTAAAGCTACTGAAATTATTGAA

CCTTCAAAACAAGATAAACCTTTGATTGAAAAATTGGCTGAAATTTATGTTAATTCATCATTTT

ATAAAGAAACTAAAGCTGAATTGCATCAATTGTCAGGAGGAGAAAAAAAAAAAAAAATTACTGT

TTTTAAAGAAATTTCATATACTACTTCATTTTGCCATCAATTGAGATGGGTTTCAAAAAGATCA

TTTAAAAATTTGTTGGGAAATCCTCAAGCTTCAATTGCTCAAATTATTGTTACTGTTGTTTTGG

GATTGGTTATTGGAGCTATTTATTTTGGATTGAAAAATGATTCAACTGGAATTCAAAATAGAGC

TGGAGTTTTGTTTTTTTTGACTACTAATCAATGCTTTTCATCAGTTTCAGCTGTTGAATTGTTT

GTTGTTGAAAAAAAATTGTTTATTCATGAATATATTTCAGGATATTATAGAGTTTCATCATATT

TTTTGGGAAAATTGTTGTCAGATTTGTTGCCTATGAGAATGTTGCCTTCAATTATTTTTACTTG

CATTGTTTATTTTATGTTGGGATTGAAAGCTAAAGCTGATGCTTTTTTTGTTATGATGTTTACT

TTGATGATGGTTGCTTATTCAGCTTCATCAATGGCTTTGGCTATTGCTGCTGGACAATCAGTTG

TTTCAGTTGCTACTTTGTTGATGACTATTTGCTTTGTTTTATGATGATTTTTTCAGGATTGTT

GGTTAATTTGACTACTATTGCTTCATGGTTGTCATGGTTGCAATATTTTTCAATTCCTAGATAT

GGATTTACTGCTTTGCAACATAATGAATTTTTGGGACAAAATTTTTGCCCTGGATTGAATGCTA

CTGGAAATAATCCTTGCAATTATGCTACTTGCACTGGAGAAGAATATTTGGTTAAACAAGGAAT

```
TGATTTGTCACCTTGGGGATTGTGGAAAAATCATGTTGCTTTGGCTTGCATGATTGTTATTTTT

TTGACTATTGCTTATTTGAAATTGTTGTTTTTGAAAAAATATTCA
```

Amino Acid
ABC transporter ABCG2
Human

SEQ ID NO. 10

```
MSSSNVEVFIPVSQGNTNGFPATASNDLKAFTEGAVLSFHNICYRVKLKSGFLPCRKPVEKEIL

SNINGIMKPGLNAILGPTGGGKSSLLDVLAARKDPSGLSGDVLINGAPRPANFKCNSGYVVQDD

VVMGTLTVRENLQFSAALRLATTMTNHEKNERINRVIQELGLDKVADSKVGTQFIRGVSGGERK

RTSIGMELITDPSILFLDEPTTGLDSSTANAVLLLLKRMSKQGRTIIFSIHQPRYSIFKLFDSL

TLLASGRLMFHGPAQEALGYFESAGYHCEAYNNPADFFLDIINGDSTAVALNREEDFKATEIIE

PSKQDKPLIEKLAEIYVNSSFYKETKAELHQLSGGEKKKKITVFKEISYTTSFCHQLRWVSKRS

FKNLLGNPQASIAQIIVTVVLGLVIGAIYFGLKNDSTGIQNRAGVLFFLTTNQCFSSVSAVELF

VVEKKLFIHEYISGYYRVSSYFLGKLLSDLLPMRMLPSIIFTCIVYFMLGLKAKADAFFVMMFT

LMMVAYSASSMALAIAAGQSVVSVATLLMTICFVFMMIFSGLLVNLTTIASWLSWLQYFSIPRY

GFTALQHNEFLGQNFCPGLNATGNNPCNYATCTGEEYLVKQGIDLSPWGLWKNHVALACMIVIF

LTIAYLKLLFLKKYS
```

DNA
MYB12-like
*Cannabis*

SEQ ID NO. 11

```
ATGAAGAAGAACAAATCAACTAGTAATAATAAGAACAACAACAGTAATAATATCATCAAAAACG

ACATCGTATCATCATCATCATCAACAACAACAACATCATCAACAACTACAGCAACATCATCATT

TCATAATGAGAAAGTTACTGTCAGTACTGATCATATTATTAATCTTGATGATAAGCAGAAACGA

CAATTATGTCGTTGTCGTTTAGAAAAAGAAGAAGAAGAAGAAGGAAGTGGTGGTTGTGGTGAGA

CAGTAGTAATGATGCTAGGGTCAGTATCTCCTGCTGCTGCTACTGCTGCTGCAGCTGGGGGCTC

ATCAAGTTGTGATGAAGACATGTTGGGTGGTCATGATCAACTGTTGTTGTTGTTGTTCTGAG

AAAAAAACGACAGAAATTTCATCAGTGGTGAACTTTAATAATAATAATAATAATAATAAGGAAA

ATGGTGACGAAGTTTCAGGACCGTACGATTATCATCATCATAAAGAAGAGGAAGAAGAAGAAGA

AGAAGATGAAGCATCTGCATCAGTAGCAGCTGTTGATGAAGGGATGTTGTTGTGCTTTGATGAC

ATAATAGATAGCCACTTGCTAAATCCAAATGAGGTTTTGACTTTAAGAGAAGATAGCCATAATG

AAGGTGGGGCAGCTGATCAGATTGACAAGACTACTTGTAATAATACTACTATTACTACTAATGA

TGATTATAACAATAACTTGATGATGTTGAGCTGCAATAATAACGGAGATTATGTTATTAGTGAT

GATCATGATGATCAGTACTGGATAGACGACGTCGTTGGAGTTGACTTTTGGAGTTGGGAGAGTT

CGACTACTACTGTTATTACCCAAGAACAAGAACAAGAACAAGATCAAGTTCAAGAACAGAAGAA

TATGTGGGATAATGAGAAAGAGAAACTGTTGTCTTTGCTATGGGATAATAGTGATAACAGCAGC

AGTTGGGAGTTACAAGATAAAAGCAATAATAATAATAATAATAATGTTCCTAACAAATGTCAAG

AGATTACCTCTGATAAAGAAAATGCTATGGTTGCATGGCTTCTCTCCTGA
```

Amino Acid
MYB12
*Cannabis*

SEQ ID NO. 12

```
MKKNKSTSNNKNNNSNNIIKNDIVSSSSSTTTTSSTTTATSSFHNEKVTVSTDHIINLDDKQKR

QLCRCRLEKEEEEGSGGCGETVVMMLGSVSPAAATAAAAGGSSSCDEDMLGGHDQLLLLCCSE

KKTTEISSVVNFNNNNNNNKENGDEVSGPYDYHHHKEEEEEEEEDEASASVAAVDEGMLLCFDD

IIDSHLLNPNEVLTLREDSHNEGGAADQIDKTTCNNTTITTNDDYNNNLMMLSCNNNGDYVISD
```

-continued

```
DHDDQYWIDDVVGVDFWSWESSTTTVITQEQEQEQDQVQEQKNMWDNEKEKLLSLLWDNSDNSS

SWELQDKSNNNNNNNVPNKCQEITSDKENAMVAWLLS

DNA
Catalase
Arabidopsis thaliana
                                                      SEQ ID NO. 13
ATGGATCCTTATAAATATAGACCTGCTTCATCATATAATTCACCTTTTTTTACTACTAATTCAG

GAGCTCCTGTTTGGAATAATAATTCATCAATGACTGTTGGACCTAGAGGATTGATTTTGTTGGA

AGATTATCATTTGGTTGAAAAATTGGCTAATTTTGATAGAGAAAGAATTCCTGAAAGAGTTGTT

CATGCTAGAGGAGCTTCAGCTAAAGGATTTTTTGAAGTTACTCATGATATTTCAAATTTGACTT

GCGCTGATTTTTTGAGAGCTCCTGGAGTTCAAACTCCTGTTATTGTTAGATTTTCAACTGTTAT

TCATGCTAGAGGATCACCTGAAACTTTGAGAGATCCTAGAGGATTTGCTGTTAAATTTTATACT

AGAGAAGGAAATTTTGATTTGGTTGGAAATAATTTTCCTGTTTTTTTTATTAGAGATGGAATGA

AATTTCCTGATATTGTTCATGCTTTGAAACCTAATCCTAAATCACATATTCAAGAAAATTGGAG

AATTTTGGATTTTTTTTCACATCATCCTGAATCATTGAATATGTTTACTTTTTTGTTTGATGAT

ATTGGAATTCCTCAAGATTATAGACATATGGATGGATCAGGAGTTAATACTTATATGTTGATTA

ATAAAGCTGGAAAAGCTCATTATGTTAAATTTCATTGGAAACCTACTTGCGGAGTTAAATCATT

GTTGGAAGAAGATGCTATTAGATTGGGAGGAACTAATCATTCACATGCTACTCAAGATTTGTAT

GATTCAATTGCTGCTGGAAATTATCCTGAATGGAAATTGTTTATTCAAATTATTGATCCTGCTG

ATGAAGATAAATTTGATTTTGATCCTTTGGATGTTACTAAAACTTGGCCTGAAGATATTTTGCC

TTTGCAACCTGTTGGAAGAATGGTTTTGAATAAAAATATTGATAATTTTTTTGCTGAAAATGAA

CAATTGGCTTTTTGCCCTGCTATTATTGTTCCTGGAATTCATTATTCAGATGATAAATTGTTGC

AAACTAGAGTTTTTTCATATGCTGATACTCAAAGACATAGATTGGGACCTAATTATTTGCAATT

GCCTGTTAATGCTCCTAAATGCGCTCATCATAATAATCATCATGAAGGATTTATGAATTTTATG

CATAGAGATGAAGAAGTTAATTATTTTCCTTCAAGATATGATCAAGTTAGACATGCTGAAAAAT

ATCCTACTCCTCCTGCTGTTTGCTCAGGAAAAAGAGAAAGATGCATTATTGAAAAGAAAATAA

TTTTAAAGAACCTGGAGAAAGATATAGAACTTTTACTCCTGAAAGACAAGAAAGATTTATTCAA

AGATGGATTGATGCTTTGTCAGATCCTAGAATTACTCATGAAATTAGATCAATTTGGATTTCAT

ATTGGTCACAAGCTGATAAATCATTGGGACAAAAATTGGCTTCAAGATTGAATGTTAGACCTTC

AATT

Amino Acid
Catalase
Arabidopsis thaliana
                                                      SEQ ID NO. 14
MDPYKYRPASSYNSPFFTTNSGAPVWNNNSSMTVGPRGLILLEDYHLVEKLANFDRERIPERVV

HARGASAKGFFEVTHDISNLTCADFLRAPGVQTPVIVRFSTVIHARGSPETLRDPRGFAVKFYT

REGNFDLVGNNFPVFFIRDGMKFPDIVHALKPNPKSHIQENWRILDFFSHHPESLNMFTFLFDD

IGIPQDYRHMDGSGVNTYMLINKAGKAHYVKFHWKPTCGVKSLLEEDAIRLGGTNHSHATQDLY

DSIAAGNYPEWKLFIQIIDPADEDKFDFDPLDVTKTWPEDILPLQPVGRMVLNKNIDNFFAENE

QLAFCPAIIVPGIHYSDDKLLQTRVFSYADTQRHRLGPNYLQLPVNAPKCAHHNNHHEGFMNFM

HRDEEVNYFPSRYDQVRHAEKYPTPPAVCSGKRERCIIEKENNFKEPGERYRTFTPERQERFIQ

RWIDALSDPRITHEIRSIWISYWSQADKSLGQKLASRLNVRPSI
```

-continued

DNA
Catalase HPII (KatE)
*Escherichia coli*

SEQ ID NO. 15

```
ATGTCGCAACATAACGAAAAGAACCCACATCAGCACCAGTCACCACTACACGATTCCAGCGAAG

CGAAACCGGGGATGGACTCACTGGCACCTGAGGACGGCTCTCATCGTCCAGCGGCTGAACCAAC

ACCGCCAGGTGCACAACCTACCGCCCCAGGGAGCCTGAAAGCCCCTGATACGCGTAACGAAAAA

CTTAATTCTCTGGAAGACGTACGCAAAGGCAGTGAAAATTATGCGCTGACCACTAATCAGGGCG

TGCGCATCGCCGACGATCAAAACTCACTGCGTGCCGGTAGCCGTGGTCCAACGCTGCTGGAAGA

TTTTATTCTGCGCGAGAAAATCACCCACTTTGACCATGAGCGCATTCCGGAACGTATTGTTCAT

GCACGCGGATCAGCCGCTCACGGTTATTTCCAGCCATATAAAAGCTTAAGCGATATTACCAAAG

CGGATTTCCTCTCAGATCCGAACAAAATCACCCCAGTATTTGTACGTTTCTCTACCGTTCAGGG

TGGTGCTGGCTCTGCTGATACCGTGCGTGATATCCGTGGCTTTGCCACCAAGTTCTATACCGAA

GAGGGTATTTTTGACCTCGTTGGCAATAACACGCCAATCTTCTTTATCCAGGATGCGCATAAAT

TCCCCGATTTTGTTCATGCGGTAAAACCAGAACCGCACTGGGCAATTCCACAAGGGCAAAGTGC

CCACGATACTTTCTGGGATTATGTTTCTCTGCAACCTGAAACTCTGCACAACGTGATGTGGGCG

ATGTCGGATCGCGGCATCCCCCGCAGTTACCGCACCATGGAAGGCTTCGGTATTCACACCTTCC

GCCTGATTAATGCCGAAGGGAAGGCAACGTTTGTACGTTTCCACTGGAAACCACTGGCAGGTAA

AGCCTCACTCGTTTGGGATGAAGCACAAAAACTCACCGGACGTGACCCGGACTTCCACCGCCGC

GAGTTGTGGGAAGCCATTGAAGCAGGCGATTTTCCGGAATACGAACTGGGCTTCCAGTTGATTC

CTGAAGAAGATGAATTCAAGTTCGACTTCGATCTTCTCGATCCAACCAAACTTATCCCGGAAGA

ACTGGTGCCCGTTCAGCGTGTCGGCAAAATGGTGCTCAATCGCAACCCGGATAACTTCTTTGCT

GAAAACGAACAGGCGGCTTTCCATCCTGGGCATATCGTGCCGGGACTGGACTTCACCAACGATC

CGCTGTTGCAGGGACGTTTGTTCTCCTATACCGATACACAAATCAGTCGTCTTGGTGGGCCGAA

TTTCCATGAGATTCCGATTAACCGTCCGACCTGCCCTTACCATAATTTCCAGCGTGACGGCATG

CATCGCATGGGGATCGACACTAACCCGGCGAATTACGAACCGAACTCGATTAACGATAACTGGC

CGCGCGAAACACCGCCGGGGCCGAAACGCGGCGGTTTTGAATCATACCAGGAGCGCGTGGAAGG

CAATAAAGTTCGCGAGCGCAGCCCATCGTTTGGCGAATATTATTCCCATCCGCGTCTGTTCTGG

CTAAGTCAGACGCCATTTGAGCAGCGCCATATTGTCGATGGTTTCAGTTTTGAGTTAAGCAAAG

TCGTTCGTCCGTATATTCGTGAGCGCGTTGTTGACCAGCTGGCGCATATTGATCTCACTCTGGC

CCAGGCGGTGGCGAAAAATCTCGGTATCGAACTGACTGACGACCAGCTGAATATCACCCCACCT

CCGGACGTCAACGGTCTGAAAAAGGATCCATCCTTAAGTTTGTACGCCATTCCTGACGGTGATG

TGAAAGGTCGCGTGGTAGCGATTTTACTTAATGATGAAGTGAGATCGGCAGACCTTCTGGCCAT

TCTCAAGGCGCTGAAGGCCAAAGGCGTTCATGCCAAACTGCTCTACTCCCGAATGGGTGAAGTG

ACTGCGGATGACGGTACGGTGTTGCCTATAGCCGCTACCTTTGCCGGTGCACCTTCGCTGACGG

TCGATGCGGTCATTGTCCCTTGCGGCAATATCGCGGATATCGCTGACAACGGCGATGCCAACTA

CTACCTGATGGAAGCCTACAAACACCTTAAACCGATTGCGCTGGCGGGTGACGCGCGCAAGTTT

AAAGCAACAATCAAGATCGCTGACCAGGGTGAAGAAGGGATTGTGGAAGCTGACAGCGCTGACG

GTAGTTTTATGGATGAACTGCTAACGCTGATGGCAGCACACCGCGTGTGGTCACGCATTCCTAA

GATTGACAAAATTCCTGCCTGA
```

Amino Acid
Catalase HPII (KatE)
*Escherichia coli*

SEQ ID NO. 16

MSQHNEKNPHQHQSPLHDSSEAKPGMDSLAPEDGSHRPAAEPTPPGAQPTAPGSLKAPDTRNEK

LNSLEDVRKGSENYALTTNQGVRIADDQNSLRAGSRGPTLLEDFILREKITHFDHERIPERIVH

ARGSAAHGYFQPYKSLSDITKADFLSDPNKITPVFVRFSTVQGGAGSADTVRDIRGFATKFYTE

EGIFDLVGNNTPIFFIQDAHKFPDFVHAVKPEPHWAIPQGQSAHDTFWDYVSLQPETLHNVMWA

MSDRGIPRSYRTMEGFGIHTFRLINAEGKATFVRFHWKPLAGKASLVWDEAQKLTGRDPDFHRR

ELWEAIEAGDFPEYELGFQLIPEEDEFKFDFDLLDPTKLIPEELVPVQRVGKMVLNRNPDNFFA

ENEQAAFHPGHIVPGLDFTNDPLLQGRLFSYTDTQISRLGGPNFHEIPINRPTCPYHNFQRDGM

HRMGIDTNPANYEPNSINDNWPRETPPGPKRGGFESYQERVEGNKVRERSPSFGEYYSHPRLFW

LSQTPFEQRHIVDGFSFELSKVVRPYIRERVVDQLAHIDLTLAQAVAKNLGIELTDDQLNITPP

PDVNGLKKDPSLSLYAIPDGDVKGRVVAILLNDEVRSADLLAILKALKAKGVHAKLLYSRMGEV

TADDGTVLPIAATFAGAPSLTVDAVIVPCGNIADIADNGDANYYLMEAYKHLKPIALAGDARKF

KATIKIADQGEEGIVEADSADGSFMDELLTLMAAHRVWSRIPKIDKIPA

DNA
Trichome-targeted CBDA synthase
*Cannabis*

SEQ ID NO. 17

ATGAAGTGCTCAACATTCTCCTTTTGGTTTGTTTGCAAGATAATATTTTCTTTTTCTCATTCA

ATATCCAAACTTCCATTGCTAATCCTCGAGAAAACTTCCTTAAATGCTTCTCGCAATATATTCC

CAATAATGCAACAAATCTAAAACTCGTATACACTCAAAACAACCCATTGTATATGTCTGTCCTA

AATTCGACAATACACAATCTTAGATTCACCTCTGACACAACCCCAAAACCACTTGTTATCGTCA

CTCCTTCACATGTCTCTCATATCCAAGGCACTATTCTATGCTCCAAGAAAGTTGGCTTGCAGAT

TCGAACTCGAAGTGGTGGTCATGATTCTGAGGGCATGTCCTACATATCTCAAGTCCCATTTGTT

ATAGTAGACTTGAGAAACATGCGTTCAATCAAAATAGATGTTCATAGCCAAACTGCATGGGTTG

AAGCCGGAGCTACCCTTGGAGAAGTTTATTATTGGGTTAATGAGAAAAATGAGAATCTTAGTTT

GGCGGCTGGGTATTGCCCTACTGTTTGCGCAGGTGGACACTTTGGTGGAGGAGGCTATGGACCA

TTGATGAGAAACTATGGCCTCGCGGCTGATAATATCATTGATGCACACTTAGTCAACGTTCATG

GAAAAGTGCTAGATCGAAAATCTATGGGGGAAGATCTCTTTTGGGCTTTACGTGGTGGTGGAGC

AGAAAGCTTCGGAATCATTGTAGCATGGAAAATTAGACTGGTTGCTGTCCCAAAGTCTACTATG

TTTAGTGTTAAAAAGATCATGGAGATACATGAGCTTGTCAAGTTAGTTAACAAATGGCAAATA

TTGCTTACAAGTATGACAAAGATTTATTACTCATGACTCACTTCATAACTAGGAACATTACAGA

TAATCAAGGGAAGAATAAGACAGCAATACACACTTACTTCTCTTCAGTTTTCCTTGGTGGAGTG

GATAGTCTAGTCGACTTGATGAACAAGAGTTTTCCTGAGTTGGGTATTAAAAAAACGGATTGCA

GACAATTGAGCTGGATTGATACTATCATCTTCTATAGTGGTGTTGTAAATTACGACACTGATAA

TTTTAACAAGGAAATTTTGCTTGATAGATCCGCTGGGCAGAACGGTGCTTTCAAGATTAAGTTA

GACTACGTTAAGAAACCAATTCCAGAATCTGTATTTGTCCAAATTTTGGAAAAATTATATGAAG

AAGATATAGGAGCTGGGATGTATGCGTTGTACCCTTACGGTGGTATAATGGATGAGATTTCAGA

ATCAGCAATTCCATTCCCTCATCGAGCTGGAATCTTGTATGAGTTATGGTACATATGTAGTTGG

GAGAAGCAAGAAGATAACGAAAAGCATCTAAACTGGATTAGAAATATTTATAACTTCATGACTC

CTTATGTGTCCAAAAATCCAAGATTGGCATATCTCAATTATAGAGACCTTGATATAGGAATAAA

TGATCCCAAGAATCCAAATAATTACACACAAGCACGTATTTGGGGTGAGAAGTATTTTGGTAAA

AATTTTGACAGGCTAGTAAAAGTGAAAACCCTGGTTGATCCCAATAACTTTTTTAGAAACGAAC

AAAGCATCCCACCTCTACCACGGCATCGTCATTAA

Amino Acid
Trichome-targeted CBDA synthase
*Cannabis*
SEQ ID NO. 18

MKCSTFSFWFVCKIIFFFFSFNIQTSIANPRENFLKCFSQYIPNNATNLKLVYTQNNPLYMSVL

NSTIHNLRFTSDTTPKPLVIVTPSHVSHIQGTILCSKKVGLQIRTRSGGHDSEGMSYISQVPFV

IVDLRNMRSIKIDVHSQTAWVEAGATLGEVYYWVNEKNENLSLAAGYCPTVCAGGHFGGGGYGP

LMRNYGLAADNIIDAHLVNVHGKVLDRKSMGEDLFWALRGGGAESFGIIVAWKIRLVAVPKSTM

FSVKKIMEIHELVKLVNKWQNIAYKYDKDLLLMTHFITRNITDNQGKNKTAIHTYFSSVFLGGV

DSLVDLMNKSFPELGIKKTDCRQLSWIDTIIFYSGVVNYDTDNFNKEILLDRSAGQNGAFKIKL

DYVKKPIPESVFVQILEKLYEEDIGAGMYALYPYGGIMDEISESAIPFPHRAGILYELWYICSW

EKQEDNEKHLNWIRNIYNFMTPYVSKNPRLAYLNYRDLDIGINDPKNPNNYTQARIWGEKYFGK

NFDRLVKVKTLVDPNNFFRNEQSIPPLPRHRH

DNA
Trichome-targeted UDP glycosyltransferase 76G1
*Stevia rebaudiana*
SEQ ID NO. 19

ATGAAGTGCTCAACATTCTCCTTTTGGTTTGTTTGCAAGATAATATTTTCTTTTTCTCATTCA

ATATCCAAACTTCCATTGCTAATCCTCGAGAAAATAAAACTGAAACTACTGTTAGAAGAAGAAG

AAGAATTATTTTGTTTCCTGTTCCTTTTCAAGGACATATTAATCCTATTTTGCAATTGGCTAAT

GTTTTGTATTCAAAAGGATTTTCAATTACTATTTTTCATACTAATTTTAATAAACCTAAAACTT

CAAATTATCCTCATTTTACTTTTAGATTTATTTTGGATAATGATCCTCAAGATGAAAGAATTTC

AAATTTGCCTACTCATGGACCTTTGGCTGGAATGAGAATTCCTATTATTAATGAACATGGAGCT

GATGAATTGAGAAGAGAATTGGAATTGTTGATGTTGGCTTCAGAAGAAGATGAAGAAGTTTCAT

GCTTGATTACTGATGCTTTGTGGTATTTTGCTCAATCAGTTGCTGATTCATTGAATTTGAGAAG

ATTGGTTTTGATGACTTCATCATTGTTTAATTTTCATGCTCATGTTTCATTGCCTCAATTTGAT

GAATTGGGATATTTGGATCCTGATGATAAAACTAGATTGGAAGAACAAGCTTCAGGATTTCCTA

TGTTGAAAGTTAAAGATATTAAATCAGCTTATTCAAATTGGCAAATTTTGAAAGAAATTTTGGG

AAAAAATGATTAAACAAACTAGAGCTTCATCAGGAGTTATTTGGAATTCATTTAAAGAATTGGAA

GAATCAGAATTGGAAACTGTTATTAGAGAAATTCCTGCTCCTTCATTTTTGATTCCTTTGCCTA

AACATTTGACTGCTTCATCATCATCATTGTTGGATCATGATAGAACTGTTTTTCAATGGTTGGA

TCAACAACCTCCTTCATCAGTTTTGTATGTTTCATTTGGATCAACTTCAGAAGTTGATGAAAAA

GATTTTTTGGAAATTGCTAGAGGATTGGTTGATTCAAAACAATCATTTTTGTGGGTTGTTAGAC

CTGGATTTGTTAAAGGATCAACTTGGGTTGAACCTTTGCCTGATGGATTTTTGGGAGAAAGAGG

AAGAATTGTTAAATGGGTTCCTCAACAAGAAGTTTTGGCTCATGGAGCTATTGGAGCTTTTTGG

ACTCATTCAGGATGGAATTCAACTTTGGAATCAGTTTGCGAAGGAGTTCCTATGATTTTTTCAG

ATTTTGGATTGGATCAACCTTTGAATGCTAGATATATGTCAGATGTTTTGAAAGTTGGAGTTTA

TTTGGAAAATGGATGGGAAGAGGAGAAATTGCTAATGCTATTAGAAGAGTTATGGTTGATGAA

GAAGGAGAATATATTAGACAAAATGCTAGAGTTTTGAAACAAAAAGCTGATGTTTCATTGATGA

AAGGAGGATCATCATATGAATCATTGGAATCATTGGTTTCATATATTTCATCATTGTAA

Amino Acid
Trichome-targeted UDP glycosyltransferase 76G1
*Stevia rebaudiana*
SEQ ID NO. 20

MKCSTFSFWFVCKIIFFFFSFNIQTSIANPRENKTETTVRRRRRIILFPVPFQGHINPILQLAN

-continued

VLYSKGFSITIFHTNFNKPKTSNYPHFTFRFILDNDPQDERISNLPTHGPLAGMRIPIINEHGA

DELRRELELLMLASEEDEEVSCLITDALWYFAQSVADSLNLRRLVLMTSSLFNFHAHVSLPQFD

ELGYLDPDDKTRLEEQASGFPMLKVKDIKSAYSNWQILKEILGKMIKQTRASSGVIWNSFKELE

ESELETVIREIPAPSFLIPLPKHLTASSSSLLDHDRTVFQWLDQQPPSSVLYVSFGSTSEVDEK

DFLEIARGLVDSKQSFLWVVRPGFVKGSTWVEPLPDGFLGERGRIVKWVPQQEVLAHGAIGAFW

THSGWNSTLESVCEGVPMIFSDFGLDQPLNARYMSDVLKVGVYLENGWERGEIANAIRRVMVDE

EGEYIRQNARVLKQKADVSLMKGGSSYESLESLVSYISSL

DNA
PM-UTR1
*Arabidopsis thaliana*
SEQ ID NO. 21
ATGGAGGTCCATGGCTCCGGATTCCGTCGAATTCTGTTGTTGGCGTTGTGTATCTCCGGATCT

GGTCCGCCTACATCTACCAAGGCGTTCTTCAAGAGACTCTGTCCACGAAGAGATTTGGTCCAGA

TGAGAAGAGGTTCGAGCATCTTGCATTCTTGAACTTAGCTCAAAGTGTAGTCTGCTTGATCTGG

TCTTATATAATGATCAAGCTCTGGTCAAATGCTGGTAACGGTGGAGCACCATGGTGGACGTATT

GGAGTGCAGGCATTACTAATACAATTGGTCCTGCCATGGGAATTGAAGCCTTGAAGTATATCAG

TTATCCAGCTCAGGTTTTGGCAAAATCGTCAAAAATGATTCCAGTTATGCTAATGGGAACTTTA

GTTTACGGAATAAGATACACTTTCCCTGAATACATGTGCACCTTTCTTGTCGCTGGAGGAGTAT

CCATCTTTGCTCTTCTTAAGACAAGCTCTAAGACAATTAGCAAGCTAGCACATCCAAATGCTCC

CCTCGGTTACGCACTTTGTTCCTTAAACCTCGCCTTTGACGGATTCACAAATGCCACACAAGAC

TCCATTGCCTCAAGGTACCCAAAAACCGAAGCGTGGGACATAATGCTGGGAATGAACTTATGGG

GCACAATATACAACATTATCTACATGTTTGGCTTGCCACAAGGGATGGATTCGAAGCAATTCAG

TTCTGTAAGCTACACCCGGAAGCGGCATGGGACATTCTAAAGTATTGTATATGCGGTGCCGTGG

GACAAAACTTCATCTTCATGACAATAAGTAACTTCGGGTCACTAGCTAACACGACCATAACCAC

GACCAGGAAGTTTGTTAGCATTGTTGTATCATCAGTAATGAGCGGAAATCCATTGTCGTTGAAG

CAATGGGGATGTGTTTCGATGGTCTTTGGTGGTTTGGCATATCAAATTTATCTTAAATGGAAGA

AATTGCAGAGAGTGGAGTGCTCCATAATGAACTTAATGTGTGGGTCTACCTGCGCCGCTTGA

DNA
Cytostolic CBDA synthase (cytCBDAs)
*Cannabis sativa*
SEQ ID NO. 22
ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAAGAT

CATGGAGATACATGAGCTTGTCAAGTTAGTTAACAAATGGCAAAATATTGCTTACAAGTATGAC

AAAGATTTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

-continued

```
GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT

TGCTTGATAGATCCGCTGGGCAGAACGGTGCTTTCAAGATTAAGTTAGACTACGTTAAGAAACC

AATTCCAGAATCTGTATTTGTCCAAATTTTGGAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAGAAGCAAGAAGATAA

CGAAAAGCATCTAAACTGGATTAGAAATATTTATAACTTCATGACTCCTTATGTGTCCAAAAAT

CCAAGATTGGCATATCTCAATTATAGAGACCTTGATATAGGAATAAATGATCCCAAGAATCCAA

ATAATTACACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCTA

CCACGGCATCGTCATTAA
```

Amino Acid
Cytostolic CBDA synthase (cytCBDAs)
*Cannabis sativa*
SEQ ID NO. 23

```
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

PRLAYLNYRDLDIGINDPKNPNNYTQARIWGEKYFGKNFDRLVKVKTLVDPNNFFRNEQSIPPL

PRHRH
```

DNA
Cytostolic-targeted UDP glycosyltransferase 76G1 (cytUTG)
*Stevia rebaudiana*
SEQ ID NO. 24

```
ATGGAAAATAAAACCGAAACCACCGTCCGCCGTCGTCGCCGTATCATTCTGTTCCCGGTCCCGT

TCCAGGGCCACATCAACCCGATTCTGCAACTGGCGAACGTGCTGTATTCGAAAGGTTTCAGCAT

CACCATCTTCCATACGAACTTCAACAAGCCGAAGACCAGCAATTACCCGCACTTTACGTTCCGT

TTTATTCTGGATAACGACCCGCAGGATGAACGCATCTCTAATCTGCCGACCCACGGCCCGCTGG

CGGGTATGCGTATTCCGATTATCAACGAACACGGCGCAGATGAACTGCGTCGCGAACTGGAACT

GCTGATGCTGGCCAGCGAAGAAGATGAAGAAGTTTCTTGCCTGATCACCGACGCACTGTGGTAT

TTTGCCCAGTCTGTTGCAGATAGTCTGAACCTGCGTCGCCTGGTCCTGATGACCAGCAGCCTGT

TCAATTTTCATGCCCACGTTAGTCTGCCGCAGTTCGATGAACTGGGTTATCTGGACCCGGATGA

CAAAACCCGCCTGGAAGAACAGGCGAGCGGCTTTCCGATGCTGAAAGTCAAGGATATTAAGTCA

GCGTACTCGAACTGGCAGATTCTGAAAGAAATCCTGGGTAAAATGATTAAGCAAACCAAAGCAA

GTTCCGGCGTCATCTGGAATAGTTTCAAAGAACTGGAAGAATCCGAACTGGAAACGGTGATTCG

TGAAATCCCGGCTCCGAGTTTTCTGATTCCGCTGCCGAAGCATCTGACCGCGAGCAGCAGCAGC

CTGCTGGATCACGACCGCACGGTGTTTCAGTGGCTGGATCAGCAACCGCCGAGTTCCGTGCTGT

ATGTTAGCTTCGGTAGTACCTCGGAAGTGGATGAAAAGGACTTTCTGGAAATCGCTCGTGGCCT

GGTTGATAGCAAACAATCTTTCCTGTGGGTGGTTCGCCCGGGTTTTGTGAAGGGCTCTACGTGG

GTTGAACCGCTGCCGGACGGCTTCCTGGGTGAACGTGGCCGCATTGTCAAATGGGTGCCGCAGC
```

-continued

```
AAGAAGTGCTGGCGCATGGCGCGATTGGCGCGTTTTGGACCCACTCCGGTTGGAACTCAACGCT

GGAATCGGTTTGTGAAGGTGTCCCGATGATTTTCTCAGATTTTGGCCTGGACCAGCCGCTGAAT

GCACGTTATATGTCGGATGTTCTGAAAGTCGGTGTGTACCTGGAAAACGGTTGGGAACGCGGCG

AAATTGCGAATGCCATCCGTCGCGTTATGGTCGATGAAGAAGGCGAATACATTCGTCAGAATGC

TCGCGTCCTGAAACAAAGGCGGACGTGAGCCTGATGAAAGGCGGTTCATCGTATGAAAGTCTG

GAATCCCTGGTTTCATACATCAGCTCTCTGTAA
```

Amino Acid
Cytostolic-targeted UDP glycosyltransferase 76G1 (cytUTG)
*Stevia rebaudiana*
SEQ ID NO. 25

```
MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTKASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL
```

Amino Acid
Glycosyltransferase (NtGT5a)
*Nicotiana tabacum*
SEQ ID NO. 26

```
MGSIGAELTKPHAVCIPYPAQGHINPMLKLAKILHHKGFHITFVNTEFNHRRLLKSRGPDSLKG

LSSFRFETIPDGLPPCEADATQDIPSLCESTTNTCLAPFRDLLAKLNDTNTSNVPPVSCIVSDG

VMSFTLAAAQELGVPEVLFWTTSACGFLGYMHYCKVIEKGYAPLKDASDLTNGYLETTLDFIPG

MKDVRLRDLPSFLRTTNPDEFMIKFVLQETERARKASAIILNTFETLEAEVLESLRNLLPPVYP

IGPLHFLVKHVDDENLKGLRSSLWKEEPECIQWLDTKEPNSVVYVNFGSITVMTPNQLIEFAWG

LANSQQTFLWIIRPDIVSGDASILPPEFVEETKNRGMLASWCSQEEVLSHPAIVGFLTHSGWNS

TLESISSGVPMICWPFFAEQQTNCWFSVTKWDVGMEIDSDVKRDEVESLVRELMVGGKGKKMKK

KAMEWKELAEASAKEHSGSSYVNIEKLVNDILLSSKH
```

DNA
Glycosyltransferase (NtGT5a)
*Nicotiana tabacum*
SEQ ID NO. 27

```
ATGGGTTCCATTGGTGCTGAATTAACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACCGACGTCTCCTTAAATCTCGTGGCCCTGATTCTCTCAAGGGT

CTTTCTTCTTTCCGTTTTGAGACCATTCCTGATGGACTTCCGCCATGTGAGGCAGATGCCACAC

AAGATATACCTTCTTTGTGTGAATCTACAACCAATACTTGCTTGGCTCCTTTTAGGGATCTTCT

TGCGAAACTCAATGATACTAACACATCTAACGTGCCACCCGTTTCGTGCATCGTCTCGGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTACTGCAAGGTTATTGAAAAAGGATATGCTCC

ACTTAAAGATGCGAGTGACTTGACAAATGGATACCTAGAGACAACATTGGATTTTATACCAGGC

ATGAAAGACGTACGTTTAAGGGATCTTCCAAGTTTCTTGAGAACTACAAATCCAGATGAATTCA

TGATCAAATTTGTCCTCCAAGAAACAGAGAGAGCAAGAAAGGCTTCTGCAATTATCCTCAACAC

ATTTGAAACACTAGAGGCTGAAGTTCTTGAATCGCTCCGAAATCTTCTTCCTCCAGTCTACCCC

ATAGGGCCCTTGCATTTTCTAGTGAAACATGTTGATGATGAGAATTTGAAGGGACTTAGATCCA
```

-continued

```
GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAGCTTATTGAGTTTGCTTGGGGA

CTTGCAAACAGCCAGCAAACATTCTTATGGATCATAAGACCTGATATTGTTTCAGGTGATGCAT

CGATTCTTCCACCCGAATTCGTGGAAGAAACGAAGAACAGAGGTATGCTTGCTAGTTGGTGTTC

ACAAGAAGAAGTACTTAGTCACCCTGCAATAGTAGGATTCTTGACTCACAGTGGATGGAATTCG

ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACAGTGATGTGAAGAG

AGATGAAGTGGAAAGCCTTGTAAGGGAATTGATGGTTGGGGGAAAAGGCAAAAAGATGAAGAAA

AAGGCAATGGAATGGAAGGAATTGGCTGAAGCATCTGCTAAAGAACATTCAGGGTCATCTTATG

TGAACATTGAAAAGTTGGTCAATGATATTCTTCTTTCATCCAAACATTAA
```

Amino Acid
Glycosyltransferase (NtGT5b)
Nicotiana tabacum
SEQ ID NO. 28
```
MGSIGAEFTKPHAVCIPYPAQGHINPMLKLAKILHHKGFHITFVNTEFNHRRLLKSRGPDSLKG

LSSFRFETIPDGLPPCDADATQDIPSLCESTTNTCLGPFRDLLAKLNDTNTSNVPPVSCIISDG

VMSFTLAAAQELGVPEVLFWTTSACGFLGYMHYYKVIEKGYAPLKDASDLTNGYLETTLDFIPC

MKDVRLRDLPSFLRTTNPDEFMIKFVLQETERARKASAIILNTYETLEAEVLESLRNLLPPVYP

IGPLHFLVKHVDDENLKGLRSSLWKEEPECIQWLDTKEPNSVVYVNFGSITVMTPNQLIEFAWG

LANSQQSFLWIIRPDIVSGDASILPPEFVEETKKRGMLASWCSQEEVLSHPAIGGFLTHSGWNS

TLESISSGVPMICWPFFAEQQTNCWFSVTKWDVGMEIDCDVKRDEVESLVRELMVGGKGKKMKK

KAMEWKELAEASAKEHSGSSYVNIEKVVNDILLSSKH
```

DNA
Glycosyltransferase (NtGT5b)
Nicotiana tabacum
SEQ ID NO. 29
```
ATGGGTTCCATTGGTGCTGAATTTACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACAGACGTCTGCTTAAATCTCGTGGCCCTGATTCTCTCAAGGGT

CTTTCTTCTTTCCGTTTTGAGACAATTCCTGATGGACTTCCGCCATGTGATGCAGATGCCACAC

AAGATATACCTTCTTTGTGTGAATCTACAACCAATACTTGCTTGGGTCCTTTTAGGGATCTTCT

TGCGAAACTCAATGATACTAACACATCTAACGTGCCACCCGTTTCGTGCATCATCTCAGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTATTACAAGGTTATTGAAAAAGGATACGCTCC

ACTTAAAGATGCGAGTGACTTGACAAATGGATACCTAGAGACAACATTGGATTTTATACCATGC

ATGAAAGACGTACGTTAAGGGATCTTCCAAGTTTCTTGAGAACTACAAATCCAGATGAATTCA

TGATCAAATTTGTCCTCCAAGAAACAGAGAGAGCAAGAAAGGCTTCTGCAATTATCCTCAACAC

ATATGAAACACTAGAGGCTGAAGTTCTTGAATCGCTCCGAAATCTTCTTCCTCCAGTCTACCCC

ATTGGGCCCTTGCATTTTCTAGTGAAACATGTTGATGATGAGAATTTGAAGGGACTTAGATCCA

GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAACTTATTGAATTTGCTTGGGGA

CTTGCAAACAGCCAACAATCATTCTTATGGATCATAAGACCTGATATTGTTTCAGGTGATGCAT

CGATTCTTCCCCCCGAATTCGTGGAAGAAACGAAGAAGAGAGGTATGCTTGCTAGTTGGTGTTC

ACAAGAAGAAGTACTTAGTCACCCTGCAATAGGAGGATTCTTGACTCACAGTGGATGGAATTCG
```

-continued

```
ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACTGTGATGTGAAGAG

GGATGAAGTGGAAAGCCTTGTAAGGGAATTGATGGTTGGGGGAAAAGGCAAAAGATGAAGAAA

AAGGCAATGGAATGGAAGGAATTGGCTGAAGCATCTGCTAAAGAACATTCAGGGTCATCTTATG

TGAACATTGAGAAGGTGGTCAATGATATTCTTCTTTCGTCCAAACATTAA
```

Amino Acid
UDP-glycosyltransferase 73C3 (NtGT4)
*Nicotiana tabacum*
SEQ ID NO. 30

```
MATQVHKLHFILFPLMAPGHMIPMIDIAKLLANRGVITTIITTPVNANRFSSTITRAIKSGLRI

QILTLKFPSVEVGLPEGCENIDMLPSLDLASKFFAAISMLKQQVENLLEGINPSPSCVISDMGF

PWTTQIAQNFNIPRIVFHGTCCFSLLCSYKILSSNILENITSDSEYFVVPDLPDRVELTKAQVS

GSTKNTTSVSSSVLKEVTEQIRLAEESSYGIVNSFEELEQVYEKEYRKARGKKVWCGPVSLC

NKEIEDLVTRGNKTAIDNQDCLKWLDNFETESVVYASLGSLSRLTLLQMVELGLGLEESNRPFV

WVLGGGDKLNDLEKWILENGFEQRIKERGVLIRGWAPQVLILSHPAIGGVLTHCGWNSTLEGIS

AGLPMVTWPLFAEQFCNEKLVVQVLKIGVSLGVKVPVKWGDEENVGVLVKKDDVKKALDKLMDE

GEEGQVRRTKAKELGELAKKAFGEGGSSYVNLTSLIEDIIEQQNHKEK
```

DNA
UDP-glycosyltransferase 73C3 (NtGT4)
*Nicotiana tabacum*
SEQ ID NO. 31

```
ATGGCAACTCAAGTGCACAAACTTCATTTCATACTATTCCCTTTAATGGCTCCAGGCCACATGA

TTCCTATGATAGACATAGCTAAACTTCTAGCAAATCGCGGTGTCATTACCACTATCATCACCAC

TCCAGTAAACGCCAATCGTTTCAGTTCAACAATTACTCGTGCCATAAAATCCGGTCTAAGAATC

CAAATTCTTACACTCAAATTTCCAAGTGTAGAAGTAGGATTACCAGAAGGTTGCGAAAATATTG

ACATGCTTCCTTCTCTTGACTTGGCTTCAAAGTTTTTTGCTGCAATTAGTATGCTGAAACAACA

AGTTGAAAATCTCTTAGAAGGAATAAATCCAAGTCCAAGTTGTGTTATTTCAGATATGGGATTT

CCTTGGACTACTCAAATTGCACAAAATTTTAATATCCCAAGAATTGTTTTTCATGGTACTTGTT

GTTTCTCACTTTTATGTTCCTATAAAATACTTTCCTCCAACATTCTTGAAAATATAACCTCAGA

TTCAGAGTATTTTGTTGTTCCTGATTTACCCGATAGAGTTGAACTAACGAAAGCTCAGGTTTCA

GGATCGACGAAAAATACTACTTCTGTTAGTTCTTCTGTATTGAAAGAAGTTACTGAGCAAATCA

GATTAGCCGAGGAATCATCATATGGTGTAATTGTTAATAGTTTTGAGGAGTTGGAGCAAGTGTA

TGAGAAAGAATATAGGAAAGCTAGAGGGAAAAAAGTTTGGTGTGTTGGTCCTGTTTCTTTGTGT

AATAAGGAAATTGAAGATTTGGTTACAAGGGGTAATAAAACTGCAATTGATAATCAAGATTGCT

TGAAATGGTTAGATAATTTTGAAACAGAATCTGTGGTTTATGCAAGTCTTGGAAGTTTATCTCG

TTTGACATTATTGCAAATGGTGGAACTTGGTCTTGGTTTAGAAGAGTCAAATAGGCCTTTTGTA

TGGGTATTAGGAGGAGGTGATAAATTAAATGATTTAGAGAAATGGATTCTTGAGAATGGATTTG

AGCAAAGAATTAAAGAAGAGGAGTTTTGATTAGAGGATGGGCTCCTCAAGTGCTTATACTTTC

ACACCCTGCAATTGGTGGAGTATTGACTCATTGCGGATGGAATTCTACATTGGAAGGTATTTCA

GCAGGATTACCAATGGTAACATGGCCACTATTTGCTGAGCAATTTTGCAATGAGAAGTTAGTAG

TCCAAGTGCTAAAAATTGGAGTGAGCCTAGGTGTGAAGGTGCCTGTCAAATGGGAGATGAGGA

AAATGTTGGAGTTTTGGTAAAAAAGGATGATGTTAAGAAAGCATTAGACAAACTAATGGATGAA

GGAGAAGAAGGACAAGTAAGAAGAACAAAAGCAAAAGAGTTAGGAGAATTGGCTAAAAAGGCAT

TTGGAGAAGGTGGTTCTTCTTATGTTAACTTAACATCTCTGATTGAAGACATCATTGAGCAACA

AAATCACAAGGAAAAATAG
```

Amino Acid
Glycosyltransferase (NtGT1b)
*Nicotiana tabacum*
SEQ ID NO. 32

MKTAELVFIPAPGMGHLVPTVEVAKQLVDRHEQLSITVLIMTIPLETNIPSYTKSLSSDYSSRI

TLLPLSQPETSVTMSSFNAINFFEYISSYKGRVKDAVSETSFSSSNSVKLAGFVIDMFCTAMID

VANEFGIPSYVFYTSSAAMLGLQLHFQSLSIECSPKVHNYVEPESEVLISTYMNPVPVKCLPGI

ILVNDESSTMFVNHARRFRETKGIMVNTFTELESHALKALSDDEKIPPIYPVGPILNLENGNED

HNQEYDAIMKWLDEKPNSSVVFLCFGSKGSFEEDQVKEIANALESSGYHFLWSLRRPPPKDKLQ

FPSEFENPEEVLPEGFFQRTKGRGKVIGWAPQLAILSHPSVGGFVSHCGWNSTLESVRSGVPIA

TWPLYAEQQSNAFQLVKDLGMAVEIKMDYREDFNTRNPPLVKAEEIEDGIRKLMDSENKIRAKV

TEMKDKSRAALLEGGSSYVALGHFVETVMKN

DNA
Glycosyltransferase (NtGT1b)
*Nicotiana tabacum*
SEQ ID NO. 33

ATGAAGACAGCAGAGTTAGTATTCATTCCTGCTCCTGGGATGGGTCACCTTGTACCAACTGTGG

AGGTGGCAAAGCAACTAGTCGACAGACACGAGCAGCTTTCGATCACAGTTCTAATCATGACAAT

TCCTTTGGAAACAAATATTCCATCATATACTAAATCACTGTCCTCAGACTACAGTTCTCGTATA

ACGCTGCTTCCACTCTCTCAACCTGAGACCTCTGTTACTATGAGCAGTTTTAATGCCATCAATT

TTTTTGAGTACATCTCCAGCTACAAGGGTCGTGTCAAAGATGCTGTTAGTGAAACCTCCTTTAG

TTCGTCAAATTCTGTGAAACTTGCAGGATTTGTAATAGACATGTTCTGCACTGCGATGATTGAT

GTAGCGAACGAGTTTGGAATCCCAAGTTATGTGTTCTACACTTCTAGTGCAGCTATGCTTGGAC

TACAACTGCATTTTCAAAGTCTTAGCATTGAATGCAGTCCGAAAGTTCATAACTACGTTGAACC

TGAATCAGAAGTTCTGATCTCAACTTACATGAATCCGGTTCCAGTCAAATGTTTGCCCGGAATT

ATACTAGTAAATGATGAAGTAGCACCATGTTTGTCAATCATGCACGAAGATTCAGGGAGACGA

AAGGAATTATGGTGAACACGTTCACTGAGCTTGAATCACACGCTTTGAAAGCCCTTTCCGATGA

TGAAAAAATCCCACCAATCTACCCAGTTGGACCTATACTTAACCTTGAAAATGGGAATGAAGAT

CACAATCAAGAATATGATGCGATTATGAAGTGGCTTGACGAGAAGCCTAATTCATCAGTGGTGT

TCTTATGCTTTGGAAGCAAGGGGTCTTTCGAAGAAGATCAGGTGAAGGAAATAGCAAATGCTCT

AGAGAGCAGTGGCTACCACTTCTTGTGGTCGCTAAGGCGACCGCCACCAAAAGACAAGCTACAA

TTCCCAAGCGAATTCGAGAATCCAGAGGAAGTCTTACCAGAGGGATTCTTTCAAAGGACTAAAG

GAAGAGGAAAGGTGATAGGATGGGCACCCCAGTTGGCTATTTTGTCTCATCCTTCAGTAGGAGG

ATTCGTGTCGCATTGTGGGTGGAATTCAACTCTGGAGAGCGTTCGAAGTGGAGTGCCGATAGCA

ACATGGCCATTGTATGCAGAGCAACAGAGCAATGCATTTCAACTGGTGAAGGATTTGGGTATGG

CAGTAGAGATTAAGATGGATTACAGGGAAGATTTTAATACGAGAAATCCACCACTGGTTAAAGC

TGAGGAGATAGAAGATGGAATTAGGAAGCTGATGGATTCAGAGAATAAAATCAGGGCTAAGGTG

ACGGAGATGAAGGACAAAAGTAGAGCAGCACTGCTGGAGGGCGGATCATCATATGTAGCTCTTG

GGCATTTTGTTGAGACTGTCATGAAAAACTAG

Amino Acid
Glycosyltransferase (NtGT1a)
*Nicotiana tabacum*
SEQ ID NO. 34

MKTTELVFIPAPGMGHLVPTVEVAKQLVDRDEQLSITVLIMTLPLETNIPSYTKSLSSDYSSRI

TLLQLSQPETSVSMSSFNAINFFEYISSYKDRVKDAVNETFSSSSSVKLKGFVIDMFCTAMIDV

ANEFGIPSYVFYTSNAAMLGLQLHFQSLSIEYSPKVHNYLDPESEVAISTYINPIPVKCLPGII

-continued

LDNDKSGTMFVNHARRFRETKGIMVNTFAELESHALKALSDDEKIPPIYPVGPILNLGDGNEDH

NQEYDMIMKWLDEQPHSSVVFLCFGSKGSFEEDQVKEIANALERSGNRFLWSLRRPPPKDTLQF

PSEFENPEEVLPVGFFQRTKGRGKVIGWAPQLAILSHPAVGGFVSHCGWNSTLESVRSGVPIAT

WPLYAEQQSNAFQLVKDLGMAVEIKMDYREDFNKTNPPLVKAEEIEDGIRKLMDSENKIRAKVM

EMKDKSRAALLEGGSSYVALGHFVETVMKN

DNA
Glycosyltransferase (NtGT1a)
*Nicotiana tabacum*
SEQ ID NO. 35

ATGAAGACAACAGAGTTAGTATTCATTCCTGCTCCTGGCATGGGTCACCTTGTACCCACTGTGG

AGGTGGCAAAGCAACTAGTCGACAGAGACGAACAGCTTTCAATCACAGTTCTCATCATGACGCT

TCCTTTGGAAACAAATATTCCATCATATACTAAATCACTGTCCTCAGACTACAGTTCTCGTATA

ACGCTGCTTCAACTTTCTCAACCTGAGACCTCTGTTAGTATGAGCAGTTTTAATGCCATCAATT

TTTTTGAGTACATCTCCAGCTACAAGGATCGTGTCAAAGATGCTGTTAATGAAACCTTTAGTTC

GTCAAGTTCTGTGAAACTCAAAGGATTTGTAATAGACATGTTCTGCACTGCGATGATTGATGTG

GCGAACGAGTTTGGAATCCCAAGTTATGTCTTCTACACTTCTAATGCAGCTATGCTTGGACTCC

AACTCCATTTTCAAAGTCTTAGTATTGAATACAGTCCGAAAGTTCATAATTACCTAGACCCTGA

ATCAGAAGTAGCGATCTCAACTTACATTAATCCGATTCCAGTCAAATGTTTGCCCGGGATTATA

CTAGACAATGATAAAAGTGGCACCATGTTCGTCAATCATGCACGAAGATTCAGG

GAGACGAAAGGAATTATGGTGAACACATTCGCTGAGCTTGAATCACACGCTTTGAAAGCCCTTT

CCGATGATGAGAAAATCCCACCAATCTACCCAGTTGGGCCTATACTTAACCTTGGAGATGGGAA

TGAAGATCACAATCAAGAATATGATATGATTATGAAGTGGCTCGACGAGCAGCCTCATTCATCA

GTGGTGTTCCTATGCTTTGGAAGCAAGGGATCTTTCGAAGAAGATCAAGTGAAGGAAATAGCAA

ATGCTCTAGAGAGAAGTGGTAACCGGTTCTTGTGGTCGCTAAGACGACCGCCACCAAAAGACAC

GCTACAATTCCCAAGCGAATTCGAGAATCCAGAGGAAGTCTTGCCGGTGGGATTCTTTCAAAGG

ACTAAAGGAAGAGGAAAGGTGATAGGATGGGCACCCCAGTTGGCTATTTTGTCTCATCCTGCAG

TAGGAGGATTCGTGTCGCATTGTGGGTGGAATTCAACTTTGGAGAGTGTTCGTAGTGGAGTACC

GATAGCAACATGGCCATTGTATGCAGAGCAACAGAGCAATGCATTTCAACTGGTGAAGGATTTG

GGGATGGCAGTGGAGATTAAGATGGATTACAGGGAAGATTTTAATAAGACAAATCCACCACTGG

TTAAAGCTGAGGAGATAGAAGATGGAATTAGGAAGCTGATGGATTCAGAGAATAAAATCAGGGC

TAAGGTGATGGAGATGAAGGACAAAAGTAGAGCAGCGTTATTAGAAGGCGGATCATCATATGTA

GCTCTCGGGCATTTTGTTGAGACTGTCATGAAAAACTAA

Amino Acid
Glycosyltransferase (NtGT3)
*Nicotiana tabacum*
SEQ ID NO. 36

MKETKKIELVFIPSPGIGHLVSTVEMAKLLIAREEQLSITVLIIQWPNDKKLDSYIQSVANFSS

RLKFIRLPQDDSIMQLLKSNIFTTFIASHKPAVRDAVADILKSESNNTLAGIVIDLFCTSMIDV

ANEFELPTYVFYTSGAATLGLHYHIQNLRDEFNKDITKYKDEPEEKLSIATYLNPFPAKCLPSV

ALDKEGGSTMFLDLAKRFRETKGIMINTFLELESYALNSLSRDKNLPPIYPVGPVLNLNNVEGD

NLGSSDQNTMKWLDDQPASSVVFLCFGSGGSFEKHQVKEIAYALESSGCRFLWSLRRPPTEDAR

FPSNYENLEEILPEGFLERTKGIGKVIGWAPQLAILSHKSTGGFVSHCGWNSTLESTYFGVPIA

TWPMYAEQQANAFQLVKDLRMGVEIKMDYRKDMKVMGKEVIVKAEEIEKAIREIMDSESEIRVK

VKEMKEKSRAAQMEGGSSYTSIGGFIQIIMENSQ

DNA

Glycosyltransferase (NtGT3)
*Nicotiana tabacum*

SEQ ID NO. 37

```
ATGAAAGAAACCAAGAAAATAGAGTTAGTCTTCATTCCTTCACCAGGAATTGGCCATTTAGTAT
CCACAGTTGAAATGGCAAAGCTTCTTATAGCTAGAGAAGAGCAGCTATCTATCACAGTCCTCAT
CATCCAATGGCCTAACGACAAGAAGCTCGATTCTTATATCCAATCAGTCGCCAATTTCAGCTCG
CGTTTGAAATTCATTCGACTCCCTCAGGATGATTCCATTATGCAGCTACTCAAAAGCAACATTT
TCACCACGTTTATTGCCAGTCATAAGCCTGCAGTTAGAGATGCTGTTGCTGATATTCTCAAGTC
AGAATCAAATAATACGCTAGCAGGTATTGTTATCGACTTGTTCTGCACCTCAATGATAGACGTG
GCCAATGAGTTCGAGCTACCAACCTATGTTTTCTACACGTCTGGTGCAGCAACCCTTGGTCTTC
ATTATCATATACAGAATCTCAGGGATGAATTTAACAAAGATATTACCAAGTACAAAGACGAACC
TGAAGAAAAACTCTCTATAGCAACATATCTCAATCCATTTCCAGCAAAATGTTTGCCGTCTGTA
GCCTTAGACAAAGAAGGTGGTTCAACAATGTTTCTTGATCTCGCAAAAAGGTTTCGAGAAACCA
AAGGTATTATGATAAACACATTTCTAGAGCTCGAATCCTATGCATTAAACTCGCTCTCACGAGA
CAAGAATCTTCCACCTATATACCCTGTCGGACCAGTATTGAACCTTAACAATGTTGAAGGTGAC
AACTTAGGTTCATCTGACCAGAATACTATGAAATGGTTAGATGATCAGCCCGCTTCATCTGTAG
TGTTCCTTTGTTTTGGTAGTGGTGGAAGCTTTGAAAAACATCAAGTTAAGGAAATAGCCTATGC
TCTGGAGAGCAGTGGGTGTCGGTTTTTGTGGTCGTTAAGGCGACCACCAACCGAAGATGCAAGA
TTTCCAAGCAACTATGAAAATCTTGAAGAAATTTTGCCAGAAGGATTCTTGGAAAGAACAAAAG
GGATTGGAAAAGTGATAGGATGGGCACCTCAGTTGGCGATTTTGTCACATAAATCGACGGGGGG
ATTTGTGTCGCACTGTGGATGGAATTCGACTTTGGAAAGTACATATTTTGGAGTGCCAATAGCA
ACCTGGCCAATGTACGCGGAGCAACAAGCGAATGCATTTCAATTGGTTAAGGATTTGAGAATGG
GAGTTGAGATTAAGATGGATTATAGGAAGGATATGAAAGTGATGGGCAAAGAAGTTATAGTGAA
AGCTGAGGAGATTGAGAAAGCAATAAGAGAAATTATGGATTCCGAGAGTGAAATTCGGGTGAAG
GTGAAAGAGATGAAGGAGAAGAGCAGAGCAGCACAAATGGAAGGTGGCTCTTCTTACACTTCTA
TTGGAGGTTTCATCCAAATTATCATGGAGAATTCTCAATAA
```

Amino Acid
Glycosyltransferase (NtGT2)
*Nicotiana tabacum*

SEQ ID NO. 38

```
MVQPHVLLVTFPAQGHINPCLQFAKRLIRMGIEVTFATSVFAHRRMAKTTTSTLSKGLNFAAFS
DGYDDGFKADEHDSQHYMSEIKSRGSKTLKDIILKSSDEGRPVTSLVYSLLLPWAAKVAREFHI
PCALLWIQPATVLDIYYYYFNGYEDAIKGSTNDPNWCIQLPRLPLLKSQDLPSFLLSSSNEEKY
SFALPTFKEQLDTLDVEENPKVLVNTFDALEPKELKAIEKYNLIGIGPLIPSTFLDGKDPLDSS
FGGDLFQKSNDYIEWLNSKANSSVVYISFGSLLNLSKNQKEEIAKGLIEIKKPFLWVIRDQENG
KGDEKEEKLSCMMELEKQGKIVPWCSQLEVLTHPSIGCFVSHCGWNSTLESLSSGVSVVAFPHW
TDQGTNAKLIEDVWKTGVRLKKNEDGVVESEEIKRCIEMVMDGGEKGEEMRRNAQKWKELAREA
VKEGGSSEMNLKAFVQEVGKGC
```

DNA
Glycosyltransferase (NtGT2)
*Nicotiana tabacum*

SEQ ID NO. 39

```
ATGGTGCAACCCCATGTCCTCTTGGTGACTTTTCCAGCACAAGGCCATATTAATCCATGTCTCC
AATTTGCCAAGAGGCTAATTAGAATGGGCATTGAGGTAACTTTTGCCACGAGCGTTTTCGCCCA
TCGTCGTATGGCAAAAACTACGACTTCCACTCTATCCAAGGGCTTAAATTTTGCGGCATTCTCT
GATGGGTACGACGATGGTTTCAAGGCCGATGAGCATGATTCTCAACATTACATGTCGGAGATAA
```

-continued

```
AAAGTCGCGGTTCTAAAACCCTAAAAGATATCATTTTGAAGAGCTCAGACGAGGGACGTCCTGT

GACATCCCTCGTCTATTCTCTTTTGCTTCCATGGGCTGCAAAGGTAGCGCGTGAATTTCACATA

CCGTGCGCGTTACTATGGATTCAACCAGCAACTGTGCTAGACATATATTATTATTACTTCAATG

GCTATGAGGATGCCATAAAAGGTAGCACCAATGATCCAAATTGGTGTATTCAATTGCCTAGGCT

TCCACTACTAAAAAGCCAAGATCTTCCTTCTTTTTACTTTCTTCTAGTAATGAAGAAAAATAT

AGCTTTGCTCTACCAACATTTAAAGAGCAACTTGACACATTAGATGTTGAAGAAAATCCTAAAG

TACTTGTGAACACATTTGATGCATTAGAGCCAAAGGAACTCAAAGCTATTGAAAAGTACAATTT

AATTGGGATTGGACCATTGATTCCTTCAACATTTTTGGACGGAAAAGACCCTTTGGATTCTTCC

TTTGGTGGTGATCTTTTTCAAAAGTCTAATGACTATATTGAATGGTTGAACTCAAAGGCTAACT

CATCTGTGGTTTATATCTCATTTGGGAGTCTCTTGAATTTGTCAAAAAATCAAAGGAGGAGAT

TGCAAAGGGTTGATAGAGATTAAAAAGCCATTCTTGTGGGTAATAAGAGATCAAGAAAATGGT

AAGGGAGATGAAAAGAAGAGAAATTAAGTTGTATGATGGAGTTGGAAAAGCAAGGGAAAATAG

TACCATGGTGTTCACAACTTGAAGTCTTAACACATCCATCTATAGGATGTTTCGTGTCACATTG

TGGATGGAATTCGACTCTGGAAAGTTTATCGTCAGGCGTGTCAGTAGTGGCATTTCCTCATTGG

ACGGATCAAGGGACAAATGCTAAACTAATTGAAGATGTTTGGAAGACAGGTGTAAGGTTGAAAA

AGAATGAAGATGGTGTGGTTGAGAGTGAAGAGATAAAAAGGTGCATAGAAATGGTAATGGATGG

TGGAGAGAAAGGAGAAGAAATGAGAAGAAATGCTCAAAAATGGAAAGAATTGGCAAGGGAAGCT

GTAAAAGAAGGCGGATCTTCGGAAATGAATCTAAAAGCTTTTGTTCAAGAAGTTGGCAAAGGTT

GCTGA
```

Amino Acid  
THCA Synthase Trichome targeting domain  
*Cannabis*

SEQ ID NO. 40

MNCSAFSFWFVCKIIFFFLSFHIQISIA

Amino Acid  
CBDA Synthase Trichome targeting domain  
*Cannabis*

SEQ ID NO. 41

MKCSTFSFWFVCKIIFFFFSFNIQTSIA

Amino Acid  
THCA Synthase  
*Cannabis*

SEQ ID NO. 42

MNCSAFSFWFVCKIIFFFLSFHIQISIANPRENFLKCFSKHIPNNVANPKLVYTQHDQLYMSIL

NSTIQNLRFISDTTPKPLVIVTPSNNSHIQATILCSKKVGLQIRTRSGGHDAEGMSYISQVPFV

VVDLRNMHSIKIDVHSQTAWVEAGATLGEVYYWINEKNENLSFPGGYCPTVGVGGHFSGGGYGA

LMRNYGLAADNIIDAHLVNVDGKVLDRKSMGEDLFWAIRGGGGENFGIIAAWKIKLVDVPSKST

IFSVKKNMEIHGLVKLFNKWQNIAYKYDKDLVLMTHFITKNITDNHGKNKTTVHGYFSSIFHGG

VDSLVDLMNKSFPELGIKKTDCKEFSWIDTTIFYSGVVNFNTANFKKEILLDRSAGKKTAFSIK

LDYVKKPIPETAMVKILEKLYEEDVGAGMYVLYPYGGIMEEISESAIPFPHRAGIMYELWYTAS

WEKQEDNEKHINWVRSVYNFTTPYVSQNPRLAYLNYRDLDLGKTNHASPNNYTQARIWGEKYFG

KNFNRLVKVKTKVDPNNFFRNEQSIPPLPPHHH

Amino Acid  
MYB8-orthologue for CAN738  
*Humulus lupulus*

SEQ ID NO. 43

MGRAPCCEKVGLKKGRWTSEEDEILTKYIQSNGEGCWRSLPKNAGLLRCGKSCRLRWINYLRAD

LKRGNISSEEEDIIIKLHSTLGNRWSLIASHLPGRTDNEIKNYWNSHLSRKIHTFRRCNNTTTH

HHHLPNLVTVTKVNLPIPKRKGGRTSRLAMKKNKSSTSNQNSSVIKNDVGSSSSTTTTSVHQRT

-continued

```
TTTTPTMDDQQKRQLSRCRLEEKEDQDGASTGTVVMMLGQAAAVGSSCDEDMLGHDQLSFLCCS

EEKTTENSMTNLKENGDHEVSGPYDYDHRYEKETSVDEGMLLCFNDIIDSNLLNPNEVLTLSEE

SLNLGGALMDTTTSTTTNNNNYSLSYNNNGDCVISDDHDQYWLDDVVGVDFWSWESSTTVTQEQ

EQEQEQEQEQEQEQEQEHHHQQDQKKNTWDNEKEKMLALLWDSDNSNWELQDNNNYHKCQEI

TSDKENAMVAWLLS
```

Amino Acid
atMYB12 - orthologue for CAN739
*Arabidopsis thaliana*
SEQ ID NO. 44
```
MGRAPCCEKVGIKRGRWTAEEDQILSNYIQSNGEGSWRSLPKNAGLKRCGKSCRLRWINYLRSD

LKRGNITPEEEELVVKLHSTLGNRWSLIAGHLPGRTDNEIKNYWNSHLSRKLHNFIRKPSISQD

VSAVIMTNASSAPPPPQAKRRLGRTSRSAMKPKIHRTKTRKTKKTSAPPEPNADVAGADKEALM

VESSGAEAELGRPCDYYGDDCNKNLMSINGDNGVLTFDDDIIDLLLDESDPGHLYTNTTCGGDG

ELHNIRDSEGARGFSDTWNQGNLDCLLQSCPSVESFLNYDHQVNDASTDEFIDWDCVWQEGSDN

NLWHEKENPDSMVSWLLDGDDEATIGNSNCENFGEPLDHDDESALVAWLLS
```

Amino Acid
MYB112-orthologue for CAN833
*Arabidopsis thaliana*
SEQ ID NO. 45
```
MNISRTEFANCKTLINHKEEVEEVEKKMEIEIRRGPWTVEEDMKLVSYISLHGEGRWNSLSRSA

GLNRTGKSCRLRWLNYLRPDIRRGDISLQEQFIILELHSRWGNRWSKIAQHLPGRTDNEIKNYW

RTRVQKHAKLLKCDVNSKQFKDTIKHLWMPRLIERIAATQSVQFTSNHYSPENSSVATATSSTS

SSEAVRSSFYGGDQVEFGTLDHMTNGGYWFNGGDTFETLCSFDELNKWLIQ
```

Amino Acid
Cytosolic targeted THCA Synthase (ctTHCAs)
*Cannabis*
SEQ ID NO. 46
```
NPRENFLKCFSKHIPNNVANPKLVYTQHDQLYMSILNSTIQNLRFISDTTPKPLVIVTPSNNSH

IQATILCSKKVGLQIRTRSGGHDAEGMSYISQVPFVVVDLRNMHSIKIDVHSQTAWVEAGATLG

EVYYWINEKNENLSFPGGYCPTVGVGGHFSGGGYGALMRNYGLAADNIIDAHLVNVDGKVLDRK

SMGEDLFWAIRGGGGENFGIIAAWKIKLVDVPSKSTIFSVKKNMEIHGLVKLFNKWQNIAYKYD

KDLVLMTHFITKNITDNHGKNKTTVHGYFSSIFHGGVDSLVDLMNKSFPELGIKKTDCKEFSWI

DTTIFYSGVVNFNTANFKKEILLDRSAGKKTAFSIKLDYVKKPIPETAMVKILEKLYEEDVGAG

MYVLYPYGGIMEEISESAIPFPHRAGIMYELWYTASWEKQEDNEKHINWVRSVYNFTTPYVSQN

PRLAYLNYRDLDLGKTNHASPNNYTQARIWGEKYFGKNFNRLVKVKTKVDPNNFFRNEQSIPPL

PPHHH
```

Amino Acid
Trichome targeted Catalase with THCA Synthase Trichome
targeting domain
*Arabidopsis thaliana*
SEQ ID NO. 47
```
MNCSAFSFWFVCKIIFFFLSFHIQISIAMDPYKYRPASSYNSPFFTTNSGAPVWNNNSSMTVGP

RGLILLEDYHLVEKLANFDRERIPERVVHARGASAKGFFEVTHDISNLTCADFLRAPGVQTPVI

VRFSTVIHARGSPETLRDPRGFAVKFYTREGNFDLVGNNFPVFFIRDGMKFPDIVHALKPNPKS

HIQENWRILDFFSHHPESLNMFTFLFDDIGIPQDYRHMDGSGVNTYMLINKAGKAHYVKFHWKP

TCGVKSLLEEDAIRLGGTNHSHATQDLYDSIAAGNYPEWKLFIQIIDPADEDKFDFDPLDVTKT

WPEDILPLQPVGRMVLNKNIDNFFAENEQLAFCPAIIVPGIHYSDDKLLQTRVFSYADTQRHRL

GPNYLQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQKLAS
```

RLNVRPSI

Amino Acid
Trichome targeted Catalase with CBDA Synthase Trichome
targeting domain
*Arabidopsis thaliana*
SEQ ID NO. 48

MKCSTFSFWFVCKIIFFFFSFNIQTSIAMDPYKYRPASSYNSPFFTTNSGAPVWNNNSSMTVGP

RGLILLEDYHLVEKLANFDRERIPERVVHARGASAKGFFEVTHDISNLTCADFLRAPGVQTPVI

VRFSTVIHARGSPETLRDPRGFAVKFYTREGNFDLVGNNFPVFFIRDGMKFPDIVHALKPNPKS

HIQENWRILDFFSHHPESLNMFTFLFDDIGIPQDYRHMDGSGVNTYMLINKAGKAHYVKFHWKP

TCGVKSLLEEDAIRLGGTNHSHATQDLYDSIAAGNYPEWKLFIQIIDPADEDKFDFDPLDVTKT

WPEDILPLQPVGRMVLNKNIDNFFAENEQLAFCPAIIVPGIHYSDDKLLQTRVFSYADTQRHRL

GPNYLQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQKLAS

RLNVRPSI

Amino Acid
Catalase HPII (KatE) with THCA Synthase Trichome targeting
domain
*Escherichia coli*
SEQ ID NO. 49

MNCSAFSFWFVCKIIFFFLSFHIQISIAMSQHNEKNPHQHQSPLHDSSEAKPGMDSLAPEDGSH

RPAAEPTPPGAQPTAPGSLKAPDTRNEKLNSLEDVRKGSENYALTTNQGVRIADDQNSLRAGSR

GPTLLEDFILREKITHFDHERIPERIVHARGSAAHGYFQPYKSLSDITKADFLSDPNKITPVFV

RFSTVQGGAGSADTVRDIRGFATKFYTEEGIFDLVGNNTPIFFIQDAHKFPDFVHAVKPEPHWA

IPQGQSAHDTFWDYVSLQPETLHNVMWAMSDRGIPRSYRTMEGFGIHTFRLINAEGKATFVRFH

WKPLAGKASLVWDEAQKLTGRDPDFHRRELWEAIEAGDFPEYELGFQLIPEEDEFKFDFDLLDP

TKLIPEELVPVQRVGKMVLNRNPDNFFAENEQAAFHPGHIVPGLDFTNDPLLQGRLFSYTDTQI

SRLGGPNFHEIPINRPTCPYHNFQRDGMHRGIDTNPANYEPNSINDNWPRETPPGPKRGGFES

YQERVEGNKVRERSPSFGEYYSHPRLFWLSQTPFEQRHIVDGFSFELSKVVRPYIRERVVDQLA

HIDLTLAQAVAKNLGIELTDDQLNITPPPDVNGLKKDPSLSLYAIPDGDVKGRVVAILLNDEVR

SADLLAILKALKAKGVHAKLLYSRMGEVTADDGTVLPIAATFAGAPSLTVDAVIVPCGNIADIA

DNGDANYYLMEAYKHLKPIALAGDARKFKATIKIADQGEEGIVEADSADGSFMDELLTLMAAHR

VWSRIPKIDKIPA

Amino Acid
Catalase HPII (KatE) with CBDA Synthase Trichome targeting
domain
*Escherichia coli*
SEQ ID NO. 50

MKCSTFSFWFVCKIIFFFFSFNIQTSIAMSQHNEKNPHQHQSPLHDSSEAKPGMDSLAPEDGSH

RPAAEPTPPGAQPTAPGSLKAPDTRNEKLNSLEDVRKGSENYALTTNQGVRIADDQNSLRAGSR

GPTLLEDFILREKITHFDHERIPERIVHARGSAAHGYFQPYKSLSDITKADFLSDPNKITPVFV

RFSTVQGGAGSADTVRDIRGFATKFYTEEGIFDLVGNNTPIFFIQDAHKFPDFVHAVKPEPHWA

IPQGQSAHDTFWDYVSLQPETLHNVMWAMSDRGIPRSYRTMEGFGIHTFRLINAEGKATFVRFH

WKPLAGKASLVWDEAQKLTGRDPDFHRRELWEAIEAGDFPEYELGFQLIPEEDEFKFDFDLLDP

TKLIPEELVPVQRVGKMVLNRNPDNFFAENEQAAFHPGHIVPGLDFTNDPLLQGRLFSYTDTQI

SRLGGPNFHEIPINRPTCPYHNFQRDGMHRGIDTNPANYEPNSINDNWPRETPPGPKRGGFES

YQERVEGNKVRERSPSFGEYYSHPRLFWLSQTPFEQRHIVDGFSFELSKVVRPYIRERVVDQLA

HIDLTLAQAVAKNLGIELTDDQLNITPPPDVNGLKKDPSLSLYAIPDGDVKGRVVAILLNDEVR

-continued

SADLLAILKALKAKGVHAKLLYSRMGEVTADDGTVLPIAATFAGAPSLTVDAVIVPCGNIADIA

DNGDANYYLMEAYKHLKPIALAGDARKFKATIKIADQGEEGIVEADSADGSFMDELLTLMAAHR

VWSRIPKIDKIPA

Amino Acid
Catalase 1
*Arabidopsis thaliana*
SEQ ID NO. 51

MDPYRVRPSSAHDSPFFTTNSGAPVWNNNSSLTVGTRGPILLEDYHLLEKLANFDRERIP

ERVVHARGASAKGFFEVTHDITQLTSADFLRGPGVQTPVIVRFSTVIHERGSPETLRDPR

GFAVKFYTREGNFDLVGNNFPVFFVRDGMKFPDMVHALKPNPKSHIQENWRILDFFSHHP

ESLHMFSFLFDDLGIPQDYRHMEGAGVNTYMLINKAGKAHYVKFHWKPTCGIKCLSDEEA

IRVGGANHSHATKDLYDSIAAGNYPQWNLFVQVMDPAHEDKFDFDPLDVTKIWPEDILPL

QPVGRLVLNKNIDNFFNENEQIAFCPALVVPGIHYSDDKLLQTRIFSYADSQRHRLGPNY

LQLPVNAPKCAHHNNHHDGFMNFMHRDEEVNYFPSRLDPVRHAEKYPTTPIVCSGNREKC

FIGKENNFKQPGERYRSWDSDRQERFVKRFVEALSEPRVTHEIRSIWISYWSQADKSLGQ

KLATRLNVRPNF

Amino Acid
Catalase 2
*Arabidopsis thaliana*
SEQ ID NO. 52

MDPYKYRPASSYNSPFFTTNSGAPVWNNNSSMTVGPRGPILLEDYHLVEKLANFDRERIP

ERVVHARGASAKGFFEVTHDISNLTCADFLRAPGVQTPVIVRFSTVIHERGSPETLRDPR

GFAVKFYTREGNFDLVGNNFPVFFIRDGMKFPDMVHALKPNPKSHIQENWRILDFFSHHP

ESLNMFTFLFDDIGIPQDYRHMDGSGVNTYMLINKAGKAHYVKFHWKPTCGVKSLLEEDA

IRVGGTNHSHATQDLYDSIAAGNYPEWKLFIQIIDPADEDKFDFDPLDVTKTWPEDILPL

QPVGRMVLNKNIDNFFAENEQLAFCPAIIVPGIHYSDDKLLQTRVFSYADTQRHRLGPNY

LQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQ

KLASRLNVRPSI

Amino Acid
Catalase 3
*Arabidopsis thaliana*
SEQ ID NO. 53

MDPYKYRPSSAYNAPFYTTNGGAPVSNNISSLTIGERGPVLLEDYHLIEKVANFTRERIP

ERVVHARGISAKGFFEVTHDISNLTCADFLRAPGVQTPVIVRFSTVVHERASPETMRDIR

GFAVKFYTREGNFDLVGNNTPVFFIRDGIQFPDVVHALKPNPKTNIQEYWRILDYMSHLP

ESLLTWCWMFDDVGIPQDYRHMEGFGVHTYTLIAKSGKVLFVKFHWKPTCGIKNLTDEEA

KVVGGANHSHATKDLHDAIASGNYPEWKLFIQTMDPADEDKFDFDPLDVTKIWPEDILPL

QPVGRLVLNRTIDNFFNETEQLAFNPGLVVPGIYYSDDKLLQCRIFAYGDTQRHRLGPNY

LQLPVNAPKCAHHNNHHEGFMNFMHRDEEINYYPSKFDPVRCAEKVPTPTNSYTGIRTKC

VIKKENNFKQAGDRYRSWAPDRQDRFVKRWVEILSEPRLTHEIRGIWISYWSQADRSLGQ

KLASRLNVRPSI

DNA
forward primer of CYP3A4
Artificial
SEQ ID NO. 54

TGCCTAATAAAGCTCCTCCTACT

DNA
reverse primer of CYP3A4

-continued

Artificial

SEQ ID NO. 55

GCTCCTGAAACAGTTCCATCTC

DNA
forward primer of P450 oxidoreductase
Artificial

SEQ ID NO. 56

GGAAGAGCTTTGGTTCCTATGT

DNA
reverse primer of P450 oxidoreductase
Artificial

SEQ ID NO. 57

GCTCCCAATTCAGCAACAATATC

DNA
forward primer of CBDA synthase
Artificial

SEQ ID NO. 58

ACATCACAATCACACAAAACTAACAAAAG

DNA
reverse primer of CBDA synthase
Artificial

SEQ ID NO. 59

GGCCATAGTTTCTCATCAATGG

DNA
forward primer of UGT76G1
Artificial

SEQ ID NO. 60

GATTGGAAGAACAAGCTTCAGGATTTCC

DNA
reverse primer of UGT76G1
Artificial

SEQ ID NO. 61

CCATCCTGAATGAGTCCAAAAAGCTC

DNA
forward primer of ABCG2
Artificial

SEQ ID NO. 62

CCTTCAGGATTGTCAGGAGATG

DNA
reverse primer of ABCG2
Artificial

SEQ ID NO. 63

GCAGGTCCATGAAACATCAATC

DNA
forward primer of Trichome-targeted CBDAs
Artificial

SEQ ID NO. 64

AAAGATCAAAAGCAAGTTCTTCACTGT

DNA
reverse primer of Trichome-targeted CBDAs
Artificial

SEQ ID NO. 65

CCATGCAGTTTGGCTATGAACATCT

DNA
forward primer of Trichome-targeted UGT
Artificial

SEQ ID NO. 66

AGTGCTCAACATTCTCCTTTTGGTT

DNA
reverse primer of Trichome-targeted UGT
Artificial

SEQ ID NO. 67

TCTGAAGCCAACATCAACAATTCCA

DNA
forward primer of Plasma membrane-targeted UTR1
Artificial

SEQ ID NO. 68

TTGTTCCTTAAACCTCGCCTTTGAC

DNA
reverse primer of Plasma membrane-targeted UTR1
Artificial
SEQ ID NO. 69
TCATTATGGAGCACTCCACTCTCTG DNA
forward primer of Cytosolic-targeted CBDA synthase
Artificial
SEQ ID NO. 70
AAAGATCAAAAGCAAGTTCTTCACTGT DNA
reverse primer of Cytosolic-targeted CBDA synthase
Artificial
SEQ ID NO. 71
ATAAACTTCTCCAAGGGTAGCTCCG DNA
forward primer of Cytosolic-targeted UGT
Artificial
SEQ ID NO. 72
AGAACTGGAAGAATCCGAACTGGAA DNA
reverse primer of Cytosolic-targeted UGT
Artificial
SEQ ID NO. 73
AAATCATCGGGACACCTTCACAAAC DNA
tonoplast targeting sequence
*Arabidopsis thaliana*
SEQ ID NO. 74
TGCTCCATAATGAACTTAATGTGTGGGTCTACCTGCGCCGCT

---

What is claimed is:

1. A method for producing water-soluble cannabinoids in a trichome comprising:
   1) introducing into a *Cannabis* plant a first nucleotide sequence, operably linked to a promoter, encoding a fusion peptide having a first domain and a second domain, wherein said first domain comprises a N-terminal cannabinoid synthase trichome targeting domain, and said second domain comprises a glycosyltransferase enzyme, and wherein said glycosyltransferase enzyme is not endogenous to *Cannabis*, and is selected from the group consisting of: nucleotide sequence according to SEQ ID NO's. 7, 24, 27, 29, 31, 33, 35, 37, and 39;
   2) introducing into the *Cannabis* plant a second nucleotide sequence, operably linked to a promoter, encoding a heterologous UDP-galactose/UDP-glucose transporter having a plasma membrane targeting sequence configured to facilitate the transport of UDP-glucose to the trichome of the *Cannabis* plant where it is used as a substrate for said glycosyltransferase enzyme, and wherein said plasma membrane targeting sequence replaces or disrupts the tonoplast targeting sequence of the UDP-galactose/UDP-glucose transporter; and
   wherein said N-terminal cannabinoid synthase trichome targeting domain is selected from the group consisting of: an N-terminal cannabidiolic acid (CBDA) synthase trichome targeting sequence; an N-terminal cannabigerolic acid (CBGA) synthase trichome targeting domain; an N-terminal cannabichromenic acid (CBCA) synthase trichome targeting domain; and an N-terminal tetrahydrocannabinolic acid (THCA) synthase trichome targeting domain.

2. The method of claim 1 wherein the first domain of said fusion peptide is selected from the group consisting of: the amino acid sequence identified as SEQ ID NO. 40, and the amino acid sequence identified as SEQ ID NO. 41.

3. The method of claim 1 wherein said fusion peptide comprises nucleotide sequence SEQ ID NO. 19.

4. The method of claim 1 wherein said plasma membrane targeting sequence comprises the nucleotide sequence according to SEQ ID NO. 74.

5. The method of claim 1 wherein said heterologous UDP-galactose/UDP-glucose transporter having a plasma membrane targeting sequence comprises the nucleotide sequence according to SEQ ID NO. 21.

\* \* \* \* \*

SEQUENCE LISTING

<160> NUMBER OF SEQ ID NOS: 74

<210> SEQ ID NO 1
<211> LENGTH: 1509
<212> TYPE: DNA
<213> ORGANISM: Homo sapien

<400> SEQUENCE: 1

```
atggctttga ttcctgattt ggctatggaa actagattgt tgttggctgt ttcattggtt      60
ttgttgtatt tgtatggaac tcattcacat ggattgttta aaaaattggg aattcctgga     120
cctactcctt tgccttttttt gggaaatatt ttgtcatatc ataaaggatt ttgcatgttt    180
gatatggaat gccataaaaa atatggaaaa gtttggggat tttatgatgg acaacaacct    240
gttttggcta ttactgatcc tgatatgatt aaaactgttt tggttaaaga atgctattca    300
gtttttacta atagaagacc ttttggacct gttggattta tgaaatcagc tatttcaatt    360
gctgaagatg aagaatggaa aagattgaga tcattgttgt cacctacttt tacttcagga    420
aaattgaaag aaatggttcc tattattgct caatatggag atgttttggt tagaaatttg    480
agaagagaag ctgaaactgg aaaacctgtt actttgaaag atgtttttgg agcttattca    540
atggatgtta ttacttcaac ttcatttgga gttaatattg attcattgaa taatcctcaa    600
gatccttttg ttgaaaatac taaaaaattg ttgagatttg attttttgga tccttttttt    660
ttgtcaatta ctgttttttcc ttttttgatt cctatttttgg aagttttgaa tatttgcgtt    720
tttcctagag aagttactaa ttttttgaga aaatcagtta aagaatgaa agaatcaaga    780
ttggaagata ctcaaaaaca tagagttgat tttttgcaat tgatgattga ttcacaaaat    840
tcaaaagaaa ctgaatcaca taaagctttg tcagatttgg aattggttgc tcaatcaatt    900
```

```
attttttattt ttgctggatg cgaaactact tcatcagttt tgtcatttat tatgtatgaa    960
ttggctactc atcctgatgt tcaacaaaaa ttgcaagaag aaattgatgc tgttttgcct   1020
aataaagctc ctcctactta tgatactgtt ttgcaaatgg aatatttgga tatggttgtt   1080
aatgaaactt tgagattgtt tcctattgct atgagattgg aaagagtttg caaaaaagat   1140
gttgaaatta atggaatgtt tattcctaaa ggagttgttg ttatgattcc ttcatatgct   1200
ttgcatagag atcctaaata ttggactgaa cctgaaaaat ttttgcctga agatttttca   1260
aaaaaaaata agataatat tgatccttat atttatactc ttttggatc aggacctaga   1320
aattgcattg gaatgagatt tgctttgatg aatatgaaat tggctttgat tagagttttg   1380
caaattttt catttaaacc ttgcaaagaa actcaaattc ctttgaaatt gtcattggga   1440
ggattgttgc aacctgaaaa acctgttgtt ttgaaagttg aatcaagaga tggaactgtt   1500
tcaggagct                                                          1509
```

<210> SEQ ID NO 2
<211> LENGTH: 503
<212> TYPE: PRT
<213> ORGANISM: Homo sapien

<400> SEQUENCE: 2

```
Met Ala Leu Ile Pro Asp Leu Ala Met Glu Thr Arg Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Leu Ser Ile Thr
    210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255
```

Lys Glu Ser Arg Leu Glu Asp Thr Gln Lys His Arg Val Asp Phe Leu
            260                 265                 270

Gln Leu Met Ile Asp Ser Gln Asn Ser Lys Glu Thr Glu Ser His Lys
        275                 280                 285

Ala Leu Ser Asp Leu Glu Leu Val Ala Gln Ser Ile Ile Phe Ile Phe
    290                 295                 300

Ala Gly Cys Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
    370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
        435                 440                 445

Leu Met Asn Met Lys Leu Ala Leu Ile Arg Val Leu Gln Asn Phe Ser
    450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
            500

<210> SEQ ID NO 3
<211> LENGTH: 2040
<212> TYPE: DNA
<213> ORGANISM: Homo sapien

<400> SEQUENCE: 3
atgattaata tgggagattc acatgttgat acttcatcaa ctgtttcaga agctgttgct      60
gaagaagttt cattgttttc aatgactgat atgatttttgt tttcattgat tgttggattg     120
ttgacttatt ggttttttgtt tagaaaaaaa aaagaagaag ttcctgaatt tactaaaatt    180
caaactttga cttcatcagt tagagaatca tcatttgttg aaaaaatgaa aaaaactgga     240
agaaatatta ttgttttttta tggatcacaa actggaactg ctgaagaatt tgctaataga   300
ttgtcaaaag atgctcatag atatggaatg agaggaatgt cagctgatcc tgaagaatat   360
gatttggctg atttgtcatc attgcctgaa attgataatg ctttggttgt ttttttgcatg   420 gctacttatg gagaaggaga tcctactgat aatgctcaag atttttatga ttggttgcaa    480
gaaactgatg ttgatttgtc aggagttaaa tttgctgtttt ttggattggg aaataaaact    540
tatgaacatt ttaatgctat gggaaaatat gttgataaaa gattggaaca attgggagct   600
caaagaattt ttgaattggg attgggagat gatgatggaa atttggaaga agatttttatt    660 acttggagag aacaattttg gttggctgtt tgcgaacatt ttggagttga agctactgga   720

```
gaagaatcat caattagaca atatgaattg gttgttcata ctgatattga tgctgctaaa    780
gtttatatgg gagaaatggg aagattgaaa tcatatgaaa atcaaaaacc tcctttgat     840
gctaaaaatc cttttttggc tgctgttact actaatagaa aattgaatca aggaactgaa    900
agacatttga tgcatttgga attggatatt tcagattcaa aaattagata tgaatcagga    960
gatcatgttg ctgtttatcc tgctaatgat tcagctttgg ttaatcaatt gggaaaaatt   1020
ttgggagctg atttggatgt tgttatgtca ttgaataatt tggatgaaga atcaaataaa   1080
aaacatcctt ttccttgccc tacttcatat agaactgctt tgacttatta tttggatatt   1140
actaatcctc ctagaactaa tgttttgtat gaattggctc aatatgcttc agaaccttca   1200
gaacaagaat tgttgagaaa atggcttca tcatcaggag aaggaaaaga attgtatttg    1260
tcatggggttg ttgaagctag aagacatatt ttggctattt tgcaagattg cccttcattg   1320
agacctccta ttgatcattt gtgcgaattg ttgcctagat tgcaagctag atattattca   1380
attgcttcat catcaaaagt tcatcctaat tcagttcata tttgcgctgt tgttgttgaa   1440
tatgaaacta aagctggaag aattaataaa ggagttgcta ctaattggtt gagagctaaa   1500
gaacctgttg agaaaatgg aggaagagct ttggttccta tgtttgttag aaaatcacaa    1560
tttagattgc ctttaaagc tactactcct gttattatgg ttggacctgg aactggagtt    1620
gctcctttta ttggatttat tcaagaaaga gcttggttga caacaagg aaaagaagtt     1680
ggagaaactt tgttgtatta tggatgcaga agatcagatg aagattattt gtatagagaa   1740
gaattggctc aatttcatag agatggagct ttgactcaat tgaatgttgc tttttcaaga   1800
gaacaatcac ataaagttta tgttcaacat ttgttgaaac aagatagaga acatttgtgg   1860
aaattgattg aaggaggagc tcatatttat gtttgcggag atgctagaaa tatggctaga   1920
gatgttcaaa atactttta tgatattgtt gctgaattgg gagctatgga acatgctcaa   1980
gctgttgatt atattaaaaa attgatgact aaaggaagat attcattgga tgtttggtca   2040
```

<210> SEQ ID NO 4
<211> LENGTH: 680
<212> TYPE: PRT
<213> ORGANISM: Homo sapien

<400> SEQUENCE: 4

```
Met Ile Asn Met Gly Asp Ser His Val Asp Thr Ser Ser Thr Val Ser
1               5                   10                  15

Glu Ala Val Ala Glu Glu Val Ser Leu Phe Ser Met Thr Asp Met Ile
            20                  25                  30

Leu Phe Ser Leu Ile Val Gly Leu Leu Thr Tyr Trp Phe Leu Phe Arg
        35                  40                  45

Lys Lys Lys Glu Glu Val Pro Glu Phe Thr Lys Ile Gln Thr Leu Thr
    50                  55                  60

Ser Ser Val Arg Glu Ser Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
            100                 105                 110

Met Ser Ala Asp Pro Glu Glu Tyr Asp Leu Ala Asp Leu Ser Ser Leu
        115                 120                 125

Pro Glu Ile Asp Asn Ala Leu Val Val Phe Cys Met Ala Thr Tyr Gly
    130                 135                 140
```

```
Glu Gly Asp Pro Thr Asp Asn Ala Gln Asp Phe Tyr Asp Trp Leu Gln
145                 150                 155                 160

Glu Thr Asp Val Asp Leu Ser Gly Val Lys Phe Ala Val Phe Gly Leu
            165                 170                 175

Gly Asn Lys Thr Tyr Glu His Phe Asn Ala Met Gly Lys Tyr Val Asp
            180                 185                 190

Lys Arg Leu Glu Gln Leu Gly Ala Gln Arg Ile Phe Glu Leu Gly Leu
        195                 200                 205

Gly Asp Asp Asp Gly Asn Leu Glu Glu Asp Phe Ile Thr Trp Arg Glu
210                 215                 220

Gln Phe Trp Leu Ala Val Cys Glu His Phe Gly Val Glu Ala Thr Gly
225                 230                 235                 240

Glu Glu Ser Ser Ile Arg Gln Tyr Glu Leu Val Val His Thr Asp Ile
            245                 250                 255

Asp Ala Ala Lys Val Tyr Met Gly Glu Met Gly Arg Leu Lys Ser Tyr
            260                 265                 270

Glu Asn Gln Lys Pro Pro Phe Asp Ala Lys Asn Pro Phe Leu Ala Ala
        275                 280                 285

Val Thr Thr Asn Arg Lys Leu Asn Gln Gly Thr Glu Arg His Leu Met
290                 295                 300

His Leu Glu Leu Asp Ile Ser Asp Ser Lys Ile Arg Tyr Glu Ser Gly
305                 310                 315                 320

Asp His Val Ala Val Tyr Pro Ala Asn Asp Ser Ala Leu Val Asn Gln
            325                 330                 335

Leu Gly Lys Ile Leu Gly Ala Asp Leu Asp Val Val Met Ser Leu Asn
            340                 345                 350

Asn Leu Asp Glu Glu Ser Asn Lys Lys His Pro Phe Pro Cys Pro Thr
        355                 360                 365

Ser Tyr Arg Thr Ala Leu Thr Tyr Tyr Leu Asp Ile Thr Asn Pro Pro
370                 375                 380

Arg Thr Asn Val Leu Tyr Glu Leu Ala Gln Tyr Ala Ser Glu Pro Ser
385                 390                 395                 400

Glu Gln Glu Leu Leu Arg Lys Met Ala Ser Ser Gly Glu Gly Lys
            405                 410                 415

Glu Leu Tyr Leu Ser Trp Val Val Glu Ala Arg Arg His Ile Leu Ala
            420                 425                 430

Ile Leu Gln Asp Cys Pro Ser Leu Arg Pro Pro Ile Asp His Leu Cys
        435                 440                 445

Glu Leu Leu Pro Arg Leu Gln Ala Arg Tyr Tyr Ser Ile Ala Ser Ser
        450                 455                 460

Ser Lys Val His Pro Asn Ser Val His Ile Cys Ala Val Val Val Glu
465                 470                 475                 480

Tyr Glu Thr Lys Ala Gly Arg Ile Asn Lys Gly Val Ala Thr Asn Trp
            485                 490                 495

Leu Arg Ala Lys Glu Pro Val Gly Glu Asn Gly Arg Ala Leu Val
        500                 505                 510

Pro Met Phe Val Arg Lys Ser Gln Phe Arg Leu Pro Phe Lys Ala Thr
        515                 520                 525

Thr Pro Val Ile Met Val Gly Pro Gly Thr Gly Val Ala Pro Phe Ile
        530                 535                 540

Gly Phe Ile Gln Glu Arg Ala Trp Leu Arg Gln Gln Gly Lys Glu Val
545                 550                 555                 560
```

```
Gly Glu Thr Leu Leu Tyr Tyr Gly Cys Arg Arg Ser Asp Glu Asp Tyr
                565                 570                 575

Leu Tyr Arg Glu Glu Leu Ala Gln Phe His Arg Asp Gly Ala Leu Thr
        580                 585                 590

Gln Leu Asn Val Ala Phe Ser Arg Glu Gln Ser His Lys Val Tyr Val
    595                 600                 605

Gln His Leu Leu Lys Gln Asp Arg Glu His Leu Trp Lys Leu Ile Glu
610                 615                 620

Gly Gly Ala His Ile Tyr Val Cys Gly Asp Ala Arg Asn Met Ala Arg
625                 630                 635                 640

Asp Val Gln Asn Thr Phe Tyr Asp Ile Val Ala Glu Leu Gly Ala Met
                645                 650                 655

Glu His Ala Gln Ala Val Asp Tyr Ile Lys Lys Leu Met Thr Lys Gly
                660                 665                 670

Arg Tyr Ser Leu Asp Val Trp Ser
        675                 680

<210> SEQ ID NO 5
<211> LENGTH: 1554
<212> TYPE: DNA
<213> ORGANISM: Cannabis sativa

<400> SEQUENCE: 5
```

| | | | | | |
|---|---|---|---|---|---|
| atgaatcctc | gagaaaactt | ccttaaatgc | ttctcgcaat | atattcccaa | taatgcaaca | 60 |
| aatctaaaac | tcgtatacac | tcaaaacaac | ccattgtata | tgtctgtcct | aaattcgaca | 120 |
| atacacaatc | ttagattcac | ctctgacaca | accccaaaac | cacttgttat | cgtcactcct | 180 |
| tcacatgtct | ctcatatcca | aggcactatt | ctatgctcca | agaaagttgg | cttgcagatt | 240 |
| cgaactcgaa | gtggtggtca | tgattctgag | ggcatgtcct | acatatctca | agtcccattt | 300 |
| gttatagtag | acttgagaaa | catgcgttca | atcaaaatag | atgttcatag | ccaaactgca | 360 |
| tgggttgaag | ccggagctac | ccttggagaa | gtttattatt | gggttaatga | aaaaatgag | 420 |
| aatcttagtt | tggcggctgg | gtattgccct | actgtttgcg | caggtggaca | ctttggtgga | 480 |
| ggaggctatg | gaccattgat | gagaaactat | ggcctcgcgg | ctgataatat | cattgatgca | 540 |
| cacttagtca | acgttcatgg | aaaagtgcta | gatcgaaaat | ctatggggga | agatctcttt | 600 |
| tgggctttac | gtggtggtgg | agcagaaagc | ttcggaatca | ttgtagcatg | gaaaattaga | 660 |
| ctggttgctg | tcccaaagtc | tactatgttt | agtgttaaaa | agatcatgga | gatacatgag | 720 |
| cttgtcaagt | tagttaacaa | atggcaaaat | attgcttaca | gtatgacaa | agatttatta | 780 |
| ctcatgactc | acttcataac | taggaacatt | acagataatc | aagggaagaa | taagacagca | 840 |
| atacacactt | acttctcttc | agttttcctt | ggtggagtgg | atagtctagt | cgacttgatg | 900 |
| aacaagagtt | ttcctgagtt | gggtattaaa | aaaacggatt | gcagacaatt | gagctggatt | 960 |
| gatactatca | tcttctatag | tggtgttgta | aattacgaca | ctgataattt | taacaaggaa | 1020 |
| attttgcttg | atagatccgc | tgggcagaac | ggtgctttca | agattaagtt | agactacgtt | 1080 |
| aagaaaccaa | ttccagaatc | tgtatttgtc | caaattttgg | aaaaattata | tgaagaagat | 1140 |
| ataggagctg | gatgtatgc | gttgtaccct | tacggtggta | aatggatga | gatttcagaa | 1200 |
| tcagcaattc | cattccctca | tcgagctgga | atcttgtatg | agttatggta | catatgtagt | 1260 |
| tgggagaagc | aagaagataa | cgaaaagcat | ctaaactgga | ttagaaatat | ttataacttc | 1320 |
| atgactcctt | atgtgtccaa | aaattcaaga | ttggcatatc | tcaattatag | agaccttgat | 1380 |
| ataggaataa | atgatcccaa | gaatccaaat | aattacacac | aagcacgtat | ttgggggtgag | 1440 | aagtattttg gtaaaaattt tgacaggcta gtaaaagtga aaaccctggt tgatcccaat    1500 aactttttta gaaacgaaca aagcatccca cctcaaccac ggcatcgtca ttaa          1554

<210> SEQ ID NO 6
<211> LENGTH: 517
<212> TYPE: PRT
<213> ORGANISM: Cannabis sativa

<400> SEQUENCE: 6

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350
```

```
Phe Lys Ile Lys Leu Asp Tyr Val Lys Lys Pro Ile Pro Glu Ser Val
            355                 360                 365
Phe Val Gln Ile Leu Glu Lys Leu Tyr Glu Glu Asp Ile Gly Ala Gly
        370                 375                 380
Met Tyr Ala Leu Tyr Pro Tyr Gly Gly Ile Met Asp Glu Ile Ser Glu
385                 390                 395                 400
Ser Ala Ile Pro Phe Pro His Arg Ala Gly Ile Leu Tyr Glu Leu Trp
                405                 410                 415
Tyr Ile Cys Ser Trp Glu Lys Gln Glu Asp Asn Glu Lys His Leu Asn
            420                 425                 430
Trp Ile Arg Asn Ile Tyr Asn Phe Met Thr Pro Tyr Val Ser Lys Asn
        435                 440                 445
Ser Arg Leu Ala Tyr Leu Asn Tyr Arg Asp Leu Asp Ile Gly Ile Asn
    450                 455                 460
Asp Pro Lys Asn Pro Asn Asn Tyr Thr Gln Ala Arg Ile Trp Gly Glu
465                 470                 475                 480
Lys Tyr Phe Gly Lys Asn Phe Asp Arg Leu Val Lys Val Lys Thr Leu
                485                 490                 495
Val Asp Pro Asn Asn Phe Phe Arg Asn Glu Gln Ser Ile Pro Pro Gln
            500                 505                 510
Pro Arg His Arg His
        515

<210> SEQ ID NO 7
<211> LENGTH: 1374
<212> TYPE: DNA
<213> ORGANISM: Stevia rebaudiana

<400> SEQUENCE: 7
atggaaaata aaactgaaac tactgttaga agaagaagaa gaattatttt gtttcctgtt      60
ccttttcaag gacatattaa tcctattttg caattggcta atgttttgta ttcaaaagga     120
ttttcaatta ctattttca tactaatttt aataaaccta aaacttcaaa ttatcctcat     180
tttactttta gatttatttt ggataatgat cctcaagatg aaagaatttc aaatttgcct     240
actcatggac ctttggctgg aatgagaatt cctattatta tgaacatgg agctgatgaa     300 ttgagaagag aattggaatt gttgatgttg gcttcagaag aagatgaaga gtttcatgc     360 ttgattactg atgctttgtg gtattttgct caatcagttg ctgattcatt gaatttgaga     420
agattggttt tgatgacttc atcattgttt aattttcatg ctcatgtttc attgcctcaa     480
tttgatgaat gggatatttt ggatcctgat gataaaacta gattggaaga caagcttca     540 ggatttccta tgttgaaagt taaagatatt aaatcagctt attcaaattg gcaaattttg     600
aaagaaattt gggaaaaat gattaaacaa actagagctt catcaggagt tatttggaat     660
tcatttaaag aattggaaga atcagaattg gaaactgtta ttagagaaat tcctgctcct     720
tcatttttga ttcctttgcc taaacatttg actgcttcat catcatcatt gttggatcat     780
gatagaactg tttttcaatg gttggatcaa caacctcctt catcagtttt gtatgtttca     840
tttggatcaa cttcagaagt tgatgaaaaa gatttttgg aaattgctag aggattggt     900 gattcaaaac aatcattttt gtgggttgtt agacctggat tgttaaagg atcaacttgg     960 gttgaacctt tgcctgatgg atttttggga gaaagaggaa gaattgttaa atgggttcct    1020
caacaagaag tttggctca tggagctatt ggagcttttt ggactcattc aggatggaat    1080
tcaactttgg aatcagtttg cgaaggagtt cctatgattt tttcagattt tggattggat    1140
```

```
caacctttga atgctagata tatgtcagat gttttgaaag ttggagttta tttggaaaat    1200
ggatgggaaa gaggagaaat tgctaatgct attagaagag ttatggttga tgaagaagga    1260
gaatatatta gacaaaatgc tagagttttg aaacaaaaag ctgatgtttc attgatgaaa    1320
ggaggatcat catatgaatc attggaatca ttggtttcat atatttcatc attg           1374
```

<210> SEQ ID NO 8
<211> LENGTH: 458
<212> TYPE: PRT
<213> ORGANISM: Stevia rebaudiana

<400> SEQUENCE: 8

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
        20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Arg Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335
```

```
Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 9
<211> LENGTH: 1965
<212> TYPE: DNA
<213> ORGANISM: Homo sapien

<400> SEQUENCE: 9
atgtcatcat caaatgttga agtttttatt cctgtttcac aaggaaatac taatggattt          60
cctgctactg cttcaaatga tttgaaagct tttactgaag gagctgtttt gtcatttcat         120
aatatttgct atagagttaa attgaaatca ggattttgc cttgcagaaa acctgttgaa          180
aaagaaattt tgtcaaatat taatggaatt atgaaacctg gattgaatgc tattttggga         240
cctactggag gaggaaaatc atcattgttg atgttttgg ctgctagaaa agatccttca          300
ggattgtcag gagatgtttt gattaatgga gctcctagac tgctaatttt aaatgcaat          360 tcaggatatg ttgttcaaga tgatgttgtt atgggaactt tgactgttag agaaaatttg         420
caattttcag ctgctttgag attggctact actatgacta atcatgaaaa aaatgaaaga         480
attaatagag ttattcaaga attgggattg ataaagttg ctgattcaaa agttggaact          540
caatttatta gaggagtttc aggaggagaa agaaaaagaa cttcaattgg aatggaattg         600
attactgatc cttcaatttt tgttttggat gaacctacta ctggattgga ttcatcaact         660
gctaatgctg ttttgttgtt gttgaaaaga atgtcaaaac aaggaagaac tattattttt         720
tcaattcatc aacctagata ttcaattttt aaattgtttg attcattgac tttgttggct         780
tcaggaagat tgatgtttca tggacctgct caagaagctt tgggatattt tgaatcagct         840
ggatatcatt gcgaagctta taataatcct gctgattttt ttttggatat tattaatgga         900
gattcaactg ctgttgcttt gaatagagaa gaagatttta agctactga aattattgaa          960 ccttcaaaac aagataaacc tttgattgaa aaattggctg aaatttatgt taattcatca        1020
ttttataaag aaactaaagc tgaattgcat caattgtcag gaggagaaaa aaaaaaaaaa        1080
attactgttt ttaaagaaat ttcatatact acttcatttt gccatcaatt gagatgggtt        1140
tcaaaaagat catttaaaaa tttgttggga atcctcaag cttcaattgc tcaaattatt         1200
gttactgttg ttttgggatt ggttattgga gctatttatt tggattgaa aaatgattca         1260 actggaattc aaaatagagc tggagttttg tttttttga ctactaatca atgcttttca         1320
tcagtttcag ctgttgaatt gtttgttgtt gaaaaaaat tgtttattca tgaatatatt         1380
tcaggatatt atagagtttc atcatatttt ttgggaaaat tgttgtcaga tttgttgcct        1440
```

```
atgagaatgt tgccttcaat tatttttact tgcattgttt atttatgtt gggattgaaa    1500 gctaaagctg atgcttttt tgttatgatg tttactttga tgatggttgc ttattcagct    1560
tcatcaatgg ctttggctat tgctgctgga caatcagttg tttcagttgc tactttgttg    1620
atgactattt gctttgtttt tatgatgatt ttttcaggat tgttggttaa tttgactact    1680
attgcttcat ggttgtcatg gttgcaatat ttttcaattc ctagatatgg atttactgct    1740
ttgcaacata atgaatttt gggacaaaat ttttgccctg gattgaatgc tactggaaat     1800
aatccttgca attatgctac ttgcactgga gaagaatatt tggttaaaca aggaattgat    1860 ttgtcaccttt ggggattgtg gaaaaatcat gttgctttgg cttgcatgat tgttattttt   1920
ttgactattg cttatttgaa attgttgttt ttgaaaaaat attca                    1965

<210> SEQ ID NO 10
<211> LENGTH: 655
<212> TYPE: PRT
<213> ORGANISM: Homo sapien

<400> SEQUENCE: 10

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
```

-continued

```
                      275                 280                 285
Asn Pro Ala Asp Phe Phe Leu Asp Ile Ile Asn Gly Asp Ser Thr Ala
    290                 295                 300
Val Ala Leu Asn Arg Glu Glu Asp Phe Lys Ala Thr Glu Ile Ile Glu
305                 310                 315                 320
Pro Ser Lys Gln Asp Lys Pro Leu Ile Glu Lys Leu Ala Glu Ile Tyr
                325                 330                 335
Val Asn Ser Ser Phe Tyr Lys Glu Thr Lys Ala Glu Leu His Gln Leu
                340                 345                 350
Ser Gly Gly Glu Lys Lys Lys Ile Thr Val Phe Lys Glu Ile Ser
                355                 360                 365
Tyr Thr Thr Ser Phe Cys His Gln Leu Arg Trp Val Ser Lys Arg Ser
    370                 375                 380
Phe Lys Asn Leu Leu Gly Asn Pro Gln Ala Ser Ile Ala Gln Ile Ile
385                 390                 395                 400
Val Thr Val Val Leu Gly Leu Val Ile Gly Ala Ile Tyr Phe Gly Leu
                405                 410                 415
Lys Asn Asp Ser Thr Gly Ile Gln Asn Arg Ala Gly Val Leu Phe Phe
                420                 425                 430
Leu Thr Thr Asn Gln Cys Phe Ser Ser Val Ser Ala Val Glu Leu Phe
                435                 440                 445
Val Val Glu Lys Lys Leu Phe Ile His Glu Tyr Ile Ser Gly Tyr Tyr
    450                 455                 460
Arg Val Ser Ser Tyr Phe Leu Gly Lys Leu Leu Ser Asp Leu Leu Pro
465                 470                 475                 480
Met Arg Met Leu Pro Ser Ile Ile Phe Thr Cys Ile Val Tyr Phe Met
                485                 490                 495
Leu Gly Leu Lys Ala Lys Ala Asp Ala Phe Phe Val Met Met Phe Thr
                500                 505                 510
Leu Met Met Val Ala Tyr Ser Ala Ser Ser Met Ala Leu Ala Ile Ala
                515                 520                 525
Ala Gly Gln Ser Val Val Ser Val Ala Thr Leu Leu Met Thr Ile Cys
    530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
                565                 570                 575
Gly Phe Thr Ala Leu Gln His Asn Glu Phe Leu Gly Gln Asn Phe Cys
                580                 585                 590
Pro Gly Leu Asn Ala Thr Gly Asn Asn Pro Cys Asn Tyr Ala Thr Cys
                595                 600                 605
Thr Gly Glu Glu Tyr Leu Val Lys Gln Gly Ile Asp Leu Ser Pro Trp
                610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
                645                 650                 655
```

<210> SEQ ID NO 11
<211> LENGTH: 1074
<212> TYPE: DNA
<213> ORGANISM: Cannabis

<400> SEQUENCE: 11

-continued

```
atgaagaaga acaaatcaac tagtaataat aagaacaaca acagtaataa tatcatcaaa      60
aacgacatcg tatcatcatc atcatcaaca acaacaacat catcaacaac tacagcaaca     120
tcatcatttc ataatgagaa agttactgtc agtactgatc atattattaa tcttgatgat     180
aagcagaaac gacaattatg tcgttgtcgt ttagaaaaag aagaagaaga agaaggaagt     240
ggtggttgtg gtgagacagt agtaatgatg ctagggtcag tatctcctgc tgctgctact     300
gctgctgcag ctgggggctc atcaagttgt gatgaagaca tgttgggtgg tcatgatcaa     360
ctgttgttgt gtgttgttc tgagaaaaaa acgacagaaa tttcatcagt ggtgaacttt     420
aataataata ataataataa taaggaaaat ggtgacgaag tttcaggacc gtacgattat     480
catcatcata agaagagga agaagaagaa gaagaagatg aagcatctgc atcagtagca     540
gctgttgatg aagggatgtt gttgtgcttt gatgacataa tagatagcca cttgctaaat     600
ccaaatgagg ttttgacttt aagagaagat agccataatg aaggtggggc agctgatcag     660
attgacaaga ctacttgtaa taatactact attactacta tgatgattta taacaataac     720
ttgatgatgt tgagctgcaa taataacgga gattatgtta ttagtgatga tcatgatgat     780
cagtactgga tagacgacgt cgttggagtt gacttttgga gttgggagag ttcgactact     840
actgttatta cccaagaaca agaacaagaa caagatcaag ttcaagaaca gaagaatatg     900
tgggataatg agaaagagaa actgttgtct ttgctatggg ataatagtga taacagcagc     960
agttgggagt tacaagataa aagcaataat aataataata ataatgttcc taacaaatgt    1020
caagagatta cctctgataa agaaaatgct atggttgcat ggcttctctc ctga          1074
```

<210> SEQ ID NO 12
<211> LENGTH: 357
<212> TYPE: PRT
<213> ORGANISM: Cannabis

<400> SEQUENCE: 12

```
Met Lys Lys Asn Lys Ser Thr Ser Asn Lys Asn Asn Asn Ser Asn
1               5                   10                  15

Asn Ile Ile Lys Asn Asp Ile Val Ser Ser Ser Ser Thr Thr Thr
                20                  25                  30

Thr Ser Ser Thr Thr Thr Ala Thr Ser Ser Phe His Asn Glu Lys Val
            35                  40                  45

Thr Val Ser Thr Asp His Ile Ile Asn Leu Asp Lys Gln Lys Arg
    50                  55                  60

Gln Leu Cys Arg Cys Arg Leu Glu Lys Glu Glu Glu Glu Gly Ser
65                  70                  75                  80

Gly Gly Cys Gly Glu Thr Val Val Met Met Leu Gly Ser Val Ser Pro
                85                  90                  95

Ala Ala Ala Thr Ala Ala Ala Gly Gly Ser Ser Cys Asp Glu
                100                 105                 110

Asp Met Leu Gly Gly His Asp Gln Leu Leu Leu Cys Cys Ser Glu
                115                 120                 125

Lys Lys Thr Thr Glu Ile Ser Ser Val Val Asn Phe Asn Asn Asn
130                 135                 140

Asn Asn Asn Lys Glu Asn Gly Asp Glu Val Ser Gly Pro Tyr Asp Tyr
145                 150                 155                 160

His His His Lys Glu Glu Glu Glu Glu Glu Asp Glu Ala Ser
                165                 170                 175

Ala Ser Val Ala Ala Val Asp Glu Gly Met Leu Leu Cys Phe Asp Asp
                180                 185                 190
```

Ile Ile Asp Ser His Leu Leu Asn Pro Asn Glu Val Leu Thr Leu Arg
        195                 200                 205

Glu Asp Ser His Asn Glu Gly Gly Ala Ala Asp Gln Ile Asp Lys Thr
    210                 215                 220

Thr Cys Asn Asn Thr Thr Ile Thr Thr Asn Asp Asp Tyr Asn Asn
225                 230                 235                 240

Leu Met Met Leu Ser Cys Asn Asn Asn Gly Asp Tyr Val Ile Ser Asp
                245                 250                 255

Asp His Asp Asp Gln Tyr Trp Ile Asp Val Val Gly Val Asp Phe
                260                 265                 270

Trp Ser Trp Glu Ser Ser Thr Thr Thr Val Ile Thr Gln Glu Gln Glu
            275                 280                 285

Gln Glu Gln Asp Gln Val Gln Glu Gln Lys Asn Met Trp Asp Asn Glu
    290                 295                 300

Lys Glu Lys Leu Leu Ser Leu Leu Trp Asp Asn Ser Asp Asn Ser Ser
305                 310                 315                 320

Ser Trp Glu Leu Gln Asp Lys Ser Asn Asn Asn Asn Asn Asn Val
                325                 330                 335

Pro Asn Lys Cys Gln Glu Ile Thr Ser Asp Lys Glu Asn Ala Met Val
            340                 345                 350

Ala Trp Leu Leu Ser
        355

<210> SEQ ID NO 13
<211> LENGTH: 1476
<212> TYPE: DNA
<213> ORGANISM: Arabidopsis thaliana

<400> SEQUENCE: 13

| | | | | | | |
|---|---|---|---|---|---|---|
| atggatcctt | ataaatatag | acctgcttca | tcatataatt | caccttttt | tactactaat | 60 |
| tcaggagctc | ctgtttggaa | taataattca | tcaatgactg | ttggacctag | aggattgatt | 120 |
| ttgttggaag | attatcattt | ggttgaaaaa | ttggctaatt | ttgatagaga | agaattcct | 180 |
| gaaagagttg | tccatgctag | aggagcttca | gctaaaggat | tttttgaagt | tactcatgat | 240 |
| atttcaaatt | tgacttgcgc | tgattttttg | agagctcctg | gagttcaaac | tcctgttatt | 300 |
| gttagatttt | caactgttat | tcatgctaga | ggatcacctg | aaactttgag | agatcctaga | 360 |
| ggatttgctg | ttaaatttta | tactagagaa | ggaaattttg | atttggttgg | aaataatttt | 420 |
| cctgtttttt | ttattagaga | tggaatgaaa | tttcctgata | ttgttcatgc | tttgaaacct | 480 |
| aatcctaaat | cacatattca | agaaaattgg | agaattttgg | atttttttc | acatcatcct | 540 |
| gaatcattga | atatgtttac | ttttttgttt | gatgatattg | gaattcctca | agattataga | 600 |
| catatggatg | gatcaggagt | taatacttat | atgttgatta | taaagctgg | aaaagctcat | 660 |
| tatgttaaat | tcattggaa | acctacttgc | ggagttaaat | cattgttgga | agaagatgct | 720 |
| attagattgg | gaggaactaa | tcattcacat | gctactcaag | atttgtatga | ttcaattgct | 780 |
| gctggaaatt | atcctgaatg | gaaattgttt | attcaaatta | ttgatcctgc | tgatgaagat | 840 |
| aaatttgatt | ttgatccttt | ggatgttact | aaaacttggc | ctgaagatat | tttgcctttg | 900 |
| caacctgttg | aagaatggt | tttgaataaa | aatattgata | atttttttgc | tgaaaatgaa | 960 |
| caattggctt | tttgccctgc | tattattgtt | cctggaattc | attattcaga | tgataaattg | 1020 |
| ttgcaaacta | gagttttttc | atatgctgat | actcaaagac | atagattggg | acctaattat | 1080 |
| ttgcaattgc | ctgttaatgc | tcctaaatgc | gctcatcata | taatcatca | tgaaggattt | 1140 |

-continued

```
atgaatttta tgcatagaga tgaagaagtt aattattttc cttcaagata tgatcaagtt   1200
agacatgctg aaaatatcc tactcctcct gctgtttgct caggaaaaag agaaagatgc     1260
attattgaaa aagaaaataa ttttaaagaa cctggagaaa gatatagaac ttttactcct    1320
gaaagacaag aaagatttat tcaaagatgg attgatgctt tgtcagatcc tagaattact    1380
catgaaatta gatcaatttg gatttcatat tggtcacaag ctgataaatc attgggacaa    1440
aaattggctt caagattgaa tgttagacct tcaatt                              1476
```

<210> SEQ ID NO 14
<211> LENGTH: 492
<212> TYPE: PRT
<213> ORGANISM: Arabidopsis thaliana

<400> SEQUENCE: 14

```
Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Ser Ser Met
            20                  25                  30

Thr Val Gly Pro Arg Gly Leu Ile Leu Leu Glu Asp Tyr His Leu Val
        35                  40                  45

Glu Lys Leu Ala Asn Phe Asp Arg Glu Arg Ile Pro Glu Arg Val Val
    50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Ala Arg Gly Ser
            100                 105                 110

Pro Glu Thr Leu Arg Asp Pro Arg Gly Phe Ala Val Lys Phe Tyr Thr
        115                 120                 125

Arg Glu Gly Asn Phe Asp Leu Val Gly Asn Asn Phe Pro Val Phe Phe
    130                 135                 140

Ile Arg Asp Gly Met Lys Phe Pro Asp Ile Val His Ala Leu Lys Pro
145                 150                 155                 160

Asn Pro Lys Ser His Ile Gln Glu Asn Trp Arg Ile Leu Asp Phe Phe
                165                 170                 175

Ser His His Pro Glu Ser Leu Asn Met Phe Thr Phe Leu Phe Asp Asp
            180                 185                 190

Ile Gly Ile Pro Gln Asp Tyr Arg His Met Asp Gly Ser Gly Val Asn
        195                 200                 205

Thr Tyr Met Leu Ile Asn Lys Ala Gly Lys Ala His Tyr Val Lys Phe
    210                 215                 220

His Trp Lys Pro Thr Cys Gly Val Lys Ser Leu Leu Glu Glu Asp Ala
225                 230                 235                 240

Ile Arg Leu Gly Gly Thr Asn His Ser His Ala Thr Gln Asp Leu Tyr
                245                 250                 255

Asp Ser Ile Ala Ala Gly Asn Tyr Pro Glu Trp Lys Leu Phe Ile Gln
            260                 265                 270

Ile Ile Asp Pro Ala Asp Glu Asp Lys Phe Asp Phe Asp Pro Leu Asp
        275                 280                 285

Val Thr Lys Thr Trp Pro Glu Asp Ile Leu Pro Leu Gln Pro Val Gly
    290                 295                 300

Arg Met Val Leu Asn Lys Asn Ile Asp Asn Phe Phe Ala Glu Asn Glu
```

```
            305                 310                 315                 320
Gln Leu Ala Phe Cys Pro Ala Ile Ile Val Pro Gly Ile His Tyr Ser
                325                 330                 335

Asp Asp Lys Leu Leu Gln Thr Arg Val Phe Ser Tyr Ala Asp Thr Gln
                340                 345                 350

Arg His Arg Leu Gly Pro Asn Tyr Leu Gln Leu Pro Val Asn Ala Pro
                355                 360                 365

Lys Cys Ala His His Asn Asn His His Glu Gly Phe Met Asn Phe Met
370                 375                 380

His Arg Asp Glu Glu Val Asn Tyr Phe Pro Ser Arg Tyr Asp Gln Val
385                 390                 395                 400

Arg His Ala Glu Lys Tyr Pro Thr Pro Pro Ala Val Cys Ser Gly Lys
                405                 410                 415

Arg Glu Arg Cys Ile Ile Glu Lys Glu Asn Asn Phe Lys Glu Pro Gly
                420                 425                 430

Glu Arg Tyr Arg Thr Phe Thr Pro Glu Arg Gln Glu Arg Phe Ile Gln
                435                 440                 445

Arg Trp Ile Asp Ala Leu Ser Asp Pro Arg Ile Thr His Glu Ile Arg
450                 455                 460

Ser Ile Trp Ile Ser Tyr Trp Ser Gln Ala Asp Lys Ser Leu Gly Gln
465                 470                 475                 480

Lys Leu Ala Ser Arg Leu Asn Val Arg Pro Ser Ile
                485                 490

<210> SEQ ID NO 15
<211> LENGTH: 2262
<212> TYPE: DNA
<213> ORGANISM: Escherichia coli

<400> SEQUENCE: 15
atgtcgcaac ataacgaaaa gaacccacat cagcaccagt caccactaca cgattccagc     60
gaagcgaaac cggggatgga ctcactggca cctgaggacg gctctcatcg tccagcggct    120
gaaccaacac cgccaggtgc acaacctacc gccccaggga gcctgaaagc ccctgatacg    180
cgtaacgaaa aacttaattc tctggaagac gtacgcaaag gcagtgaaaa ttatgcgctg    240
accactaatc agggcgtgcg catcgccgac gatcaaaact cactgcgtgc cggtagccgt    300
ggtccaacgc tgctggaaga ttttattctg cgcgagaaaa tcacccactt tgaccatgag    360
cgcattccgg aacgtattgt tcatgcacgc ggatcagccg ctcacggtta tttccagcca    420
tataaaagct taagcgatat taccaaagcg gatttcctct cagatccgaa caaaatcacc    480
ccagtatttg tacgtttctc taccgttcag ggtggtgctg gctctgctga taccgtgcgt    540
gatatccgtg gctttgccac caagttctat accgaagagg gtattttga cctcgttggc    600 aataacacgc caatcttctt tatccaggat gcgcataaat ccccgatttt gttcatgcg    660 gtaaaaccag aaccgcactg gcaattccca agggcaaa gtgcccacga cttttctgg    720 gattatgttt ctctgcaacc tgaaactctg cacaacgtga tgtgggcgat gtcggatcgc    780
ggcatccccc gcagttaccg caccatggaa ggcttcggta ttcacacctt ccgcctgatt    840
aatgccgaag gaaggcaac gtttgtacgt ttccactgga accactggc aggtaaagcc    900 tcactcgttt gggatgaagc acaaaaactc accggacgtg acccggactt ccaccgccgc    960
gagttgtggg aagccattga agcaggcgat tttccggaat acgaactggg cttccagttg   1020
attcctgaag aagatgaatt caagttcgac ttcgatcttc tcgatccaac caaacttatc   1080
```

-continued

```
ccggaagaac tggtgcccgt tcagcgtgtc ggcaaaatgg tgctcaatcg caacccggat    1140
aacttctttg ctgaaaacga acaggcggct ttccatcctg gcatatcgt gccgggactg     1200 gacttcacca acgatccgct gttgcaggga cgtttgttct cctataccga tacacaaatc    1260
agtcgtcttg gtgggccgaa tttccatgag attccgatta accgtccgac ctgcccttac    1320
cataatttcc agcgtgacgg catgcatcgc atggggatcg acactaaccc ggcgaattac    1380
gaaccgaact cgattaacga taactggccg cgcgaaacac cgccggggcc gaaacgcggc    1440
ggttttgaat cataccagga gcgcgtggaa ggcaataaag ttcgcgagcg cagcccatcg    1500
tttggcgaat attattccca tccgcgtctg ttctggctaa gtcagacgcc atttgagcag    1560
cgccatattg tcgatggttt cagttttgag ttaagcaaag tcgttcgtcc gtatattcgt    1620
gagcgcgttg ttgaccagct ggcgcatatt gatctcactc tggcccaggc ggtggcgaaa    1680
aatctcggta tcgaactgac tgacgaccag ctgaatatca ccccacctcc ggacgtcaac    1740
ggtctgaaaa aggatccatc cttaagtttg tacgccattc ctgacggtga tgtgaaaggt    1800
cgcgtggtag cgatttact taatgatgaa gtgagatcgg cagaccttct ggccattctc     1860
aaggcgctga aggccaaagg cgttcatgcc aaactgctct actcccgaat gggtgaagtg    1920
actgcggatg acggtacggt gttgcctata gccgctacct tgccggtgc accttcgctg     1980 acggtcgatg cggtcattgt cccttgcggc aatatcgcgg atatcgctga acggcgat      2040 gccaactact acctgatgga agcctacaaa caccttaaac cgattgcgct ggcggggtgac   2100 gcgcgcaagt ttaaagcaac aatcaagatc gctgaccagg gtgaagaagg gattgtggaa    2160
gctgacagcg ctgacggtag ttttatggat gaactgctaa cgctgatggc agcacaccgc    2220
gtgtggtcac gcattcctaa gattgacaaa attcctgcct ga                       2262
```

<210> SEQ ID NO 16
<211> LENGTH: 753
<212> TYPE: PRT
<213> ORGANISM: Escherichia coli

<400> SEQUENCE: 16

```
Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
```

```
                165                 170                 175
Asp Thr Val Arg Asp Ile Arg Gly Phe Ala Thr Lys Phe Tyr Thr Glu
                180                 185                 190

Glu Gly Ile Phe Asp Leu Val Gly Asn Asn Thr Pro Ile Phe Phe Ile
                195                 200                 205

Gln Asp Ala His Lys Phe Pro Asp Phe Val His Ala Val Lys Pro Glu
            210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
                275                 280                 285

Val Arg Phe His Trp Lys Pro Leu Ala Gly Lys Ala Ser Leu Val Trp
        290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Phe Asp Phe Asp
            340                 345                 350

Leu Leu Asp Pro Thr Lys Leu Ile Pro Glu Glu Leu Val Pro Val Gln
            355                 360                 365

Arg Val Gly Lys Met Val Leu Asn Arg Asn Pro Asp Asn Phe Phe Ala
        370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
            420                 425                 430

Ile Asn Arg Pro Thr Cys Pro Tyr His Asn Phe Gln Arg Asp Gly Met
        435                 440                 445

His Arg Met Gly Ile Asp Thr Asn Pro Ala Asn Tyr Glu Pro Asn Ser
    450                 455                 460

Ile Asn Asp Asn Trp Pro Arg Glu Thr Pro Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
            500                 505                 510

Leu Ser Gln Thr Pro Phe Glu Gln Arg His Ile Val Asp Gly Phe Ser
        515                 520                 525

Phe Glu Leu Ser Lys Val Val Arg Pro Tyr Ile Arg Glu Arg Val Val
        530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
                565                 570                 575

Pro Asp Val Asn Gly Leu Lys Lys Asp Pro Ser Leu Ser Leu Tyr Ala
            580                 585                 590
```

-continued

Ile Pro Asp Gly Asp Val Lys Gly Arg Val Val Ala Ile Leu Leu Asn
        595                 600                 605

Asp Glu Val Arg Ser Ala Asp Leu Leu Ala Ile Leu Lys Ala Leu Lys
610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
            645                 650                 655

Ala Pro Ser Leu Thr Val Asp Ala Val Ile Val Pro Cys Gly Asn Ile
        660                 665                 670

Ala Asp Ile Ala Asp Asn Gly Asp Ala Asn Tyr Tyr Leu Met Glu Ala
        675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Gly Ile Val Glu
705                 710                 715                 720

Ala Asp Ser Ala Asp Gly Ser Phe Met Asp Glu Leu Leu Thr Leu Met
            725                 730                 735

Ala Ala His Arg Val Trp Ser Arg Ile Pro Lys Ile Asp Lys Ile Pro
            740                 745                 750

Ala

<210> SEQ ID NO 17
<211> LENGTH: 1635
<212> TYPE: DNA
<213> ORGANISM: Cannabis

<400> SEQUENCE: 17

| | | |
|---|---|---|
| atgaagtgct caacattctc cttttggttt gtttgcaaga taatattttt cttttctca | 60 |
| ttcaatatcc aaacttccat tgctaatcct cgagaaaact tccttaaatg cttctcgcaa | 120 |
| tatattccca ataatgcaac aaatctaaaa ctcgtataca ctcaaaacaa cccattgtat | 180 |
| atgtctgtcc taaattcgac aatacacaat cttagattca cctctgacac aaccccaaaa | 240 |
| ccacttgtta tcgtcactcc ttcacatgtc tctcatatcc aaggcactat tctatgctcc | 300 |
| aagaaagttg gcttgcagat tcgaactcga agtggtggtc atgattctga gggcatgtcc | 360 |
| tacatatctc aagtcccatt tgttatagta gacttgagaa acatgcgttc aatcaaaata | 420 |
| gatgttcata gccaaactgc atgggttgaa gccggagcta cccttggaga agtttattat | 480 |
| tgggttaatg agaaaaatga gaatcttagt ttggcggctg gtattgccc tactgtttgc | 540 |
| gcaggtggac actttggtgg aggaggctat ggaccattga tgagaaacta ggcctcgcg | 600 |
| gctgataata tcattgatgc acacttagtc aacgttcatg aaaagtgct agatcgaaaa | 660 |
| tctatggggg aagatctctt ttgggcttta cgtggtggtg gagcagaaag cttcggaatc | 720 |
| attgtagcat ggaaaattag actggttgct gtcccaaagt ctactatgtt tagtgttaaa | 780 |
| aagatcatgg agatacatga gcttgtcaag ttagttaaca aatggcaaaa tattgcttac | 840 |
| aagtatgaca aagatttatt actcatgact cacttcataa ctaggaacat tacagataat | 900 |
| caagggaaga ataagacagc aatacacact tacttctctt cagttttcct tggtggagtg | 960 |
| gatagtctag tcgacttgat gaacaagagt tttcctgagt tgggtattaa aaaaacggat | 1020 |
| tgcagacaat tgagctggat tgatactatc atcttctata gtggtgttgt aaattacgac | 1080 |
| actgataatt ttaacaagga aattttgctt gatagatccg ctgggcagaa cggtgctttc | 1140 |

```
aagattaagt tagactacgt taagaaacca attccagaat ctgtatttgt ccaaattttg    1200
gaaaaattat atgaagaaga tataggagct gggatgtatg cgttgtaccc ttacggtggt    1260
ataatggatg agatttcaga atcagcaatt ccattccctc atcgagctgg aatcttgtat    1320
gagttatggt acatatgtag ttgggagaag caagaagata acgaaaagca tctaaactgg    1380
attagaaata tttataactt catgactcct tatgtgtcca aaaatccaag attggcatat    1440
ctcaattata gagaccttga tataggaata aatgatccca agaatccaaa taattacaca    1500
caagcacgta tttggggtga agtatttt ggtaaaaatt ttgacaggct agtaaaagtg    1560
aaaaccctgg ttgatcccaa taactttttt agaaacgaac aaagcatccc acctctacca    1620
cggcatcgtc attaa                                                    1635
```

<210> SEQ ID NO 18
<211> LENGTH: 544
<212> TYPE: PRT
<213> ORGANISM: Cannabis

<400> SEQUENCE: 18

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
                20                  25                  30

Asn Phe Leu Lys Cys Phe Ser Gln Tyr Ile Pro Asn Asn Ala Thr Asn
            35                  40                  45

Leu Lys Leu Val Tyr Thr Gln Asn Asn Pro Leu Tyr Met Ser Val Leu
        50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
            260                 265                 270

Asn Lys Trp Gln Asn Ile Ala Tyr Lys Tyr Asp Lys Asp Leu Leu Leu
        275                 280                 285
```

```
Met Thr His Phe Ile Thr Arg Asn Ile Thr Asp Asn Gln Gly Lys Asn
    290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
                340                 345                 350

Tyr Ser Gly Val Val Asn Tyr Asp Thr Asp Asn Phe Asn Lys Glu Ile
            355                 360                 365

Leu Leu Asp Arg Ser Ala Gly Gln Asn Gly Ala Phe Lys Ile Lys Leu
    370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
                420                 425                 430

Pro His Arg Ala Gly Ile Leu Tyr Glu Leu Trp Tyr Ile Cys Ser Trp
            435                 440                 445

Glu Lys Gln Glu Asp Asn Glu Lys His Leu Asn Trp Ile Arg Asn Ile
    450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495

Asn Asn Tyr Thr Gln Ala Arg Ile Trp Gly Glu Lys Tyr Phe Gly Lys
            500                 505                 510

Asn Phe Asp Arg Leu Val Lys Val Lys Thr Leu Val Asp Pro Asn Asn
    515                 520                 525

Phe Phe Arg Asn Glu Gln Ser Ile Pro Pro Leu Pro Arg His Arg His
530                 535                 540

<210> SEQ ID NO 19
<211> LENGTH: 1467
<212> TYPE: DNA
<213> ORGANISM: Stevia rebaudiana

<400> SEQUENCE: 19
atgaagtgct caacattctc cttttggttt gtttgcaaga taatattttt cttttctca       60 ttcaatatcc aaacttccat tgctaatcct cgagaaaata aaactgaaac tactgttaga     120
agaagaagaa gaattatttt gtttcctgtt ccttttcaag acatattaa tcctattttg      180 caattggcta atgttttgta ttcaaaagga ttttcaatta ctattttca tactaatttt     240 aataaaccta aacttcaaa ttatcctcat tttactttta gatttatttt ggataatgat     300
cctcaagatg aaagaatttc aaatttgcct actcatggac ctttggctgg aatgagaatt    360
cctattatta tgaacatgg agctgatgaa ttgagaagag aattggaatt gttgatgttg     420
gcttcagaag aagatgaaga agtttcatgc ttgattactg atgctttgtg gtattttgct   480
caatcagttg ctgattcatt gaatttgaga agattggttt tgatgacttc atcattgttt   540
aattttcatg ctcatgtttc attgcctcaa tttgatgaat tgggatattt ggatcctgat   600
gataaaacta gattggaaga acaagcttca ggatttccta tgttgaaagt taaagatatt   660
```

-continued

```
aaatcagctt attcaaattg gcaaattttg aaagaaattt tgggaaaaat gattaaacaa    720
actagagctt catcaggagt tatttggaat tcatttaaag aattggaaga atcagaattg    780
gaaactgtta ttagagaaat tcctgctcct tcattttga ttcctttgcc taaacatttg    840
actgcttcat catcatcatt gttggatcat gatagaactg ttttcaatg gttggatcaa    900 caacctcctt catcagtttt gtatgtttca tttggatcaa cttcagaagt tgatgaaaaa    960 gatttttgg aaattgctag aggattggtt gattcaaaac aatcatttt gtgggttgtt   1020 agacctggat ttgttaaagg atcaacttgg gttgaaccct tgcctgatgg atttttggga   1080
gaaagaggaa gaattgttaa atgggttcct caacaagaag ttttggctca tggagctatt   1140
ggagcttttt ggactcattc aggatggaat tcaactttgg aatcagtttg cgaaggagtt   1200
cctatgattt tttcagattt tggattggat caacctttga atgctagata tatgtcagat   1260
gttttgaaag ttggagttta tttggaaaat ggatgggaaa gaggagaaat tgctaatgct   1320
attagaagag ttatggttga tgaagaagga gaatatatta gacaaaatgc tagagttttg   1380
aaacaaaaag ctgatgtttc attgatgaaa ggaggatcat catatgaatc attggaatca   1440
ttggtttcat atatttcatc attgtaa                                     1467
```

<210> SEQ ID NO 20
<211> LENGTH: 488
<212> TYPE: PRT
<213> ORGANISM: Stevia rebaudiana

<400> SEQUENCE: 20

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
                20                  25                  30

Asn Lys Thr Glu Thr Thr Val Arg Arg Arg Arg Ile Ile Leu Phe
            35                  40                  45

Pro Val Pro Phe Gln Gly His Ile Asn Pro Ile Leu Gln Leu Ala Asn
        50                  55                  60

Val Leu Tyr Ser Lys Gly Phe Ser Ile Thr Ile Phe His Thr Asn Phe
65                  70                  75                  80

Asn Lys Pro Lys Thr Ser Asn Tyr Pro His Phe Thr Phe Arg Phe Ile
                85                  90                  95

Leu Asp Asn Asp Pro Gln Asp Glu Arg Ile Ser Asn Leu Pro Thr His
            100                 105                 110

Gly Pro Leu Ala Gly Met Arg Ile Pro Ile Ile Asn Glu His Gly Ala
        115                 120                 125

Asp Glu Leu Arg Arg Glu Leu Glu Leu Leu Met Leu Ala Ser Glu Glu
    130                 135                 140

Asp Glu Glu Val Ser Cys Leu Ile Thr Asp Ala Leu Trp Tyr Phe Ala
145                 150                 155                 160

Gln Ser Val Ala Asp Ser Leu Asn Leu Arg Arg Leu Val Leu Met Thr
                165                 170                 175

Ser Ser Leu Phe Asn Phe His Ala His Val Ser Leu Pro Gln Phe Asp
            180                 185                 190

Glu Leu Gly Tyr Leu Asp Pro Asp Asp Lys Thr Arg Leu Glu Glu Gln
        195                 200                 205

Ala Ser Gly Phe Pro Met Leu Lys Val Lys Asp Ile Lys Ser Ala Tyr
    210                 215                 220

Ser Asn Trp Gln Ile Leu Lys Glu Ile Leu Gly Lys Met Ile Lys Gln
```

```
                      225                 230                 235                 240
        Thr Arg Ala Ser Ser Gly Val Ile Trp Asn Ser Phe Lys Glu Leu Glu
                        245                 250                 255

Glu Ser Glu Leu Glu Thr Val Ile Arg Glu Ile Pro Ala Pro Ser Phe
                        260                 265                 270

Leu Ile Pro Leu Pro Lys His Leu Thr Ala Ser Ser Ser Ser Leu Leu
                        275                 280                 285

Asp His Asp Arg Thr Val Phe Gln Trp Leu Asp Gln Gln Pro Pro Ser
                        290                 295                 300

Ser Val Leu Tyr Val Ser Phe Gly Ser Thr Ser Glu Val Asp Glu Lys
        305                 310                 315                 320

Asp Phe Leu Glu Ile Ala Arg Gly Leu Val Asp Ser Lys Gln Ser Phe
                        325                 330                 335

Leu Trp Val Val Arg Pro Gly Phe Val Lys Gly Ser Thr Trp Val Glu
                        340                 345                 350

Pro Leu Pro Asp Gly Phe Leu Gly Glu Arg Gly Arg Ile Val Lys Trp
                        355                 360                 365

Val Pro Gln Gln Glu Val Leu Ala His Gly Ala Ile Gly Ala Phe Trp
                        370                 375                 380

Thr His Ser Gly Trp Asn Ser Thr Leu Glu Ser Val Cys Glu Gly Val
        385                 390                 395                 400

Pro Met Ile Phe Ser Asp Phe Gly Leu Asp Gln Pro Leu Asn Ala Arg
                        405                 410                 415

Tyr Met Ser Asp Val Leu Lys Val Gly Val Tyr Leu Glu Asn Gly Trp
                        420                 425                 430

Glu Arg Gly Glu Ile Ala Asn Ala Ile Arg Arg Val Met Val Asp Glu
                        435                 440                 445

Glu Gly Glu Tyr Ile Arg Gln Asn Ala Arg Val Leu Lys Gln Lys Ala
                        450                 455                 460

Asp Val Ser Leu Met Lys Gly Gly Ser Ser Tyr Glu Ser Leu Glu Ser
        465                 470                 475                 480

Leu Val Ser Tyr Ile Ser Ser Leu
                        485

<210> SEQ ID NO 21
<211> LENGTH: 1022
<212> TYPE: DNA
<213> ORGANISM: Arabidopsis thaliana

<400> SEQUENCE: 21
atggaggtcc atggctccgg attccgtcga attctgttgt tggcgttgtg tatctccggg      60
atctggtccg cctacatcta ccaaggcgtt cttcaagaga ctctgtccac gaagagattt     120
ggtccagatg agaagaggtt cgagcatctt gcattcttga acttagctca agtgtagtc      180 tgcttgatct ggtcttatat aatgatcaag ctctggtcaa atgctggtaa cggtggagca     240
ccatggtgga cgtattggag tgcaggcatt actaatacaa ttggtcctgc catgggaatt     300
gaagccttga gtatatcag ttatccagct caggttttgg caaaatcgtc aaaaatgatt      360
ccagttatgc taatgggaac tttagtttac ggaataagat acactttccc tgaatacatg     420
tgcacctttc ttgtcgctgg aggagtatcc atctttgctc ttcttaagac aagctctaag     480
acaattagca agctagcaca tccaaatgct cccctcggtt acgcactttg ttccttaaac     540
ctcgcctttg acggattcac aaatgccaca caagactcca ttgcctcaag gtacccaaaa     600
accgaagcgt gggacataat gctgggaatg aacttatggg gcacaatata caacattatc     660
```

-continued

```
tacatgtttg gcttgccaca agggatggat tcgaagcaat tcagttctgt aagctacacc      720
cggaagcggc atgggacatt ctaaagtatt gtatatgcgg tgccgtggga caaaacttca      780
tcttcatgac aataagtaac ttcgggtcac tagctaacac gaccataacc acgaccagga      840
agtttgttag cattgttgta tcatcagtaa tgagcggaaa tccattgtcg ttgaagcaat      900
ggggatgtgt ttcgatggtc tttggtggtt tggcatatca aatttatctt aaatggaaga      960
aattgcagag agtggagtgc tccataatga acttaatgtg tgggtctacc tgcgccgctt     1020
ga                                                                    1022
```

<210> SEQ ID NO 22
<211> LENGTH: 1554
<212> TYPE: DNA
<213> ORGANISM: Cannabis sativa

<400> SEQUENCE: 22

```
atgaatcctc gagaaaactt ccttaaatgc ttctcgcaat atattcccaa taatgcaaca       60
aatctaaaac tcgtatacac tcaaaacaac ccattgtata tgtctgtcct aaattcgaca      120
atacacaatc ttagattcac ctctgacaca accccaaaac cacttgttat cgtcactcct      180
tcacatgtct ctcatatcca aggcactatt ctatgctcca agaaagttgg cttgcagatt      240
cgaactcgaa gtggtggtca tgattctgag ggcatgtcct acatatctca agtcccattt      300
gttatagtag acttgagaaa catgcgttca atcaaaatag atgttcatag ccaaactgca      360
tgggttgaag ccggagctac ccttggagaa gtttattatt gggttaatga aaaaatgag      420 aatcttagtt tggcggctgg gtattgccct actgtttgcg caggtggaca ctttggtgga      480
ggaggctatg gaccattgat gagaaactat ggcctcgcgg ctgataatat cattgatgca      540
cacttagtca acgttcatgg aaaagtgcta gatcgaaaat ctatggggga agatctcttt      600
tgggctttac gtggtggtgg agcagaaagc ttcggaatca ttgtagcatg gaaaattaga      660
ctggttgctg tcccaaagtc tactatgttt agtgttaaaa agatcatgga gatacatgag      720
cttgtcaagt tagttaacaa atggcaaaat attgcttaca gtatgacaa agatttatta      780 ctcatgactc acttcataac taggaacatt acagataatc aagggaagaa taagacagca      840
atacacactt acttctcttc agttttcctt ggtggagtgg atagtctagt cgacttgatg      900
aacaagagtt ttcctgagtt gggtattaaa aaaacggatt gcagacaatt gagctggatt      960
gatactatca tcttctatag tggtgttgta aattacgaca ctgataattt taacaaggaa     1020
attttgcttg atagatccgc tgggcagaac ggtgctttca agattaagtt agactacgtt     1080
aagaaaccaa ttccagaatc tgtatttgtc caaattttgg aaaaattata tgaagaagat     1140
ataggagctg gatgtatgc gttgtacct acggtggta atggatga gatttcagaa          1200 tcagcaattc cattccctca tcgagctgga atcttgtatg agttatggta catatgtagt     1260
tgggagaagc aagaagataa cgaaaagcat ctaaactgga ttagaaatat ttataacttc     1320
atgactcctt atgtgtccaa aaatccaaga ttggcatatc tcaattatag agaccttgat     1380
ataggaataa atgatcccaa gaatccaaat aattacacac aagcacgtat ttggggtgag     1440
aagtattttg gtaaaaattt tgacaggcta gtaaaagtga aaaccctggt tgatcccaat     1500
aactttttta gaaacgaaca aagcatccca cctctaccac ggcatcgtca ttaa           1554
```

<210> SEQ ID NO 23
<211> LENGTH: 517
<212> TYPE: PRT

<213> ORGANISM: Cannabis sativa

<400> SEQUENCE: 23

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365

Phe Val Gln Ile Leu Glu Lys Leu Tyr Glu Glu Asp Ile Gly Ala Gly
    370                 375                 380

Met Tyr Ala Leu Tyr Pro Tyr Gly Gly Ile Met Asp Glu Ile Ser Glu
385                 390                 395                 400
```

```
Ser Ala Ile Pro Phe Pro His Arg Ala Gly Ile Leu Tyr Glu Leu Trp
            405                 410                 415

Tyr Ile Cys Ser Trp Glu Lys Gln Glu Asp Asn Glu Lys His Leu Asn
        420                 425                 430

Trp Ile Arg Asn Ile Tyr Asn Phe Met Thr Pro Tyr Val Ser Lys Asn
        435                 440                 445

Pro Arg Leu Ala Tyr Leu Asn Tyr Arg Asp Leu Asp Ile Gly Ile Asn
    450                 455                 460

Asp Pro Lys Asn Pro Asn Asn Tyr Thr Gln Ala Arg Ile Trp Gly Glu
465                 470                 475                 480

Lys Tyr Phe Gly Lys Asn Phe Asp Arg Leu Val Lys Val Lys Thr Leu
                485                 490                 495

Val Asp Pro Asn Asn Phe Phe Arg Asn Glu Gln Ser Ile Pro Pro Leu
                500                 505                 510

Pro Arg His Arg His
        515

<210> SEQ ID NO 24
<211> LENGTH: 1377
<212> TYPE: DNA
<213> ORGANISM: Stevia rebaudiana

<400> SEQUENCE: 24
atggaaaata aaaccgaaac caccgtccgc cgtcgtcgcc gtatcattct gttcccggtc    60
ccgttccagg ccacatcaa cccgattctg caactggcga acgtgctgta ttcgaaaggt   120
ttcagcatca ccatcttcca tacgaacttc aacaagccga agaccagcaa ttacccgcac   180
tttacgttcc gttttattct ggataacgac ccgcaggatg aacgcatctc taatctgccg   240
acccacggcc cgctggcggg tatgcgtatt ccgattatca cgaacacgg cgcagatgaa   300 ctgcgtcgcg aactggaact gctgatgctg ccagcgaag aagatgaaga gtttcttgc   360 ctgatcaccg acgcactgtg gtattttgcc cagtctgttg cagatagtct gaacctgcgt   420
cgcctggtcc tgatgaccag cagcctgttc aattttcatg cccacgttag tctgccgcag   480
ttcgatgaac tgggttatct ggaccccggat gacaaaaccc gcctggaaga acaggcgagc   540
ggctttccga tgctgaaagt caaggatatt aagtcagcgt actcgaactg gcagattctg   600
aaagaaatcc tgggtaaaat gattaagcaa accaaagcaa gttccggcgt catcctggaat   660 agtttcaaag aactggaaga atccgaactg gaaacggtga ttcgtgaaat cccggctccg   720
agtttctcga ttccgctgcc gaagcatctg accgcgagca gcagcagcct gctggatcac   780
gaccgcacgg tgtttcagtg gctggatcag caaccgccga gttccgtgct gtatgttagc   840
ttcggtagta cctcggaagt ggatgaaaag gactttctgg aaatcgctcg tggcctggtt   900
gatagcaaac aatctttcct gtgggtggtt cgcccgggtt ttgtgaaggg ctctacgtgg   960
gttgaaccgc tgccggacgg cttcctgggt gaacgtggcc gcattgtcaa atgggtgccg  1020
cagcaagaag tgctggcgca tgcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377
```

```
<210> SEQ ID NO 25
<211> LENGTH: 458
<212> TYPE: PRT
<213> ORGANISM: Stevia rebaudiana

<400> SEQUENCE: 25
```

| | | | | | | | | | | | | | | | |
|---|---|---|---|---|---|---|---|---|---|---|---|---|---|---|---|
| Met | Glu | Asn | Lys | Thr | Glu | Thr | Thr | Val | Arg | Arg | Arg | Arg | Ile | Ile | |
| 1 | | | | 5 | | | | | 10 | | | | | 15 | |
| Leu | Phe | Pro | Val | Pro | Phe | Gln | Gly | His | Ile | Asn | Pro | Ile | Leu | Gln | Leu |
| | | | 20 | | | | | 25 | | | | | 30 | | |
| Ala | Asn | Val | Leu | Tyr | Ser | Lys | Gly | Phe | Ser | Ile | Thr | Ile | Phe | His | Thr |
| | | 35 | | | | | 40 | | | | | 45 | | | |
| Asn | Phe | Asn | Lys | Pro | Lys | Thr | Ser | Asn | Tyr | Pro | His | Phe | Thr | Phe | Arg |
| | 50 | | | | | 55 | | | | | 60 | | | | |
| Phe | Ile | Leu | Asp | Asn | Asp | Pro | Gln | Asp | Glu | Arg | Ile | Ser | Asn | Leu | Pro |
| 65 | | | | | 70 | | | | | 75 | | | | | 80 |
| Thr | His | Gly | Pro | Leu | Ala | Gly | Met | Arg | Ile | Pro | Ile | Ile | Asn | Glu | His |
| | | | | 85 | | | | | 90 | | | | | 95 | |
| Gly | Ala | Asp | Glu | Leu | Arg | Arg | Glu | Leu | Glu | Leu | Leu | Met | Leu | Ala | Ser |
| | | | 100 | | | | | 105 | | | | | 110 | | |
| Glu | Glu | Asp | Glu | Glu | Val | Ser | Cys | Leu | Ile | Thr | Asp | Ala | Leu | Trp | Tyr |
| | | | | 115 | | | | | 120 | | | | | 125 | |
| Phe | Ala | Gln | Ser | Val | Ala | Asp | Ser | Leu | Asn | Leu | Arg | Arg | Leu | Val | Leu |
| | 130 | | | | | 135 | | | | | 140 | | | | |
| Met | Thr | Ser | Ser | Leu | Phe | Asn | Phe | His | Ala | His | Val | Ser | Leu | Pro | Gln |
| 145 | | | | | 150 | | | | | 155 | | | | | 160 |
| Phe | Asp | Glu | Leu | Gly | Tyr | Leu | Asp | Pro | Asp | Asp | Lys | Thr | Arg | Leu | Glu |
| | | | | 165 | | | | | 170 | | | | | 175 | |
| Glu | Gln | Ala | Ser | Gly | Phe | Pro | Met | Leu | Lys | Val | Lys | Asp | Ile | Lys | Ser |
| | | | 180 | | | | | 185 | | | | | 190 | | |
| Ala | Tyr | Ser | Asn | Trp | Gln | Ile | Leu | Lys | Glu | Ile | Leu | Gly | Lys | Met | Ile |
| | | | | 195 | | | | | 200 | | | | | 205 | |
| Lys | Gln | Thr | Lys | Ala | Ser | Ser | Gly | Val | Ile | Trp | Asn | Ser | Phe | Lys | Glu |
| | 210 | | | | | 215 | | | | | 220 | | | | |
| Leu | Glu | Glu | Ser | Glu | Leu | Glu | Thr | Val | Ile | Arg | Glu | Ile | Pro | Ala | Pro |
| 225 | | | | | 230 | | | | | 235 | | | | | 240 |
| Ser | Phe | Leu | Ile | Pro | Leu | Pro | Lys | His | Leu | Thr | Ala | Ser | Ser | Ser | Ser |
| | | | | 245 | | | | | 250 | | | | | 255 | |
| Leu | Leu | Asp | His | Asp | Arg | Thr | Val | Phe | Gln | Trp | Leu | Asp | Gln | Gln | Pro |
| | | | 260 | | | | | 265 | | | | | 270 | | |
| Pro | Ser | Ser | Val | Leu | Tyr | Val | Ser | Phe | Gly | Ser | Thr | Ser | Glu | Val | Asp |
| | | 275 | | | | | 280 | | | | | 285 | | | |
| Glu | Lys | Asp | Phe | Leu | Glu | Ile | Ala | Arg | Gly | Leu | Val | Asp | Ser | Lys | Gln |
| | 290 | | | | | 295 | | | | | 300 | | | | |
| Ser | Phe | Leu | Trp | Val | Val | Arg | Pro | Gly | Phe | Val | Lys | Gly | Ser | Thr | Trp |
| 305 | | | | | 310 | | | | | 315 | | | | | 320 |
| Val | Glu | Pro | Leu | Pro | Asp | Gly | Phe | Leu | Gly | Glu | Arg | Gly | Arg | Ile | Val |
| | | | | 325 | | | | | 330 | | | | | 335 | |
| Lys | Trp | Val | Pro | Gln | Gln | Glu | Val | Leu | Ala | His | Gly | Ala | Ile | Gly | Ala |
| | | | 340 | | | | | 345 | | | | | 350 | | |
| Phe | Trp | Thr | His | Ser | Gly | Trp | Asn | Ser | Thr | Leu | Glu | Ser | Val | Cys | Glu |
| | | 355 | | | | | 360 | | | | | 365 | | | |
| Gly | Val | Pro | Met | Ile | Phe | Ser | Asp | Phe | Gly | Leu | Asp | Gln | Pro | Leu | Asn |
| | 370 | | | | | 375 | | | | | 380 | | | | |

```
Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
    450                 455

<210> SEQ ID NO 26
<211> LENGTH: 485
<212> TYPE: PRT
<213> ORGANISM: Nicotiana tabacum

<400> SEQUENCE: 26

Met Gly Ser Ile Gly Ala Glu Leu Thr Lys Pro His Ala Val Cys Ile
1               5                   10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Leu Lys Ser Arg Gly Pro Asp Ser Leu Lys Gly
    50                  55                  60

Leu Ser Ser Phe Arg Phe Glu Thr Ile Pro Asp Gly Leu Pro Pro Cys
65                  70                  75                  80

Glu Ala Asp Ala Thr Gln Asp Ile Pro Ser Leu Cys Glu Ser Thr Thr
                85                  90                  95

Asn Thr Cys Leu Ala Pro Phe Arg Asp Leu Leu Ala Lys Leu Asn Asp
            100                 105                 110

Thr Asn Thr Ser Asn Val Pro Pro Val Ser Cys Ile Val Ser Asp Gly
        115                 120                 125

Val Met Ser Phe Thr Leu Ala Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Cys Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Gly
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Phe Glu Thr Leu Glu
225                 230                 235                 240

Ala Glu Val Leu Glu Ser Leu Arg Asn Leu Leu Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Pro Glu Cys Ile Gln
        275                 280                 285

Trp Leu Asp Thr Lys Glu Pro Asn Ser Val Val Tyr Val Asn Phe Gly
290                 295                 300
```

```
Ser Ile Thr Val Met Thr Pro Asn Gln Leu Ile Glu Phe Ala Trp Gly
305                 310                 315                 320

Leu Ala Asn Ser Gln Gln Thr Phe Leu Trp Ile Ile Arg Pro Asp Ile
            325                 330                 335

Val Ser Gly Asp Ala Ser Ile Leu Pro Pro Glu Phe Val Glu Glu Thr
        340                 345                 350

Lys Asn Arg Gly Met Leu Ala Ser Trp Cys Ser Gln Glu Glu Val Leu
    355                 360                 365

Ser His Pro Ala Ile Val Gly Phe Leu Thr His Ser Gly Trp Asn Ser
370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
            405                 410                 415

Val Gly Met Glu Ile Asp Ser Asp Val Lys Arg Asp Glu Val Glu Ser
        420                 425                 430

Leu Val Arg Glu Leu Met Val Gly Lys Gly Lys Lys Met Lys Lys
    435                 440                 445

Lys Ala Met Glu Trp Lys Glu Leu Ala Glu Ala Ser Lys Glu His
450                 455                 460

Ser Gly Ser Ser Tyr Val Asn Ile Glu Lys Leu Val Asn Asp Ile Leu
465                 470                 475                 480

Leu Ser Ser Lys His
            485

<210> SEQ ID NO 27
<211> LENGTH: 1458
<212> TYPE: DNA
<213> ORGANISM: Nicotiana tabacum

<400> SEQUENCE: 27
atgggttcca ttggtgctga attaacaaag ccacatgcag tttgcatacc atatcccgcc      60
caaggccata ttaaccccat gttaaagcta gccaaaatcc ttcatcacaa aggctttcac     120 atcactttg tcaatactga atttaaccac cgacgtctcc ttaaatctcg tggccctgat      180
tctctcaagg gtctttcttc tttccgtttt gagaccattc ctgatggact tccgccatgt     240
gaggcagatg ccacacaaga tataccttct ttgtgtgaat ctacaaccaa tacttgcttg     300
gctcctttta gggatcttct tgcgaaactc aatgatacta acacatctaa cgtgccaccc     360
gtttcgtgca tcgtctcgga tggtgtcatg agcttcacct tagccgctgc acaagaattg     420
ggagtccctg aagttctgtt ttggaccact agtgcttgtg gtttcttagg ttacatgcat     480
tactgcaagg ttattgaaaa aggatatgct ccacttaaag atgcgagtga cttgacaaat     540
ggatacctag agacaacatt ggattttata ccaggcatga agacgtacg tttaagggat      600 cttccaagtt tcttgagaac tacaaatcca tgaattca tgatcaaatt tgtcctccaa       660
gaaacagaga gagcaagaaa ggcttctgca attatcctca acacatttga aacactagag     720
gctgaagttc ttgaatcgct ccgaaatctt cttcctccag tctaccccat agggcccttg     780
cattttctag tgaaacatgt tgatgatgag aatttgaagg acttagatc cagcctttgg     840 aaagaggaac cagagtgtat acaatggctt gataccaaag aaccaaattc tgttgtttat     900
gttaactttg gaagcattac tgttatgact cctaatcagc ttattgagtt tgcttggga     960 cttgcaaaca gccagcaaac attcttatgg atcataagac ctgatattgt ttcaggtgat    1020
```

```
gcatcgattc ttccacccga attcgtggaa gaaacgaaga acagaggtat gcttgctagt   1080
tggtgttcac aagaagaagt acttagtcac cctgcaatag taggattctt gactcacagt   1140
ggatggaatt cgacactcga agtataagc agtggggtgc ctatgatttg ctggccattt     1200
ttcgctgaac agcaaacaaa ttgttggttt tccgtcacta atgggatgt tggaatggag    1260 attgacagtg atgtgaagag agatgaagtg gaaagccttg taagggaatt gatggttggg   1320
ggaaaaggca aaaagatgaa gaaaaaggca atggaatgga aggaattggc tgaagcatct   1380
gctaaagaac attcagggtc atcttatgtg aacattgaaa agttggtcaa tgatattctt   1440
ctttcatcca aacattaa                                                  1458
```

<210> SEQ ID NO 28
<211> LENGTH: 485
<212> TYPE: PRT
<213> ORGANISM: Nicotiana tabacum

<400> SEQUENCE: 28

```
Met Gly Ser Ile Gly Ala Glu Phe Thr Lys Pro His Ala Val Cys Ile
1               5                  10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Leu Lys Ser Arg Gly Pro Asp Ser Leu Lys Gly
    50                  55                  60

Leu Ser Ser Phe Arg Phe Glu Thr Ile Pro Asp Gly Leu Pro Pro Cys
65                  70                  75                  80

Asp Ala Asp Ala Thr Gln Asp Ile Pro Ser Leu Cys Glu Ser Thr Thr
                85                  90                  95

Asn Thr Cys Leu Gly Pro Phe Arg Asp Leu Leu Ala Lys Leu Asn Asp
            100                 105                 110

Thr Asn Thr Ser Asn Val Pro Pro Val Ser Cys Ile Ile Ser Asp Gly
        115                 120                 125

Val Met Ser Phe Thr Leu Ala Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Tyr Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Cys
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Tyr Glu Thr Leu Glu
225                 230                 235                 240

Ala Glu Val Leu Glu Ser Leu Arg Asn Leu Leu Pro Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Pro Glu Cys Ile Gln
        275                 280                 285

Trp Leu Asp Thr Lys Glu Pro Asn Ser Val Val Tyr Val Asn Phe Gly
```

Ser Ile Thr Val Met Thr Pro Asn Gln Leu Ile Glu Phe Ala Trp Gly
305                 310                 315                 320

Leu Ala Asn Ser Gln Gln Ser Phe Leu Trp Ile Ile Arg Pro Asp Ile
                325                 330                 335

Val Ser Gly Asp Ala Ser Ile Leu Pro Pro Glu Phe Val Glu Thr
                340                 345                 350

Lys Lys Arg Gly Met Leu Ala Ser Trp Cys Ser Gln Glu Val Leu
            355                 360                 365

Ser His Pro Ala Ile Gly Gly Phe Leu Thr His Ser Gly Trp Asn Ser
370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
                405                 410                 415

Val Gly Met Glu Ile Asp Cys Asp Val Lys Arg Asp Glu Val Glu Ser
            420                 425                 430

Leu Val Arg Glu Leu Met Val Gly Gly Lys Gly Lys Met Lys Lys
            435                 440                 445

Lys Ala Met Glu Trp Lys Glu Leu Ala Glu Ala Ser Ala Lys Glu His
            450                 455                 460

Ser Gly Ser Ser Tyr Val Asn Ile Glu Lys Val Val Asn Asp Ile Leu
465                 470                 475                 480

Leu Ser Ser Lys His
                485

<210> SEQ ID NO 29
<211> LENGTH: 1458
<212> TYPE: DNA
<213> ORGANISM: Nicotiana tabacum

<400> SEQUENCE: 29
atgggttcca ttggtgctga atttacaaag ccacatgcag tttgcatacc atatcccgcc     60
caaggccata ttaaccccat gttaaagcta gccaaaatcc ttcatcacaa aggctttcac    120
atcactttg tcaatactga atttaaccac agacgtctgc ttaaatctcg tggccctgat    180
tctctcaagg gtcttctcttc tttccgtttt gagacaattc ctgatggact ccgccatgt    240
gatgcagatg ccacacaaga tataccttct ttgtgtgaat ctacaaccaa tacttgcttg    300
ggtccttta gggatcttct tgcgaaactc aatgatacta acacatctaa cgtgccaccc    360
gtttcgtgca tcatctcaga tggtgtcatg agcttcacct tagccgctgc acaagaattg    420
ggagtccctg aagttctgtt ttggaccact agtgcttgtg gtttcttagg ttacatgcat    480
tattacaagg ttattgaaaa aggatacgct ccacttaaag atgcgagtga cttgacaaat    540
ggatacctag acaacatt ggatttata ccatgcatga agacgtacg tttaagggat    600
cttccaagtt tcttgagaac tacaaatcca gatgaattca tgatcaaatt tgtcctccaa    660
gaaacagaga gagcaagaaa ggcttctgca attatcctca acacatatga aacactagag    720
gctgaagttc ttgaatcgct ccgaaatctt cttcctccag tctacccat ggggcccttg    780
cattttctag tgaaacatgt tgatgatgag aattgaagg acttagatc cagcctttgg    840
aaagaggaac cagagtgtat acaatggctt gataccaaag aaccaaattc tgttgtttat    900
gttaactttg gaagcattac tgttatgact cctaatcaac ttattgaatt tgcttgggga    960
cttgcaaaca gccaacaatc attcttatgg atcataagac ctgatattgt ttcaggtgat   1020

-continued

```
gcatcgattc ttccccccga attcgtggaa gaaacgaaga agagaggtat gcttgctagt    1080
tggtgttcac aagaagaagt acttagtcac cctgcaatag gaggattctt gactcacagt    1140
ggatggaatt cgacactcga agtataagc agtggggtgc ctatgatttg ctggccattt     1200
ttcgctgaac agcaaacaaa ttgttggttt tccgtcacta aatgggatgt tggaatggag    1260
attgactgtg atgtgaagag ggatgaagtg gaaagccttg taagggaatt gatggttggg    1320
ggaaaaggca aaaagatgaa gaaaaaggca atggaatgga aggaattggc tgaagcatct    1380
gctaaagaac attcagggtc atcttatgtg aacattgaga aggtggtcaa tgatattctt    1440
ctttcgtcca aacattaa                                                  1458
```

<210> SEQ ID NO 30
<211> LENGTH: 496
<212> TYPE: PRT
<213> ORGANISM: Nicotiana tabacum

<400> SEQUENCE: 30

```
Met Ala Thr Gln Val His Lys Leu His Phe Ile Leu Phe Pro Leu Met
1               5                   10                  15

Ala Pro Gly His Met Ile Pro Met Ile Asp Ile Ala Lys Leu Leu Ala
            20                  25                  30

Asn Arg Gly Val Ile Thr Thr Ile Thr Thr Pro Val Asn Ala Asn
        35                  40                  45

Arg Phe Ser Ser Thr Ile Thr Arg Ala Ile Lys Ser Gly Leu Arg Ile
    50                  55                  60

Gln Ile Leu Thr Leu Lys Phe Pro Ser Val Glu Val Gly Leu Pro Glu
65                  70                  75                  80

Gly Cys Glu Asn Ile Asp Met Leu Pro Ser Leu Asp Leu Ala Ser Lys
                85                  90                  95

Phe Phe Ala Ala Ile Ser Met Leu Lys Gln Gln Val Glu Asn Leu Leu
            100                 105                 110

Glu Gly Ile Asn Pro Ser Pro Ser Cys Val Ile Ser Asp Met Gly Phe
        115                 120                 125

Pro Trp Thr Thr Gln Ile Ala Gln Asn Phe Asn Ile Pro Arg Ile Val
    130                 135                 140

Phe His Gly Thr Cys Cys Phe Ser Leu Leu Cys Ser Tyr Lys Ile Leu
145                 150                 155                 160

Ser Ser Asn Ile Leu Glu Asn Ile Thr Ser Asp Ser Glu Tyr Phe Val
                165                 170                 175

Val Pro Asp Leu Pro Asp Arg Val Glu Leu Thr Lys Ala Gln Val Ser
            180                 185                 190

Gly Ser Thr Lys Asn Thr Thr Ser Val Ser Ser Val Leu Lys Glu
        195                 200                 205

Val Thr Glu Gln Ile Arg Leu Ala Glu Glu Ser Ser Tyr Gly Val Ile
    210                 215                 220

Val Asn Ser Phe Glu Glu Leu Glu Gln Val Tyr Glu Lys Glu Tyr Arg
225                 230                 235                 240

Lys Ala Arg Gly Lys Lys Val Trp Cys Val Gly Pro Val Ser Leu Cys
                245                 250                 255

Asn Lys Glu Ile Glu Asp Leu Val Thr Arg Gly Asn Lys Thr Ala Ile
            260                 265                 270

Asp Asn Gln Asp Cys Leu Lys Trp Leu Asp Asn Phe Glu Thr Glu Ser
        275                 280                 285
```

```
Val Val Tyr Ala Ser Leu Gly Ser Leu Ser Arg Leu Thr Leu Leu Gln
    290                 295                 300

Met Val Glu Leu Gly Leu Gly Leu Glu Glu Ser Asn Arg Pro Phe Val
305                 310                 315                 320

Trp Val Leu Gly Gly Asp Lys Leu Asn Asp Leu Glu Lys Trp Ile
                325                 330                 335

Leu Glu Asn Gly Phe Glu Gln Arg Ile Lys Glu Arg Gly Val Leu Ile
                340                 345                 350

Arg Gly Trp Ala Pro Gln Val Leu Ile Leu Ser His Pro Ala Ile Gly
                355                 360                 365

Gly Val Leu Thr His Cys Gly Trp Asn Ser Thr Leu Glu Gly Ile Ser
    370                 375                 380

Ala Gly Leu Pro Met Val Thr Trp Pro Leu Phe Ala Glu Gln Phe Cys
385                 390                 395                 400

Asn Glu Lys Leu Val Val Gln Val Leu Lys Ile Gly Val Ser Leu Gly
                405                 410                 415

Val Lys Val Pro Val Lys Trp Gly Asp Glu Asn Val Gly Val Leu
                420                 425                 430

Val Lys Lys Asp Asp Val Lys Lys Ala Leu Asp Lys Leu Met Asp Glu
                435                 440                 445

Gly Glu Glu Gly Gln Val Arg Arg Thr Lys Ala Lys Glu Leu Gly Glu
    450                 455                 460

Leu Ala Lys Lys Ala Phe Gly Glu Gly Gly Ser Ser Tyr Val Asn Leu
465                 470                 475                 480

Thr Ser Leu Ile Glu Asp Ile Ile Glu Gln Gln Asn His Lys Glu Lys
                485                 490                 495

<210> SEQ ID NO 31
<211> LENGTH: 1491
<212> TYPE: DNA
<213> ORGANISM: Nicotiana tabacum

<400> SEQUENCE: 31
atggcaactc aagtgcacaa acttcatttc atactattcc ctttaatggc tccaggccac      60
atgattccta tgatagacat agctaaactt ctagcaaatc gcggtgtcat taccactatc     120
atcaccactc agtaaacgc caatcgtttc agttcaacaa ttactcgtgc cataaaatcc     180
ggtctaagaa tccaaattct tacactcaaa tttccaagtg tagaagtagg attaccagaa     240
ggttgcgaaa atattgacat gcttccttct cttgacttgg cttcaaagtt ttttgctgca     300
attagtatgc tgaaacaaca agttgaaaat ctcttagaag gaataaatcc aagtccaagt     360
tgtgttattt cagatatggg atttccttgg actactcaaa ttgcacaaaa ttttaatatc     420
ccaagaattg ttttcatgg tacttgttgt ttctcacttt tatgttccta taaatactt     480
tcctccaaca ttcttgaaaa ataaccctca gattcagagt attttgttgt tcctgattta     540
cccgatagag ttgaactaac gaaagctcag gtttcaggat cgacgaaaaa tactacttct     600
gttagttctt ctgtattgaa agaagttact gagcaaatca gattagccga ggaatcatca     660
tatggtgtaa ttgttaatag ttttgaggag ttggagcaag tgtatgagaa agaatatagg     720
aaagctagag ggaaaaaagt ttggtgtgtt ggtcctgttt ctttgtgtaa taggaaaatt     780
gaagatttgg ttacaagggg taataaaact gcaattgata tcaagattg cttgaaatgg     840
ttagataatt ttgaaacaga atctgtggtt tatgcaagtc ttggaagttt atctcgtttg     900
acattattgc aaatggtgga acttggtctt ggtttagaag agtcaaatag gccttttgta     960
```

-continued

```
tgggtattag gaggaggtga taaattaaat gatttagaga aatggattct tgagaatgga    1020
tttgagcaaa gaattaaaga aagaggagtt ttgattagag gatgggctcc tcaagtgctt    1080
atactttcac accctgcaat tggtggagta ttgactcatt gcggatggaa ttctacattg    1140
gaaggtattt cagcaggatt accaatggta acatggccac tatttgctga gcaattttgc    1200
aatgagaagt tagtagtcca agtgctaaaa attggagtga gcctaggtgt gaaggtgcct    1260
gtcaaatggg gagatgagga aaatgttgga gttttggtaa aaaaggatga tgttaagaaa    1320
gcattagaca aactaatgga tgaaggagaa gaaggacaag taagaagaac aaaagcaaaa    1380
gagttaggag aattggctaa aaaggcattt ggagaaggtg gttcttctta tgttaactta    1440
acatctctga ttgaagacat cattgagcaa caaaatcaca aggaaaaata g             1491
```

<210> SEQ ID NO 32
<211> LENGTH: 479
<212> TYPE: PRT
<213> ORGANISM: Nicotiana tabacum

<400> SEQUENCE: 32

```
Met Lys Thr Ala Glu Leu Val Phe Ile Pro Ala Pro Gly Met Gly His
1               5                   10                  15

Leu Val Pro Thr Val Glu Val Ala Lys Gln Leu Val Asp Arg His Glu
                20                  25                  30

Gln Leu Ser Ile Thr Val Leu Ile Met Thr Ile Pro Leu Glu Thr Asn
            35                  40                  45

Ile Pro Ser Tyr Thr Lys Ser Leu Ser Ser Asp Tyr Ser Ser Arg Ile
        50                  55                  60

Thr Leu Leu Pro Leu Ser Gln Pro Glu Thr Ser Val Thr Met Ser Ser
65                  70                  75                  80

Phe Asn Ala Ile Asn Phe Phe Glu Tyr Ile Ser Ser Tyr Lys Gly Arg
                85                  90                  95

Val Lys Asp Ala Val Ser Glu Thr Ser Phe Ser Ser Asn Ser Val
                100                 105                 110

Lys Leu Ala Gly Phe Val Ile Asp Met Phe Cys Thr Ala Met Ile Asp
            115                 120                 125

Val Ala Asn Glu Phe Gly Ile Pro Ser Tyr Val Phe Tyr Thr Ser Ser
        130                 135                 140

Ala Ala Met Leu Gly Leu Gln Leu His Phe Gln Ser Leu Ser Ile Glu
145                 150                 155                 160

Cys Ser Pro Lys Val His Asn Tyr Val Glu Pro Glu Ser Glu Val Leu
                165                 170                 175

Ile Ser Thr Tyr Met Asn Pro Val Pro Val Lys Cys Leu Pro Gly Ile
            180                 185                 190

Ile Leu Val Asn Asp Glu Ser Ser Thr Met Phe Val Asn His Ala Arg
        195                 200                 205

Arg Phe Arg Glu Thr Lys Gly Ile Met Val Asn Thr Phe Thr Glu Leu
    210                 215                 220

Glu Ser His Ala Leu Lys Ala Leu Ser Asp Asp Glu Lys Ile Pro Pro
225                 230                 235                 240

Ile Tyr Pro Val Gly Pro Ile Leu Asn Leu Glu Asn Gly Asn Glu Asp
                245                 250                 255

His Asn Gln Glu Tyr Asp Ala Ile Met Lys Trp Leu Asp Glu Lys Pro
            260                 265                 270

Asn Ser Ser Val Val Phe Leu Cys Phe Gly Ser Lys Gly Ser Phe Glu
        275                 280                 285
```

```
Glu Asp Gln Val Lys Glu Ile Ala Asn Ala Leu Glu Ser Ser Gly Tyr
        290                 295                 300

His Phe Leu Trp Ser Leu Arg Arg Pro Pro Lys Asp Lys Leu Gln
305                 310                 315                 320

Phe Pro Ser Glu Phe Glu Asn Pro Glu Glu Val Leu Pro Glu Gly Phe
                325                 330                 335

Phe Gln Arg Thr Lys Gly Arg Gly Lys Val Ile Gly Trp Ala Pro Gln
            340                 345                 350

Leu Ala Ile Leu Ser His Pro Ser Val Gly Gly Phe Val Ser His Cys
            355                 360                 365

Gly Trp Asn Ser Thr Leu Glu Ser Val Arg Ser Gly Val Pro Ile Ala
        370                 375                 380

Thr Trp Pro Leu Tyr Ala Glu Gln Gln Ser Asn Ala Phe Gln Leu Val
385                 390                 395                 400

Lys Asp Leu Gly Met Ala Val Glu Ile Lys Met Asp Tyr Arg Glu Asp
                405                 410                 415

Phe Asn Thr Arg Asn Pro Pro Leu Val Lys Ala Glu Glu Ile Glu Asp
            420                 425                 430

Gly Ile Arg Lys Leu Met Asp Ser Glu Asn Lys Ile Arg Ala Lys Val
            435                 440                 445

Thr Glu Met Lys Asp Lys Ser Arg Ala Ala Leu Leu Glu Gly Gly Ser
        450                 455                 460

Ser Tyr Val Ala Leu Gly His Phe Val Glu Thr Val Met Lys Asn
465                 470                 475

<210> SEQ ID NO 33
<211> LENGTH: 1440
<212> TYPE: DNA
<213> ORGANISM: Nicotiana tabacum

<400> SEQUENCE: 33
atgaagacag cagagttagt attcattcct gctcctggga tgggtcacct tgtaccaact     60
gtggaggtgg caaagcaact agtcgacaga cacgagcagc tttcgatcac agttctaatc    120
atgacaattc ctttggaaac aaatattcca tcatatacta atcactgtc ctcagactac     180 agttctcgta taacgctgct tccactctct caacctgaga cctctgttac tatgagcagt    240
tttaatgcca tcaattttt tgagtacatc tccagctaca agggtcgtgt caaagatgct    300
gttagtgaaa cctcctttag ttcgtcaaat tctgtgaaac ttgcaggatt tgtaatagac    360
atgttctgca ctgcgatgat tgatgtagcg aacgagtttg gaatcccaag ttatgtgttc    420
tacacttcta gtgcagctat gcttggacta caactgcatt ttcaaagtct tagcattgaa    480
tgcagtccga aagttcataa ctacgttgaa cctgaatcag aagttctgat ctcaacttac    540
atgaatccgg ttccagtcaa atgtttgccc ggaattatac tagtaaatga tgaaagtagc    600
accatgtttg tcaatcatgc acgaagattc agggagacga aaggaattat ggtgaacacg    660
ttcactgagc ttgaatcaca cgctttgaaa gcccttccg atgatgaaaa atcccacca    720 atctacccag ttggacctat acttaacctt gaaatgggga tgaagatca caatcaagaa    780 tatgatgcga ttatgaagtg gcttgacgag aagcctaatt catcagtggt gttcttatgc    840
tttggaagca aggggtctt cgaagaagat caggtgaagg aaatagcaaa tgctctagag    900
agcagtggct accacttctt gtggtcgcta aggcgaccgc caccaaaaga caagctacaa    960
ttcccaagcg aattcgagaa tccagaggaa gtcttaccag agggattctt tcaaaggact   1020
```

```
aaaggaagag gaaaggtgat aggatgggca ccccagttgg ctattttgtc tcatccttca     1080
gtaggaggat tcgtgtcgca ttgtgggtgg aattcaactc tggagagcgt tcgaagtgga     1140
gtgccgatag caacatggcc attgtatgca gagcaacaga gcaatgcatt tcaactggtg     1200
aaggatttgg gtatggcagt agagattaag atggattaca gggaagattt taatacgaga     1260
aatccaccac tggttaaagc tgaggagata gaagatggaa ttaggaagct gatggattca     1320
gagaataaaa tcagggctaa ggtgacggag atgaaggaca aaagtagagc agcactgctg     1380
gagggcggat catcatatgt agctcttggg cattttgttg agactgtcat gaaaaactag     1440
```

<210> SEQ ID NO 34
<211> LENGTH: 478
<212> TYPE: PRT
<213> ORGANISM: Nicotiana tabacum

<400> SEQUENCE: 34

```
Met Lys Thr Thr Glu Leu Val Phe Ile Pro Ala Pro Gly Met Gly His
1               5                   10                  15

Leu Val Pro Thr Val Glu Val Ala Lys Gln Leu Val Asp Arg Asp Glu
                20                  25                  30

Gln Leu Ser Ile Thr Val Leu Ile Met Thr Leu Pro Leu Glu Thr Asn
            35                  40                  45

Ile Pro Ser Tyr Thr Lys Ser Leu Ser Ser Asp Tyr Ser Ser Arg Ile
        50                  55                  60

Thr Leu Leu Gln Leu Ser Gln Pro Glu Thr Ser Val Ser Met Ser Ser
65                  70                  75                  80

Phe Asn Ala Ile Asn Phe Phe Glu Tyr Ile Ser Ser Tyr Lys Asp Arg
                85                  90                  95

Val Lys Asp Ala Val Asn Glu Thr Phe Ser Ser Ser Ser Val Lys
                100                 105                 110

Leu Lys Gly Phe Val Ile Asp Met Phe Cys Thr Ala Met Ile Asp Val
            115                 120                 125

Ala Asn Glu Phe Gly Ile Pro Ser Tyr Val Phe Tyr Thr Ser Asn Ala
        130                 135                 140

Ala Met Leu Gly Leu Gln Leu His Phe Gln Ser Leu Ser Ile Glu Tyr
145                 150                 155                 160

Ser Pro Lys Val His Asn Tyr Leu Asp Pro Glu Ser Glu Val Ala Ile
                165                 170                 175

Ser Thr Tyr Ile Asn Pro Ile Pro Val Lys Cys Leu Pro Gly Ile Ile
            180                 185                 190

Leu Asp Asn Asp Lys Ser Gly Thr Met Phe Val Asn His Ala Arg Arg
        195                 200                 205

Phe Arg Glu Thr Lys Gly Ile Met Val Asn Thr Phe Ala Glu Leu Glu
    210                 215                 220

Ser His Ala Leu Lys Ala Leu Ser Asp Asp Glu Lys Ile Pro Pro Ile
225                 230                 235                 240

Tyr Pro Val Gly Pro Ile Leu Asn Leu Gly Asp Gly Asn Glu Asp His
                245                 250                 255

Asn Gln Glu Tyr Asp Met Ile Met Lys Trp Leu Asp Glu Gln Pro His
            260                 265                 270

Ser Ser Val Val Phe Leu Cys Phe Gly Ser Lys Gly Ser Phe Glu Glu
        275                 280                 285

Asp Gln Val Lys Glu Ile Ala Asn Ala Leu Glu Arg Ser Gly Asn Arg
    290                 295                 300
```

```
Phe Leu Trp Ser Leu Arg Arg Pro Pro Lys Asp Thr Leu Gln Phe
305                 310                 315                 320

Pro Ser Glu Phe Glu Asn Pro Glu Val Leu Pro Val Gly Phe Phe
            325                 330                 335

Gln Arg Thr Lys Gly Arg Gly Lys Val Ile Gly Trp Ala Pro Gln Leu
            340                 345                 350

Ala Ile Leu Ser His Pro Ala Val Gly Gly Phe Val Ser His Cys Gly
                355                 360                 365

Trp Asn Ser Thr Leu Glu Ser Val Arg Ser Gly Val Pro Ile Ala Thr
    370                 375                 380

Trp Pro Leu Tyr Ala Glu Gln Gln Ser Asn Ala Phe Gln Leu Val Lys
385                 390                 395                 400

Asp Leu Gly Met Ala Val Glu Ile Lys Met Asp Tyr Arg Glu Asp Phe
                405                 410                 415

Asn Lys Thr Asn Pro Pro Leu Val Lys Ala Glu Ile Glu Asp Gly
            420                 425                 430

Ile Arg Lys Leu Met Asp Ser Glu Asn Lys Ile Arg Ala Lys Val Met
                435                 440                 445

Glu Met Lys Asp Lys Ser Arg Ala Ala Leu Leu Glu Gly Gly Ser Ser
450                 455                 460

Tyr Val Ala Leu Gly His Phe Val Glu Thr Val Met Lys Asn
465                 470                 475
```

<210> SEQ ID NO 35
<211> LENGTH: 1437
<212> TYPE: DNA
<213> ORGANISM: Nicotiana tabacum
<400> SEQUENCE: 35

```
atgaagacaa cagagttagt attcattcct gctcctggca tgggtcacct tgtacccact      60
gtggaggtgg caaagcaact agtcgacaga gacgaacagc tttcaatcac agttctcatc    120
atgacgcttc ctttggaaac aaatattcca tcatatacta atcactgtc ctcagactac     180
agttctcgta taacgctgct tcaactttct caacctgaga cctctgttag tatgagcagt    240
tttaatgcca tcaattttt tgagtacatc tccagctaca aggatcgtgt caaagatgct    300
gttaatgaaa cctttagttc gtcaagttct gtgaaactca aggatttgt aatagacatg    360
ttctgcactg cgatgattga tgtggcgaac gagtttggaa tcccaagtta tgtcttctac    420
acttctaatg cagctatgct tggactccaa ctccattttc aaagtcttag tattgaatac    480
agtccgaaag ttcataatta cctagaccct gaatcagaag tagcgatctc aacttacatt    540
aatccgattc cagtcaaatg tttgcccggg attatactag acaatgataa agtggcacc     600
atgttcgtca atcatgcacg aagattcagg gagacgaaag gaattatggt gaacacattc    660
gctgagcttg aatcacacgc tttgaaagcc ctttccgatg atgagaaaat cccaccaatc    720
tacccagttg ggcctatact taaccttgga gatgggaatg aagatcacaa tcaagaatat    780
gatatgatta tgaagtggct cgacgagcag cctcattcat cagtggtgtt cctatgcttt    840
ggaagcaagg gatctttcga agaagatcaa gtgaaggaaa tagcaaatgc tctagagaga    900
agtggtaacc ggttcttgtg gtcgctaaga cgaccgccac caaaagacac gctacaattc    960
ccaagcgaat tcgagaatcc agaggaagtc ttgccggtgg gattctttca aaggactaaa   1020
ggaagaggaa aggtgatagg atgggcaccc cagttggcta ttttgtctca tcctgcagta   1080
ggaggattcg tgtcgcattg tgggtggaat tcaactttgg agagtgttcg tagtggagta   1140
```

-continued

```
ccgatagcaa catggccatt gtatgcagag caacagagca atgcatttca actggtgaag    1200
gatttgggga tggcagtgga gattaagatg gattacaggg aagattttaa taagacaaat    1260
ccaccactgg ttaaagctga ggagatagaa gatggaatta ggaagctgat ggattcagag    1320
aataaaatca gggctaaggt gatggagatg aaggacaaaa gtagagcagc gttattagaa    1380
ggcggatcat catatgtagc tctcgggcat tttgttgaga ctgtcatgaa aaactaa       1437
```

<210> SEQ ID NO 36
<211> LENGTH: 482
<212> TYPE: PRT
<213> ORGANISM: Nicotiana tabacum
<400> SEQUENCE: 36

```
Met Lys Glu Thr Lys Lys Ile Glu Leu Val Phe Ile Pro Ser Pro Gly
1               5                   10                  15

Ile Gly His Leu Val Ser Thr Val Glu Met Ala Lys Leu Leu Ile Ala
            20                  25                  30

Arg Glu Glu Gln Leu Ser Ile Thr Val Leu Ile Ile Gln Trp Pro Asn
        35                  40                  45

Asp Lys Lys Leu Asp Ser Tyr Ile Gln Ser Val Ala Asn Phe Ser Ser
    50                  55                  60

Arg Leu Lys Phe Ile Arg Leu Pro Gln Asp Asp Ser Ile Met Gln Leu
65                  70                  75                  80

Leu Lys Ser Asn Ile Phe Thr Thr Phe Ile Ala Ser His Lys Pro Ala
                85                  90                  95

Val Arg Asp Ala Val Ala Asp Ile Leu Lys Ser Glu Ser Asn Asn Thr
            100                 105                 110

Leu Ala Gly Ile Val Ile Asp Leu Phe Cys Thr Ser Met Ile Asp Val
        115                 120                 125

Ala Asn Glu Phe Glu Leu Pro Thr Tyr Val Phe Tyr Thr Ser Gly Ala
    130                 135                 140

Ala Thr Leu Gly Leu His Tyr His Ile Gln Asn Leu Arg Asp Glu Phe
145                 150                 155                 160

Asn Lys Asp Ile Thr Lys Tyr Lys Asp Glu Pro Glu Glu Lys Leu Ser
                165                 170                 175

Ile Ala Thr Tyr Leu Asn Pro Phe Pro Ala Lys Cys Leu Pro Ser Val
            180                 185                 190

Ala Leu Asp Lys Glu Gly Gly Ser Thr Met Phe Leu Asp Leu Ala Lys
        195                 200                 205

Arg Phe Arg Glu Thr Lys Gly Ile Met Ile Asn Thr Phe Leu Glu Leu
210                 215                 220

Glu Ser Tyr Ala Leu Asn Ser Leu Ser Arg Asp Lys Asn Leu Pro Pro
225                 230                 235                 240

Ile Tyr Pro Val Gly Pro Val Leu Asn Leu Asn Asn Val Glu Gly Asp
                245                 250                 255

Asn Leu Gly Ser Ser Asp Gln Asn Thr Met Lys Trp Leu Asp Asp Gln
            260                 265                 270

Pro Ala Ser Ser Val Val Phe Leu Cys Phe Gly Ser Gly Gly Ser Phe
        275                 280                 285

Glu Lys His Gln Val Lys Glu Ile Ala Tyr Ala Leu Glu Ser Ser Gly
    290                 295                 300

Cys Arg Phe Leu Trp Ser Leu Arg Arg Pro Pro Thr Glu Asp Ala Arg
305                 310                 315                 320

Phe Pro Ser Asn Tyr Glu Asn Leu Glu Glu Ile Leu Pro Glu Gly Phe
```

```
                    325                 330                 335
Leu Glu Arg Thr Lys Gly Ile Gly Lys Val Ile Gly Trp Ala Pro Gln
                340                 345                 350
Leu Ala Ile Leu Ser His Lys Ser Thr Gly Gly Phe Val Ser His Cys
            355                 360                 365
Gly Trp Asn Ser Thr Leu Glu Ser Thr Tyr Phe Gly Val Pro Ile Ala
        370                 375                 380
Thr Trp Pro Met Tyr Ala Glu Gln Gln Ala Asn Ala Phe Gln Leu Val
385                 390                 395                 400
Lys Asp Leu Arg Met Gly Val Glu Ile Lys Met Asp Tyr Arg Lys Asp
                405                 410                 415
Met Lys Val Met Gly Lys Glu Val Ile Val Lys Ala Glu Glu Ile Glu
                420                 425                 430
Lys Ala Ile Arg Glu Ile Met Asp Ser Glu Ser Glu Ile Arg Val Lys
            435                 440                 445
Val Lys Glu Met Lys Glu Lys Ser Arg Ala Ala Gln Met Glu Gly Gly
        450                 455                 460
Ser Ser Tyr Thr Ser Ile Gly Gly Phe Ile Gln Ile Ile Met Glu Asn
465                 470                 475                 480
Ser Gln
```

<210> SEQ ID NO 37
<211> LENGTH: 1449
<212> TYPE: DNA
<213> ORGANISM: Nicotiana tabacum

<400> SEQUENCE: 37

| | | | | | |
|---|---|---|---|---|---|
| atgaaagaaa | ccaagaaaat | agagttagtc | ttcattcctt | caccaggaat | tggccattta    60 |
| gtatccacag | ttgaaatggc | aaagcttctt | atagctagag | aagagcagct | atctatcaca   120 |
| gtcctcatca | tccaatggcc | taacgacaag | aagctcgatt | cttatatcca | atcagtcgcc   180 |
| aatttcagct | cgcgtttgaa | attcattcga | ctccctcagg | atgattccat | tatgcagcta   240 |
| ctcaaaagca | acatttttcac | cacgtttatt | gccagtcata | agcctgcagt | tagagatgct   300 |
| gttgctgata | ttctcaagtc | agaatcaaat | aatacgctag | caggtattgt | tatcgacttg   360 |
| ttctgcacct | caatgataga | cgtggccaat | gagttcgagc | taccaaccta | tgttttctac   420 |
| acgtctggtg | cagcaaccct | tggtcttcat | tatcatatac | agaatctcag | ggatgaattt   480 |
| aacaaagata | ttaccaagta | caaagacgaa | cctgaagaaa | actctctat | agcaacatat   540 |
| ctcaatccat | ttccagcaaa | atgtttgccg | tctgtagcct | tagacaaaga | aggtggttca   600 |
| acaatgtttc | ttgatctcgc | aaaaaggttt | cgagaaacca | aaggtattat | gataaacaca   660 |
| tttctagagc | tcgaatccta | tgcattaaac | tcgctctcac | gagacaagaa | tcttccacct   720 |
| atataccctg | tcggaccagt | attgaacctt | aacaatgttg | aaggtgacaa | cttaggttca   780 |
| tctgaccaga | atactatgaa | atggttagat | gatcagcccg | cttcatctgt | agtgttcctt   840 |
| tgttttggta | gtggtggaag | ctttgaaaaa | catcaagtta | aggaaatagc | ctatgctctg   900 |
| gagagcagtg | ggtgtcggtt | tttgtggtcg | ttaaggcgac | caccaaccga | agatgcaaga   960 |
| tttccaagca | actatgaaaa | tcttgaagaa | attttgccag | aaggattctt | ggaaagaaca  1020 |
| aaagggattg | gaaaagtgat | aggatgggca | cctcagttgg | cgattttgtc | acataaatcg  1080 |
| acgggggat | ttgtgtcgca | ctgtggatgg | aattcgactt | tggaaagtac | atattttgga  1140 |
| gtgccaatag | caacctggcc | aatgtacgcg | gagcaacaag | cgaatgcatt | tcaattggtt  1200 |

```
aaggatttga gaatgggagt tgagattaag atggattata ggaaggatat gaaagtgatg    1260
ggcaaagaag ttatagtgaa agctgaggag attgagaaag caataagaga aattatggat    1320
tccgagagtg aaattcgggt gaaggtgaaa gagatgaagg agaagagcag agcagcacaa    1380
atggaaggtg ctcttcttta cacttctatt ggaggtttca tccaaattat catggagaat    1440
tctcaataa                                                            1449
```

<210> SEQ ID NO 38
<211> LENGTH: 470
<212> TYPE: PRT
<213> ORGANISM: Nicotiana tabacum

<400> SEQUENCE: 38

```
Met Val Gln Pro His Val Leu Leu Val Thr Phe Pro Ala Gln Gly His
1               5                   10                  15

Ile Asn Pro Cys Leu Gln Phe Ala Lys Arg Leu Ile Arg Met Gly Ile
                20                  25                  30

Glu Val Thr Phe Ala Thr Ser Val Phe Ala His Arg Arg Met Ala Lys
            35                  40                  45

Thr Thr Thr Ser Thr Leu Ser Lys Gly Leu Asn Phe Ala Ala Phe Ser
        50                  55                  60

Asp Gly Tyr Asp Asp Gly Phe Lys Ala Asp Glu His Asp Ser Gln His
65                  70                  75                  80

Tyr Met Ser Glu Ile Lys Ser Arg Gly Ser Lys Thr Leu Lys Asp Ile
                85                  90                  95

Ile Leu Lys Ser Ser Asp Glu Gly Arg Pro Val Thr Ser Leu Val Tyr
            100                 105                 110

Ser Leu Leu Leu Pro Trp Ala Ala Lys Val Ala Arg Glu Phe His Ile
        115                 120                 125

Pro Cys Ala Leu Leu Trp Ile Gln Pro Ala Thr Val Leu Asp Ile Tyr
    130                 135                 140

Tyr Tyr Tyr Phe Asn Gly Tyr Glu Asp Ala Ile Lys Gly Ser Thr Asn
145                 150                 155                 160

Asp Pro Asn Trp Cys Ile Gln Leu Pro Arg Leu Pro Leu Leu Lys Ser
                165                 170                 175

Gln Asp Leu Pro Ser Phe Leu Leu Ser Ser Asn Glu Glu Lys Tyr
            180                 185                 190

Ser Phe Ala Leu Pro Thr Phe Lys Glu Gln Leu Asp Thr Leu Asp Val
        195                 200                 205

Glu Glu Asn Pro Lys Val Leu Val Asn Thr Phe Asp Ala Leu Glu Pro
    210                 215                 220

Lys Glu Leu Lys Ala Ile Glu Lys Tyr Asn Leu Ile Gly Ile Gly Pro
225                 230                 235                 240

Leu Ile Pro Ser Thr Phe Leu Asp Gly Lys Asp Pro Leu Asp Ser Ser
                245                 250                 255

Phe Gly Gly Asp Leu Phe Gln Lys Ser Asn Asp Tyr Ile Glu Trp Leu
            260                 265                 270

Asn Ser Lys Ala Asn Ser Ser Val Val Tyr Ile Ser Phe Gly Ser Leu
        275                 280                 285

Leu Asn Leu Ser Lys Asn Gln Lys Glu Ile Ala Lys Gly Leu Ile
    290                 295                 300

Glu Ile Lys Lys Pro Phe Leu Trp Val Ile Arg Asp Gln Glu Asn Gly
305                 310                 315                 320

Lys Gly Asp Glu Lys Glu Glu Lys Leu Ser Cys Met Met Glu Leu Glu
```

```
            325                 330                 335
Lys Gln Gly Lys Ile Val Pro Trp Cys Ser Gln Leu Glu Val Leu Thr
            340                 345                 350

His Pro Ser Ile Gly Cys Phe Val His Cys Gly Trp Asn Ser Thr
            355                 360                 365

Leu Glu Ser Leu Ser Ser Gly Val Ser Val Val Ala Phe Pro His Trp
            370                 375                 380

Thr Asp Gln Gly Thr Asn Ala Lys Leu Ile Glu Asp Val Trp Lys Thr
385                 390                 395                 400

Gly Val Arg Leu Lys Lys Asn Glu Asp Gly Val Val Glu Ser Glu Glu
            405                 410                 415

Ile Lys Arg Cys Ile Glu Met Val Met Asp Gly Glu Lys Gly Glu
            420                 425                 430

Glu Met Arg Arg Asn Ala Gln Lys Trp Lys Glu Leu Ala Arg Glu Ala
            435                 440                 445

Val Lys Glu Gly Gly Ser Ser Glu Met Asn Leu Lys Ala Phe Val Gln
            450                 455                 460

Glu Val Gly Lys Gly Cys
465                 470

<210> SEQ ID NO 39
<211> LENGTH: 1413
<212> TYPE: DNA
<213> ORGANISM: Nicotiana tabacum

<400> SEQUENCE: 39
atggtgcaac cccatgtcct cttggtgact tttccagcac aaggccatat taatccatgt    60
ctccaatttg ccaagaggct aattagaatg ggcattgagg taacttttgc cacgagcgtt   120
ttcgcccatc gtcgtatggc aaaaactacg acttccactc tatccaaggg cttaaatttt   180
gcggcattct ctgatgggta cgacgatggt ttcaaggccg atgagcatga ttctcaacat   240
tacatgtcgg agataaaaag tcgcggttct aaaacccaa aagatatcat tttgaagagc   300
tcagacgagg acgtcctgt gacatccctc gtctattctc ttttgcttcc atgggctgca   360
aaggtagcgc gtgaatttca cataccgtgc gcgttactat ggattcaacc agcaactgtg   420
ctagacatat attattatta cttcaatggc tatgaggatg ccataaaagg tagcaccaat   480
gatccaaatt ggtgtattca attgcctagg cttccactac taaaaagcca agatcttcct   540
tcttttttac tttcttctag taatgaagaa aaatatagct tgctctacc aacatttaaa   600
gagcaacttg acacattaga tgttgaagaa atcctaaag tacttgtgaa cacatttgat   660
gcattagagc caaaggaact caaagctatt gaaaagtaca atttaattgg gattggacca   720
ttgattcctt caacattttt ggacggaaaa gacccttgg attcttcctt tggtggtgat   780
cttttttcaaa agtctaatga ctatattgaa tggttgaact caaaggctaa ctcatctgtg   840
gtttatatct catttgggag tctcttgaat ttgtcaaaaa atcaaaagga ggagattgca   900
aaagggttga tagagattaa aaagccattc ttgtgggtaa taagagatca agaaaatggt   960
aaggagatg aaaagaaga gaaattaagt tgtatgatgg agttggaaaa gcaagggaaa  1020
atagtaccat ggtgttcaca acttgaagtc ttaacacatc catctatagg atgtttcgtg  1080
tcacattgtg gatggaattc gactctggaa agtttatcgt caggcgtgtc agtagtggca  1140
tttcctcatt ggacggatca agggacaaat gctaaactaa ttgaagatgt ttggaagaca  1200
ggtgtaaggt tgaaaaagaa tgaagatggt gtggttgaga gtgaagagat aaaaaggtgc  1260
```

```
atagaaatgg taatggatgg tggagagaaa ggagaagaaa tgagaagaaa tgctcaaaaa   1320
tggaaagaat tggcaaggga agctgtaaaa gaaggcggat cttcggaaat gaatctaaaa   1380
gcttttgttc aagaagttgg caaaggttgc tga                                1413
```

<210> SEQ ID NO 40
<211> LENGTH: 28
<212> TYPE: PRT
<213> ORGANISM: Cannabis

<400> SEQUENCE: 40

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala
            20                  25
```

<210> SEQ ID NO 41
<211> LENGTH: 28
<212> TYPE: PRT
<213> ORGANISM: Cannabis

<400> SEQUENCE: 41

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala
            20                  25
```

<210> SEQ ID NO 42
<211> LENGTH: 545
<212> TYPE: PRT
<213> ORGANISM: Cannabis

<400> SEQUENCE: 42

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
```

195                 200                 205
Leu Val Asn Val Asp Gly Lys Val Leu Asp Arg Lys Ser Met Gly Glu
    210                 215                 220

Asp Leu Phe Trp Ala Ile Arg Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415

Tyr Pro Tyr Gly Gly Ile Met Glu Glu Ile Ser Glu Ser Ala Ile Pro
            420                 425                 430

Phe Pro His Arg Ala Gly Ile Met Tyr Glu Leu Trp Tyr Thr Ala Ser
        435                 440                 445

Trp Glu Lys Gln Glu Asp Asn Glu Lys His Ile Asn Trp Val Arg Ser
    450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asn
        515                 520                 525

Asn Phe Phe Arg Asn Glu Gln Ser Ile Pro Pro Leu Pro Pro His His
    530                 535                 540

His
545

<210> SEQ ID NO 43
<211> LENGTH: 462
<212> TYPE: PRT
<213> ORGANISM: Humulus lupulus

<400> SEQUENCE: 43

Met Gly Arg Ala Pro Cys Cys Glu Lys Val Gly Leu Lys Lys Gly Arg
1               5                   10                  15

Trp Thr Ser Glu Glu Asp Glu Ile Leu Thr Lys Tyr Ile Gln Ser Asn
            20                  25                  30

Gly Glu Gly Cys Trp Arg Ser Leu Pro Lys Asn Ala Gly Leu Leu Arg
            35                  40                  45

Cys Gly Lys Ser Cys Arg Leu Arg Trp Ile Asn Tyr Leu Arg Ala Asp
            50                  55                  60

Leu Lys Arg Gly Asn Ile Ser Ser Glu Glu Asp Ile Ile Ile Lys
65                  70                  75                  80

Leu His Ser Thr Leu Gly Asn Arg Trp Ser Leu Ile Ala Ser His Leu
                85                  90                  95

Pro Gly Arg Thr Asp Asn Glu Ile Lys Asn Tyr Trp Asn Ser His Leu
            100                 105                 110

Ser Arg Lys Ile His Thr Phe Arg Arg Cys Asn Asn Thr Thr Thr His
            115                 120                 125

His His His Leu Pro Asn Leu Val Thr Val Thr Lys Val Asn Leu Pro
        130                 135                 140

Ile Pro Lys Arg Lys Gly Gly Arg Thr Ser Arg Leu Ala Met Lys Lys
145                 150                 155                 160

Asn Lys Ser Ser Thr Ser Asn Gln Asn Ser Ser Val Ile Lys Asn Asp
                165                 170                 175

Val Gly Ser Ser Ser Thr Thr Thr Ser Val His Gln Arg Thr
            180                 185                 190

Thr Thr Thr Thr Pro Thr Met Asp Asp Gln Gln Lys Arg Gln Leu Ser
            195                 200                 205

Arg Cys Arg Leu Glu Glu Lys Glu Asp Gln Asp Gly Ala Ser Thr Gly
            210                 215                 220

Thr Val Val Met Met Leu Gly Gln Ala Ala Val Gly Ser Ser Cys
225                 230                 235                 240

Asp Glu Asp Met Leu Gly His Asp Gln Leu Ser Phe Leu Cys Cys Ser
                245                 250                 255

Glu Glu Lys Thr Thr Glu Asn Ser Met Thr Asn Leu Lys Glu Asn Gly
            260                 265                 270

Asp His Glu Val Ser Gly Pro Tyr Asp Tyr Asp His Arg Tyr Glu Lys
            275                 280                 285

Glu Thr Ser Val Asp Glu Gly Met Leu Leu Cys Phe Asn Asp Ile Ile
            290                 295                 300

Asp Ser Asn Leu Leu Asn Pro Asn Glu Val Leu Thr Leu Ser Glu Glu
305                 310                 315                 320

Ser Leu Asn Leu Gly Gly Ala Leu Met Asp Thr Thr Thr Ser Thr Thr
                325                 330                 335

Thr Asn Asn Asn Asn Tyr Ser Leu Ser Tyr Asn Asn Asn Gly Asp Cys
            340                 345                 350

Val Ile Ser Asp Asp His Asp Gln Tyr Trp Leu Asp Asp Val Val Gly
            355                 360                 365

Val Asp Phe Trp Ser Trp Glu Ser Ser Thr Thr Val Thr Gln Glu Gln
            370                 375                 380

Glu Gln Glu Gln Glu Gln Glu Gln Glu Gln Glu Gln Glu Gln Glu Gln
385                 390                 395                 400

Glu Gln Glu His His Gln Gln Asp Gln Lys Lys Asn Thr Trp Asp
                405                 410                 415

Asn Glu Lys Glu Lys Met Leu Ala Leu Leu Trp Asp Ser Asp Asn Ser
            420                 425                 430

Asn Trp Glu Leu Gln Asp Asn Asn Tyr His Lys Cys Gln Glu Ile

```
                   435                 440                 445
Thr Ser Asp Lys Glu Asn Ala Met Val Ala Trp Leu Leu Ser
    450                 455                 460

<210> SEQ ID NO 44
<211> LENGTH: 371
<212> TYPE: PRT
<213> ORGANISM: Arabidopsis thaliana

<400> SEQUENCE: 44

Met Gly Arg Ala Pro Cys Cys Glu Lys Val Gly Ile Lys Arg Gly Arg
1               5                   10                  15

Trp Thr Ala Glu Glu Asp Gln Ile Leu Ser Asn Tyr Ile Gln Ser Asn
                20                  25                  30

Gly Glu Gly Ser Trp Arg Ser Leu Pro Lys Asn Ala Gly Leu Lys Arg
            35                  40                  45

Cys Gly Lys Ser Cys Arg Leu Arg Trp Ile Asn Tyr Leu Arg Ser Asp
        50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
                85                  90                  95

Pro Gly Arg Thr Asp Asn Glu Ile Lys Asn Tyr Trp Asn Ser His Leu
            100                 105                 110

Ser Arg Lys Leu His Asn Phe Ile Arg Lys Pro Ser Ile Ser Gln Asp
        115                 120                 125

Val Ser Ala Val Ile Met Thr Asn Ala Ser Ser Ala Pro Pro Pro
130                 135                 140

Gln Ala Lys Arg Arg Leu Gly Arg Thr Ser Arg Ser Ala Met Lys Pro
145                 150                 155                 160

Lys Ile His Arg Thr Lys Thr Arg Lys Thr Lys Thr Ser Ala Pro
                165                 170                 175

Pro Glu Pro Asn Ala Asp Val Ala Gly Ala Asp Lys Glu Ala Leu Met
            180                 185                 190

Val Glu Ser Ser Gly Ala Glu Ala Glu Leu Gly Arg Pro Cys Asp Tyr
        195                 200                 205

Tyr Gly Asp Asp Cys Asn Lys Asn Leu Met Ser Ile Asn Gly Asp Asn
    210                 215                 220

Gly Val Leu Thr Phe Asp Asp Ile Ile Asp Leu Leu Leu Asp Glu
225                 230                 235                 240

Ser Asp Pro Gly His Leu Tyr Thr Asn Thr Thr Cys Gly Gly Asp Gly
                245                 250                 255

Glu Leu His Asn Ile Arg Asp Ser Glu Gly Ala Arg Gly Phe Ser Asp
            260                 265                 270

Thr Trp Asn Gln Gly Asn Leu Asp Cys Leu Leu Gln Ser Cys Pro Ser
        275                 280                 285

Val Glu Ser Phe Leu Asn Tyr Asp His Gln Val Asn Asp Ala Ser Thr
    290                 295                 300

Asp Glu Phe Ile Asp Trp Asp Cys Val Trp Gln Glu Gly Ser Asp Asn
305                 310                 315                 320

Asn Leu Trp His Glu Lys Glu Asn Pro Asp Ser Met Val Ser Trp Leu
                325                 330                 335

Leu Asp Gly Asp Asp Glu Ala Thr Ile Gly Asn Ser Asn Cys Glu Asn
            340                 345                 350
```

-continued

Phe Gly Glu Pro Leu Asp His Asp Glu Ser Ala Leu Val Ala Trp
         355                 360                 365

Leu Leu Ser
         370

<210> SEQ ID NO 45
<211> LENGTH: 243
<212> TYPE: PRT
<213> ORGANISM: Arabidopsis thaliana

<400> SEQUENCE: 45

Met Asn Ile Ser Arg Thr Glu Phe Ala Asn Cys Lys Thr Leu Ile Asn
1               5                   10                  15

His Lys Glu Glu Val Glu Val Glu Lys Lys Met Glu Ile Glu Ile
            20                  25                  30

Arg Arg Gly Pro Trp Thr Val Glu Glu Asp Met Lys Leu Val Ser Tyr
        35                  40                  45

Ile Ser Leu His Gly Glu Gly Arg Trp Asn Ser Leu Ser Arg Ser Ala
    50                  55                  60

Gly Leu Asn Arg Thr Gly Lys Ser Cys Arg Leu Arg Trp Leu Asn Tyr
65                  70                  75                  80

Leu Arg Pro Asp Ile Arg Arg Gly Asp Ile Ser Leu Gln Glu Gln Phe
                85                  90                  95

Ile Ile Leu Glu Leu His Ser Arg Trp Gly Asn Arg Trp Ser Lys Ile
            100                 105                 110

Ala Gln His Leu Pro Gly Arg Thr Asp Asn Glu Ile Lys Asn Tyr Trp
        115                 120                 125

Arg Thr Arg Val Gln Lys His Ala Lys Leu Leu Lys Cys Asp Val Asn
    130                 135                 140

Ser Lys Gln Phe Lys Asp Thr Ile Lys His Leu Trp Met Pro Arg Leu
145                 150                 155                 160

Ile Glu Arg Ile Ala Ala Thr Gln Ser Val Gln Phe Thr Ser Asn His
                165                 170                 175

Tyr Ser Pro Glu Asn Ser Ser Val Ala Thr Ala Thr Ser Ser Thr Ser
            180                 185                 190

Ser Ser Glu Ala Val Arg Ser Ser Phe Tyr Gly Gly Asp Gln Val Glu
        195                 200                 205

Phe Gly Thr Leu Asp His Met Thr Asn Gly Gly Tyr Trp Phe Asn Gly
    210                 215                 220

Gly Asp Thr Phe Glu Thr Leu Cys Ser Phe Asp Glu Leu Asn Lys Trp
225                 230                 235                 240

Leu Ile Gln

<210> SEQ ID NO 46
<211> LENGTH: 517
<212> TYPE: PRT
<213> ORGANISM: Cannabis

<400> SEQUENCE: 46

Asn Pro Arg Glu Asn Phe Leu Lys Cys Phe Ser Lys His Ile Pro Asn
1               5                   10                  15

Asn Val Ala Asn Pro Lys Leu Val Tyr Thr Gln His Asp Gln Leu Tyr
            20                  25                  30

Met Ser Ile Leu Asn Ser Thr Ile Gln Asn Leu Arg Phe Ile Ser Asp
        35                  40                  45

Thr Thr Pro Lys Pro Leu Val Ile Val Thr Pro Ser Asn Asn Ser His

-continued

```
                50                  55                  60
Ile Gln Ala Thr Ile Leu Cys Ser Lys Lys Val Gly Leu Gln Ile Arg
 65                  70                  75                  80

Thr Arg Ser Gly Gly His Asp Ala Glu Gly Met Ser Tyr Ile Ser Gln
                     85                  90                  95

Val Pro Phe Val Val Asp Leu Arg Asn Met His Ser Ile Lys Ile
                100                 105                 110

Asp Val His Ser Gln Thr Ala Trp Val Glu Ala Gly Ala Thr Leu Gly
                115                 120                 125

Glu Val Tyr Tyr Trp Ile Asn Glu Lys Asn Glu Asn Leu Ser Phe Pro
            130                 135                 140

Gly Gly Tyr Cys Pro Thr Val Gly Val Gly Gly His Phe Ser Gly Gly
145                 150                 155                 160

Gly Tyr Gly Ala Leu Met Arg Asn Tyr Gly Leu Ala Ala Asp Asn Ile
                165                 170                 175

Ile Asp Ala His Leu Val Asn Val Asp Gly Lys Val Leu Asp Arg Lys
                180                 185                 190

Ser Met Gly Glu Asp Leu Phe Trp Ala Ile Arg Gly Gly Gly Gly Glu
                195                 200                 205

Asn Phe Gly Ile Ile Ala Ala Trp Lys Ile Lys Leu Val Asp Val Pro
210                 215                 220

Ser Lys Ser Thr Ile Phe Ser Val Lys Lys Asn Met Glu Ile His Gly
225                 230                 235                 240

Leu Val Lys Leu Phe Asn Lys Trp Gln Asn Ile Ala Tyr Lys Tyr Asp
                245                 250                 255

Lys Asp Leu Val Leu Met Thr His Phe Ile Thr Lys Asn Ile Thr Asp
                260                 265                 270

Asn His Gly Lys Asn Lys Thr Thr Val His Gly Tyr Phe Ser Ser Ile
                275                 280                 285

Phe His Gly Gly Val Asp Ser Leu Val Asp Leu Met Asn Lys Ser Phe
                290                 295                 300

Pro Glu Leu Gly Ile Lys Lys Thr Asp Cys Lys Glu Phe Ser Trp Ile
305                 310                 315                 320

Asp Thr Thr Ile Phe Tyr Ser Gly Val Val Asn Phe Asn Thr Ala Asn
                325                 330                 335

Phe Lys Lys Glu Ile Leu Leu Asp Arg Ser Ala Gly Lys Lys Thr Ala
                340                 345                 350

Phe Ser Ile Lys Leu Asp Tyr Val Lys Lys Pro Ile Pro Glu Thr Ala
                355                 360                 365

Met Val Lys Ile Leu Glu Lys Leu Tyr Glu Glu Asp Val Gly Ala Gly
            370                 375                 380

Met Tyr Val Leu Tyr Pro Tyr Gly Gly Ile Met Glu Glu Ile Ser Glu
385                 390                 395                 400

Ser Ala Ile Pro Phe Pro His Arg Ala Gly Ile Met Tyr Glu Leu Trp
                405                 410                 415

Tyr Thr Ala Ser Trp Glu Lys Gln Glu Asp Asn Glu Lys His Ile Asn
                420                 425                 430

Trp Val Arg Ser Val Tyr Asn Phe Thr Thr Pro Tyr Val Ser Gln Asn
                435                 440                 445

Pro Arg Leu Ala Tyr Leu Asn Tyr Arg Asp Leu Asp Leu Gly Lys Thr
                450                 455                 460

Asn His Ala Ser Pro Asn Asn Tyr Thr Gln Ala Arg Ile Trp Gly Glu
465                 470                 475                 480
```

Lys Tyr Phe Gly Lys Asn Phe Asn Arg Leu Val Lys Val Lys Thr Lys
            485                 490                 495

Val Asp Pro Asn Asn Phe Arg Asn Glu Gln Ser Ile Pro Pro Leu
            500                 505                 510

Pro Pro His His His
            515

<210> SEQ ID NO 47
<211> LENGTH: 520
<212> TYPE: PRT
<213> ORGANISM: Arabidopsis thaliana

<400> SEQUENCE: 47

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Met Asp Pro Tyr
                20                  25                  30

Lys Tyr Arg Pro Ala Ser Ser Tyr Asn Ser Pro Phe Phe Thr Thr Asn
            35                  40                  45

Ser Gly Ala Pro Val Trp Asn Asn Asn Ser Ser Met Thr Val Gly Pro
        50                  55                  60

Arg Gly Leu Ile Leu Leu Glu Asp Tyr His Leu Val Glu Lys Leu Ala
65                  70                  75                  80

Asn Phe Asp Arg Glu Arg Ile Pro Glu Arg Val Val His Ala Arg Gly
                85                  90                  95

Ala Ser Ala Lys Gly Phe Phe Glu Val Thr His Asp Ile Ser Asn Leu
            100                 105                 110

Thr Cys Ala Asp Phe Leu Arg Ala Pro Gly Val Gln Thr Pro Val Ile
        115                 120                 125

Val Arg Phe Ser Thr Val Ile His Ala Arg Gly Ser Pro Glu Thr Leu
130                 135                 140

Arg Asp Pro Arg Gly Phe Ala Val Lys Phe Tyr Thr Arg Glu Gly Asn
145                 150                 155                 160

Phe Asp Leu Val Gly Asn Asn Phe Pro Val Phe Phe Ile Arg Asp Gly
                165                 170                 175

Met Lys Phe Pro Asp Ile Val His Ala Leu Lys Pro Asn Pro Lys Ser
            180                 185                 190

His Ile Gln Glu Asn Trp Arg Ile Leu Asp Phe Phe Ser His His Pro
        195                 200                 205

Glu Ser Leu Asn Met Phe Thr Phe Leu Phe Asp Asp Ile Gly Ile Pro
210                 215                 220

Gln Asp Tyr Arg His Met Asp Gly Ser Gly Val Asn Thr Tyr Met Leu
225                 230                 235                 240

Ile Asn Lys Ala Gly Lys Ala His Tyr Val Lys Phe His Trp Lys Pro
                245                 250                 255

Thr Cys Gly Val Lys Ser Leu Leu Glu Glu Asp Ala Ile Arg Leu Gly
            260                 265                 270

Gly Thr Asn His Ser His Ala Thr Gln Asp Leu Tyr Asp Ser Ile Ala
        275                 280                 285

Ala Gly Asn Tyr Pro Glu Trp Lys Leu Phe Ile Gln Ile Ile Asp Pro
290                 295                 300

Ala Asp Glu Asp Lys Phe Asp Phe Asp Pro Leu Asp Val Thr Lys Thr
305                 310                 315                 320

Trp Pro Glu Asp Ile Leu Pro Leu Gln Pro Val Gly Arg Met Val Leu 325                 330                 335
Asn Lys Asn Ile Asp Asn Phe Phe Ala Glu Asn Glu Gln Leu Ala Phe
                340                 345                 350
Cys Pro Ala Ile Ile Val Pro Gly Ile His Tyr Ser Asp Asp Lys Leu
                355                 360                 365
Leu Gln Thr Arg Val Phe Ser Tyr Ala Asp Thr Gln Arg His Arg Leu
            370                 375                 380
Gly Pro Asn Tyr Leu Gln Leu Pro Val Asn Ala Pro Lys Cys Ala His
385                 390                 395                 400
His Asn Asn His His Glu Gly Phe Met Asn Phe Met His Arg Asp Glu
                405                 410                 415
Glu Val Asn Tyr Phe Pro Ser Arg Tyr Asp Gln Val Arg His Ala Glu
                420                 425                 430
Lys Tyr Pro Thr Pro Pro Ala Val Cys Ser Gly Lys Arg Glu Arg Cys
                435                 440                 445
Ile Ile Glu Lys Glu Asn Asn Phe Lys Glu Pro Gly Glu Arg Tyr Arg
            450                 455                 460
Thr Phe Thr Pro Glu Arg Gln Glu Arg Phe Ile Gln Arg Trp Ile Asp
465                 470                 475                 480
Ala Leu Ser Asp Pro Arg Ile Thr His Glu Ile Arg Ser Ile Trp Ile
                485                 490                 495
Ser Tyr Trp Ser Gln Ala Asp Lys Ser Leu Gly Gln Lys Leu Ala Ser
                500                 505                 510
Arg Leu Asn Val Arg Pro Ser Ile
            515                 520

<210> SEQ ID NO 48
<211> LENGTH: 520
<212> TYPE: PRT
<213> ORGANISM: Arabidopsis thaliana

<400> SEQUENCE: 48

Met Lys Cys Ser Thr Phe Ser Phe Trp Phe Val Cys Lys Ile Ile Phe
1               5                   10                  15
Phe Phe Phe Ser Phe Asn Ile Gln Thr Ser Ile Ala Met Asp Pro Tyr
                20                  25                  30
Lys Tyr Arg Pro Ala Ser Ser Tyr Asn Ser Pro Phe Phe Thr Thr Asn
            35                  40                  45
Ser Gly Ala Pro Val Trp Asn Asn Ser Ser Met Thr Val Gly Pro
        50                  55                  60
Arg Gly Leu Ile Leu Leu Glu Asp Tyr His Leu Val Glu Lys Leu Ala
65                  70                  75                  80
Asn Phe Asp Arg Glu Arg Ile Pro Glu Arg Val Val His Ala Arg Gly
                85                  90                  95
Ala Ser Ala Lys Gly Phe Phe Glu Val Thr His Asp Ile Ser Asn Leu
            100                 105                 110
Thr Cys Ala Asp Phe Leu Arg Ala Pro Gly Val Gln Thr Pro Val Ile
        115                 120                 125
Val Arg Phe Ser Thr Val Ile His Ala Arg Gly Ser Pro Glu Thr Leu
    130                 135                 140
Arg Asp Pro Arg Gly Phe Ala Val Lys Phe Tyr Thr Arg Glu Gly Asn
145                 150                 155                 160
Phe Asp Leu Val Gly Asn Asn Phe Pro Val Phe Phe Ile Arg Asp Gly
                165                 170                 175

Met Lys Phe Pro Asp Ile Val His Ala Leu Lys Pro Asn Pro Lys Ser
            180                 185                 190

His Ile Gln Glu Asn Trp Arg Ile Leu Asp Phe Phe Ser His His Pro
        195                 200                 205

Glu Ser Leu Asn Met Phe Thr Phe Leu Phe Asp Asp Ile Gly Ile Pro
    210                 215                 220

Gln Asp Tyr Arg His Met Asp Gly Ser Gly Val Asn Thr Tyr Met Leu
225                 230                 235                 240

Ile Asn Lys Ala Gly Lys Ala His Tyr Val Lys Phe His Trp Lys Pro
                245                 250                 255

Thr Cys Gly Val Lys Ser Leu Leu Glu Glu Asp Ala Ile Arg Leu Gly
            260                 265                 270

Gly Thr Asn His Ser His Ala Thr Gln Asp Leu Tyr Asp Ser Ile Ala
        275                 280                 285

Ala Gly Asn Tyr Pro Glu Trp Lys Leu Phe Ile Gln Ile Asp Pro
    290                 295                 300

Ala Asp Glu Asp Lys Phe Asp Phe Asp Pro Leu Asp Val Thr Lys Thr
305                 310                 315                 320

Trp Pro Glu Asp Ile Leu Pro Leu Gln Pro Val Gly Arg Met Val Leu
                325                 330                 335

Asn Lys Asn Ile Asp Asn Phe Phe Ala Glu Asn Glu Gln Leu Ala Phe
            340                 345                 350

Cys Pro Ala Ile Ile Val Pro Gly Ile His Tyr Ser Asp Asp Lys Leu
        355                 360                 365

Leu Gln Thr Arg Val Phe Ser Tyr Ala Asp Thr Gln Arg His Arg Leu
    370                 375                 380

Gly Pro Asn Tyr Leu Gln Leu Pro Val Asn Ala Pro Lys Cys Ala His
385                 390                 395                 400

His Asn Asn His His Glu Gly Phe Met Asn Phe Met His Arg Asp Glu
                405                 410                 415

Glu Val Asn Tyr Phe Pro Ser Arg Tyr Asp Gln Val Arg His Ala Glu
            420                 425                 430

Lys Tyr Pro Thr Pro Pro Ala Val Cys Ser Gly Lys Arg Glu Arg Cys
        435                 440                 445

Ile Ile Glu Lys Glu Asn Asn Phe Lys Glu Pro Gly Glu Arg Tyr Arg
    450                 455                 460

Thr Phe Thr Pro Glu Arg Gln Glu Arg Phe Ile Gln Arg Trp Ile Asp
465                 470                 475                 480

Ala Leu Ser Asp Pro Arg Ile Thr His Glu Ile Arg Ser Ile Trp Ile
                485                 490                 495

Ser Tyr Trp Ser Gln Ala Asp Lys Ser Leu Gly Gln Lys Leu Ala Ser
            500                 505                 510

Arg Leu Asn Val Arg Pro Ser Ile
        515                 520

<210> SEQ ID NO 49
<211> LENGTH: 781
<212> TYPE: PRT
<213> ORGANISM: Escherichia coli

<400> SEQUENCE: 49

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Met Ser Gln His
            20                  25                  30

```
Asn Glu Lys Asn Pro His Gln His Gln Ser Pro Leu His Asp Ser Ser
     35                  40                  45

Glu Ala Lys Pro Gly Met Asp Ser Leu Ala Pro Glu Asp Gly Ser His
 50                  55                  60

Arg Pro Ala Ala Glu Pro Thr Pro Pro Gly Ala Gln Pro Thr Ala Pro
 65                  70                  75                  80

Gly Ser Leu Lys Ala Pro Asp Thr Arg Asn Glu Lys Leu Asn Ser Leu
                 85                  90                  95

Glu Asp Val Arg Lys Gly Ser Glu Asn Tyr Ala Leu Thr Thr Asn Gln
             100                 105                 110

Gly Val Arg Ile Ala Asp Asp Gln Asn Ser Leu Arg Ala Gly Ser Arg
         115                 120                 125

Gly Pro Thr Leu Leu Glu Asp Phe Ile Leu Arg Glu Lys Ile Thr His
     130                 135                 140

Phe Asp His Glu Arg Ile Pro Glu Arg Ile Val His Ala Arg Gly Ser
145                 150                 155                 160

Ala Ala His Gly Tyr Phe Gln Pro Tyr Lys Ser Leu Ser Asp Ile Thr
                 165                 170                 175

Lys Ala Asp Phe Leu Ser Asp Pro Asn Lys Ile Thr Pro Val Phe Val
             180                 185                 190

Arg Phe Ser Thr Val Gln Gly Gly Ala Gly Ser Ala Asp Thr Val Arg
         195                 200                 205

Asp Ile Arg Gly Phe Ala Thr Lys Phe Tyr Thr Glu Glu Gly Ile Phe
     210                 215                 220

Asp Leu Val Gly Asn Asn Thr Pro Ile Phe Phe Ile Gln Asp Ala His
225                 230                 235                 240

Lys Phe Pro Asp Phe Val His Ala Val Lys Pro Glu Pro His Trp Ala
                 245                 250                 255

Ile Pro Gln Gly Gln Ser Ala His Asp Thr Phe Trp Asp Tyr Val Ser
             260                 265                 270

Leu Gln Pro Glu Thr Leu His Asn Val Met Trp Ala Met Ser Asp Arg
         275                 280                 285

Gly Ile Pro Arg Ser Tyr Arg Thr Met Glu Gly Phe Gly Ile His Thr
     290                 295                 300

Phe Arg Leu Ile Asn Ala Glu Gly Lys Ala Thr Phe Val Arg Phe His
305                 310                 315                 320

Trp Lys Pro Leu Ala Gly Lys Ala Ser Leu Val Trp Asp Glu Ala Gln
                 325                 330                 335

Lys Leu Thr Gly Arg Asp Pro Asp Phe His Arg Arg Glu Leu Trp Glu
             340                 345                 350

Ala Ile Glu Ala Gly Asp Phe Pro Glu Tyr Glu Leu Gly Phe Gln Leu
         355                 360                 365

Ile Pro Glu Glu Asp Glu Phe Lys Phe Asp Phe Asp Leu Leu Asp Pro
     370                 375                 380

Thr Lys Leu Ile Pro Glu Glu Leu Val Pro Val Gln Arg Val Gly Lys
385                 390                 395                 400

Met Val Leu Asn Arg Asn Pro Asp Asn Phe Phe Ala Glu Asn Glu Gln
                 405                 410                 415

Ala Ala Phe His Pro Gly His Ile Val Pro Gly Leu Asp Phe Thr Asn
             420                 425                 430

Asp Pro Leu Leu Gln Gly Arg Leu Phe Ser Tyr Thr Asp Thr Gln Ile
         435                 440                 445
```

```
Ser Arg Leu Gly Gly Pro Asn Phe His Glu Ile Pro Ile Asn Arg Pro
    450                 455                 460

Thr Cys Pro Tyr His Asn Phe Gln Arg Asp Gly Met His Arg Met Gly
465                 470                 475                 480

Ile Asp Thr Asn Pro Ala Asn Tyr Glu Pro Asn Ser Ile Asn Asp Asn
                485                 490                 495

Trp Pro Arg Glu Thr Pro Gly Pro Lys Arg Gly Gly Phe Glu Ser
            500                 505                 510

Tyr Gln Glu Arg Val Glu Gly Asn Lys Val Arg Glu Arg Ser Pro Ser
        515                 520                 525

Phe Gly Glu Tyr Tyr Ser His Pro Arg Leu Phe Trp Leu Ser Gln Thr
    530                 535                 540

Pro Phe Glu Gln Arg His Ile Val Asp Gly Phe Ser Phe Glu Leu Ser
545                 550                 555                 560

Lys Val Val Arg Pro Tyr Ile Arg Glu Arg Val Val Asp Gln Leu Ala
                565                 570                 575

His Ile Asp Leu Thr Leu Ala Gln Ala Val Ala Lys Asn Leu Gly Ile
            580                 585                 590

Glu Leu Thr Asp Asp Gln Leu Asn Ile Thr Pro Pro Asp Val Asn
        595                 600                 605

Gly Leu Lys Lys Asp Pro Ser Leu Ser Leu Tyr Ala Ile Pro Asp Gly
    610                 615                 620

Asp Val Lys Gly Arg Val Val Ala Ile Leu Leu Asn Asp Glu Val Arg
625                 630                 635                 640

Ser Ala Asp Leu Leu Ala Ile Leu Lys Ala Leu Lys Ala Lys Gly Val
                645                 650                 655

His Ala Lys Leu Leu Tyr Ser Arg Met Gly Glu Val Thr Ala Asp Asp
            660                 665                 670

Gly Thr Val Leu Pro Ile Ala Ala Thr Phe Ala Gly Ala Pro Ser Leu
        675                 680                 685

Thr Val Asp Ala Val Ile Val Pro Cys Gly Asn Ile Ala Asp Ile Ala
    690                 695                 700

Asp Asn Gly Asp Ala Asn Tyr Tyr Leu Met Glu Ala Tyr Lys His Leu
705                 710                 715                 720

Lys Pro Ile Ala Leu Ala Gly Asp Ala Arg Lys Phe Lys Ala Thr Ile
                725                 730                 735

Lys Ile Ala Asp Gln Gly Glu Glu Gly Ile Val Glu Ala Asp Ser Ala
            740                 745                 750

Asp Gly Ser Phe Met Asp Glu Leu Leu Thr Leu Met Ala Ala His Arg
        755                 760                 765

Val Trp Ser Arg Ile Pro Lys Ile Asp Lys Ile Pro Ala
    770                 775                 780

<210> SEQ ID NO 50
<211> LENGTH: 781
<212> TYPE: PRT
<213> ORGANISM: Escherichia coli

<400> SEQUENCE: 50

Met Lys Cys Ser Thr Phe Ser Trp Phe Val Cys Lys Ile Ile Phe
1               5                   10                  15

Phe Phe Phe Ser Phe Asn Ile Gln Thr Ser Ile Ala Met Ser Gln His
                20                  25                  30

Asn Glu Lys Asn Pro His Gln His Gln Ser Pro Leu His Asp Ser Ser
            35                  40                  45
```

```
Glu Ala Lys Pro Gly Met Asp Ser Leu Ala Pro Asp Gly Ser His
        50                  55                  60

Arg Pro Ala Ala Glu Pro Thr Pro Gly Ala Gln Pro Thr Ala Pro
65                  70                  75                  80

Gly Ser Leu Lys Ala Pro Asp Thr Arg Asn Glu Lys Leu Asn Ser Leu
                85                  90                  95

Glu Asp Val Arg Lys Gly Ser Glu Asn Tyr Ala Leu Thr Thr Asn Gln
                100                 105                 110

Gly Val Arg Ile Ala Asp Asp Gln Asn Ser Leu Arg Ala Gly Ser Arg
                115                 120                 125

Gly Pro Thr Leu Leu Glu Asp Phe Ile Leu Arg Glu Lys Ile Thr His
        130                 135                 140

Phe Asp His Glu Arg Ile Pro Glu Arg Ile Val His Ala Arg Gly Ser
145                 150                 155                 160

Ala Ala His Gly Tyr Phe Gln Pro Tyr Lys Ser Leu Ser Asp Ile Thr
                165                 170                 175

Lys Ala Asp Phe Leu Ser Asp Pro Asn Lys Ile Thr Pro Val Phe Val
                180                 185                 190

Arg Phe Ser Thr Val Gln Gly Gly Ala Gly Ser Ala Asp Thr Val Arg
        195                 200                 205

Asp Ile Arg Gly Phe Ala Thr Lys Phe Tyr Thr Glu Glu Gly Ile Phe
210                 215                 220

Asp Leu Val Gly Asn Asn Thr Pro Ile Phe Phe Ile Gln Asp Ala His
225                 230                 235                 240

Lys Phe Pro Asp Phe Val His Ala Val Lys Pro Glu Pro His Trp Ala
                245                 250                 255

Ile Pro Gln Gly Gln Ser Ala His Asp Thr Phe Trp Asp Tyr Val Ser
                260                 265                 270

Leu Gln Pro Glu Thr Leu His Asn Val Met Trp Ala Met Ser Asp Arg
        275                 280                 285

Gly Ile Pro Arg Ser Tyr Arg Thr Met Glu Gly Phe Gly Ile His Thr
        290                 295                 300

Phe Arg Leu Ile Asn Ala Glu Gly Lys Ala Thr Phe Val Arg Phe His
305                 310                 315                 320

Trp Lys Pro Leu Ala Gly Lys Ala Ser Leu Val Trp Asp Glu Ala Gln
                325                 330                 335

Lys Leu Thr Gly Arg Asp Pro Asp Phe His Arg Arg Glu Leu Trp Glu
                340                 345                 350

Ala Ile Glu Ala Gly Asp Phe Pro Glu Tyr Glu Leu Gly Phe Gln Leu
                355                 360                 365

Ile Pro Glu Glu Asp Glu Phe Lys Phe Asp Phe Asp Leu Leu Asp Pro
        370                 375                 380

Thr Lys Leu Ile Pro Glu Glu Leu Val Pro Val Gln Arg Val Gly Lys
385                 390                 395                 400

Met Val Leu Asn Arg Asn Pro Asp Asn Phe Phe Ala Glu Asn Glu Gln
                405                 410                 415

Ala Ala Phe His Pro Gly His Ile Val Pro Gly Leu Asp Phe Thr Asn
                420                 425                 430

Asp Pro Leu Leu Gln Gly Arg Leu Phe Ser Tyr Thr Asp Thr Gln Ile
        435                 440                 445

Ser Arg Leu Gly Gly Pro Asn Phe His Glu Ile Pro Ile Asn Arg Pro
        450                 455                 460
```

```
Thr Cys Pro Tyr His Asn Phe Gln Arg Asp Gly Met His Arg Met Gly
465                 470                 475                 480

Ile Asp Thr Asn Pro Ala Asn Tyr Glu Pro Asn Ser Ile Asn Asp Asn
                485                 490                 495

Trp Pro Arg Glu Thr Pro Pro Gly Pro Lys Arg Gly Gly Phe Glu Ser
            500                 505                 510

Tyr Gln Glu Arg Val Glu Gly Asn Lys Val Arg Glu Arg Ser Pro Ser
        515                 520                 525

Phe Gly Glu Tyr Tyr Ser His Pro Arg Leu Phe Trp Leu Ser Gln Thr
    530                 535                 540

Pro Phe Glu Gln Arg His Ile Val Asp Gly Phe Ser Phe Glu Leu Ser
545                 550                 555                 560

Lys Val Val Arg Pro Tyr Ile Arg Glu Arg Val Val Asp Gln Leu Ala
                565                 570                 575

His Ile Asp Leu Thr Leu Ala Gln Ala Val Ala Lys Asn Leu Gly Ile
            580                 585                 590

Glu Leu Thr Asp Asp Gln Leu Asn Ile Thr Pro Pro Asp Val Asn
        595                 600                 605

Gly Leu Lys Lys Asp Pro Ser Leu Ser Leu Tyr Ala Ile Pro Asp Gly
    610                 615                 620

Asp Val Lys Gly Arg Val Val Ala Ile Leu Leu Asn Asp Glu Val Arg
625                 630                 635                 640

Ser Ala Asp Leu Leu Ala Ile Leu Lys Ala Leu Lys Ala Lys Gly Val
                645                 650                 655

His Ala Lys Leu Leu Tyr Ser Arg Met Gly Glu Val Thr Ala Asp Asp
            660                 665                 670

Gly Thr Val Leu Pro Ile Ala Ala Thr Phe Ala Gly Ala Pro Ser Leu
        675                 680                 685

Thr Val Asp Ala Val Ile Val Pro Cys Gly Asn Ile Ala Asp Ile Ala
    690                 695                 700

Asp Asn Gly Asp Ala Asn Tyr Tyr Leu Met Glu Ala Tyr Lys His Leu
705                 710                 715                 720

Lys Pro Ile Ala Leu Ala Gly Asp Ala Arg Lys Phe Lys Ala Thr Ile
                725                 730                 735

Lys Ile Ala Asp Gln Gly Glu Gly Ile Val Glu Ala Asp Ser Ala
            740                 745                 750

Asp Gly Ser Phe Met Asp Glu Leu Leu Thr Leu Met Ala Ala His Arg
        755                 760                 765

Val Trp Ser Arg Ile Pro Lys Ile Asp Lys Ile Pro Ala
    770                 775                 780

<210> SEQ ID NO 51
<211> LENGTH: 492
<212> TYPE: PRT
<213> ORGANISM: Arabidopsis thaliana

<400> SEQUENCE: 51

Met Asp Pro Tyr Arg Val Arg Pro Ser Ser Ala His Asp Ser Pro Phe
1               5                   10                  15

Phe Thr Thr Asn Ser Gly Ala Pro Val Trp Asn Asn Ser Ser Leu
            20                  25                  30

Thr Val Gly Thr Arg Gly Pro Ile Leu Leu Glu Asp Tyr His Leu Leu
        35                  40                  45

Glu Lys Leu Ala Asn Phe Asp Arg Glu Arg Ile Pro Glu Arg Val Val
    50                  55                  60
```

```
His Ala Arg Gly Ala Ser Ala Lys Gly Phe Phe Glu Val Thr His Asp
 65                  70                  75                  80

Ile Thr Gln Leu Thr Ser Ala Asp Phe Leu Arg Gly Pro Gly Val Gln
                 85                  90                  95

Thr Pro Val Ile Val Arg Phe Ser Thr Val Ile His Glu Arg Gly Ser
            100                 105                 110

Pro Glu Thr Leu Arg Asp Pro Arg Gly Phe Ala Val Lys Phe Tyr Thr
            115                 120                 125

Arg Glu Gly Asn Phe Asp Leu Val Gly Asn Asn Phe Pro Val Phe Phe
130                 135                 140

Val Arg Asp Gly Met Lys Phe Pro Asp Met Val His Ala Leu Lys Pro
145                 150                 155                 160

Asn Pro Lys Ser His Ile Gln Glu Asn Trp Arg Ile Leu Asp Phe Phe
                165                 170                 175

Ser His His Pro Glu Ser Leu His Met Phe Ser Phe Leu Phe Asp Asp
            180                 185                 190

Leu Gly Ile Pro Gln Asp Tyr Arg His Met Glu Gly Ala Gly Val Asn
            195                 200                 205

Thr Tyr Met Leu Ile Asn Lys Ala Gly Lys Ala His Tyr Val Lys Phe
210                 215                 220

His Trp Lys Pro Thr Cys Gly Ile Lys Cys Leu Ser Asp Glu Glu Ala
225                 230                 235                 240

Ile Arg Val Gly Gly Ala Asn His Ser His Ala Thr Lys Asp Leu Tyr
                245                 250                 255

Asp Ser Ile Ala Ala Gly Asn Tyr Pro Gln Trp Asn Leu Phe Val Gln
            260                 265                 270

Val Met Asp Pro Ala His Glu Asp Lys Phe Asp Phe Asp Pro Leu Asp
            275                 280                 285

Val Thr Lys Ile Trp Pro Glu Asp Ile Leu Pro Leu Gln Pro Val Gly
            290                 295                 300

Arg Leu Val Leu Asn Lys Asn Ile Asp Asn Phe Phe Asn Glu Asn Glu
305                 310                 315                 320

Gln Ile Ala Phe Cys Pro Ala Leu Val Val Pro Gly Ile His Tyr Ser
                325                 330                 335

Asp Asp Lys Leu Leu Gln Thr Arg Ile Phe Ser Tyr Ala Asp Ser Gln
            340                 345                 350

Arg His Arg Leu Gly Pro Asn Tyr Leu Gln Leu Pro Val Asn Ala Pro
            355                 360                 365

Lys Cys Ala His His Asn Asn His His Asp Gly Phe Met Asn Phe Met
370                 375                 380

His Arg Asp Glu Glu Val Asn Tyr Phe Pro Ser Arg Leu Asp Pro Val
385                 390                 395                 400

Arg His Ala Glu Lys Tyr Pro Thr Thr Pro Ile Val Cys Ser Gly Asn
                405                 410                 415

Arg Glu Lys Cys Phe Ile Gly Lys Glu Asn Asn Phe Lys Gln Pro Gly
            420                 425                 430

Glu Arg Tyr Arg Ser Trp Asp Ser Asp Arg Gln Glu Arg Phe Val Lys
            435                 440                 445

Arg Phe Val Glu Ala Leu Ser Glu Pro Arg Val Thr His Glu Ile Arg
450                 455                 460

Ser Ile Trp Ile Ser Tyr Trp Ser Gln Ala Asp Lys Ser Leu Gly Gln
465                 470                 475                 480
```

```
Lys Leu Ala Thr Arg Leu Asn Val Arg Pro Asn Phe
            485                 490

<210> SEQ ID NO 52
<211> LENGTH: 492
<212> TYPE: PRT
<213> ORGANISM: Arabidopsis thaliana

<400> SEQUENCE: 52

Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Asn Ser Ser Met
                20                  25                  30

Thr Val Gly Pro Arg Gly Pro Ile Leu Leu Glu Asp Tyr His Leu Val
            35                  40                  45

Glu Lys Leu Ala Asn Phe Asp Arg Glu Arg Ile Pro Glu Arg Val Val
    50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Glu Arg Gly Ser
            100                 105                 110

Pro Glu Thr Leu Arg Asp Pro Arg Gly Phe Ala Val Lys Phe Tyr Thr
        115                 120                 125

Arg Glu Gly Asn Phe Asp Leu Val Gly Asn Asn Phe Pro Val Phe Phe
    130                 135                 140

Ile Arg Asp Gly Met Lys Phe Pro Asp Met Val His Ala Leu Lys Pro
145                 150                 155                 160

Asn Pro Lys Ser His Ile Gln Glu Asn Trp Arg Ile Leu Asp Phe Phe
                165                 170                 175

Ser His His Pro Glu Ser Leu Asn Met Phe Thr Phe Leu Phe Asp Asp
            180                 185                 190

Ile Gly Ile Pro Gln Asp Tyr Arg His Met Asp Gly Ser Gly Val Asn
        195                 200                 205

Thr Tyr Met Leu Ile Asn Lys Ala Gly Lys Ala His Tyr Val Lys Phe
    210                 215                 220

His Trp Lys Pro Thr Cys Gly Val Lys Ser Leu Leu Glu Glu Asp Ala
225                 230                 235                 240

Ile Arg Val Gly Gly Thr Asn His Ser His Ala Thr Gln Asp Leu Tyr
                245                 250                 255

Asp Ser Ile Ala Ala Gly Asn Tyr Pro Glu Trp Lys Leu Phe Ile Gln
            260                 265                 270

Ile Ile Asp Pro Ala Asp Glu Asp Lys Phe Asp Phe Asp Pro Leu Asp
        275                 280                 285

Val Thr Lys Thr Trp Pro Glu Asp Ile Leu Pro Leu Gln Pro Val Gly
    290                 295                 300

Arg Met Val Leu Asn Lys Asn Ile Asp Asn Phe Phe Ala Glu Asn Glu
305                 310                 315                 320

Gln Leu Ala Phe Cys Pro Ala Ile Ile Val Pro Gly Ile His Tyr Ser
                325                 330                 335

Asp Asp Lys Leu Leu Gln Thr Arg Val Phe Ser Tyr Ala Asp Thr Gln
            340                 345                 350

Arg His Arg Leu Gly Pro Asn Tyr Leu Gln Leu Pro Val Asn Ala Pro
        355                 360                 365
```

-continued

Lys Cys Ala His His Asn Asn His His Glu Gly Phe Met Asn Phe Met
    370                 375                 380

His Arg Asp Glu Glu Val Asn Tyr Phe Pro Ser Arg Tyr Asp Gln Val
385                 390                 395                 400

Arg His Ala Glu Lys Tyr Pro Thr Pro Pro Ala Val Cys Ser Gly Lys
                405                 410                 415

Arg Glu Arg Cys Ile Ile Glu Lys Glu Asn Asn Phe Lys Glu Pro Gly
                420                 425                 430

Glu Arg Tyr Arg Thr Phe Thr Pro Glu Arg Gln Glu Arg Phe Ile Gln
            435                 440                 445

Arg Trp Ile Asp Ala Leu Ser Asp Pro Arg Ile Thr His Glu Ile Arg
    450                 455                 460

Ser Ile Trp Ile Ser Tyr Trp Ser Gln Ala Asp Lys Ser Leu Gly Gln
465                 470                 475                 480

Lys Leu Ala Ser Arg Leu Asn Val Arg Pro Ser Ile
                485                 490

<210> SEQ ID NO 53
<211> LENGTH: 492
<212> TYPE: PRT
<213> ORGANISM: Arabidopsis thaliana

<400> SEQUENCE: 53

Met Asp Pro Tyr Lys Tyr Arg Pro Ser Ser Ala Tyr Asn Ala Pro Phe
1               5                   10                  15

Tyr Thr Thr Asn Gly Gly Ala Pro Val Ser Asn Asn Ile Ser Ser Leu
            20                  25                  30

Thr Ile Gly Glu Arg Gly Pro Val Leu Leu Glu Asp Tyr His Leu Ile
        35                  40                  45

Glu Lys Val Ala Asn Phe Thr Arg Glu Arg Ile Pro Glu Arg Val Val
    50                  55                  60

His Ala Arg Gly Ile Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Val His Glu Arg Ala Ser
            100                 105                 110

Pro Glu Thr Met Arg Asp Ile Arg Gly Phe Ala Val Lys Phe Tyr Thr
        115                 120                 125

Arg Glu Gly Asn Phe Asp Leu Val Gly Asn Asn Thr Pro Val Phe Phe
    130                 135                 140

Ile Arg Asp Gly Ile Gln Phe Pro Asp Val Val His Ala Leu Lys Pro
145                 150                 155                 160

Asn Pro Lys Thr Asn Ile Gln Glu Tyr Trp Arg Ile Leu Asp Tyr Met
                165                 170                 175

Ser His Leu Pro Glu Ser Leu Leu Thr Trp Cys Trp Met Phe Asp Asp
            180                 185                 190

Val Gly Ile Pro Gln Asp Tyr Arg His Met Glu Gly Phe Gly Val His
        195                 200                 205

Thr Tyr Thr Leu Ile Ala Lys Ser Gly Lys Val Leu Phe Val Lys Phe
    210                 215                 220

His Trp Lys Pro Thr Cys Gly Ile Lys Asn Leu Thr Asp Glu Glu Ala
225                 230                 235                 240

Lys Val Val Gly Gly Ala Asn His Ser His Ala Thr Lys Asp Leu His

```
            245                 250                 255
Asp Ala Ile Ala Ser Gly Asn Tyr Pro Glu Trp Lys Leu Phe Ile Gln
            260                 265                 270

Thr Met Asp Pro Ala Asp Glu Asp Lys Phe Asp Phe Asp Pro Leu Asp
        275                 280                 285

Val Thr Lys Ile Trp Pro Glu Asp Ile Leu Pro Leu Gln Pro Val Gly
    290                 295                 300

Arg Leu Val Leu Asn Arg Thr Ile Asp Asn Phe Phe Asn Glu Thr Glu
305                 310                 315                 320

Gln Leu Ala Phe Asn Pro Gly Leu Val Val Pro Gly Ile Tyr Tyr Ser
                325                 330                 335

Asp Asp Lys Leu Leu Gln Cys Arg Ile Phe Ala Tyr Gly Asp Thr Gln
            340                 345                 350

Arg His Arg Leu Gly Pro Asn Tyr Leu Gln Leu Pro Val Asn Ala Pro
        355                 360                 365

Lys Cys Ala His His Asn Asn His His Glu Gly Phe Met Asn Phe Met
    370                 375                 380

His Arg Asp Glu Glu Ile Asn Tyr Tyr Pro Ser Lys Phe Asp Pro Val
385                 390                 395                 400

Arg Cys Ala Glu Lys Val Pro Thr Pro Thr Asn Ser Tyr Thr Gly Ile
                405                 410                 415

Arg Thr Lys Cys Val Ile Lys Lys Glu Asn Asn Phe Lys Gln Ala Gly
            420                 425                 430

Asp Arg Tyr Arg Ser Trp Ala Pro Asp Arg Gln Asp Arg Phe Val Lys
        435                 440                 445

Arg Trp Val Glu Ile Leu Ser Glu Pro Arg Leu Thr His Glu Ile Arg
    450                 455                 460

Gly Ile Trp Ile Ser Tyr Trp Ser Gln Ala Asp Arg Ser Leu Gly Gln
465                 470                 475                 480

Lys Leu Ala Ser Arg Leu Asn Val Arg Pro Ser Ile
                485                 490

<210> SEQ ID NO 54
<211> LENGTH: 23
<212> TYPE: DNA
<213> ORGANISM: Artificial Sequence
<220> FEATURE:
<223> OTHER INFORMATION: Forward primer of CYP3A4

<400> SEQUENCE: 54
tgcctaataa agctcctcct act                                          23

<210> SEQ ID NO 55
<211> LENGTH: 22
<212> TYPE: DNA
<213> ORGANISM: Artificial Sequence
<220> FEATURE:
<223> OTHER INFORMATION: Reverse primer of CYP3A4

<400> SEQUENCE: 55
gctcctgaaa cagttccatc tc                                           22

<210> SEQ ID NO 56
<211> LENGTH: 22
<212> TYPE: DNA
<213> ORGANISM: Artificial Sequence
<220> FEATURE:
<223> OTHER INFORMATION: Forward primer of P450 oxidoreductase
```

<400> SEQUENCE: 56
ggaagagctt tggttcctat gt                                        22

<210> SEQ ID NO 57
<211> LENGTH: 23
<212> TYPE: DNA
<213> ORGANISM: Artificial Sequence
<220> FEATURE:
<223> OTHER INFORMATION: Reverse primer of P450 oxidoreductase

<400> SEQUENCE: 57
gctcccaatt cagcaacaat atc                                       23

<210> SEQ ID NO 58
<211> LENGTH: 29
<212> TYPE: DNA
<213> ORGANISM: Artificial Sequence
<220> FEATURE:
<223> OTHER INFORMATION: Forward primer CBDA synthase

<400> SEQUENCE: 58
acatcacaat cacacaaaac taacaaaag                                 29

<210> SEQ ID NO 59
<211> LENGTH: 22
<212> TYPE: DNA
<213> ORGANISM: Artificial Sequence
<220> FEATURE:
<223> OTHER INFORMATION: Reverse primer of CBDA synthase

<400> SEQUENCE: 59
ggccatagtt tctcatcaat gg                                        22

<210> SEQ ID NO 60
<211> LENGTH: 28
<212> TYPE: DNA
<213> ORGANISM: Artificial Sequence
<220> FEATURE:
<223> OTHER INFORMATION: Forward primer of UGT76G1

<400> SEQUENCE: 60
gattggaaga acaagcttca ggatttcc                                  28

<210> SEQ ID NO 61
<211> LENGTH: 26
<212> TYPE: DNA
<213> ORGANISM: Artificial Sequence
<220> FEATURE:
<223> OTHER INFORMATION: Reverse primer of UGT76G1

<400> SEQUENCE: 61
ccatcctgaa tgagtccaaa aagctc                                    26

<210> SEQ ID NO 62
<211> LENGTH: 22
<212> TYPE: DNA
<213> ORGANISM: Artificial Sequence
<220> FEATURE:
<223> OTHER INFORMATION: Forward primer of ABCG2

<400> SEQUENCE: 62
ccttcaggat tgtcaggaga tg                                        22

<210> SEQ ID NO 63
<211> LENGTH: 22

```
<212> TYPE: DNA
<213> ORGANISM: Artificial Sequence
<220> FEATURE:
<223> OTHER INFORMATION: Reverse primer of ABCG2

<400> SEQUENCE: 63
gcaggtccat gaaacatcaa tc                                             22

<210> SEQ ID NO 64
<211> LENGTH: 27
<212> TYPE: DNA
<213> ORGANISM: Artificial Sequence
<220> FEATURE:
<223> OTHER INFORMATION: Forward primer of Trichome-targeted CBDAs

<400> SEQUENCE: 64
aaagatcaaa agcaagttct tcactgt                                        27

<210> SEQ ID NO 65
<211> LENGTH: 25
<212> TYPE: DNA
<213> ORGANISM: Artificial Sequence
<220> FEATURE:
<223> OTHER INFORMATION: Reverse primer of Trichome-targeted CBDAs

<400> SEQUENCE: 65
ccatgcagtt tggctatgaa catct                                          25

<210> SEQ ID NO 66
<211> LENGTH: 25
<212> TYPE: DNA
<213> ORGANISM: Artificial Sequence
<220> FEATURE:
<223> OTHER INFORMATION: Forward primer of Trichome-targeted UGT

<400> SEQUENCE: 66
agtgctcaac attctccttt tggtt                                          25

<210> SEQ ID NO 67
<211> LENGTH: 25
<212> TYPE: DNA
<213> ORGANISM: Artificial Sequence
<220> FEATURE:
<223> OTHER INFORMATION: Reverse primer of Trichome-targeted UGT

<400> SEQUENCE: 67
tctgaagcca acatcaacaa ttcca                                          25

<210> SEQ ID NO 68
<211> LENGTH: 25
<212> TYPE: DNA
<213> ORGANISM: Artificial Sequence
<220> FEATURE:
<223> OTHER INFORMATION: Forward primer of Plasma membrane-targeted UTRI

<400> SEQUENCE: 68
ttgttcctta aacctcgcct ttgac                                          25

<210> SEQ ID NO 69
<211> LENGTH: 25
<212> TYPE: DNA
<213> ORGANISM: Artificial Sequence
<220> FEATURE:
<223> OTHER INFORMATION: Reverse primer of Plasma membrane-targeted UTRI

<400> SEQUENCE: 69
```

```
tcattatgga gcactccact ctctg                                        25

<210> SEQ ID NO 70
<211> LENGTH: 27
<212> TYPE: DNA
<213> ORGANISM: Artificial Sequence
<220> FEATURE:
<223> OTHER INFORMATION: Forward primer of Cytosolic-targeted CBDA
      synthase

<400> SEQUENCE: 70
aaagatcaaa agcaagttct tcactgt                                      27

<210> SEQ ID NO 71
<211> LENGTH: 25
<212> TYPE: DNA
<213> ORGANISM: Artificial Sequence
<220> FEATURE:
<223> OTHER INFORMATION: Reverse primer of Cytosolic-targeted CBDA
      synthase

<400> SEQUENCE: 71
ataaacttct ccaagggtag ctccg                                        25

<210> SEQ ID NO 72
<211> LENGTH: 25
<212> TYPE: DNA
<213> ORGANISM: Artificial Sequence
<220> FEATURE:
<223> OTHER INFORMATION: Forward primer of Cytosolic-targeted UGT

<400> SEQUENCE: 72
agaactggaa gaatccgaac tggaa                                        25

<210> SEQ ID NO 73
<211> LENGTH: 25
<212> TYPE: DNA
<213> ORGANISM: Artificial Sequence
<220> FEATURE:
<223> OTHER INFORMATION: Reverse primer of Cytosolic-targeted UGT

<400> SEQUENCE: 73
aaatcatcgg gacaccttca caaac                                        25

<210> SEQ ID NO 74
<211> LENGTH: 42
<212> TYPE: DNA
<213> ORGANISM: Arabidopsis thaliana

<400> SEQUENCE: 74
tgctccataa tgaacttaat gtgtgggtct acctgcgccg ct                     42
```